US007928238B2

(12) United States Patent
Rano et al.

(10) Patent No.: US 7,928,238 B2
(45) Date of Patent: Apr. 19, 2011

(54) 1,2,3,4-TETRAHYDRO-QUINOLINE DERIVATIVES AS CETP INHIBITORS

(75) Inventors: Thomas Rano, Branchburg, NJ (US); Gee-Hong Kuo, Scotch Plains, NJ (US); Ellen Sieber-McMaster, Langhorne, PA (US); Keith T. Demarest, Flemington, NJ (US); Patricia Pelton, Long Valley, NJ (US); Aihua Wang, Jamison, PA (US)

(73) Assignee: Janssen Pharmaceutica NV (BE)

( * ) Notice: Subject to any disclaimer, the term of this patent is extended or adjusted under 35 U.S.C. 154(b) by 335 days.

(21) Appl. No.: 11/746,755

(22) Filed: May 10, 2007

(65) Prior Publication Data

US 2007/0265304 A1    Nov. 15, 2007

Related U.S. Application Data

(60) Provisional application No. 60/799,468, filed on May 11, 2006, provisional application No. 60/871,153, filed on Dec. 21, 2006.

(51) Int. Cl.
*C07D 453/04* (2006.01)
*A01N 43/42* (2006.01)

(52) U.S. Cl. ......... 546/134; 514/279; 514/183; 546/112

(58) Field of Classification Search ................... 514/183
See application file for complete search history.

(56) References Cited

U.S. PATENT DOCUMENTS

| | | | |
|---|---|---|---|
| 5,580,885 | A | 12/1996 | King et al. |
| 5,616,537 | A | 4/1997 | Yokota et al. |
| 5,770,544 | A | 6/1998 | Yokota et al. |
| 6,051,601 | A | 4/2000 | Dombroski et al. |
| 6,093,573 | A | 7/2000 | Beamer et al. |
| 6,262,074 | B1 | 7/2001 | Otten et al. |
| 6,476,075 | B1 | 11/2002 | Sikorski et al. |
| 6,479,436 | B1 | 11/2002 | Otten et al. |
| 6,642,228 | B1 | 11/2003 | Hayashi et al. |
| 6,713,508 | B2 | 3/2004 | Sahoo et al. |
| 7,015,219 | B2 | 3/2006 | Dickson et al. |
| 7,125,891 | B2 | 10/2006 | Breslin et al. |
| 2002/0013314 | A1 | 1/2002 | Zhu et al. |
| 2003/0162777 | A1 | 8/2003 | Leonardi et al. |
| 2003/0181446 | A1 | 9/2003 | Leonardi et al. |
| 2004/0034089 | A1 | 2/2004 | Breslin et al. |
| 2004/0039018 | A1 | 2/2004 | Ruggeri |
| 2005/0113368 | A1 | 5/2005 | Bhuniya et al. |
| 2006/0276509 | A1 | 12/2006 | Breslin et al. |

FOREIGN PATENT DOCUMENTS

| | | |
|---|---|---|
| EP | 0 198 264 A2 | 3/1986 |
| EP | 0 801 060 A1 | 3/1997 |
| WO | WO 93/05038 | 3/1993 |
| WO | WO 94/01415 | 1/1994 |
| WO | WO 96/11920 | 4/1996 |
| WO | WO 96/15099 | 5/1996 |
| WO | WO 98/12180 | 3/1998 |
| WO | WO 98/12192 | 3/1998 |
| WO | WO 00/78716 A1 | 12/2000 |
| WO | WO 01/12187 A2 | 2/2001 |
| WO | WO 01/57003 A1 | 8/2001 |
| WO | WO 02/36116 A2 | 5/2002 |
| WO | WO 03/031436 A1 | 4/2003 |
| WO | WO 2004/037788 A1 | 5/2004 |
| WO | WO 2004/072041 A1 | 8/2004 |
| WO | WO 2004/072042 A1 | 8/2004 |

OTHER PUBLICATIONS

Hesler et al., J. Biol. Chem., 262:2275-2282, 1987.
Au-Young and Fielding, Proc. Natl. Acad. Sci., 89:4094-4098, 1992.
Bruce et al., Curr. Opin. Struct. Biol., 8:426-434, 1998.
Marcel et al., Journal of Clinical Investigation, 85:10-17, 1990.
McPherson et al., Arteriosclerosis and Thrombosis: A Jounral of Vascular Biology, 11(4):797-804, 1991.
Nishida et al., Journal of Biological Chemistry, 268(22):16352-60, 1993.
Guerin et al., Arteriosclerosis and Thrombosis: A Journal of Vascular Biology, 14(5):679-85, 1994.
Guerin et al., Arteriosclerosis and Thrombosis: A Journal of Vascular Biology, 14(2):199-206, 1994.
Packard and Shepard, ARterscler. Thromb. Vasc. Biol., 17:3542-3556, 1997.
Guerin et al., European Journal of Clinical Investigation, 26(6):485-94, 1996.
Guerin et al, Arterioscloerosis, Thrombosis and Vascular Biology, 20(1):189-97, 2001.
Sugano et al., Journal of Biological Chemistry, 273(9):5033-6, 1998.
Rittershaus et al., Arteriosclerosis, Thrombosis and Vascular Biology, 20(9):2106-2112, 2000.
Whitlock et al., Journal of Cinical Investigation, 84(1):129-37, 1989.
Okamoto et al., Nature, 406:203-207, 2000.
Huang et al., Clin. Sci., 103(6):587-594, 2002.
DeGrooth et al., Circulation, 105(18):2159-2165, 2002.
Brousseau et al., New England Journal of Medicine, 350(15):1505-1515, 2004.
Berge et al., "Pharmaceutical Salts.", J. Pharm.Sci., 1977, vol. 66(1), pp. 1-19.
Connolly et al., "Sterospecific Inhibition of CETP by Chiral *N,N*-Disubstituted Trifluoro-3-amino-2-propanols.", Biochemistry, 2000, vol. 39, pp. 13870-13879.
Gould P.L., "Salt Selection for Basic Drugs.", International J. Pharm., 1986, vol. 33, pp. 201-217.
Still et al., "Rapid Chromatographic Technique for Preparative Separations with Moderate Resolution.", J. Org. Chem., 1978, vol. 43(14), pp. 2923-2925.
Tashiro et al., "Preparation of Bromobenzoic Acids From the Corresponding Bromotoluenes Via the Krohke Method.", Organic Preparations and Procedures International, 1984, vol. 16(5), pp. 379-383.
International Search Report, International U.S. Appl. No. PCT/US2007/068628, Date of Mailing of International Search Report, Apr. 28, 2008.
Written Opinion of International Search Authority relating to International Application No. PCT/US2007/068628, Date of Mailing of Written Opinion, Apr. 28, 2008.
Translation of EP0198264.

*Primary Examiner* — James D. Anderson
*Assistant Examiner* — Meghan Finn

(57) ABSTRACT

The invention is directed to compounds of Formula (I) described herein useful as CETP inhibitors, compositions containing them, and methods of using them.

57 Claims, No Drawings

1,2,3,4-TETRAHYDRO-QUINOLINE DERIVATIVES AS CETP INHIBITORS

CROSS-REFERENCE TO RELATED APPLICATIONS

This Application claims priority to United States Provisional Patent Applications No. 60/799,468, filed May 11, 2006, and 60/871,153, filed Dec. 21, 2006, which are hereby incorporated by reference in their entireties.

FIELD OF THE INVENTION

The present invention is directed to compounds useful as CETP inhibitors, compositions containing them, and methods of using them, for example, for the treatment of disorders and conditions modulated by cholesteryl ester transfer protein (CETP).

STATEMENT REGARDING FEDERALLY SPONSORED RESEARCH OR DEVELOPMENT

The research and development of the invention described below was not federally sponsored.

BACKGROUND OF THE INVENTION

Cholesterol homeostasis is maintained by dietary intake, biosynthesis, metabolism to bile acids, absorption and a process known as reverse cholesterol transport (RCT). Cholesterol is transported in the blood by lipoproteins, which contain different apolipoproteins that are recognized by different receptors on the liver and cells such as macrophages. RCT is involved in the movement of cholesterol from peripheral tissues to the liver for excretion. This pathway may represent up to 70% of the flux of cholesterol to the liver. Inherent in this process is the remodeling of the lipoprotein particles. A key player in RCT is the cholesteryl ester transfer protein (CETP), a glycoprotein that mediates the transfer of cholesteryl ester from the cardioprotective High Density Lipoprotein (HDL) particles to the pro-atherogenic LDL (Low Density Lipoprotein), VLDL (Very Low Density Lipoprotein) and IDL (Intermediate Density Lipoprotein).

CETP is a glycoprotein with a molecular weight of about 74 kDa and a primary sequence containing 476 amino acids. Although the amino acid sequence would suggest the protein to be highly hydrophobic, most of the hydrophobic residues reside mainly on the interior, as the protein is soluble in water (Hesler et al., J. Biol. Chem., 262:2275-2282, 1987). This hydrophobic pocket allows for the binding of neutral lipids (Au-Young and Fielding, Proc. Natl. Acad. Sci., 89:4094-4098, 1992). Using the crystallographic structure of a related protein, BPI (bactericidal/permeability increasing protein) with about 20% homology to CETP, a model of CETP was published by Bruce et al., Curr. Opin. Struct. Biol., 8:426-434, 1998. The C-terminal residues were predicted to form an amphipathic helix that covers the opening of an N-terminal pocket. Lipid transfer is thought to occur through a disordering of the lipids in the lipoprotein surface followed by flipping open of the hydrophobic pocket with entry of the neutral lipid.

CETP facilitates exchange and net transfer of neutral lipids, mainly cholesteryl esters and triglycerides between plasma lipoproteins. Phospholipids can also be transferred to a lesser degree. CETP inhibitors have emerged with the potential to increase HDL cholesterol (HDL-C) to levels exceeding those of the currently available therapies.

In normal human plasma, the CETP concentration is around 1-3 µg/ml; however, in patients with hypercholesterolemia, or mixed hyperlipidemias with hypertriglyceridemia, the CETP concentrations have been reported to be 2-3 fold higher (Marcel et al., Journal of Clinical Investigation, 85:10-17, 1990, and McPherson et al., Arteriosclerosis and Thrombosis: A Journal of Vascular Biology, 11 (4):797-804, 1991). Plasma CETP activity is modulated by a variety of factors including: plasma CETP concentration, plasma levels of lipoprotein acceptors and donors, plasma triglyceride levels, physical exercise, alcohol and smoking. Circulating CETP is associated with HDL, VLDL and LDL particles (Nishida et al., Journal of Biological Chemistry, 268(22):16352-60, 1993). Most seems to be associated with HDL and only about 1% is reported to be present in free form.

In patients with Type IIa hypercholesterolemia (familial hypercholesterolemia, LDL-C>160 mg/dL), elevated levels of CETP have been reported as well as increased transfer of cholesteryl ester from HDL to VLDL and LDL (Guerin et al., Arteriosclerosis and Thrombosis: A Journal of Vascular Biology, 14(5):679-85, 1994, and Guerin et al., Arteriosclerosis and Thrombosis: A Journal of Vascular Biology, 14(2):199-206, 1994) thereby generating the smaller more dense LDL particles, which are considered to be atherogenic. Type IV hypertriglyceridemia is characterized by elevated levels of VLDL and VLDL remnants with plasma triglycerides measuring >150 mg/dL. Associated with these elevations are reduced levels of HDL and apoA-I. This may be due to an increase in the CETP-mediated transfer of cholesterol esters to VLDL. This results in the formation of large VLDL1 subfractions, which are the preferential precursors of small dense proatherogenic LDL particles (Packard and Shepard, Arterscler. Thromb. Vasc. Biol., 17:3542-3556, 1997). Type IIB is a mixed hyperlipidemia characterized by simultaneous elevations in both plasma cholesterol and triglycerides with increases in VLDL and LDL and decreases in HDL. The LDL particles are shifted to the small dense LDL 4 and 5 subfractions. Plasma CETP concentrations are elevated and a higher rate of transfer activity has also been reported (Guerin et al., European Journal of Clinical Investigation, 26(6):485-94, 1996). In the case of secondary dyslipidemias such as those found in diabetes, there are also reports of elevated CETP activity particularly in the presence of hypertriglyceridemia (Guerin et al, Arterioscloerosis, Thrombosis and Vascular Biology, 20(1):189-97, 2001).

The first studies with CETP inhibitors were done in rabbits, which express high levels of CETP and are highly susceptible to atherosclerosis when fed a high cholesterol diet. Anti-sense oligonucleotides, antibodies, vaccines and small molecule inhibitors have been tested (Sugano et al., Journal of Biological Chemistry, 273(9):5033-6, 1996; Rittershaus et al., Arteriosclerosis, Thrombosis and Vascular Biology, 20(9):2106-2112, 2000; Whitlock et al., Journal of Clinical Investigation, 84(1):129-37, 1989; and Okamoto et al., Nature, 406:203-207, 2000). These studies showed that inhibition of CETP increased plasma HDL-C levels and particle size as well as decreasing aortic cholesterol content and lesion development. Administration of the small molecule inhibitor JTT-705, which irreversibly inactivated CETP by binding to a crucial cysteine residue (Cys13), to rabbits at a dose of 30 mg/kg inhibited CETP activity, increased HDL-C (+90%), reduced non-HDL-C cholesterol and lesion size (−50% and −70%, respectively, Okamoto et al., Nature, 406:203-207, 2000). However, in another study where rabbits had severe hypercholesterolemia, JTT-705 was not efficacious in preventing lesion development (Huang et al., Clin. Sci., 103(6):587-594, 2002). Interestingly there were significant elevations of plasma triglycerides in this study with JTT-705 treatment. In later clinical studies, JTT-705 was found to raise HDL-C, modestly lower LDL-C and not alter triglyceride levels (De-Grooth et al., Circulation, 105(18):2159-2165, 2002). A more potent CETP inhibitor, Torcetrapib, has shown positive results in Phase II trials, particularly in combination with Atorvastatin (Brousseau et al., New England Journal of Medicine, 350(15):1505-1515, 2004). All references cited herein are hereby incorporated by reference in their entireties.

There is a continuing need for new CETP inhibitors. There is a further need for new CETP inhibitors that increase HDL-C, increase the ratio of HDL-C/total cholesterol, increase the ratio of HCL-C/LDL-C, and/or lower LDL-C and/or lower non-HDL-C cholesterol.

It is an object of the present invention to provide compounds that are CETP inhibitors. It is also an object of the invention to provide a method of treating or ameliorating a condition mediated by CETP. It is a further object of the invention to provide a useful pharmaceutical composition comprising a compound of the present invention useful as a CETP inhibitor.

SUMMARY OF THE INVENTION

In one aspect, the present invention is directed to a compound of Formula (I):

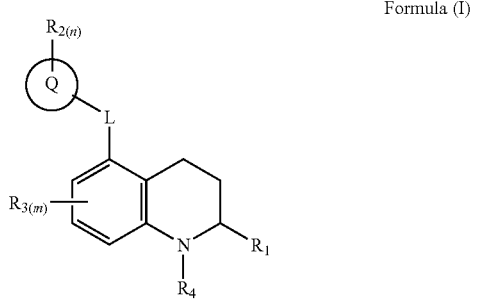

Formula (I)

wherein:
L is a covalent bond or O;
Q is $C_{6-10}$ aryl or 5- or 6-membered heteroaryl;
n is 0 to 3;
m is 0 to 3;
$R_1$ is $C_{1-10}$ alkyl, $C_{2-10}$ alkenyl, $C_{2-10}$ alkynyl, $C_{2-10}$cycloalkyl, 5- or 6-membered heteroaryl, wherein each of $C_{1-10}$ alkyl, $C_{2-10}$ alkenyl, $C_{2-10}$ alkynyl, $C_{3-10}$cycloalkyl, 5- or 6-membered heteroaryl may be optionally substituted;
or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated $C_{1-4}$alkoxy, optionally substituted $C_{1-4}$ alkylthio, halo, cyano, and hydroxy, or
$R_a$ and $R_b$ together with the carbon atoms of the phenyl ring to which they are attached form an optionally substituted 5- or 6-membered heterocyclyl fused to the phenyl ring;
each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;

each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;
$R_4$ is $C_{1-10}$ alkyl optionally substituted with 1-3 members independently selected from halo, oxo, hydroxy, halogenated $C_{1-4}$alkyl, $C_{1-4}$ alkoxy, $C_{3-8}$ cycloalkyl, CN, tert-butyldimethylsilyloxy, heterocyclyl and —$NR_cR_d$, wherein $R_c$ and $R_d$ are independently selected from H, optionally substituted $C_{1-3}$ alkyl, —$C(O)C_{1-3}$alkyl, —$C(O)O$—$C_{1-3}$ alkyl, and —$SO_2C_{1-3}$alkyl; or
$R_4$ is $C_{1-6}$alkyl substituted with heteroaryl or phenyl substituted with 1 to 3 members independently selected from halo, hydroxy, $C_{1-3}$alkyl, halogenated $C_{1-3}$alkyl, $C_{1-4}$alkoxy, or halogenated $C_{1-4}$alkoxy;
and enantiomers, diastereomers, tautomers, solvates, or pharmaceutically acceptable salts thereof.

In another aspect, the present invention is directed to pharmaceutical compositions containing one or more compounds of Formula (I), enantiomers, diastereomers, tautomers, solvates, or pharmaceutically acceptable salts thereof as described herein admixed with a pharmaceutically acceptable carrier, excipient or diluent, wherein the compositions can be used to treat a condition directly or indirectly mediated by CETP.

In yet another aspect, the present invention is directed to a method of treating or preventing a disease or condition in a mammal which disease or condition is affected by the modulation of CETP, which method comprises administering to a mammal in need of such treatment or prevention a therapeutically effective amount of one or more compounds of Formula (I), enantiomers, diastereomers, tautomers, solvates, or pharmaceutically acceptable salts thereof as described herein.

In a further aspect, the present invention is directed to a method for treating or preventing a disease or condition selected from atherosclerosis, peripheral vascular disease, dyslipidemia (including hypertriglyceridemia, hypercholesterolemia, mixed hyperlipidemia, and hypo-HDL-cholesterolemia), hyper-LDL-cholesterolemia hyperbetaliproteinemia, hypoalphalipoproteinemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and Metabolic Syndrome, said method comprising the step of administering to a mammal in need of such treatment a therapeutically effective amount of a compound of Formula (I), or an enantiomer, diastereomer, tautomer, solvate, or pharmaceutically acceptable salt thereof.

DETAILED DESCRIPTION OF THE INVENTION

As used herein, the following underlined terms are intended to have the following meanings unless otherwise noted:

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

"$C_{a-b}$" (where a and b are integers) refers to a radical containing from a to b carbon atoms inclusive. For example, $C_{1-3}$ denotes a radical containing 1, 2 or 3 carbon atoms.

"Alkyl" whether used alone or as part of a substituent group refers to straight and branched carbon chains having 1 to 10 carbon atoms or any number within this range. Typical alkyl groups include, but are not limited to, methyl, ethyl, propyl, and butyl. In preferred embodiments, the alkyl group is $C_{1-8}$ alkyl, with $C_{1-3}$alkyl being particularly preferred. The term "alkoxy" refers to an —Oalkyl substituent group, wherein alkyl is defined supra. Similarly, the terms "alkenyl" and "alkynyl" refer to straight and branched carbon chains having 2 to 10 carbon atoms or any number within this range, wherein an alkenyl chain has at least one double bond in the chain and an alkynyl chain has at least one triple bond in the chain.

The term "cycloalkyl" refers to saturated or partially unsaturated, monocyclic or polycyclic hydrocarbon rings of from 3 to 20 carbon atom members (preferably from 3 to 14 carbon atom members). Examples of such rings include, but are not limited to, cyclopropyl, cyclobutyl, cyclopentyl, cyclohexyl, cycloheptyl or adamantyl.

In certain embodiments, wherein the alkyl, alkenyl, alkynyl, alkoxy, and/or cycloalkyl as defined herein can be optionally substituted, such alkyl, alkenyl, alkynyl and cycloalkyl can be substituted with one, two or three groups independently selected from halo (F, Cl, Br, or I), oxo, cyano, amino, alkoxy, cycloalkyl, carboxy, hydroxy, heterocyclyl, and halogenatedalkyl; and/or one group selected from optionally substituted aryl and optionally substituted heteroaryl.

"Halogenated alkyl" refers to a saturated branched or straight chain alkyl radical derived by removal of at least 1 hydrogen atom from the parent alkyl and substituting it with a halogen; the parent alkyl chain contains from 1 to 10 carbon atoms with 1 or more hydrogen atoms substituted with halogen atoms up to and including substitution of all hydrogen atoms with halogen. Preferred halogenated alkyl groups are fluorinated alkyls, including trifluoromethyl substituted alkyls and perfluorinated alkyls; more preferred fluorinated alkyls include trifluoromethyl, perfluoroethyl, 1,1,2,2-tetrafluoroethyl, 2,2,2-trifluoroethyl, perfluoropropyl, 1,1,2,2,3,3-Hexafluoro-propyl, 3,3,3-trifluoroprop-1-yl, 3,3,3-trifluoroprop-2-yl; a particularly preferred fluorinated alkyls are trifluoromethyl and 1,1,2,2-tetrafluoroethyl.

"Halogenated alkoxy" refers to a radical derived from a halogenated alkyl radical attached to an oxygen atom having one open valence for attachment to a parent structure. Preferred halogenated alkoxy groups are fluorinated alkoxy groups, including trifluoromethoxy and 1,1,2,2-tetrafluoroethoxy.

"Alkylthio" refers to an alkyl group as defined herein attached through one or more sulfur (S) atoms. For example, an alkylthio group can include —S—$C_{1-6}$alkyl optionally substituted with, for example, one, two, or three groups selected from, halo (F, Cl, Br, or I), amino, alkoxy, carboxy, and hydroxy.

"Oxo" whether used alone or as part of a substituent group refers to an O═ to either a carbon or a sulfur atom. For example, phthalimide and saccharin are examples of compounds with oxo substituents.

The term "aryl" refers to an unsaturated monocyclic or polycyclic ring, preferably an aromatic monocyclic ring of 6 carbon members or to an unsaturated, aromatic polycyclic ring of from 10 to 14 carbon members. Preferred aryl groups for the practice of this invention are phenyl and naphthalenyl. In certain embodiments, the aryl ring is a $C_{6-10}$aryl. "Ph" when used herein refers to phenyl. In certain embodiments, wherein the aryl is optionally substituted, the aryl can be substituted with one, two or three groups independently selected from optionally substituted alkyl, halogenated alkyl, optionally substituted alkenyl, optionally substituted alkynyl, halo, —CHO, cyano, amino, optionally substituted alkoxy, halogenated alkoxy, carboxy, hydroxy, and optionally substituted heterocyclyl.

The term "arylalkyl" means an alkyl group substituted with an aryl group (e.g., benzyl, phenylethyl, naphthylmethyl). Similarly, the term "arylalkoxy" indicates an alkoxy group substituted with an aryl group (e.g., benzyloxy). In particularly preferred embodiments, the alkyl moiety of the arylalkyl group is ($C_{1-3}$) and the aryl moiety is ($C_{6-10}$).

"Heterocyclyl" or "heterocycle" is a 3- to 8-member, preferably 5-7 membered saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 1,3-dioxolane, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone. A "heterocyclyl" can be a partially unsaturated ring such as 2-pyrroline, 3-pyrroline, 2-imidazoline, 2-pyrazoline, or indolinone. In certain embodiments, wherein the "heterocyclyl" or "heterocycle" is optionally substituted, the "heterocyclyl" or "heterocycle" can be substituted with, one, two or three groups independently selected from $C_{1-6}$alkyl, halogenated $C_{1-6}$alkyl, $C_{2-6}$alkenyl, $C_{2-6}$alkynyl, halo, hydroxy, —CN, and/or one group selected from aryl, heteroaryl, heterocyclyl, —$SO_3H$, —C(O)OH, —C(O)O—$C_{1-4}$alkyl, C(O)NR'R", —OR', —SR', —C(O)R', —N(R')(R"), —S(O)$_2$—R', and —S(O)$_2$—N(R')(R"), wherein R' and R" are independently selected from H, $C_{1-6}$-alkyl, aryl, and heteroaryl.

"Heteroaryl" refers to a monovalent heteroaromatic radical derived by the removal of one hydrogen atom from a single atom of a parent heteroaromatic ring system. Preferably, the term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclic ring. For such compounds in which the heteroaryl ring is fused to a moiety as described above, the point of attachment is through the heteroaryl ring portion of the compound. Examples of heteroaryl groups include, and are not limited to, furyl, thienyl, pyrrolyl, oxazolyl, thiazolyl, tetrazolyl, imidazolyl, pyrazolyl, isoxazolyl, isothiazolyl, oxadiazolyl, triazolyl, thiadiazolyl, pyranyl, pyridinyl, pyridazinyl, pyrimidinyl or pyrazinyl; fused heteroaryl groups include indolyl, isoindolyl, indolinyl, isoindolinyl, indolizinyl, benzofuryl, benzothienyl, indazolyl, benzimidazolyl, benzthiazolyl, benzoxazolyl, benzisoxazolyl, benzothiadiazolyl, benzotriazolyl, purinyl, quinolizinyl, quinoxalinyl, quinolinyl, isoquinolinyl or quinazolinyl. Preferred are thienyl, oxazolyl, thiazolyl, isoxazolyl, pyridinyl, and pyridazinyl. In certain embodiments, wherein the heteroaryl is optionally substituted, the heteroaryl can be optionally substituted with one, two or three groups independently selected from alkyl, halogenatedalkyl, alkenyl, alkynyl, halo, —CHO, cyano, amino, optionally substituted alkoxy, halogenatedalkoxy, carboxy, hydroxy, and heterocyclyl.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "halogen" or "halo" refers to fluorine, chlorine, bromine and iodine. Substituents that are substituted with multiple halogens are substituted in a manner that provides compounds, which are stable.

Throughout this disclosure, unless otherwise indicated, the terminal portion of the designated side chain is described first, followed by the adjacent functionality toward the point of attachment. Thus, for example, a "phenyl$C_{1-6}$alkylaminocarbonyl$C_{1-6}$alkyl" substituent refers to a group of the formula

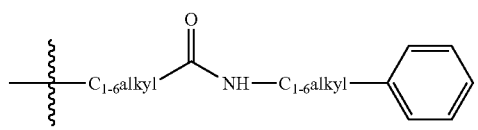

The present invention is further directed to compositions comprising a compound of Formula (I) for uses as CETP inhibitors:

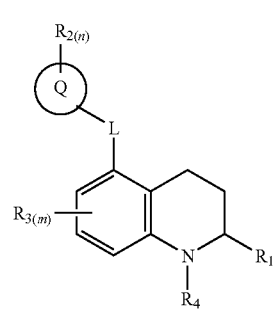

Formula (I)

wherein:
L is a covalent bond or O;
Q is $C_{6-10}$ aryl or 5- or 6-membered heteroaryl;
n is 0 to 3;
m is 0 to 3;
$R_1$ is $C_{1-10}$ alkyl, $C_{2-10}$ alkenyl, $C_{2-10}$ alkynyl, $C_{3-10}$cycloalkyl, 5- or 6-membered heteroaryl, wherein each of $C_{1-10}$ alkyl, $C_{2-10}$ alkenyl, $C_{2-10}$ alkynyl, $C_{3-10}$cycloalkyl, 5- or 6-membered heteroaryl may be optionally substituted;
or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated $C_{1-4}$alkoxy, optionally substituted $C_{1-4}$alkylthio, halo, cyano, and hydroxy, or
$R_a$ and $R_b$ together with the carbon atoms of the phenyl ring to which they are attached form an optionally substituted 5- or 6-membered heterocyclyl fused to the phenyl ring;
each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;
each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;
$R_4$ is $C_{1-10}$ alkyl optionally substituted with 1-3 members independently selected from halo, oxo, hydroxy, halogenated $C_{1-4}$alkyl, $C_{1-4}$ alkoxy, $C_{3-8}$ cycloalkyl, CN, tert-butyldimethylsilyloxy, heterocyclyl and —NR$_c$R$_d$, wherein R$_c$ and R$_d$ are independently selected from H, optionally substituted $C_{1-3}$ alkyl, —C(O)$C_{1-3}$alkyl, —C(O)O—$C_{1-3}$ alkyl, and —SO$_2$C$_{1-3}$alkyl; or
$R_4$ is $C_{1-6}$alkyl substituted with heteroaryl or phenyl substituted with 1 to 3 members independently selected from halo, hydroxy, $C_{1-3}$alkyl, halogenated $C_{1-3}$alkyl, $C_{1-4}$alkoxy, or halogenated $C_{1-4}$alkoxy;
and enantiomers, diastereomers, tautomers, solvates, or pharmaceutically acceptable salts thereof.

Particularly, the present invention features a compound of Formula (I) wherein m is 0.

Particularly, the present invention features a compound of Formula (I) wherein n is 1 or 2.

Particularly, the present invention features a compound of Formula (I) wherein L is a covalent bond.

Particularly, the present invention features a compound of Formula (I) wherein Q is phenyl.

Particularly, the present invention features a compound of Formula (I) wherein Q is thienyl or pyridinyl.

Particularly, the present invention features a compound of Formula (I) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

Particularly, the present invention features a compound of Formula (I) wherein $R_1$ is phenyl substituted with halogenated $C_{1-4}$alkyl or halogenated $C_{1-4}$alkoxy, preferably phenyl substituted with —$OCF_2CF_2H$, —$CF_3$, or —$OCF_3$.

Particularly, the present invention features a compound of Formula (I) wherein n is 1 and $R_2$ is selected from halo, halogenated $C_{1-4}$alkyl, and halogenated $C_{1-4}$alkoxy, preferably $R_2$ is —$OCF_2CF_2H$ or —$OCF_3$.

Particularly, the present invention features a compound of Formula (I) wherein $R_4$ is $C_{1-5}$ alkyl optionally substituted with 1 or 2 members each independently selected from halo, oxo, hydroxy, halogenated $C_{1-4}$alkyl, and heterocyclyl; preferably $R_4$ is $C_{1-3}$ alkyl substituted with 2 members each independently selected from halo, hydroxy, and halogenated $C_{1-3}$alkyl; more preferably $R_4$ is $C_{1-3}$ alkyl substituted with 2 members each independently selected from fluoro, hydroxy, and fluorinated $C_{1-3}$alkyl.

In particular, the present invention is directed to a compound of Formula (I) wherein
Q is phenyl;
m is 0;
n is 1 or 2;
L is a covalent bond;
$R_1$ is phenyl optionally substituted with $C_{1-4}$ alkyl, halogenated $C_{1-4}$alkyl,
$C_{1-4}$alkoxy, halogenated $C_{1-4}$ alkoxy, halo, or cyano;
Each $R_2$ is independently selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; and
$R_4$ is $C_{1-6}$ alkyl substituted with 1-3 members independently selected from halo, hydroxy, halogenated $C_{1-4}$alkyl, $C_{1-4}$alkoxy, halogenated $C_{1-4}$alkoxy, and heterocyclyl.

In particular, the present invention is directed to a compound of Formula (I) wherein
Q is 5- or 6-membered heteroaryl selected from thienyl and pyridinyl;
n is 0;
m is 0; and
L is a covalent bond.

In particular, the present invention is directed to a compound of Formula (I) as shown above, wherein (n) is 1; (m) is 0; and the Q-$R_2$ group is

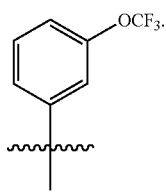

In particular, the present invention is directed to a compound of Formula (I) as shown above, wherein (m) is 0; and $R_1$ is

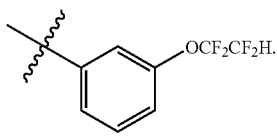

In particular, the present invention is directed to a compound of Formula (I) as shown above wherein (m) is 0, and $R_4$ is

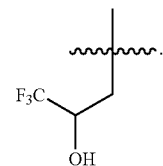

In particular, the present invention is directed to a compound of Formula (I) wherein
Q is phenyl;
m is 0;
n is 1 or 2;
L is a covalent bond;
$R_1$ is —$CH_2CH_3$, cyclohexyl, thienyl, or phenyl optionally substituted with —$OCF_2CF_2H$, —$CF_3$, —F, —$OCH_3$, —CN, —Cl, or —$OCF_3$;
Each $R_2$ is independently selected from —$OCF_3$, —$CF_3$, —Cl, —F, —$CH_3$, —CN, —OH, —$OCH_3$, —C(O)H, —$CH(CH_3)_2$, —$OCH(CH_3)_2$, and —$CH_2CH_3$; and
$R_4$ is $C_{1-5}$ alkyl optionally substituted with 1-3 members independently selected from —OH, halogenated $C_{1-3}$alkyl, and $C_{1-4}$alkoxy.

In particular, the present invention is directed to a compound of Formula (I) wherein
Q is thienyl or pyridinyl;
m is 0;
n is 0;
L is a covalent bond;
$R_1$ is —$CH_2CH_3$, cyclohexyl, thienyl, or phenyl optionally substituted with —$OCF_2CF_2H$, —$CF_3$, —F, —$OCH_3$, —CN, —CL, or —$OCF_3$;
Each $R_2$ is independently selected from —$OCF_3$, —$CF_3$, —Cl, —F, —$CH_3$, —CN, —OH, —$OCH_3$, —C(O)H, —$CH(CH_3)_2$, —$OCH(CH_3)_2$, and —$CH_2CH_3$; and
$R_4$ is $C_{1-5}$ alkyl optionally substituted with 1-3 members independently selected from —OH, halogenated $C_{1-3}$alkyl, and $C_{1-4}$alkoxy.

In particular, the present invention is directed to a compound of Formula (I) as shown above wherein:

(a) $R_1$ is $C_{1-6}$alkyl or $C_{3-10}$cycloalkyl, preferably —$CH_2CH_3$ or
(b) $R_1$ is phenyl optionally substituted with 1 or 2 members selected from $R_a$ and $R_b$, wherein
$R_a$ and $R_b$ are independently selected from the group consisting of $C_{1-4}$ alkyl, halogenated $C_{1-4}$ alkyl, $C_{1-4}$ alkoxy, halogenated $C_{1-4}$ alkoxy, cyano, and hydroxy, or $R_a$ and $R_b$ together with the carbon atoms they are attached to form 5- or 6-membered heterocyclyl fused to the phenyl ring;

preferably $R_1$ is phenyl,

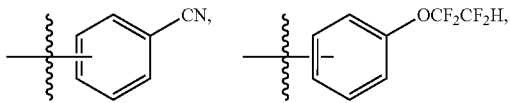

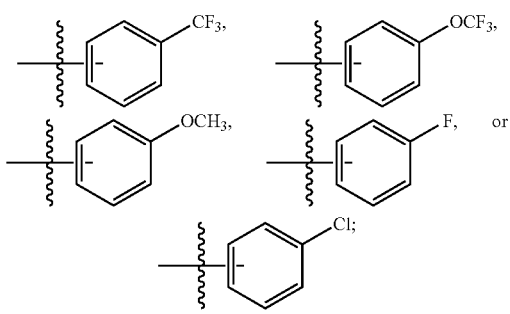

(c) $R_1$ is 5- or 6-membered heteroaryl, preferably (d) L is a covalent bond;

(e) L is O;

(f) Q is $C_{6-10}$ aryl, and preferably Q is phenyl;

(g) Q is 5- or 6-membered heteroaryl; preferably thienyl, oxazolyl, thiazolyl, isoxazolyl, pyridinyl, and pyridazinyl; and more preferably thienyl and pyridinyl;

(h) each $R_2$ is independently selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; preferably —CH$_3$, —CH$_2$CH$_3$, —C(O)H, —O—CH$_3$, —O—CF$_3$, —O—CH(CH$_3$)$_2$, —CH(CH$_3$)$_2$, CN, OH, F, Cl, and —CF$_3$;

(i) n is 0, 1, or 2;

(j) m is 0;

(k) $R_4$ is $C_{1-5}$ alkyl optionally substituted with 1-3 members independently selected from halo, oxo, hydroxy, halogenated $C_{1-3}$alkyl, $C_{1-4}$ alkoxy, $C_{3-8}$ cycloalkyl, CN, heterocyclyl, heteroaryl, and —NR$_c$R$_d$, wherein
  $R_c$ and $R_d$ are independently selected from H, $C_{1-3}$ alkyl, and —C(O)O—$C_{1-13}$ alkyl;

(l) $R_4$ is $C_{1-6}$ alkyl optionally substituted with 1-3 members independently selected from oxo, halo, hydroxy, halogenated $C_{1-5}$alkyl $C_{1-4}$ alkoxy, and 5- or 6-membered heterocyclyl; preferably selected from oxo, F, Cl, hydroxy, —O—CH$_3$, and

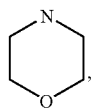

and more particularly $R_4$ is halogenated $C_{1-3}$ alkyl substituted with OH, preferably

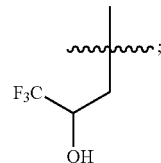

and enantiomers, diastereomers, tautomers, solvates, or pharmaceutically acceptable salts thereof; or any possible combinations of examples (a)-(l) above.

More particularly, the present invention is directed to a compound of Formula (I) as shown above wherein:

m is 0;

n is 0, 1, or 2;

$R_1$ is —CH$_2$CH$_3$,

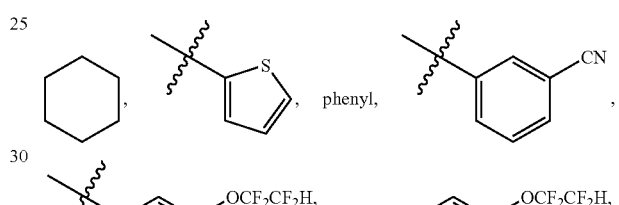

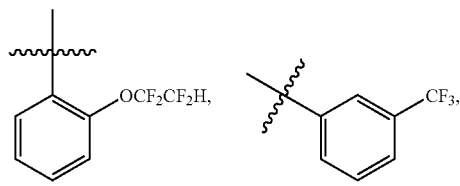

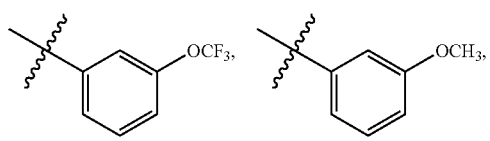

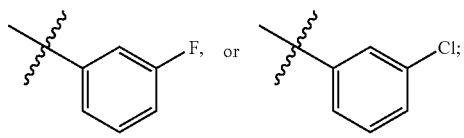

each $R_2$ is independently selected from —CH$_3$, —CH$_2$CH$_3$, —C(O)H, —O—CH$_3$, —O—CF$_3$, —O—CH(CH$_3$)$_2$, —CH(CH$_3$)$_2$, CN, OH, F, Cl, and —CF$_3$;

$R_4$ is $C_{1-5}$ alkyl optionally substituted with 1-3 members independently selected from —CF$_3$, oxo, hydroxy, —CH$_3$, and

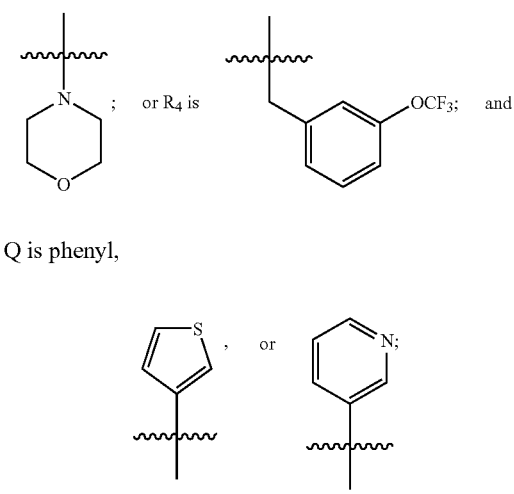

Q is phenyl, and enantiomers, diastereomers, tautomers, solvates, or pharmaceutically acceptable salts thereof.

In one aspect, the present invention is directed to a compound of Formula (Ia):

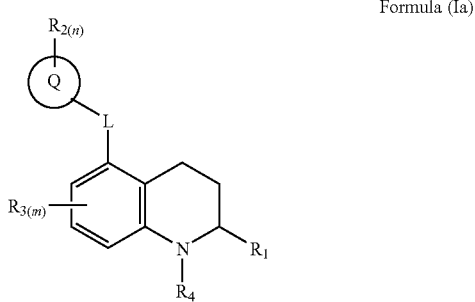

Formula (Ia)

wherein:

L is a covalent bond or O;

Q is phenyl, naphthalenyl, or a heteroaryl selected from the group consisting of thienyl, oxazolyl, thiazolyl, isoxazolyl, pyridinyl, and pyridazinyl;

n is 0 to 3;

m is 0 to 3;

$R_1$ is $C_{1-10}$ alkyl, $C_{2-10}$alkenyl, $C_{3-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with 1 to 3 substituents independently selected from halo, cyano, hydroxy, oxo, $C_{1-3}$alkyl, and $C_{1-3}$alkoxy;

or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated $C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated $C_{1-4}$alkylthio, halo, cyano, and hydroxy, or $R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyano, and hydroxy;

each $R_2$ is independently selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;

each $R_3$ is independently selected from the group consisting of $C_{1-4}$ alkyl, $C_{1-4}$ alkoxy, halo, cyano, and hydroxy;

$R_4$ is $C_{1-10}$ alkyl, halogenated $C_{1-10}$alkyl, or phenyl$C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated $C_{1-4}$ alkoxy, $C_{3-8}$ cycloalkyl, cyano, heterocyclyl, and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and —SO$_2C_{1-3}$alkyl;

and enantiomers, diastereomers, tautomers, solvates, or pharmaceutically acceptable salts thereof.

Particularly, the present invention features a compound of Formula (Ia) wherein m is 0.

Particularly, the present invention features a compound of Formula (Ia) wherein n is 1 or 2.

Particularly, the present invention features a compound of Formula (Ia) wherein L is a covalent bond.

Particularly, the present invention features a compound of Formula (Ia) wherein Q is phenyl.

Particularly, the present invention features a compound of Formula (Ia) wherein Q is thienyl or pyridinyl.

Particularly, the present invention features a compound of Formula (Ia) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

Particularly, the present invention features a compound of Formula (Ia) wherein $R_1$ is phenyl substituted with halogenated $C_{1-4}$alkyl or halogenated $C_{1-4}$alkoxy; preferably $R_1$ is phenyl substituted with —OCF$_2$CF$_2$H, —CF$_3$, or —OCF$_3$.

Particularly, the present invention features a compound of Formula (Ia) wherein n is 1 and $R_2$ is selected from halo, halogenated $C_{1-4}$alkyl, and halogenated $C_{1-4}$alkoxy, preferably $R_2$ is —OCF$_2$CF$_2$H or —OCF$_3$.

Particularly, the present invention features a compound of Formula (Ia) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

Particularly, the present invention features a compound of Formula (Ia) wherein $R_4$ is halogenated $C_{1-4}$ alkyl substituted with oxo, hydroxy, $C_{1-4}$alkoxy, or cyano; preferably $R_4$ is fluorinated$C_{1-3}$ alkyl substituted oxo, hydroxy, $C_{1-4}$alkoxy, or cyano; more preferably $R_4$ is fluorinated$C_{1-3}$ alkyl substituted with hydroxy.

Particularly, the present invention features a compound of Formula (Ia) wherein $R_4$ is phenyl$C_{1-3}$ alkyl wherein the phenyl group is substituted with hydroxy, $C_{1-4}$alkoxy, cyano, or halogenated $C_{1-4}$ alkoxy; preferably $R_4$ is phenyl$C_{1-3}$ alkyl wherein the phenyl group is substituted with halogenated $C_{1-4}$ alkoxy.

In particular, the present invention is directed to a compound of Formula (Ia) wherein Q is phenyl;

m is 0;

n is 1 or 2;

L is a covalent bond;

$R_1$ is phenyl optionally substituted with $C_{1-4}$ alkyl, halogenated $C_{1-4}$alkyl, $C_{1-4}$alkoxy, halogenated $C_{1-4}$ alkoxy, halo, or cyano;

Each $R_2$ is independently selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; and $R_4$ is $C_{1-5}$ alkyl substituted with 1 to 2 members independently selected from hydroxy, $C_{1-4}$alkoxy, oxo, halogenated $C_{1-4}$alkoxy, heterocyclyl, $C_{3-8}$cycloalkyl, and cyano; or $R_4$ is halogenated $C_{1-4}$ alkyl substituted with hydroxy, $C_{1-4}$alkoxy, oxo, or cyano.

In particular, the present invention is directed to a compound of Formula (Ia) wherein
Q is a heteroaryl selected from thienyl and pyridinyl;
n is 0;
m is 0; and
L is a covalent bond.

In particular, the present invention is directed to a compound of Formula (Ia) as shown above, wherein (n) is 1; (m) is 0; and the Q-$R_2$ group is

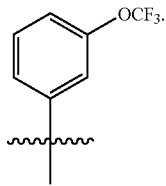

In particular, the present invention is directed to a compound of Formula (Ia) as shown above, wherein (m) is 0; and $R_1$ is

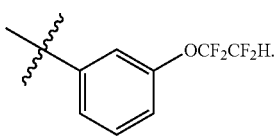

In particular, the present invention is directed to a compound of Formula (Ia) as shown above wherein (m) is 0, and $R_4$ is

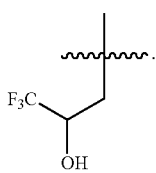

In particular, the present invention is directed to a compound of Formula (Ia) wherein
Q is phenyl;
m is 0;
n is 1 or 2;
L is a covalent bond;
$R_1$ is —CH$_2$CH$_3$, cyclohexyl, thienyl, or phenyl optionally substituted with —OCF$_2$CF$_2$H, —CF$_3$, —F, —OCH$_3$, —CN, —Cl, or —OCF$_3$;
Each $R_2$ is independently selected from —OCF$_3$, —CF$_3$, —Cl, —F, —CH$_3$, —CN, —OH, —OCH$_3$, —C(O)H, —CH(CH$_3$)$_2$, —OCH(CH$_3$)$_2$, and —CH$_2$CH$_3$; and
$R_4$ is $C_{1-6}$alkyl optionally substituted with 1 to 2 members independently selected from —OH, —OCH$_3$, and $C_{1-4}$alkoxy; or $R_4$ is halogenated $C_{1-4}$ alkyl substituted with hydroxy, $C_{1-4}$alkoxy, oxo, or cyano.

In particular, the present invention is directed to a compound of Formula (Ia) wherein
Q is phenyl;
m is 0;
n is 1 or 2;
L is a covalent bond;
$R_1$ is —CH$_2$CH$_3$, cyclohexyl, thienyl, or phenyl substituted at the 3-position with —OCF$_2$CF$_2$H, —CF$_3$, —F, —OCH$_3$, —CN, —Cl, or —OCF$_3$;
Each $R_2$ is independently selected from —OCF$_3$, —CF$_3$, —Cl, —F, —CH$_3$, —CN, —OH, —OCH$_3$, —C(O)H, —CH(CH$_3$)$_2$, —OCH(CH$_3$)$_2$, and —CH$_2$CH$_3$; and
$R_4$ is fluorinated $C_{1-4}$ alkyl substituted with hydroxy, $C_{1-4}$alkoxy, oxo, or cyano.

In particular, the present invention is directed to a compound of Formula (Ia) wherein
Q is thienyl or pyridinyl;
m is 0;
n is 0;
L is a covalent bond;
$R_1$ is —CH$_2$CH$_3$, cyclohexyl, thienyl, or phenyl optionally substituted with —OCF$_2$CF$_2$H, —CF$_3$, —F, —OCH$_3$, —CN, —CL, or —OCF$_3$;
Each $R_2$ is independently selected from —OCF$_3$, —CF$_3$, —Cl, —F, —CH$_3$, —CN, —OH, —OCH$_3$, —C(O)H, —CH(CH$_3$)$_2$, —OCH(CH$_3$)$_2$, and —CH$_2$CH$_3$; and
$R_4$ is $C_{1-6}$ alkyl optionally substituted with 1-2 members independently selected from —OH, —OCH$_3$, and $C_{1-4}$alkoxy; or $R_4$ is halogenated $C_{1-4}$ alkyl substituted with hydroxy, $C_{1-4}$alkoxy, oxo, or cyano.

In particular, the present invention is directed to a compound of Formula (Ia) as shown above wherein:
(a) $R_1$ is $C_{1-6}$alkyl or $C_{3-10}$cycloalkyl, preferably —CH$_2$CH$_3$ or

(b) $R_1$ is phenyl optionally substituted with 1 or 2 members selected from $R_a$ and $R_b$, wherein
$R_a$ and $R_b$ are independently selected from the group consisting of $C_{1-4}$ alkyl, halogenated $C_{1-4}$ alkyl, $C_{1-4}$ alkoxy, halogenated $C_{1-4}$ alkoxy, cyano, and hydroxy, or
$R_a$ and $R_b$ together with the carbon atoms they are attached to form 5- or 6-membered heterocyclyl fused to the phenyl ring;
preferably $R_1$ is phenyl,

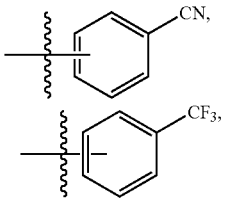

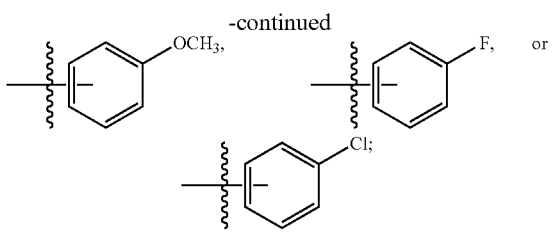

(c) $R_1$ is 5- or 6-membered heteroaryl, preferably

(d) L is a covalent bond;
(e) L is O;
(f) Q is phenyl;
(g) Q is a heteroaryl selected from the group consisting of thienyl, oxazolyl, thiazolyl, isoxazolyl, pyridinyl, and pyridazinyl; and more preferably thienyl and pyridinyl;
(h) each $R_2$ is independently selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; preferably —$CH_3$, —$CH_2CH_3$, —C(O)H, —O—$CH_3$, —O—$CF_3$, —O—$CH(CH_3)_2$, —$CH(CH_3)_2$, CN, OH, F, Cl, and —$CF_3$;
(i) n is 0, 1, or 2;
(j) m is 0;
(k) $R_4$ is $C_{1-5}$ alkyl optionally substituted with 1 or 2 members independently selected from oxo, hydroxy, cyano, $C_{1-4}$alkoxy, heterocyclyl, and —$NR_cR_d$, wherein $R_c$ and $R_d$ are independently selected from H, $C_{1-3}$ alkyl, and —C(O)O—$C_{1-3}$ alkyl;
(l) $R_4$ is halogenated $C_{1-4}$ alkyl optionally substituted with oxo, hydroxy, $C_{1-4}$ alkoxy, or cyano; preferably $R_4$ is fluorinated$C_{1-3}$alkyl substituted with hydroxy; more preferably $R_4$ is

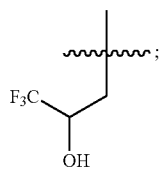

and enantiomers, diastereomers, tautomers, solvates, or pharmaceutically acceptable salts thereof; or any possible combinations of examples (a)-(l) above.

More particularly, the present invention is directed to a compound of Formula (Ia) as shown above wherein:
m is 0;
n is 0, 1, or 2;
$R_1$ is —$CH_2CH_3$,

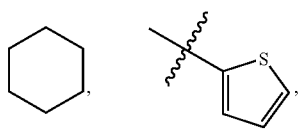

phenyl,

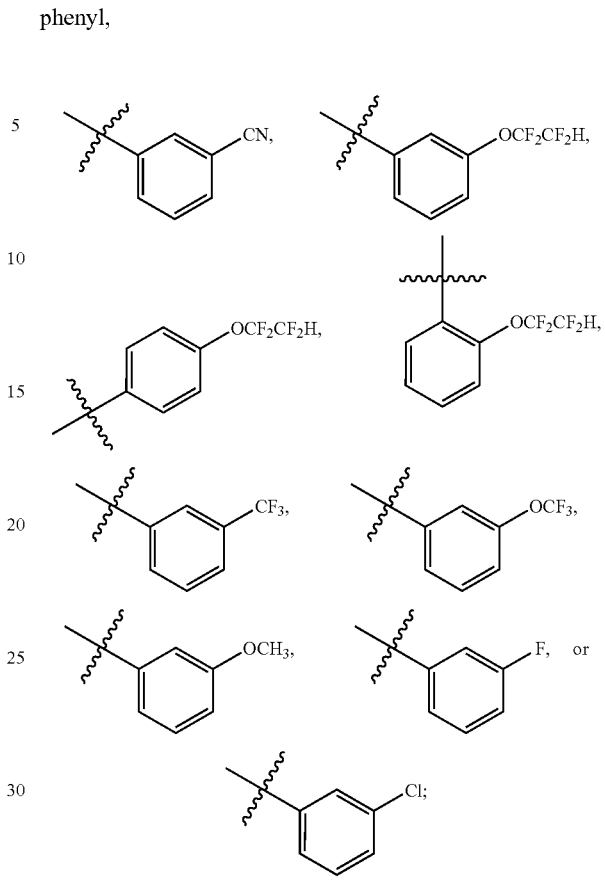

each $R_2$ is independently selected from —$CH_3$, —$CH_2CH_3$, —C(O)H, —O—$CH_3$, —O—$CF_3$, —O—$CH(CH_3)_2$, —$CH(CH_3)_2$, CN, OH, F, Cl, and —$CF_3$;

$R_4$ is halogenated $C_{1-4}$alkyl substituted with oxo, hydroxy, or —O—$CH_3$; and Q is phenyl,

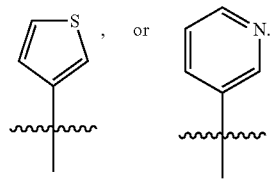

In particular, the present invention is further directed to a compound of Formula (Ia) wherein (a) m is 0
(b) n is 1, 2, or 3
(c) m and n are both 0;
(d) m is 0 and n is 1;
(e) m is 0 and n is 2;
(f) L is a bond;
(g) L is O;

(h) R₁ is
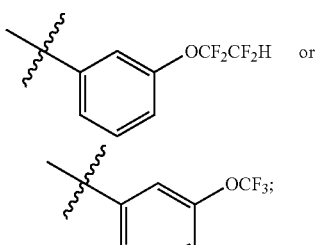 or
(i) R₁ is
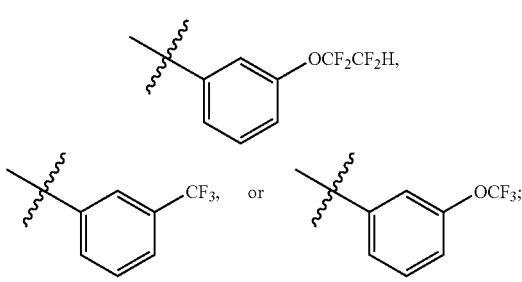
(j) R₁ is
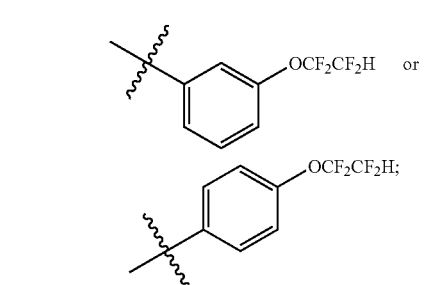
(k) R₁ is
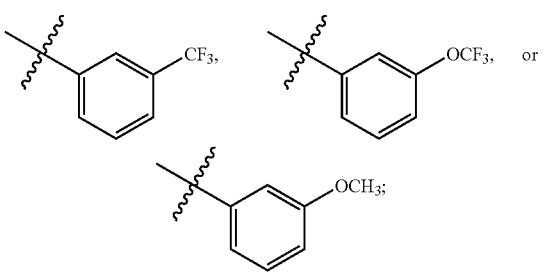
(l) R₁ is
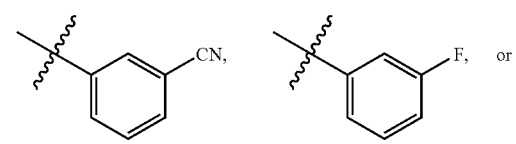
-continued
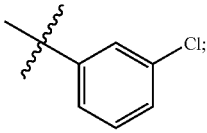
(m) R₁ is —CH₂CH₃,
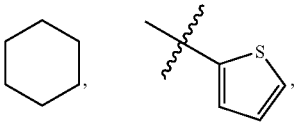
or phenyl;
(n) Q is phenyl or naphthalenyl;
(o) Q is phenyl;
(p) Q is a selected from the group consisting of thienyl, thiazolyl, oxazolyl, isoxazolyl, pyridinyl, and pyridizinyl;
(q) Q is
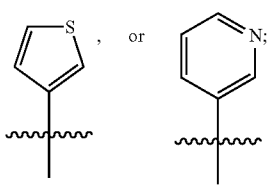
(r) n is 1 and Q is
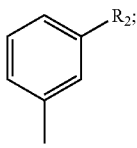
(s) n is 1 and Q is
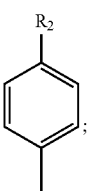
(t) n is 2 and Q is
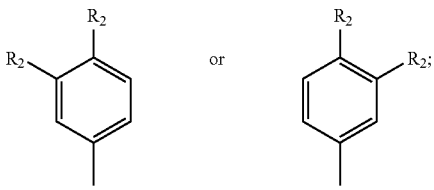

(u) n is 2 and Q is

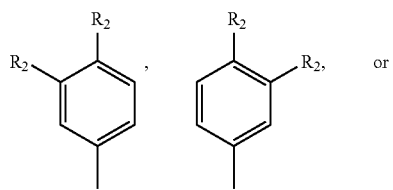

(v) R$_2$ is —O—CF$_3$;
(w) R$_2$ is F;
(x) R$_2$ is —CH$_3$, —CH$_2$CH$_3$, or —CH(CH$_3$)$_2$;
(y) R$_2$ is —C(O)H, CN, OH,
(z) R$_2$ is —O—CH(CH$_3$)$_2$, F, Cl, or —CF$_3$;
(aa) R$_2$ is —O—CH$_3$, —O—CF$_3$, or —O—CH(CH$_3$)$_2$;
(bb) R$_4$ is C$_{1-5}$alkyl substituted with 1 or 2 members independently selected from oxo, hydroxy, and —O—CH$_3$;
(cc) R$_4$ is halogenated C$_{1-4}$ alkyl substituted with oxo, hydroxy, or —O—CH$_3$;
(dd) R$_4$ is —CH$_2$CH(OH)CF$_3$;
(ee) R$_4$ is —CH$_2$CH(OH)CF$_3$;
(ff) R$_4$ is —CH$_2$CH(OH)CH(CH$_3$)$_2$;
(gg) R$_4$ is

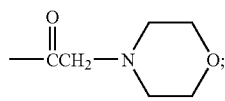

(hh) m is 0, n is 1, and L is a bond;
(ii) m is 0, n is 2, and L is a bond;
(jj) m is 0, n is 1, L is a bond, and R$_1$ is

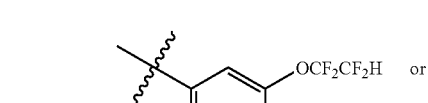

(kk) m is 0, n is 1, L is a bond, Q is phenyl, and R$_1$ is

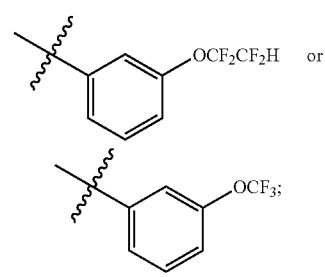

(ll) m is 0, n is 1, L is a bond, R$_1$ is

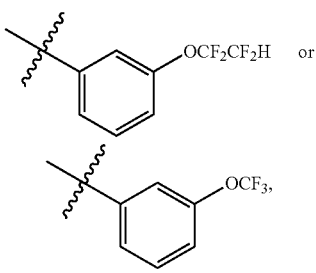

and Q is

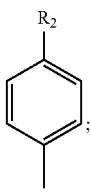

(mm) m is 0, n is 1, L is a bond, R$_1$ is

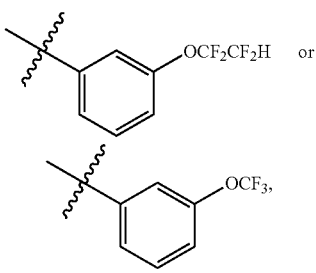

and Q is

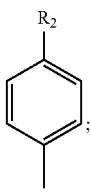

(nn) m is 0, n is 1, L is a bond, Q is phenyl, and R$_1$ is

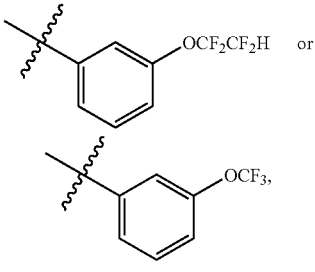

and R$_2$ is —O—CF$_3$;

(oo) m is 0, n is 1, L is a bond, Q is phenyl, and $R_1$ is

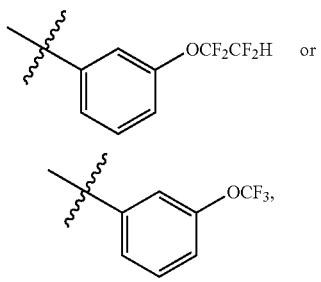

and $R_2$ is F;

(pp) m is 0, n is 1, L is a bond, Q is phenyl, and $R_1$ is

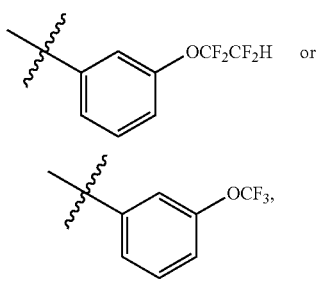

and $R_2$ is —CH$_3$, —CH$_2$CH$_3$, —CH(CH$_3$)$_2$, —C(O)H, CN, OH, —O—CH(CH$_3$)$_2$, F, Cl, —CF$_3$, —CH$_3$, —O—CF$_3$, or —O—CH(CH$_3$)$_2$;

(qq) m is 0, n is 1, L is a bond, Q is

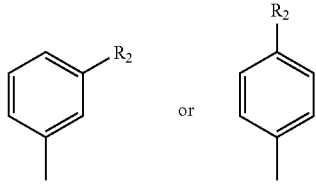

and $R_2$ is —O—CF$_3$ or F;

(rr) m is 0, n is 1, L is a bond, Q is

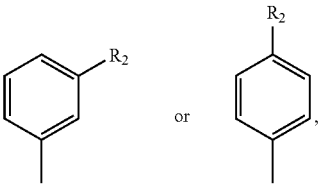

and $R_2$ is —CH$_3$, —CH$_2$CH$_3$, —CH(CH$_3$)$_2$, —C(O)H, CN, OH, —O—CH(CH$_3$)$_2$, F, Cl, —CF$_3$, —O—CH$_3$, —O—CF$_3$, or —O—CH(CH$_3$)$_2$; or enantiomers, diastereomers, tautomers, solvates, or pharmaceutically acceptable salts thereof; or any possible combinations of (a)-(rr) above.

In another aspect, the present invention is further directed to a compound of Formula (Ib):

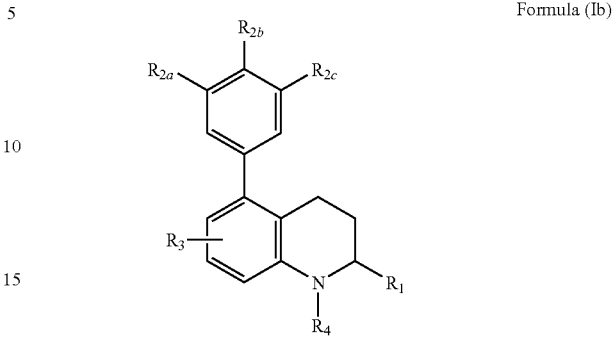

Formula (Ib)

wherein:

$R_1$ is $C_{1-10}$ alkyl, $C_{2-10}$alkenyl, $C_{2-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with halo, cyano, or hydroxy, oxo, $C_{1-3}$alkyl, or $C_{1-3}$alkoxy;

or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated $C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated $C_{1-4}$alkylthio, halo, cyano, and hydroxy, or $R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyano, and hydroxy;

each of $R_{2a}$, $R_{2b}$, and $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;

$R_3$ is absent or selected from the group consisting of $C_{1-4}$ alkyl, $C_{1-4}$ alkoxy, halo, cyano, and hydroxy;

$R_4$ is $C_{1-10}$ alkyl, halogenated $C_{1-10}$alkyl, or phenyl $C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated $C_{1-4}$ alkoxy, $C_{3-8}$ cycloalkyl, cyano, heterocyclyl, and —NR$_c$R$_d$, wherein $R_c$ and $R_d$ are independently selected from H, optionally substituted $C_{1-3}$ alkyl, —C(O)C$_{1-3}$alkyl, —C(O)O—C$_{1-3}$ alkyl, and —SO$_2$C$_{1-3}$alkyl;

and enantiomers, diastereomers, tautomers, solvates, or pharmaceutically acceptable salts thereof.

Particularly, the present invention features a compound of Formula (Ib) wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

Particularly, the present invention features a compound of Formula (Ib) wherein $R_1$ is phenyl substituted with halogenated $C_{1-4}$alkyl or halogenated $C_{1-4}$alkoxy; preferably $R_1$ is phenyl substituted with —OCF$_2$CF$_2$H, —CF$_3$, or —OCF$_3$.

Particularly, the present invention features a compound of Formula (Ib) wherein $R_{2a}$ and $R_{2b}$ are both absent and $R_{2c}$ is selected from halo, halogenated $C_{1-4}$alkyl, and halogenated $C_{1-4}$alkoxy, preferably $R_{2c}$ is —OCF$_2$CF$_2$H or —OCF$_3$.

Particularly, the present invention features a compound of Formula (Ib) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

Particularly, the present invention features a compound of Formula (Ib) wherein $R_4$ is halogenated $C_{1-4}$ alkyl substituted with oxo, hydroxy, $C_{1-4}$alkoxy, or cyano; preferably $R_4$ is fluorinated $C_{1-4}$ alkyl substituted with oxo, hydroxy, $C_{1-4}$alkoxy, or cyano; more preferably $R_4$ is fluorinated $C_{1-3}$ alkyl substituted with hydroxy.

Particularly, the present invention features a compound of Formula (Ib) wherein $R_4$ is phenyl$C_{1-3}$ alkyl wherein the phenyl group is substituted with hydroxy, $C_{1-4}$alkoxy, cyano, or halogenated $C_{1-4}$ alkoxy, preferably $R_4$ is phenyl$C_{1-3}$ alkyl wherein the phenyl group is substituted with halogenated $C_{1-4}$ alkoxy.

In particular, the present invention is directed to a compound of Formula (Ib) wherein
- $R_1$ is phenyl optionally substituted with $C_{1-4}$ alkyl, halogenated $C_{1-4}$alkyl,
  $C_{1-4}$alkoxy, halogenated $C_{1-4}$ alkoxy, halo, or cyano;
- Each $R_{2a}$, $R_{2b}$, and $R_{2c}$ is independently absent or selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H;
- $R_3$ is absent; and
- $R_4$ is $C_{1-5}$ alkyl substituted with 1 to 2 members independently selected from hydroxy, $C_{1-4}$alkoxy, oxo, halogenated $C_{1-4}$alkoxy, heterocyclyl, $C_{3-8}$cycloalkyl, cyano; or $R_4$ is halogenated $C_{1-4}$ alkyl substituted with hydroxy, $C_{1-4}$alkoxy, oxo, or cyano.

In particular, the present invention is directed to a compound of Formula (Ib) wherein
- $R_1$ is phenyl optionally substituted at the 3-position with $C_{1-4}$ alkyl, halogenated $C_{1-4}$alkyl,
  $C_{1-4}$alkoxy, halogenated $C_{1-4}$ alkoxy, halo, or cyano;
- Each $R_{2a}$, $R_{2b}$, and $R_{2c}$ is independently absent or selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H;
- $R_3$ is absent; and
- $R_4$ is fluorinated $C_{1-4}$ alkyl substituted with hydroxy, $C_{1-4}$alkoxy, oxo, or cyano.

In particular, the present invention is directed to a compound of Formula (Ib) as shown above wherein:
(a) $R_1$ is $C_{1-6}$alkyl or $C_{3-10}$cycloalkyl, preferably —CH$_2$CH$_3$ or

(b) $R_1$ is phenyl optionally substituted with 1 or 2 members selected from $R_a$ and $R_b$, wherein
  $R_a$ and $R_b$ are independently selected from the group consisting of $C_{1-4}$ alkyl, halogenated $C_{1-4}$ alkyl, $C_{1-4}$ alkoxy, halogenated $C_{1-4}$ alkoxy, cyano, and hydroxy, or
  $R_a$ and $R_b$ together with the carbon atoms they are attached to form 5- or 6-membered heterocyclyl fused to the phenyl ring;
preferably $R_1$ is phenyl,

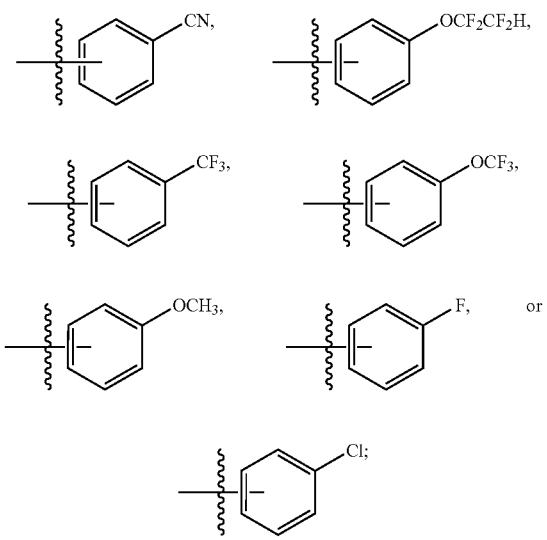

(c) $R_1$ is 5- or 6-membered heteroaryl, preferably

(d) each of $R_{2a}$, $R_{2b}$, and $R_{2c}$ is independently absent or selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; preferably —CH$_3$, —CH$_2$CH$_3$, —C(O)H, —O—CH$_3$, —O—CF$_3$, —O—CH(CH$_3$)$_2$, —CH(CH$_3$)$_2$, CN, OH, F, Cl, and —CF$_3$;

(e) $R_3$ is absent;

(f) $R_4$ is $C_{1-5}$ alkyl optionally substituted with 1 or 2 members independently selected from oxo, hydroxy, cyano, $C_{1-4}$alkoxy, heterocyclyl, and —NR$_c$R$_d$, wherein
  $R_c$ and $R_d$ are independently selected from H, $C_{1-3}$ alkyl, and —C(O)O—$C_{1-3}$ alkyl;

(g) $R_4$ is halogenated $C_{1-4}$ alkyl optionally substituted with oxo, hydroxy, $C_{1-4}$ alkoxy, or cyano; preferably $R_4$ is fluorinated$C_{1-3}$alkyl substituted with hydroxy; more preferably $R_4$ is

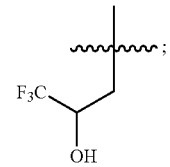

and enantiomers, diastereomers, tautomers, solvates, or pharmaceutically acceptable salts thereof; or any possible combinations of examples (a)-(g) above.

In another aspect, the present invention is further directed to a compound of Formula (Ic):

Formula (Ic)

wherein:
- each $R_{2a}$, $R_{2b}$, $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;
- $R_4$ is $C_{1-10}$ alkyl, halogenated $C_{1-10}$alkyl, or phenyl $C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of halo, oxo, hydroxy, $C_{1-4}$ alkoxy, $C_{3-8}$ cycloalkyl, cyano, heterocyclyl, heteroaryl, tert-butyldimethylsilyloxy, and —NR$_c$R$_d$, wherein
  - R$_c$ and R$_d$ are independently selected from H, optionally substituted $C_{1-3}$ alkyl, —C(O)C$_{1-3}$alkyl, —C(O)O—C$_{1-3}$ alkyl, and SO$_2$C$_{1-3}$alkyl;
- $R_5$ is selected from the group consisting of $C_{1-4}$ alkyl, halogenated $C_{1-4}$alkyl, $C_{1-4}$ alkoxy, halogenated $C_{1-4}$alkoxy, $C_{1-4}$ alkylthio, halo, cyano, and hydroxy;

and enantiomers, diastereomers, tautomers, solvates, or pharmaceutically acceptable salts thereof.

In particular, the present invention is directed to a compound of Formula (Ic) wherein $R_{2a}$ is absent or halo, preferably $R_{2a}$ is absent.

In particular, the present invention is directed to a compound of Formula (Ic) wherein $R_{2b}$ is absent, halo, $C_{1-4}$ alkoxy, halogenated $C_{1-4}$alkoxy, $C_{1-4}$ alkyl, or halogenated $C_{1-4}$ alkyl; preferably $R_{2b}$ is absent, halo, —OCF$_3$, —CF$_3$; more preferably $R_{2b}$ is absent.

In particular, the present invention is directed to a compound of Formula (Ic) wherein $R_{2c}$ is halo, hydroxy, cyano, $C_{1-4}$ alkoxy, halogenated $C_{1-4}$alkoxy, $C_{1-4}$ alkyl, or halogenated $C_{1-4}$ alkyl; preferably $R_{2c}$ is halo or halogenated $C_{1-4}$alkoxy; more preferably $R_{2c}$ is —OCF$_3$ or F.

In particular, the present invention is directed to a compound of Formula (Ic) wherein $R_4$ is $C_{1-5}$ alkyl substituted with 1 or 2 members each independently selected from oxo, hydroxy, $C_{1-4}$alkoxy, cyano, and heterocyclyl; preferably $R_4$ is $C_{1-3}$ alkyl substituted with hydroxy, $C_{1-4}$alkoxy, or cyano.

In particular, the present invention is directed to a compound of Formula (Ic) wherein $R_4$ is halogenated $C_{1-4}$ alkyl substituted with oxo, hydroxy, $C_{1-4}$alkoxy, or cyano.

In particular, the present invention is directed to a compound of Formula (Ic) wherein $R_4$ is fluorinated $C_{1-4}$ alkyl substituted with oxo, hydroxy, $C_{1-4}$alkoxy, or cyano; preferably $R_4$ is fluorinated$C_{1-3}$ alkyl substituted with hydroxy; more preferably $R_4$ is In particular, the present invention is directed to a compound of Formula (Ic) wherein $R_4$ is phenyl$C_{1-3}$ alkyl wherein the phenyl group is substituted with hydroxy, $C_{1-4}$alkoxy, cyano, or halogenated $C_{1-4}$ alkoxy, preferably $R_4$ is phenyl$C_{1-3}$ alkyl wherein the phenyl group is substituted with halogenated $C_{1-4}$ alkoxy.

In particular, the present invention is directed to a compound of Formula (Ic) wherein $R_5$ is $C_{1-4}$ alkyl, halogenated $C_{1-4}$alkyl, $C_{1-4}$ alkoxy, halogenated $C_{1-4}$ alkoxy, $C_{1-4}$ alkylthio, halo, cyano, or hydroxy; preferably $R_5$ is halogenated $C_{1-4}$alkyl, halogenated $C_{1-4}$ alkoxy, or halo; more preferably $R_5$ is —OCF$_3$ or —OCF$_2$CF$_2$H.

In particular, the present invention is directed to a compound selected from the group consisting of:
1-[2,5-Bis-(3-trifluoromethoxy-phenyl)-3,4-dihydro-2H-quinolin-1-yl]-2-morpholin-4-yl-ethanone;
1,1,1-Trifluoro-3-[2-[3-(1,1,2,2-tetrafluoro-ethoxy)-phenyl]-5-(3-trifluoromethoxy-phenyl)-3,4-dihydro-2H-quinolin-1-yl]-propan-2-ol;
1,1,1-Trifluoro-3-[2-[3-(1,1,2,2-tetrafluoro-ethoxy)-phenyl]-5-(4-trifluoromethyl-phenyl)-3,4-dihydro-2H-quinolin-1-yl]-propan-2-ol;
3-{5-(4-Chloro-3-methyl-phenyl)-2-[3-(1,1,2,2-tetrafluoro-ethoxy)-phenyl]-3,4-dihydro-2H-quinolin-1-yl}-1,1,1-trifluoro-propan-2-ol;
1,1,1-Trifluoro-3-[2-[3-(1,1,2,2-tetrafluoro-ethoxy)-phenyl]-5-(4-trifluoromethoxy-phenyl)-3,4-dihydro-2H-quinolin-1-yl]-propan-2-ol;
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzonitrile;
1,1,1-Trifluoro-3-{5-(3-fluoro-phenyl)-2-[3-(1,1,2,2-tetrafluoro-ethoxy)-phenyl]-3,4-dihydro-2H-quinolin-1-yl}-propan-2-ol;
1,1,1-Trifluoro-3-[2-[3-(1,1,2,2-tetrafluoro-ethoxy)-phenyl]-5-(3-trifluoromethyl-phenyl)-]3,4-dihydro-2H-quinolin-1-yl]-propan-2-ol;
3-{5-(3-Chloro-phenyl)-2-[3-(1,1,2,2-tetrafluoro-ethoxy)-phenyl]-3,4-dihydro-2H-quinolin-1-yl}-1,1,1-trifluoro-propan-2-ol;
1,1,1-Trifluoro-3-[5-(3-trifluoromethoxy-phenyl)-2-(3-trifluoromethyl-phenyl)-3,4-dihydro-2H-quinolin-1-yl]-propan-2-ol;
1,1,1-Trifluoro-3-[2-phenyl-5-(3-trifluoromethoxy-phenyl)-3,4-dihydro-2H-quinolin-1-yl]-propan-2-ol;
1,1,1-Trifluoro-3-[2-[4-(1,1,2,2-tetrafluoro-ethoxy)-phenyl]-5-(3-trifluoromethoxy-phenyl)-3,4-dihydro-2H-quinolin-1-yl]-propan-2-ol;
1,1,1-Trifluoro-3-[2-(3-fluoro-phenyl)-5-(3-trifluoromethoxy-phenyl)-3,4-dihydro-2H-quinolin-1-yl]-propan-2-ol;
1,1,1-Trifluoro-3-[2-(3-methoxy-phenyl)-5-(3-trifluoromethoxy-phenyl)-3,4-dihydro-2H-quinolin-1-yl]-propan-2-ol;
3-[1-(3,3,3-Trifluoro-2-hydroxy-propyl)-5-(3-trifluoromethoxy-phenyl)-1,2,3,4-tetrahydro-quinolin-2-yl]-benzonitrile;

3-[2-(3-Chloro-phenyl)-5-(3-trifluoromethoxy-phenyl)-3,4-dihydro-2H-quinolin-1-yl]-1,1,1-trifluoro-propan-2-ol;

3-[2,5-Bis-(3-trifluoromethoxy-phenyl)-3,4-dihydro-2H-quinolin-1-yl]-1,1,1-trifluoro-propan-2-ol;

1,1,1-Trifluoro-3-[2-thiophen-2-yl-5-(3-trifluoromethoxy-phenyl)-3,4-dihydro-2H-quinolin-1-yl]-propan-2-ol;

3-[2-Ethyl-5-(3-trifluoromethoxy-phenyl)-3,4-dihydro-2H-quinolin-1-yl]-1,1,1-trifluoro-propan-2-ol;

3-[2-Cyclohexyl-5-(3-trifluoromethoxy-phenyl)-3,4-dihydro-2H-quinolin-1-yl]-1,1,1-trifluoro-propan-2-ol;

2-Ethyl-1-(3-trifluoromethoxy-benzyl)-5-(3-trifluoromethoxy-phenyl)-1,2,3,4-tetrahydro-quinoline;

(αR,2R)-5-(3-Chlorophenyl)-3,4-dihydro-α-methyl-2-[3-(trifluoromethoxy)phenyl]-1(2H)-quinolineethanol;

(αR,2S)-5-(3-Chlorophenyl)-3,4-dihydro-α-methyl-2-[3-(trifluoromethoxy)phenyl]-1(2H)-quinolineethanol;

3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-phenol;

1-[3-(tert-Butyl-dimethyl-silanyloxy)-propyl]-2,5-bis-(3-trifluoromethoxy-phenyl)-1,2,3,4-tetrahydro-quinoline;

1-[2,5-Bis-(3-trifluoromethoxy-phenyl)-3,4-dihydro-2H-quinolin-1-yl]-3-methyl-butan-2-ol;

1-[2,5-Bis-(3-trifluoromethoxy-phenyl)-3,4-dihydro-2H-quinolin-1-yl]-3-chloro-propan-2-ol;

1-[2,5-Bis-(3-trifluoromethoxy-phenyl)-3,4-dihydro-2H-quinolin-1-yl]-3-fluoro-propan-2-ol;

(αS,2R)-3,4-Dihydro-α-(methoxymethyl)-2,5-bis-[3-(trifluoromethoxy)phenyl]-1(2H)-quinolineethanol;

(αS,2S)-3,4-Dihydro-α-(methoxymethyl)-2,5-bis-[3-(trifluoromethoxy)phenyl]-1(2H)-quinolineethanol;

(αR,2R)-3,4-Dihydro-α-methyl-2,5-bis-[3-(trifluoromethoxy)phenyl]-1(2H)-quinolineethanol;

(αR,2S)-3,4-Dihydro-α-methyl-2,5-bis-[3-(trifluoromethoxy)phenyl]-1(2H)-quinolineethanol;

(αR,2R)-5-(3-Fluorophenyl)-3,4-dihydro-α-methyl-2-[3-(trifluoromethoxy)phenyl]-1(2H)-quinolineethanol;

(αR,2S)-5-(3-Fluorophenyl)-3,4-dihydro-α-methyl-2-[3-(trifluoromethoxy)phenyl]-1(2H)-quinolineethanol;

1,1,1-Trifluoro-3-[5-(3-fluoro-phenyl)-2-(3-trifluoromethoxy-phenyl)-3,4-dihydro-2H-quinolin-1-yl]-propan-2-ol;

(αR,2R)-3,4-Dihydro-5-(3-methoxyphenyl)-α-methyl-2-[3-(trifluoromethoxy)phenyl]-1(2H)-quinolineethanol;

(αR,2S)-3,4-Dihydro-5-(3-methoxyphenyl)-α-methyl-2-[3-(trifluoromethoxy)phenyl]-1(2H)-quinolineethanol;

(αR,2S)-3,4-Dihydro-5-(3-methoxyphenyl)-α-methyl-2-[3-(trifluoromethoxy)phenyl]-1(2H)-quinolineethanol;

(αS,2R)-3,4-Dihydro-α-methyl-2-[3-(1,1,2,2-tetrafluoroethoxy)phenyl]-5-[3-(trifluoromethoxy)phenyl]-1(2H)-quinolineethanol;

(αS,2S)-3,4-Dihydro-α-methyl-2-[3-(1,1,2,2-tetrafluoroethoxy)phenyl]-5-[3-(trifluoromethoxy)phenyl]-1(2H)-quinolineethanol;

3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzaldehyde;

1,1,1-Trifluoro-3-{2-[3-(1,1,2,2-tetrafluoro-ethoxy)-phenyl]-5-thiophen-3-yl-3,4-dihydro-2H-quinolin-1-yl}-propan-2-ol;

1,1,1-Trifluoro-3-{5-(3-isopropyl-phenyl)-2-[3-(1,1,2,2-tetrafluoro-ethoxy)-phenyl]-3,4-dihydro-2H-quinolin-1-yl}-propan-2-ol;

1,1,1-Trifluoro-3-{5-(3-isopropoxy-phenyl)-2-[3-(1,1,2,2-tetrafluoro-ethoxy)-phenyl]-3,4-dihydro-2H-quinolin-1-yl}-propan-2-ol;

(αR,2R)-3,4-Dihydro-α-methyl-2-[3-(1,1,2,2-tetrafluoroethoxy)phenyl]-5-[3-(trifluoromethoxy)phenyl]-1(2H)-quinolineethanol;

1,1,1-Trifluoro-3-{5-(3-methoxy-phenyl)-2-[3-(1,1,2,2-tetrafluoro-ethoxy)-phenyl]-3,4-dihydro-2H-quinolin-1-yl}-propan-2-ol;

1,1,1-Trifluoro-3-{2-[3-(1,1,2,2-tetrafluoro-ethoxy)-phenyl]-5-thiophen-2-yl-3,4-dihydro-2H-quinolin-1-yl}-propan-2-ol;

1,1,1-Trifluoro-3-{5-pyridin-3-yl-2-[3-(1,1,2,2-tetrafluoro-ethoxy)-phenyl]-3,4-dihydro-2H-quinolin-1-yl}-propan-2-ol;

(αR,2R)-5-(3-Fluorophenyl)-3,4-dihydro-α-methyl-2-[3-(1,1,2,2-tetrafluoroethoxy)phenyl]-1(2H)-quinolineethanol;

(2R, αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2R, αR)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2S, αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2S, αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2S, αR)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2R, αS)-3,4-Dihydro-2-[3-(1,1,2,2-tetrafluoroethoxy)phenyl]-5-[3-fluoro)phenyl]-α-(trifluoromethyl)-1(2H)-quinolineethanol;

(2R, αS)-3,4-Dihydro-2-[3-(1,1,2,2-tetrafluoroethoxy)phenyl]-5-[3-(fluoro)phenyl]-α-(trifluoromethyl)-1(2H)-quinolineethanol;

(2R, αS)-3,4-Dihydro-2-[3-(1,1,2,2-tetrafluoroethoxy)phenyl]-5-[3-methoxy)phenyl]-α-(trifluoromethyl)-1(2H)-quinolineethanol;

3-{5-(4-Chloro-3-ethyl-phenoxy)-2-[3-(1,1,2,2-tetrafluoro-ethoxy)-phenyl]-3,4-dihydro-2H-quinolin-1-yl}-1,1,1-trifluoro-propan-2-ol;

3-{5-(2,3-Dichloro-phenoxy)-2-[3-(1,1,2,2-tetrafluoro-ethoxy)-phenyl]-3,4-dihydro-2H-quinolin-1-yl}-1,1,1-trifluoro-propan-2-ol;

1,1,1-Trifluoro-3-[2-[2-(1,1,2,2-tetrafluoro-ethoxy)-phenyl]-5-(3-trifluoromethoxy-phenyl)-3,4-dihydro-2H-quinolin-1-yl]-propan-2-ol; and enantiomers, diastereomers, tautomers, solvates, or pharmaceutically acceptable salts thereof.

In particular, the present invention is directed to a compound of Formula (I), (Ia), (Ib) or (Ic) selected from the compounds shown in Table 1 below and enantiomers, diastereomers, tautomers, solvates, or pharmaceutically acceptable salts thereof.

More particularly, the present invention is directed to a compound selected from:

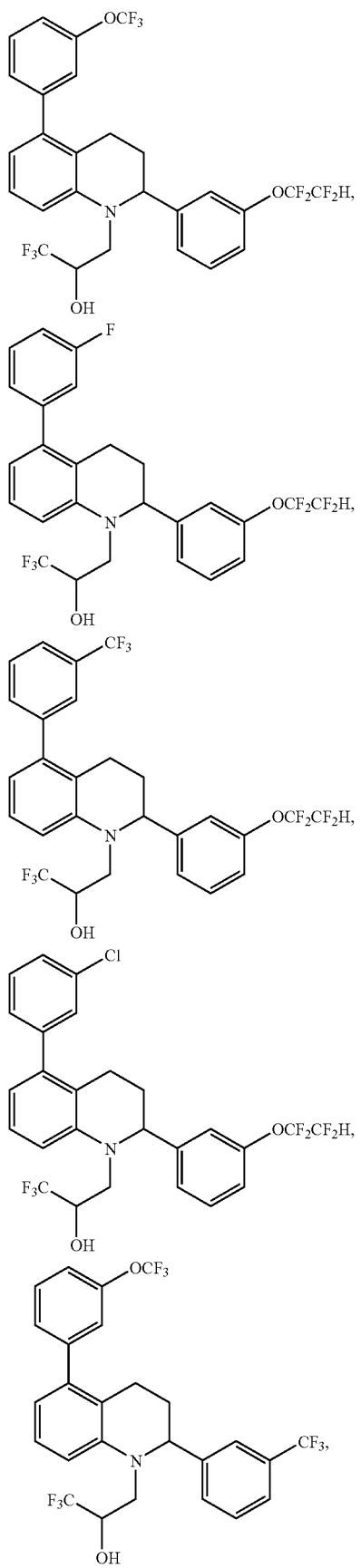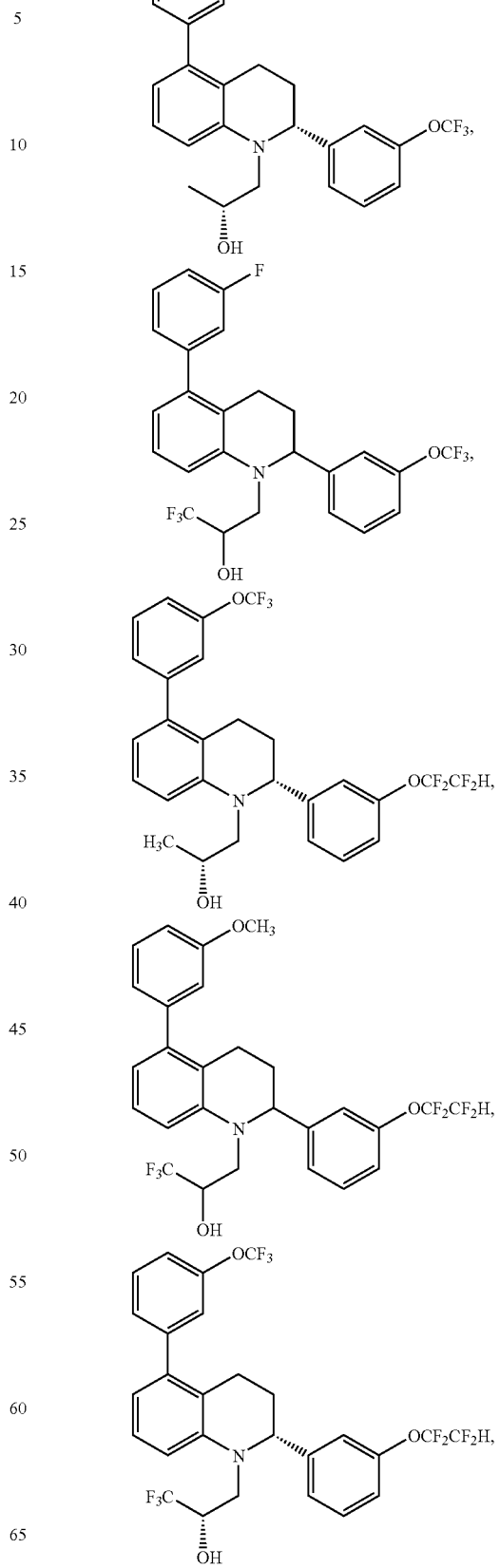

-continued

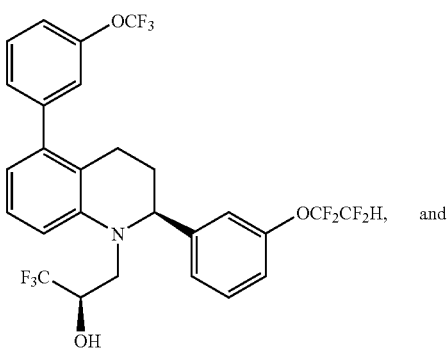

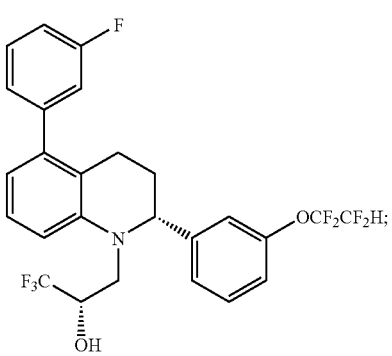

and enantiomers, diastereomers, tautomers, solvates, or pharmaceutically acceptable salts thereof.

In particular, the present invention is directed to a compound of the formula 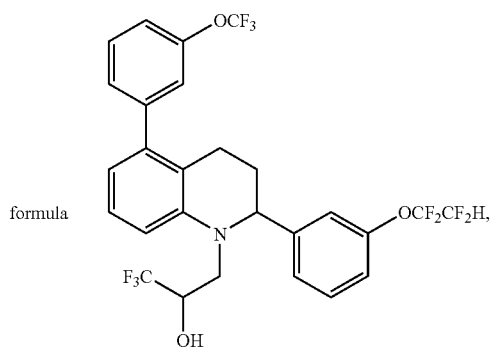

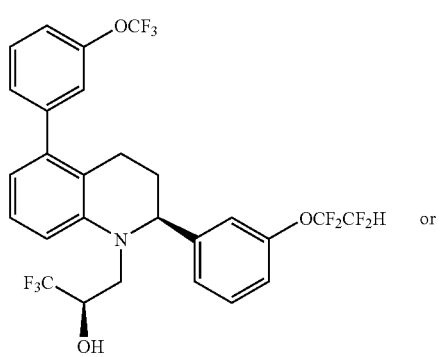 or

-continued

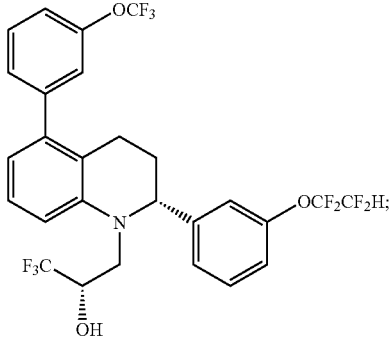

and solvates, or pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985. Representative hydroxy group prodrug forms include, but are not limited to, $C_{1-4}$alkylethers, substituted $C_{1-4}$alkylethers, and $C_{1-4}$alkyl esters.

Another embodiment of the present invention is a composition comprising the dextrorotatory enantiomer of a compound of the present invention, wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{(\text{mass levorotatory})}{(\text{mass dextrorotatory}) + (\text{mass levorotatory})} \times 100$$

Another embodiment of the present invention is a composition comprising the levorotatory enantiomer of a compound of the present invention wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{(\text{mass dextrorotatory})}{(\text{mass dextrorotatory}) + (\text{mass levorotatory})} \times 100$$

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

In another aspect, the present invention is directed to pharmaceutical compositions containing one or more compounds, salts or solvates of the present invention as described herein admixed with a pharmaceutically acceptable carrier, excipient or diluent, wherein the compositions can be used to treat a condition directly or indirectly mediated by CETP.

Even though the compounds of the present invention (including their enantiomers, diastereomers, tautomers, pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of the present invention and one or more pharmaceutically acceptable carriers, excipients or diluents.

By way of example, in the pharmaceutical compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the present invention can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions may be administered in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

The instant pharmaceutical composition will generally contain a per dosage unit (e.g., tablet, capsule, powder, injection, teaspoonful and the like) from about 0.001 to about 50 mg/kg. In one embodiment, the instant pharmaceutical composition contains a per dosage unit of from about 0.01 to about 20 mg/kg of compound, and preferably from about 0.05 to about 10 mg/kg. Methods are known in the art for determining therapeutically effective doses for the instant pharmaceutical composition. The therapeutically effective amount for administering the pharmaceutical composition to a human, for example, can be determined by persons skilled in the art by the use of established animal models.

A therapeutically effective amount for use of the instant compound of a pharmaceutical composition thereof comprises a dose range of from about 0.01 mg to about 1,000 mg, preferably from about 10 to about 800 mg, in particular from about 25 mg to about 750 mg, or more particularly, a dose range of from about 50 mg to about 400 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing 0.01, 0.05, 0.1, 0.5, 1.0, 2.5, 5.0, 10.0, 15.0, 25.0, 50.0, 100, 150, 200, 250, and 500 milligrams of the active ingredient for the symptomatic adjustment of the dosage to the subject to be treated. In certain embodiments, an effective amount of the drug may be supplied at a dosage level of from about 0.01 mg/kg to about 100 mg/kg of body weight per day, or any range therein. Preferably, the range is from about 0.5 to about 50.0 mg/kg of body weight per day, or any range therein. More preferably, from about 1.0 to about 5.0 mg/kg of body weight per day, or any range therein. The compounds may be administered on a regimen of 1 to 4 times per day.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of the present invention may be administered in any of the foregoing compositions and dosage regimens or by means of those compositions and dosage regimens established in the art whenever use of the compounds of the invention as CETP inhibitors is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiments, the present invention is further directed to a process for preparation of the compounds of the present invention.

As inhibitors of CETP, the compounds of the present invention are useful in methods for treating, preventing, or inhibiting the progression of, a disease or condition in a mammal which disease or condition is affected by the inhibition of CETP. Such methods comprise administering to a mammal in need of such treatment or prevention a therapeutically effective amount of a compound of the present invention, or a pharmaceutically acceptable salt or solvate thereof as described herein.

The present invention is also directed to a method of treating or preventing a disease or condition in a subject, particularly a mammal including human, which disease or condition is affected by the modulation of CETP. Therefore, in yet another aspect, the present invention is directed to a method of treating or preventing a disease or condition in a subject which disease or condition is affected by the modulation of CETP, which method comprises administering to a subject in need of such treatment or prevention a therapeutically effective amount of a compound of the present invention, pharmaceutically acceptable salt or solvate thereof as described herein.

In a further aspect, the present invention is directed to a method of increasing HDL-C (HDL cholesterol) in a subject, which method comprises administering to a subject in need thereof a therapeutically effective amount of a compound of the present invention, pharmaceutically acceptable salt or solvate thereof as described herein.

In a further aspect, the present invention is directed to a method of increasing the ratio of HDL-C/LDL-C in a subject, which method comprises administering to a subject in need thereof a therapeutically effective amount of a compound of the present invention, pharmaceutically acceptable salt or solvate thereof as described herein.

In a further aspect, the present invention is directed to a method of increasing the ratio of HDL-C/total cholesterol in a subject, which method comprises administering to a subject in need thereof a therapeutically effective amount of a compound of the present invention, pharmaceutically acceptable salt or solvate thereof as described herein.

In a further aspect, the present invention is directed to a method of lowering either or both of LDL-C (LDL cholesterol) and non-HDL-C cholesterol in a subject, which method comprises administering to a subject in need thereof a therapeutically effective amount of a compound of the present invention, pharmaceutically acceptable salt or solvate thereof as described herein.

Examples of the disease or condition intended to be within the scope of the present invention include, but are not limited to, atherosclerosis, peripheral vascular disease, dyslipidemia (including hypertriglyceridemia, hypercholesterolemia, mixed hyperlipidemia, and hypo-HDL-cholesterolemia), hyper-LDL-cholesterolemia hyperbetaliproteinemia, hypoalphalipoproteinemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity and Metabolic Syndrome.

Preferably the compounds of the present invention are useful for the treatment of dyslipidemia (including hypertriglyceridemia, hypercholesterolemia, mixed hyperlipidemia, and hypo-HDL-cholesterolemia) and atherosclerosis.

While the present invention comprises compositions comprising one or more of the compounds of the present invention, the present invention also comprises compositions comprising intermediates used in the manufacture of compounds of the present invention.

The compounds of the present invention, pharmaceutically acceptable salts or solvates thereof can also be useful in combination therapy with one or more additional compounds, said additional compound being, for example, an HMG-CoA reductase inhibitor, an microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor, a bile acid sequestrant, and/or an "antihypertensive agent" (examples of an antihypertensive agent include, a calcium channel blocker, an ACE inhibitor, an A-II (Angiotensin-II receptor) antagonist, a diuretic, a beta-adrenergic receptor blocker, an alpha-adrenergic receptor blocker, or a vasodilator).

The term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that treats or inhibits in a subject the onset or progression of a disease or condition as being sought by a researcher, veterinarian, medical doctor or other clinician. Thus in another aspect, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

In certain embodiments, this invention provides a method for treating or preventing in a subject one or more diseases or conditions as described herein, said method comprising (a) administering to said subject a jointly effective amount of a compound of Formula (I), (Ia), (Ib), or (Ic) or an enantiomer, diastereomer, tautomer, or pharmaceutically acceptable salt thereof as described herein; and (b) administering to said subject a jointly effective amount of an HMG-CoA reductase inhibitor, an microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor, a bile acid sequestrant, or an antihypertensive agent.

said co-administration being in any order and the combined jointly effective amounts providing the desired therapeutic or prophylactic effect.

In certain embodiments, this invention provides a method for treating or preventing in a subject one or more diseases or conditions as described herein, said method comprising (a) administering to said subject a jointly effective amount of a compound of Formula (I), (Ia), (Ib) or (Ic) or an enantiomer, diastereomer, tautomer, or pharmaceutically acceptable salt thereof as described herein; and (b) administering to said subject a jointly effective amount of an HMG-CoA reductase inhibitor, said co-administration being in any order and the combined jointly effective amounts providing the desired therapeutic or prophylactic effect.

Such administration encompasses co-administration of these therapeutic agents in a substantially simultaneous manner, such as in a single capsule having a fixed ratio of active ingredients or in multiple, separate capsules for each agent. In addition, such administration also encompasses use of each type of therapeutic agent in a sequential manner.

The HMG-CoA reductase inhibitor for use in the present invention may be any HMG-CoA reductase inhibitor which is preferably capable of lower plasma concentrations of low-density lipoprotein, total cholesterol, or both. In a preferred aspect, the HMG-CoA reductase inhibitor is from a class of therapeutics commonly called statins. Examples of HMG-CoA reductase inhibitors that may be used include but are not limited to lovastatin (Mevacor®), simvastatin (Zocor®), pravastatin (Pravachol®), lactones of pravastatin, fluvastatin (Lescol®), lactones of fluvastatin, atorvastatin (Lipitor®), lactones of atorvastatin, cerivastatin (also known as rivastatin and Baychol®), lactones of cerivastatin, rosuvastatin (Crestor®), lactones of rosuvastatin, itavastatin, nisvastatin, visastatin, atavastatin, bervastatin, compactin, dihydrocompactin, dalvastatin, fluindostatin, pitivastatin, mevastatin, and velostatin (also referred to as synvinolin), and pharmaceutically acceptable forms thereof. Preferably the HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof.

In one embodiment the present invention provides a combination therapy comprising the use of a first amount of a compound of Formula (I), (Ia), (Ib) or (Ic) or an enantiomer, diastereomer, tautomer, or pharmaceutically acceptable salt thereof as described herein and a second amount of an HMG CoA reductase inhbitor compound useful in the prophylaxis or treatment of hyperlipidemia, atherosclerosis, or hypercholesterolemia, wherein said first and second amounts together comprise an anti-hyperlipidemic condition effective amount, an anti-atherosclerotic condition effective amount, or an anti-hypercholesterolemic condition effective amount of the compounds.

General Synthetic Methods

Representative compounds of the present invention can be synthesized in accordance with the general synthetic methods described below as well as the illustrative examples that follow. Since the schemes are an illustration, the invention should not be construed as being limited by the chemical reactions and conditions expressed. The preparation of the various starting materials used in the schemes is well within the skill of persons versed in the art.

General Scheme 1 (Method A)

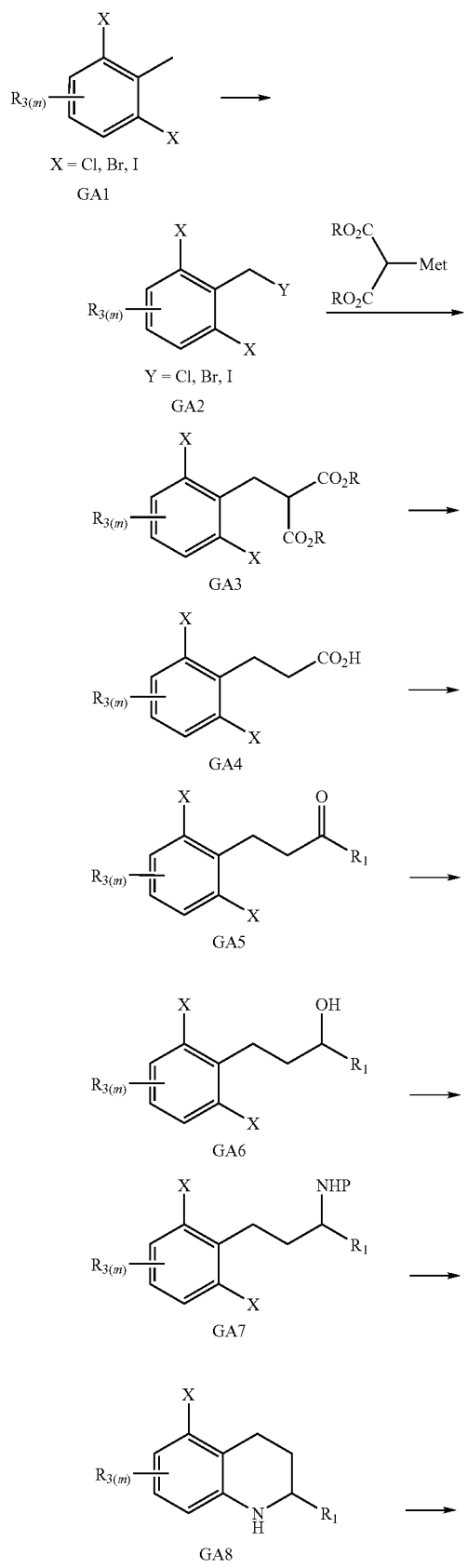

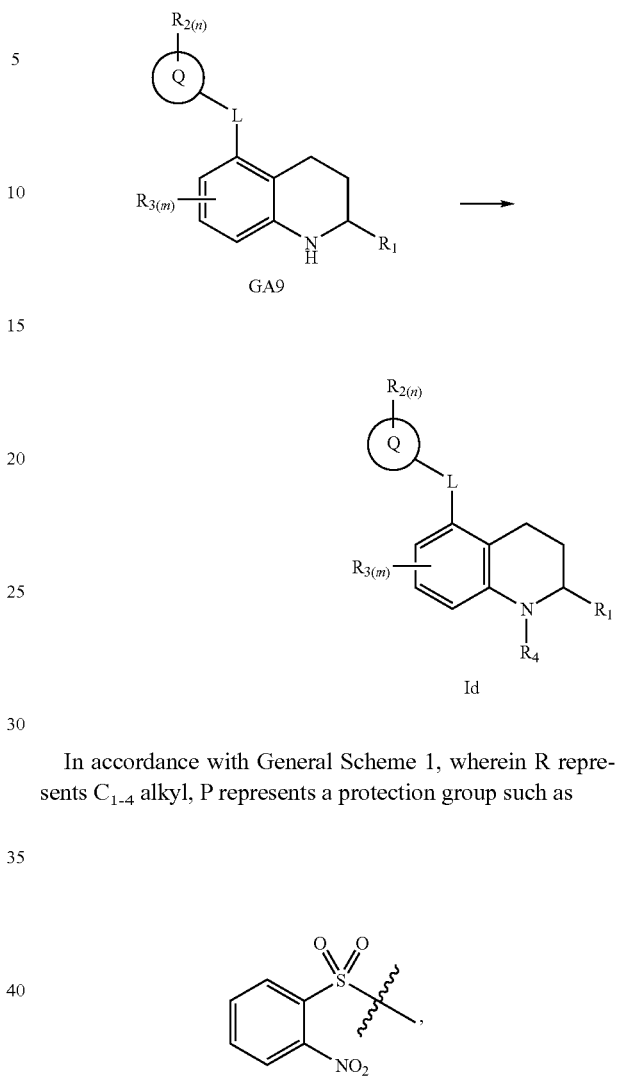

In accordance with General Scheme 1, wherein R represents $C_{1-4}$ alkyl, P represents a protection group such as Met is a metal such as Na, $R_3$ is $C_{1-4}$ alkyl, $C_{1-4}$ alkoxy, halo, or cyano, and $R_1$, $R_2$, $R_4$, m, n, L, and Q are as described herein, halogenation of a suitable starting material GA1 can provide GA2. Displacement of the halogen atom of GA2 with a metal salt (such as sodium) of malonate gives GA3, decarboxylation of which, followed by hydrolysis, gives GA4. Conversion of the carboxylic acid to the acid chloride followed by palladium-catalyzed acylation of it with the organotin or organoboron (or organozinc) compound gives GA5. Reduction of GA5 gives the alcohol GA6. Mesylation of GA6 followed by azide displacement, reduction and protection further gives GA7. Metal-catalyzed ring closure of GA7 followed by deprotection gives GA8. Transition metal-catalyzed cross-coupling of GA8 gives GA9. Alkylation of GA9 with different electrophile gives compounds of Formula (Id). When $R_3$ is OH, one can first protect the OH of GA1 as OTBS-GA1, then follow the same sequences described above in General Scheme 1 to give compounds of Formula (II),

II

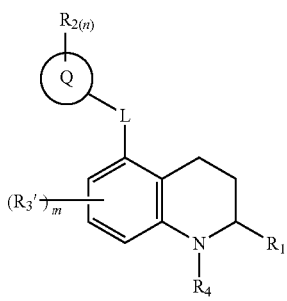

wherein $R_3'$ is OTBS and $R_1$, $R_2$, $R_4$, m, n, L, and Q are as described herein, followed by removal of the TBS protection group to give compounds of Formula (Ie):

Ie

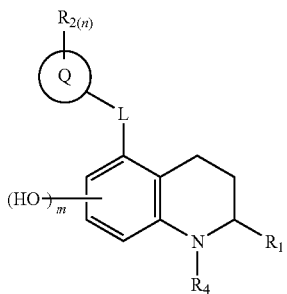

General Scheme 2 (Method B)

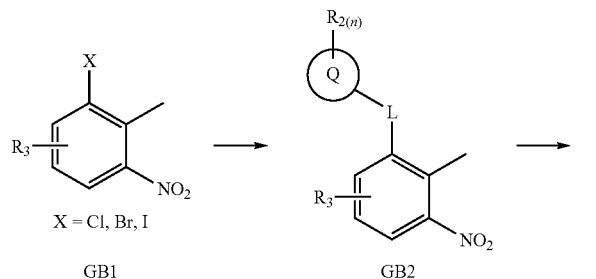

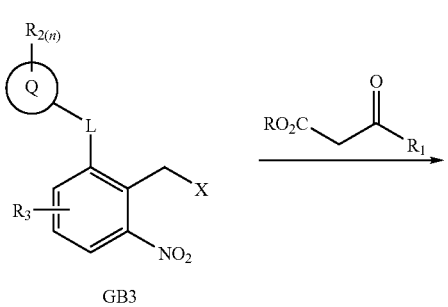

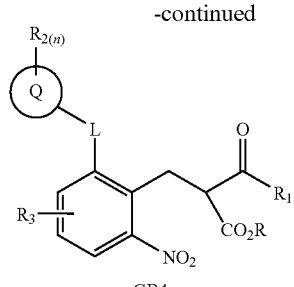
GB4

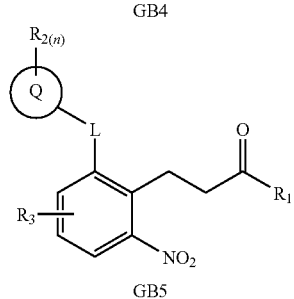
GB5

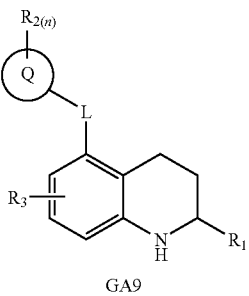
GA9

An alternate method B can be used to synthesize GA9 as shown in General Scheme 2, wherein R represents $C_{1-4}$ alkyl and $R_1$, $R_2$, $R_3$, L, and Q are as described herein. Transition metal-catalyzed cross-coupling of GB1 gives GB2. Halogenation of GB2 gives GB3. Alkylation of GB3 with beta-keto ester gives GB4. Decarboxylation of GB4 gives GB5. Hydrogenation of GB5 gives GA9 directly. In the case of $R_3$=OH, one can first protect the OH of GB1 as OTBS-GB1, then follow the same sequences as just described above to give compounds of Formula (II),

II

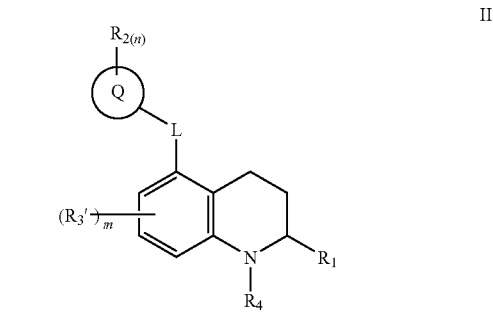

wherein $R_3'$ is OTBS and $R_1$, $R_2$, $R_4$, m, n, L, and Q are as described herein.

Compounds of the present invention that are chiral may be separated into their enantiomers by chromatography on a chiral stationary phase. Alternatively, the basic compounds of the present invention may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

ABBREVIATIONS

Ac=$CH_3C(O)$—
Aq=aqueous
CETP=cholesteryl ester transfer protein
Cpd, Cmpd=compound
con=concentration
DCE=dichloroethane
DCM=dichloromethane
DIPEA/DIEA=diisopropylethyl amine
DMF=N,N-dimethylformamide
DMSO=dimethylsulfoxide
DPPF=diphenylphosphinoferrocene
Et=ethyl
EtOAc=ethyl acetate
h or hr=hour(s)
HATU=N-[(dimethylamino)(3H-1,2,3-triazolo(4,5-b)pyridine-3-yloxy)methylene]-N-methylmethanaminium hexafluorophosphate
HDL=High Density Lipoprotein
HDL-C=high density lipoprotein cholesterol
HFIPA=hexafluoroisopropyl alcohol
IDL=Intermediate Density Lipoprotein
LAH=lithium aluminum hydride
LDL=Low Density Lipoprotein
LDL-C=Low Density Lipoprotein cholesterol
LiN(TMS)$_2$=Lithium bis(trimethylsilyl)amide
Me=methyl
min=minute(s)
NBS=N-bromosuccinimide
Pd/C=Palladium on Carbon Catalyst
Pd$_2$(OAc)$_2$=Palladium(II)acetate
Pd(PPh$_3$)$_4$=Tetrakistriphenylphosphine palladium (0)
Ph=phenyl
PPA=polyphosphoric acid
psi=pascal per square inch
Rf=retention time
RT or rt=room temperature
t-Boc=tert-butoxycarbonyl
TBSO=tert-butyldimethylsilyloxy
t-Bu=tert-butyl
TEA=triethylamine
TFA=trifluoroacetic acid
THF=tetrahydrofuran
TLC=(thin layer chromatography)
TMS=trimethylsilyl
TMSOTf=trimethylsilyl triflate
Tol=toluene
VLDL=Very Low Density Lipoprotein
Yb(OTf)$_3$=Ytterbium tristriflate

EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

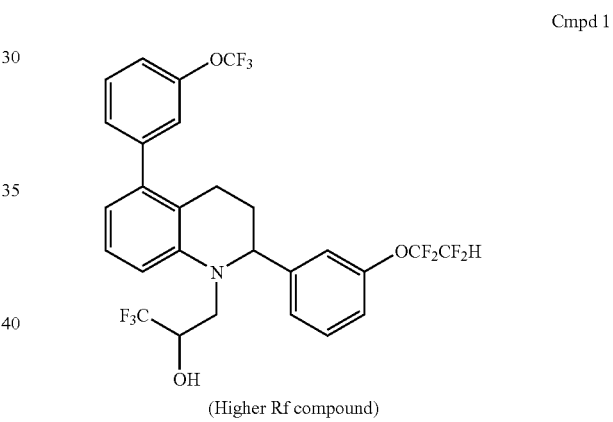

Cmpd 1

(Higher Rf compound)

1,1,1-Trifluoro-3-[2-[3-(1,1,2,2-tetrafluoro-ethoxy)-phenyl]-5-(3-trifluoromethoxy-phenyl)-3,4-dihydro-2H-quinolin-1-yl]-propan-2-ol

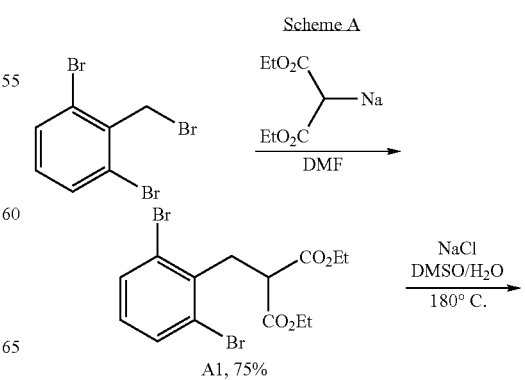

Scheme A

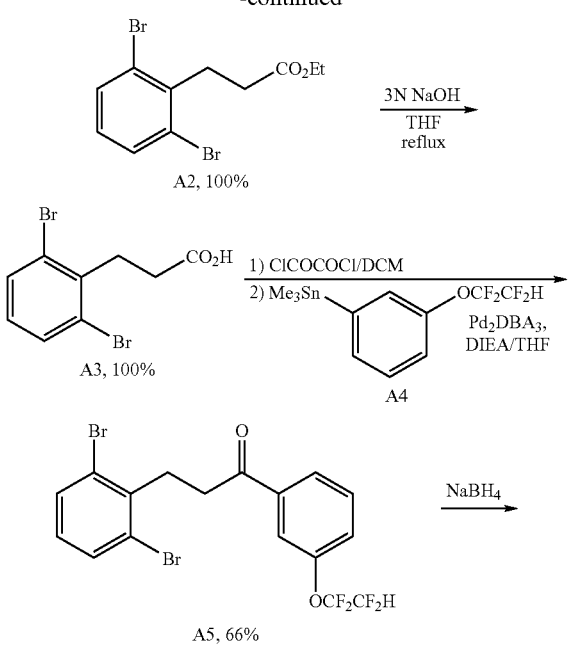
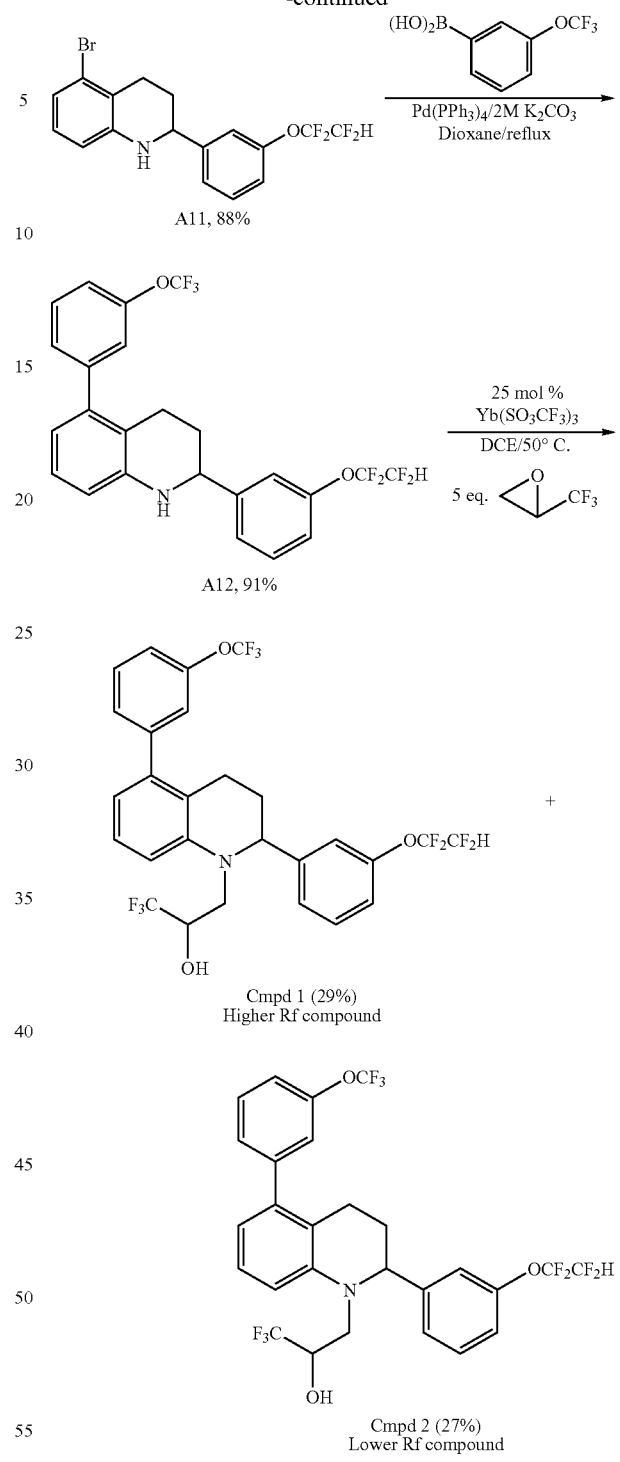
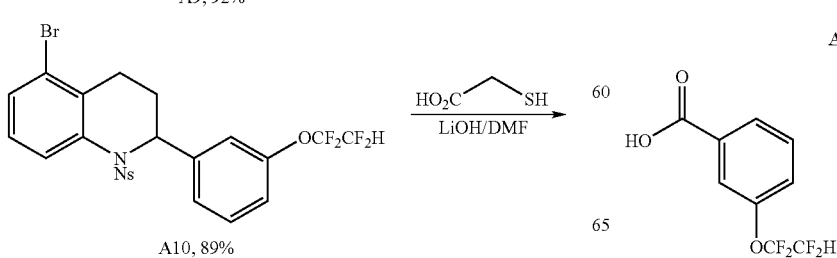

-continued
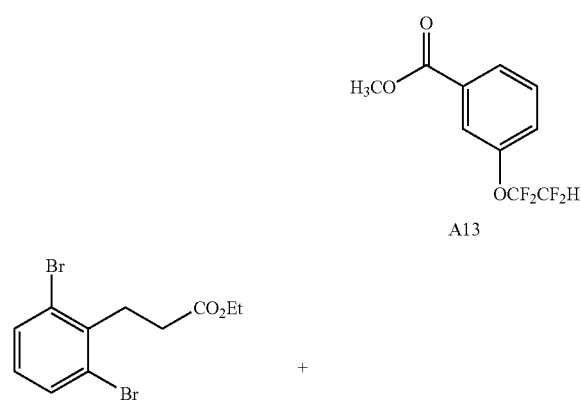
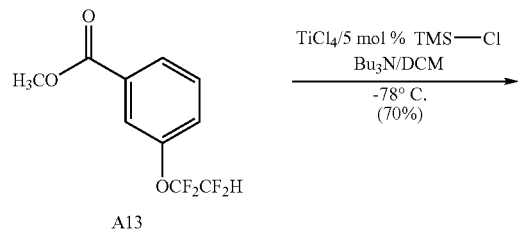
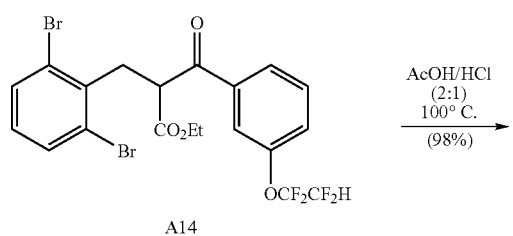
Alternate Route to A12
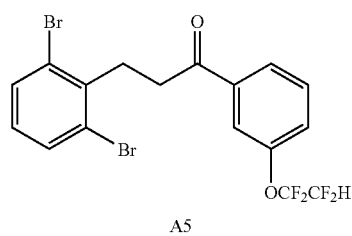
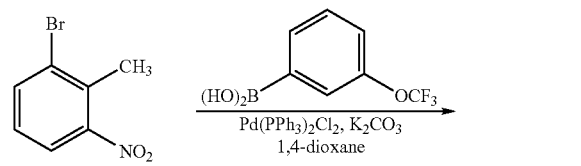
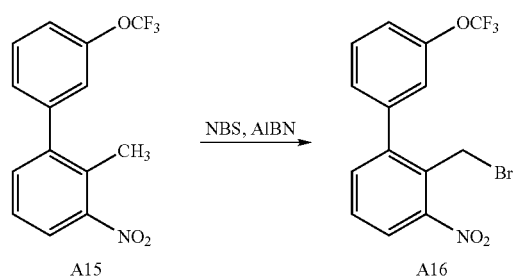
-continued
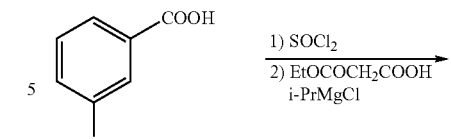
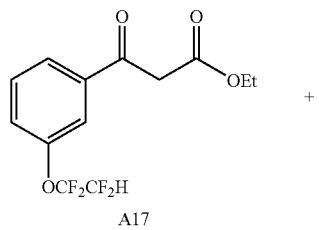
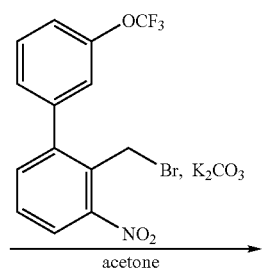

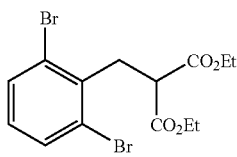

2-(2,6-Dibromo-benzyl)-malonic acid diethyl ester

To a solution of sodium diethyl malonate (2.40 g, 13.2 mmol) in DMF (15 mL) under a $N_2$ atmosphere was added 1,3-dibromo-2-bromomethyl-benzene (4.56 g, 13.9 mmol). After stirring at room temperature for 2 h, ether was added and the solution was washed with $H_2O$ and brine, dried ($MgSO_4$), concentrated and purified by column chromatography to afford 4.28 g (75%) of A1 as an oil: $^1H$ NMR (300 MHz, $CDCl_3$) δ 7.51 (d, J=8.0 Hz, 2H), 6.95 (t, J=8.0 Hz, 1H), 4.18 (q, J=7.1 Hz, 4H), 3.84 (t, J=7.7 Hz, 1H), 3.63 (d, J=7.7 Hz, 2H), 1.21 (t, J=7.1 Hz, 6H); MS (ES) m/z: 409 (M+H$^+$).

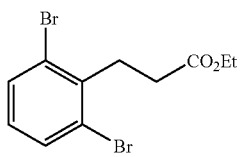

3-(2,6-Dibromo-phenyl)-propionic acid ethyl ester

A mixture of A1 (4.2 g, 10.3 mmol), sodium chloride (602 mg, 10.3 mmol) and $H_2O$ (371 mg, 20.6 mmol) in DMSO (75 mL) was heated at 180° C. for 1 h. After cooling to room temperature, the reaction mixture was poured into EtOAc (500 mL) and washed with $H_2O$ and brine, dried ($MgSO_4$) and concentrated to afford 3.49 g (100%) A2 as an oil: $^1H$ NMR (300 MHz, $CDCl_3$) δ 7.51 (d, J=8.0 Hz, 2H), 6.93 (t, J=8.0 Hz, 1H), 4.18 (q, J=7.1 Hz, 2H), 3.33 (m, 2H), 2.57 (m, 2H), 1.28 (t, J=7.1 Hz, 3H); MS (ES) m/z: 337 (M+H$^+$).

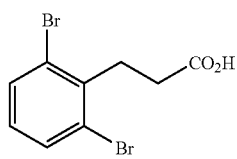

3-(2,6-Dibromo-phenyl)-propionic acid

A mixture of A2 (3.46 g, 10.3 mmol) and 3 M sodium hydroxide (25 mL, 75 mmol) in THF (25 mL) was heated at reflux for 5 h. Upon cooling to 0° C., the reaction mixture was acidified with concentrated HCl followed by extraction with EtOAc. The combined organic phases were then washed with brine, dried ($MgSO_4$) and concentrated to afford 3.29 g (100%) A3 as a white solid: $^1H$ NMR (300 MHz, $CDCl_3$) δ 7.52 (d, J=8.0 Hz, 2H), 6.95 (t, J=8.0 Hz, 1H), 3.35 (m, 2H), 2.65 (m, 2H); MS (ES) m/z: 307 (M−H$^+$).

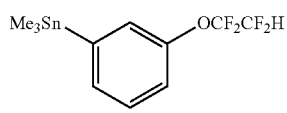

Trimethyl-[3-(1,1,2,2-tetrafluoro-ethoxy)-phenyl]-stannane

A mixture of 1-bromo-3-(1,1,2,2-tetrafluoro-ethoxy)-benzene (3.87 g, 14.1 mmol), hexamethylditin (5.11 g, 15.6 mmol), $PPh_3$ (110 mg, 0.423 mmol) in toluene (70 mL) under a $N_2$ atmosphere was degassed by bubbling $N_2$ through the solution for 15 min. Pd(PPh$_3$)$_4$ (814 mg, 0.7 mmol) was added and the reaction mixture was heated at 80° C. for 2 h. After cooling to room temperature, the reaction mixture was poured into EtOAc (500 mL). The solution was then washed with $H_2O$ and brine, dried ($MgSO_4$), concentrated and purified by column chromatography (2% EtOAc/Hex) to afford 3.76 g (67%) A4 as an oil: $^1H$ NMR (300 MHz, $CDCl_3$) δ 7.37-7.29 (m, 3H), 7.16-7.13 (m, 1H), 5.91 (tt, J=53.2, 2.9 Hz, 1H), 0.31 (s, 9H).

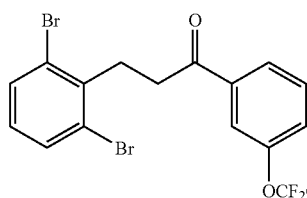

3-(2,6-Dibromo-phenyl)-1-[3-(1,1,2,2-tetrafluoro-ethoxy)-phenyl]-propan-1-one

To a solution of A3 (3.27 g, 10.6 mmol) in $CH_2Cl_2$ (45 mL) under a $N_2$ atmosphere was added 2M oxalyl chloride in $CH_2Cl_2$ (7.95 mL, 15.9 mmol). After stirring at room temperature for 18 h, the solution was concentrated to give 3.26 g of acid chloride which was used without further purification.

To a solution of the above intermediate (3.26 g, 9.98 mmol) in dry THF (50 mL) at 0° C. under a $N_2$ atmosphere was added N,N-diisopropylethylamine (2.6 mL, 15.0 mmol), A4 (4.27 g, 12.0 mmol) and Pd$_2$(dba)$_3$ (456 mg, 0.499 mmol). After heating at 50° C. for about 30 min, the reaction mixture was cooled and poured into EtOAc (300 mL) and washed with saturated NaHCO$_3$, $H_2O$ and brine, dried ($MgSO_4$), concentrated and purified by column chromatography (5% EtOAc/Hex) to afford 3.20 g (66%) of A5 as an oil: $^1H$ NMR (300 MHz, $CDCl_3$) δ 7.94-7.89 (m, 1H), 7.83 (s, 1H), 7.55-7.40 (m, 4H), 6.96 (t, J=8.0 Hz, 1H), 5.93 (tt, J=53.0, 2.8 Hz, 1H), 3.47-3.40 (m, 2H), 3.25-3.20 (m, 2H); MS (ES) m/z: 485 (M+H$^+$).

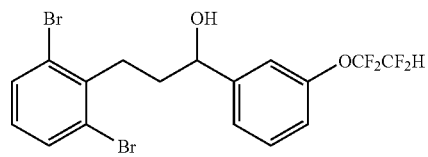

3-(2,6-Dibromo-phenyl)-1-[3-(1,1,2,2-tetrafluoro-ethoxy)-phenyl]-propan-1-ol

To a solution of A5 (3.04 g, 6.27 mmol) in EtOH (50 mL) under a $N_2$ atmosphere was added NaBH$_4$ (118 mg, 12.5 mmol). After 1 h the reaction was cooled to 0° C. and quenched with several drops of glacial AcOH. The EtOH was evaporated and the residue was dissolved in EtOAc. The organic phase was washed with saturated NaHCO₃, water and brine, dried (MgSO₄), concentrated and purified by column chromatography (10%-15%-20% EtOAc/Hex) to provide 2.89 g (95%) of A6 as an oil: ¹H NMR (300 MHz, CDCl₃) δ 7.48 (d, J=8.0 Hz, 2H), 7.41-7.28 (m, 3H), 7.14 (d, J=7.7 Hz, 1H), 6.89 (t, J=8.0 Hz, 1H), 5.91 (tt, J=53.1, 2.8 Hz, 1H), 4.86 (dd, J=10.1, 6.2 Hz, 1H), 3.19-3.05 (m, 1H), 3.03-2.92 (m, 1H), 2.09-1.95 (m, 3H); MS (ES) m/z: 509 (M+Na⁺).

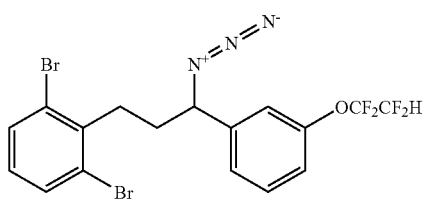

A7

To a solution of A6 (2.89 g, 5.94 mmol) in CH₂Cl₂ (30 mL) under a N₂ atmosphere at 0° C. was added triethylamine (1.66 mL, 11.9 mmol) and methanesulfonyl chloride (0.690 mL, 8.9 mmol). The cooling bath was removed and the solution was stirred at room temperature for 2 h. The reaction mixture was poured into EtOAc and washed with 1 N HCl, water, saturated NaHCO₃ and brine. The organic layer was dried (MgSO₄) and concentrated to give the mesylate as a crude intermediate.

A mixture of the above crude mesylate and sodium azide (1.93 g, 29.7 mmol) in DMF (45 mL) under a N₂ atmosphere was heated at 50° C. for ~1 h. After cooling to room temperature, the reaction mixture was poured into EtOAc (500 mL), the solution was then washed with H₂O, saturated NaHCO₃ solution and brine, dried (MgSO₄) and concentrated to afford 2.90 g (95% for two steps) A7 as an oil: ¹H NMR (300 MHz, CDCl₃) δ 7.48 (d, J=8.0 Hz, 2H), 7.42 (t, J=7.9 Hz, 1H), 7.31-7.19 (m, 3H), 6.90 (t, J=8.0 Hz, 1H), 5.92 (tt, J=53.1, 2.8 Hz, 1H), 4.60 (t, J=6.9 Hz, 1H), 3.15-3.05 (m, 1H), 2.99-2.82 (m, 1H), 2.09-1.97 (m, 2H); MS (ES) m/z: 484 (M−N₂+H⁺).

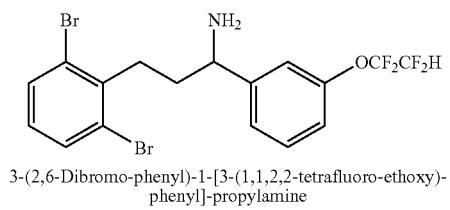

A8

3-(2,6-Dibromo-phenyl)-1-[3-(1,1,2,2-tetrafluoro-ethoxy)-phenyl]-propylamine

To a solution of A7 (2.90 g, 5.67 mmol) in 1,2-dichloroethane (38 mL) under a N₂ atmosphere was added Me₂S.BHCl₂ (1.64 mL, 14.2 mmol) dropwise. The solution was stirred at room temperature for 0.5 h and then heated at 50° C. for 1.5 h. The reaction was cooled to 0° C., then 6 N HCl (10 mL) was added. The reaction mixture was then heated at reflux for 1 h. Upon cooling to 0° C., the solution was basified with 3 N NaOH and extracted several times with CHCl₃. The combined organic phases were dried (MgSO₄), concentrated and purified by column chromatography (100% EtOAc) to provide 2.69 g (98%) A8 as an oil: ¹H NMR (300 MHz, CDCl₃) δ 7.46 (d, J=8.2 Hz, 2H), 7.39-7.26 (m, 3H), 7.14-7.10 (m, 1 H), 6.88 (t, J=8.0 Hz, 1H), 5.91 (tt, J=53.1, 2.9 Hz, 1H), 4.08 (t, J=6.6 Hz, 1H), 3.09-3.00 (m, 1H), 2.90-2.80 (m, 1H), 1.98-1.88 (m, 2H), 1.57 (brs, 2H); MS (ES) m/z: 486 (M+H⁺).

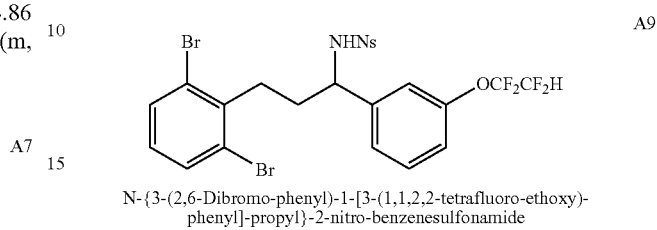

A9

N-{3-(2,6-Dibromo-phenyl)-1-[3-(1,1,2,2-tetrafluoro-ethoxy)-phenyl]-propyl}-2-nitro-benzenesulfonamide To a solution of A8 (2.67 g, 5.50 mmol) and triethylamine (1.53 mL, 11.0 mmol) in dichloromethane (27 mL) under a N₂ atmosphere was added NsCl (1.34 g, 6.05 mmol) under N₂. The reaction mixture was stirred at room temperature for 1 h and then poured into EtOAc/Et₂O. The solution was washed with saturated NaHCO₃, H₂O and brine, dried (MgSO₄), concentrated and purified by column chromatography (5%-10%-15%-20% EtOAc/Hex) to afford 3.54 g (95%) A9 as an oil: ¹H NMR (400 MHz, CDCl₃) δ 7.72 (d, J=8.0 Hz, 1H), 7.66 (d, J=7.9 Hz, 1H), 7.55-7.33 (m, 4H), 7.13-7.08 (m, 2H), 7.01 (s, 1H), 6.95-6.88 (m, 2H), 5.96 (d, J=8.9 Hz, 1H), 5.86 (tt, J=53.1, 2.8 Hz, 1H), 4.69 (dd, J=16.0, 7.8 Hz, 1H), 3.19-3.11 (m, 1H), 2.88-2.80 (m, 1H), 2.14-1.94 (m, 2H); MS (ES) m/z: 693 (M+Na⁺).

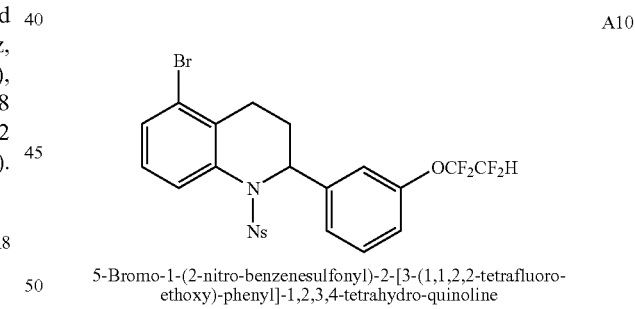

A10

5-Bromo-1-(2-nitro-benzenesulfonyl)-2-[3-(1,1,2,2-tetrafluoro-ethoxy)-phenyl]-1,2,3,4-tetrahydro-quinoline A mixture of A9 (3.54 g, 5.26 mmol), CuI (2.00 g, 10.5 mmol) and CsOAc (5.04 g, 26.3 mmol) in DMSO (52 mL) under a N₂ atmosphere was heated at 95° C. for 24 h. After cooling to room temperature, the reaction mixture was poured into EtOAc (400 mL), washed with saturated NH₄Cl (3×), water, Na₂S₂O₃ solution and brine, dried (MgSO₄) concentrated and purified by column chromatography (25% EtOAc/Hex) to afford 2.99 g (96%) A10 as an oil: ¹H NMR (400 MHz, CDCl₃) δ 7.81 (d, J=8.1 Hz, 1H), 7.73-7.69 (m, 1H), 7.63-7.50 (m, 3H), 7.43 (d, J=8.0 Hz, 1H), 7.39-7.09 (m, 5H), 5.88 (tt, J=53.1, 2.9 Hz, 1H), 5.62 (t, J=6.9 Hz, 1H), 2.74-2.66 (m, 1H), 2.47-2.39 (m, 1H), 2.35-2.27 (m, 1H), 2.05-1.96 (m, 1H); MS (ES) m/z: 589 (M).

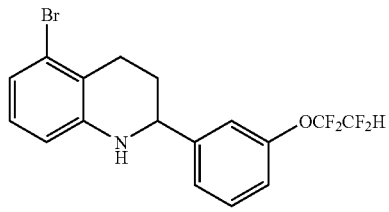

5-Bromo-2-[3-(1,1,2,2-tetrafluoro-ethoxy)-phenyl]-1,2,3,4-tetrahydro-quinoline

To a solution of A10 (2.99 g, 5.06 mmol) in DMF (25 mL) under a N$_2$ atmosphere was added thioacetic acid (0.707 mL, 10.1 mmol) and powdered LiOH (485 mg, 20.2 mmol). The reaction mixture was stirred at room temperature for ~6 h and then poured into EtOAc, washed with saturated NaHCO$_3$, H$_2$O and brine, dried (MgSO$_4$), concentrated and purified by column chromatography (25% EtOAc/Hex) to afford 1.80 g (88%) A11 as an oil: $^1$H NMR (300 MHz, CDCl$_3$) δ 7.37 (t, J=7.8 Hz, 1H), 7.30-7.21 (m, 2H), 7.15 (d, J=7.9 Hz, 1H), 6.95-6.71 (m, 2H), 6.51 (d, J=7.8 Hz, 1H), 5.90 (tt, J=53.1, 2.8 Hz, 1H), 4.40 (dd, J=9.3, 3.1 Hz, 1 H), 4.13 (brs, 1H), 2.88-2.79 (m, 2H), 2.21-2.11 (m, 1H), 2.05-1.90 (m, 1H); MS (ES) m/z: 406 (M+2).

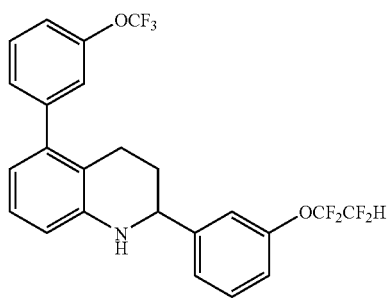

2-[3-(1,1,2,2-Tetrafluoro-ethoxy)-phenyl]-5-(3-trifluoromethoxy-phenyl)-1,2,3,4-tetrahydro-quinoline Under a N$_2$ atmosphere, a mixture of A11 (30 mg, 0.074 mmol), 3-trifluoromethoxy-phenyl-boronic acid (30 mg, 0.148 mmol), Pd(PPh$_3$)$_4$ (9 mg, 0.0074 mmol) and 2 N K$_2$CO$_3$ (0.11 mL, 0.22 mmol) in 1,4-dioxane (0.75 mL) was heated at reflux for 2 h. After cooling to room temperature, EtOAc was added and the solution was washed with Na$_2$HCO$_3$, H$_2$O and brine. The organic layer was dried (MgSO$_4$), concentrated and purified by column chromatography to give 33 mg (91%) of A12 as a clear oil: $^1$H NMR (400 MHz, CDCl$_3$) δ 7.42-7.30 (m, 4H), 7.25 (m, 1H), 7.21-7.08 (m, 4 H), 6.62 (s, 1H), 6.60 (s, 1H), 5.90 (tt, J=53.1, 2.8 Hz, 1H), 4.51 (dd, J=8.9, 3.3 Hz, 1H), 4.20 (brs, 1H), 2.81-2.71 (m, 1H), 2.53 (dt, J=16.6, 4.8 Hz, 1H), 2.10-2.02 (m, 1H), 1.92-1.82 (m, 1H); MS (ES) m/z: 486 (M+H$^+$).

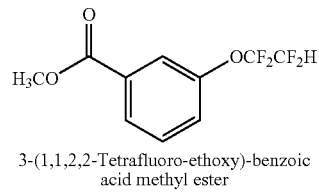

3-(1,1,2,2-Tetrafluoro-ethoxy)-benzoic acid methyl ester

To 3-(1,1,2,2-tetrafluoro-ethoxy)-benzoic acid (10 g; 41.9 mmol) in 20 mL of DCM and 30 mL of MeOH cooled to 0° C. was added TMS-diazomethane (2M; 35 mL). The reaction was stirred for 10 minutes, followed by removal of the solvent in vacuo. Purification by column chromatography provided 9.1 g (86%) of A13: $^1$H NMR (400 MHz, CDCl$_3$) δ 3.94 (s, 3H), 5.93 (tt, J=53.1, 2.8 Hz, 1H), 7.40-7.50 (m. 2H), 7.88 (s, 1H), 7.97 (d, J=8.9 Hz, 1H).

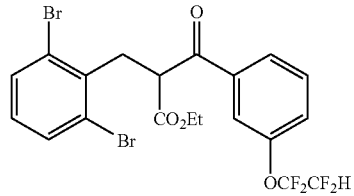

2-(2,6-Dibromo-benzyl)-3-oxo-3-[3-(1,1,2,2-tetrafluoro-ethoxy)-phenyl]-propionic acid ethyl ester To A2 (308 mg; 0.95 mmol) and A13 (725 mg; 2.87 mmol) in anhydrous PhMe (2.5 mL) under an atmosphere of N$_2$ cooled to 0° C. was added TiCl$_4$ (2.87 mL; 2.87 mmol), TMSOTf (8.6 uL; 0.0475 mmol) and Bu$_3$N (1.01 mL; 4.27 mmol). The ice bath was removed. After 10 minutes, A2 was completely consumed. The ice bath was replaced and the reaction was quenched with water. EtOAc was added and the mixture separated. The organic layer was washed with water (2×), saturated sodium bicarbonate solution (2×), water and brine. The organic layer was dried (MgSO$_4$), concentrated and purified by column chromatography (0-5% EtOAc/Hexanes) to provide A14 (364 mg) in 70% yield; $^1$H NMR (400 MHz, CDCl$_3$) δ 1.09 (t, 3H), 3.69 ½ ABX (J$_{ab}$=14.4 Hz, J$_{ax}$=5.9 Hz, 1H), 3.80½ ABX (J$_{ab}$=14.4 Hz, J$_{ax}$=8.6 Hz, 1H), 4.08-4.15 (m, 2H), 4.70 (dd, J=8.5, 6.1 Hz, 1H), 5.93 (tt, J=53.1, 2.8 Hz, 1H), 6.91 (t, J=8.0 Hz, 1H), 7.37-7.50 (m, 4H), 7.75 (s, 1H), 7.78 (d, J=7.46 Hz 1H).

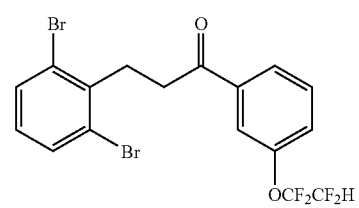

3-(2,6-Dibromo-phenyl)-1-[3-(1,1,2,2-tetrafluoro-ethoxy)-phenyl]-propan-1-one

A14 (369 mg; 0.663 mmol) was heated in a 2:1 mixture of AcOH/conc. HCl (5 mL) for 1 hour under an atmosphere of N$_2$. After cooling, water was added and extraction with EtOAc followed. The organic layer was washed with water (3x), 1N NaOH (1x), water (1x) and brine. The organic layer was dried (MgSO$_4$) and concentrated to provide A5 (~305 mg) in near quantitative yield. The compound was identical in all respects to A5 which was prepared employing the original method.

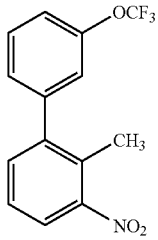

A15

2-Methyl-3-nitro-3'-trifluoromethoxy-biphenyl

A mixture of 2-bromo-6-nitrotoluene (21.5 g, 99.5 mmol), 3-trifluoromethoxylbenzeneboronic acid (27.0 g, 131.1 mmol), Pd(PPh$_3$)$_2$Cl$_2$ (3.50 g, 5.0 mmol) and 2M K$_2$CO$_3$ (120 mL, 240 mmol) in dioxane (330 mL) was degassed with N$_2$ and then heated at 100° C. for 3 h. After cooling to room temperature, the reaction mixture was passed through Celite and partitioned between EtOAc and H$_2$O. The combined organic phases were dried (MgSO$_4$), concentrated and purified by column chromatography (1-10% EtOAc/Heaxane) to give A15 (28.27 g, 96%) as light yellow oil: $^1$H NMR (300 MHz, CDCl$_3$) δ 7.85 (d, J=7.82 Hz, 1H), 7.74-7.38 (m, 3H), 7.31-7.23 (m, 2H), 7.19 (s, 1H), 2.37 (s, 3H).

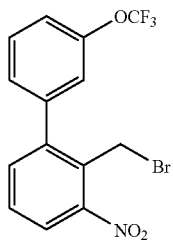

A16

2-Bromomethyl-3-nitro-3'-trifluoromethoxy-biphenyl

A mixture of A15 (26.1 g, 87.8 mmol), NBS (20.3 g, 114 mmol), AIBN (1.44 g, 8.77 mmol) was degassed with N$_2$ and then heated at 85° C. After 20 min, it began to react vigorously. After 2 h, the temperature was raised to 90° C. and the mixture was heated for 3 h. After cooling to room temperature, the reaction mixture was diluted with hexane. The solid was filtered off and the filtrate was concentrated to give A16 (31.47 g, 95%) as yellow oil: $^1$H NMR (300 MHz, CDCl$_3$) δ 8.00 (dd, J=2.03, 2.04, 1H), 7.58-7.49 (m, 3H), 7.41-7.28 (m, 3H), 4.69 (s, 2H).

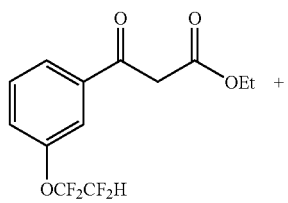

A17 & A18

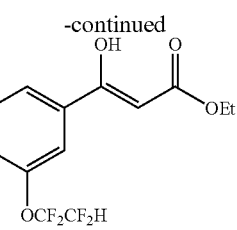

3-Oxo-3-[3-(1,1,2,2-tetrafluoro-ethoxy)-phenyl]-propionic acid ethyl ester
3-Hydroxy-3-[3-(1,1,2,2-tetrafluoro-ethoxy)-phenyl]-acrylic acid ethyl ester To an ice-cooled solution of 3-tetrafluoroethoxy-benzoic acid (40 g, 0.17 mol) was added SOCl$_2$ (59 mL, 0.81 mol) dropwise. After addition, the ice-bath was removed and the mixture was stirred at room temperature for 3 h followed by heating at 50° C. for 2 h and then 75° C. for 3 h. Then the reaction mixture was stirred at room temperature overnight. SOCl$_2$ was removed in rotary evaporator. To the residue was added dry toluene and concentrated (20 ml×3). After on high vacuum line for 5 hours, the acyl chloride was obtained as a clear oil (41 g, 95%).

To a solution of EtOCOCH$_2$COOH (16.1 g, 0.122 mol) in THF (120 mL) at −78° C. was added i-PrMgCl (2.0 M in THF, 122 mL, 0.244 mol) dropwise through an additional funnel. After stirring at −78° C. for 1 h, the acyl chloride (20.9 g, 0.0815 mol) in THF (80 mL) was added via an addition funnel. The reaction mixture was stirred at −78° C. for 1 h. The cooling bath was removed and the mixture was stirred at room temperature for 2 h. The reaction flask was cooled in ice-bath, and 1 N HCl (~100 mL, till pH<1) was added dropwise. Upon addition of 1 N HCl, some precipitate formed and stirring became difficult, then the precipitate dissolved during further addition of 1 N HCl. The organic layer was separated and the aqueous layer was extracted with EtOAc. The combined organic phases were dried, concentrated and purified by column chromatography to give 21.8 g (83%) of a tautomeric mixture of A17 an A18: MS (ES) m/z: 331 (M+Na$^+$).

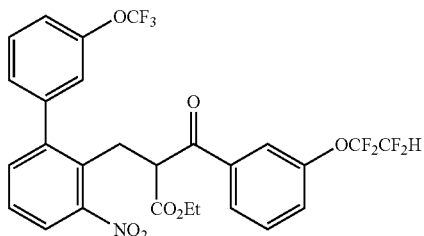

A19

2-(3-Nitro-3'-trifluoromethoxy-biphenyl-2-ylmethyl)-3-oxo-3-[3-(1,1,2,2-tetrafluoro-ethoxy)-phenyl]-propionic acid ethyl ester To a mixture of A17 and A18 (13.5 g, 43.8 mmol) and benzyl bromide (15.7 g, 41.7 mmol) in 270 mL acetone was added K$_2$CO$_3$ (8.66 g, 62.6 mmol)). After stirring at room temperature for 1 h, TLC (15% EtOAc in hexane) indicated the reaction was complete. The reaction mixture was filtered through Celite and the solid was washed with EtOAc. The filtrate was concentrated and purified by column chromatography to give 22 g (87%) of A19 as a yellow oil: $^1$H NMR (300

MHz, CDCl$_3$) δ 7.85 (dd, J=6.5, 2.7 Hz, 1H), 7.59-7.54 (m, 2H), 7.48-7.36 (m, 5H), 7.26-7.21 (m, 2 H), 7.14 (s, 1H), 5.92 (tt, J=53.0, 2.5 Hz, 1H), 4.21 (t, J=7.0 Hz, 1H), 4.02-3.82 (m, 2H), 3.74-3.59 (m, 2H), 0.96 (t, J=7.1 Hz, 3H); MS (ES) m/z: 626 (M+Na$^+$).

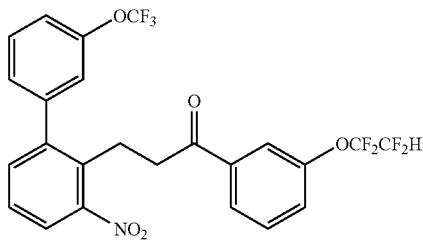

A20

3-(3-Nitro-3'-trifluoromethoxy-biphenyl-2-yl)-1-[3-(1,1,2,2-tetrafluoro-ethoxy)-phenyl]-propan-1-one To A19 (22.5 g, 37.3 mmol) was added concentrated HCl (85 mL) and HOAc (140 mL). After heating at 100° C. for 9 h, TLC (20% EtOAc/hexane) showed that the reaction was complete. After cooling down to room temperature, HOAc was evaporated through rotary evaporator. The residue was diluted with water (200 mL) and cooled in an ice-bath. To the mixture was added 6 N NaOH (~80 mL) until judged basic by pH paper. The aqueous solution was extracted with EtOAc (×3), and the combined organic extractions were dried (Na$_2$SO$_4$), concentrated and purified by column chromatography to give 18.4 g (93%) of the product as a yellow oil: $^1$H NMR (400 MHz, CDCl$_3$) δ 7.91-7.84 (dd, J=5.5, 4.0 Hz, 1H), 7.69 (m, 1H), 7.64 (s, 1H), 7.49-7.39 (m, 5H), 7.27-7.22 (m, 2H), 7.17 (s, 1H), 5.91 (tt, J=53.0, 2.7 Hz, 1H), 3.21-3.08 (m, 4H); MS (ES) m/z: 554 (M+Na$^+$).

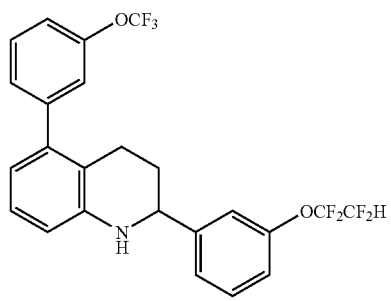

A12

2-[3-(1,1,2,2-Tetrafluoro-ethoxy)-phenyl]-5-(3-trifluoromethoxy-phenyl)-1,2,3,4-tetrahydro-quinoline A mixture of A20 (5.7 g, 10.7 mmol) and 10% Pd/C (615 mg) in EtOAc (~100 mL) was shaken in Parr-shaker under 50 psi H$_2$ for 19 h. The reaction mixture was filtered through Celite and the solid was washed with EtOAc. The filtrate was concentrated and dried under vacuum to give 5.2 g (100%) of A12.

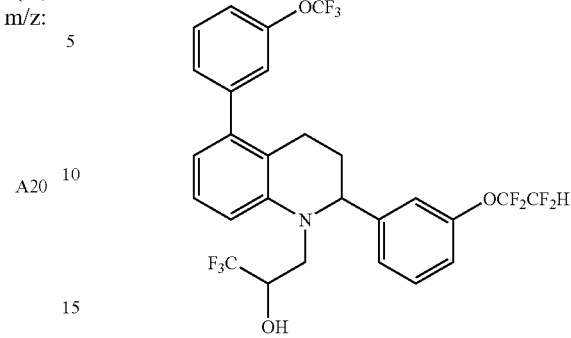

Cmpd 1

Higher Rf compound
1,1,1-Trifluoro-3-[2-[3-(1,1,2,2-tetrafluoro-ethoxy)-phenyl]-5-(3-trifluoromethoxy-phenyl)-3,4-dihydro-2H-quinolin-1-yl]-propan-2-ol To a solution of A12 (33 mg, 0.068 mmol) and 1,1,1-trifluoro-2,3-epoxy-propane (38 mg, 0.34 mmol) in DCE (0.45 mL) under a N$_2$ atmosphere was added Yb(OTf)$_3$ (10.5 mg, 0.0169 mmol). The reaction mixture was heated at 50° C. for 48 h and then cooled to ambient temperature. EtOAc was added and the solution was washed with saturated NaHCO$_3$, H$_2$O and brine, dried (MgSO$_4$), concentrated and purified by column chromatography to get 12 mg (29%) of compound 1 as an oil: $^1$H NMR (400 MHz, CDCl$_3$) δ 7.40-7.20 (m, 2H), 7.28-7.10 (m, 6 H), 7.04 (s, 1H), 6.73 (d, J=8.3 Hz, 1H), 6.67 (d, J=7.4 Hz, 1H), 5.89 (tt, J=53.1, 2.8 Hz, 1H), 4.89 (t, J=4.4 Hz, 1H), 4.42 (m, 1H), 3.91 (d, J=15.5 Hz, 1H), 3.30 (dd, J=15.6, 9.7 Hz, 1H), 2.48 (dt, J=16.3, 4.4 Hz, 1 H), 2.42-2.31 (m, 2H), 2.19-2.09 (m, 1H), 2.00-1.92 (m, 1H); MS (ES) m/z: 598 (M+H$^+$).

Example 2

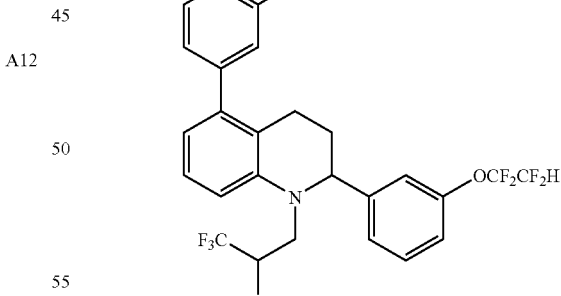

Cmpd 2

Lower Rf compound
1,1,1-Trifluoro-3-[2-[3-(1,1,2,2-tetrafluoro-ethoxy)-phenyl]-5-(3-trifluoromethoxy-phenyl)-3,4-dihydro-2H-quinolin-1-yl]-propan-2-ol Compound 2 was isolated as the other diasteriomer (Lower Rf; 27%) in the synthesis of compound 1. $^1$H NMR (400 MHz, CDCl$_3$) δ 7.40-7.32 (m, 2H), 7.28-7.09 (m, 6H), 7.02 (s, 1H), 6.89 (d, J=8.3 Hz, 1H), 6.68 (d, J=7.4 Hz, 1H), 5.89 (tt, J=53.1, 2.8 Hz, 1H), 4.61 (t, J=4.3 Hz, 1H), 4.34 (m, 1H), 3.80 (dd, J=15.7, 6.5 Hz, 1H), 3.51 (dd, J=15.7, 5.4 Hz, 1 H), 2.48-2.33 (m, 2H), 2.24 (d, J=5.0 Hz, 1H), 2.17-2.08 (m, 1H), 1.99-1.91 (m, 1H); MS (ES) m/z: 598 (M+H$^+$).

Example 3

Cmpd 3

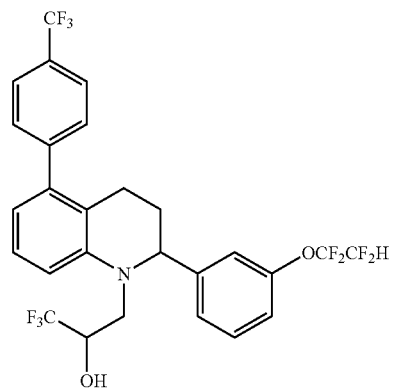

(Higher Rf compound)
1,1,1-Trifluoro-3-[2-[3-(1,1,2,2-tetrafluoro-ethoxy)-phenyl]-5-(4-trifluoromethyl-phenyl)-3,4-dihydro-2H-quinolin-1-yl]-propan-2-ol Scheme B

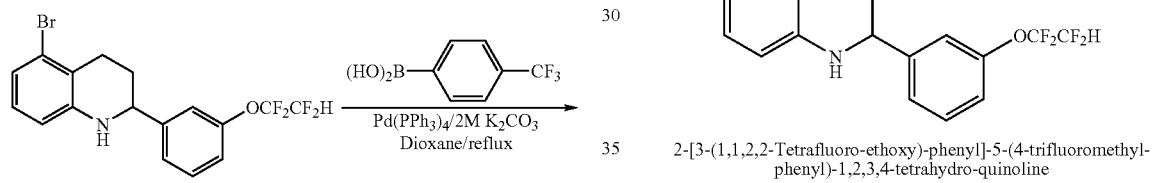

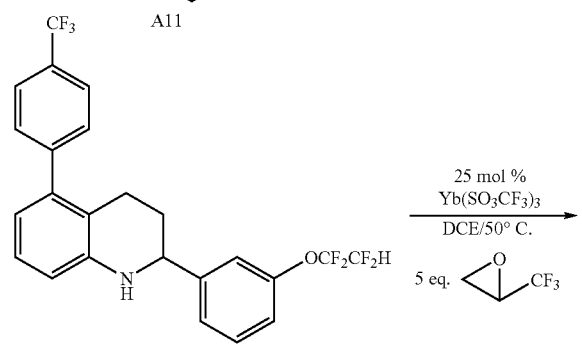

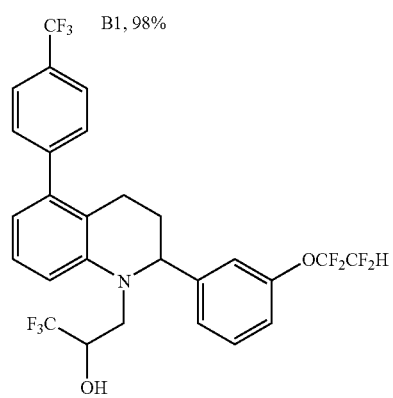

Cmpd 3, 32%
Higher Rf compound

+

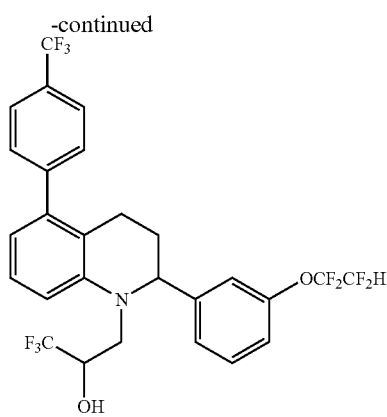

Cmpd 4, 34%
Lower Rf compound

B1

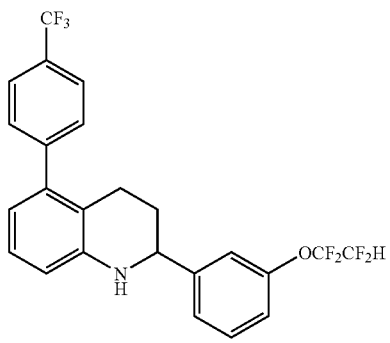

2-[3-(1,1,2,2-Tetrafluoro-ethoxy)-phenyl]-5-(4-trifluoromethyl-phenyl)-1,2,3,4-tetrahydro-quinoline Replacing 3-trifluoromethoxy-phenyl-boronic acid with 4-trifluoromethyl-phenyl-boronic acid and following the same procedure as in the preparation of A12 gave B1: $^1$H NMR (400 MHz, CDCl$_3$) δ 7.64 (d, J=8.1 Hz, 2H), 7.44 (d, J=8.1 Hz, 2H), 7.37 (t, J=7.8 Hz, 1H), 7.30 (d, J=7.8 Hz, 1H), 7.25 (s, 1H), 7.19-7.09 (m, 2H), 6.64-6.59 (m, 2H), 5.90 (tt, J=53.1, 2.8 Hz, 1H), 4.51 (dd, J=8.8, 3.4 Hz, 1H), 4.22 (brs, 1H), 2.80-2.70 (m, 1H), 2.52 (dt, J=16.6, 5.0 Hz, 1H), 2.10-2.02 (m, 1H), 1.92-1.82 (m, 1H); MS (ES) m/z: 470 (M+H$^+$).

Cmpd 3

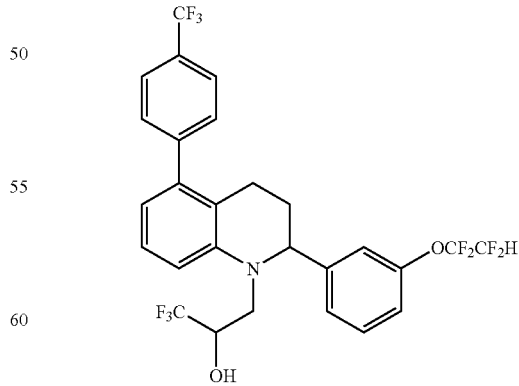

Higher Rf compound
1,1,1-Trifluoro-3-[2-[3-(1,1,2,2-tetrafluoro-ethoxy)-phenyl]-5-(4-trifluoromethyl-phenyl)-3,4-dihydro-2H-quinolin-1-yl]-propan-2-ol Replacing A12 with B1 and following the same procedure as in the preparation of compounds 1 and 2 gave compounds 3 and 4. $^1$H NMR (400 MHz, CDCl$_3$) δ 7.61 (d, J=8.1 Hz, 2H), 7.39-7.31 (m, 3H), 7.23 (t, J=8.1 Hz, 1H), 7.18 (m, 2H), 7.03 (s, 1H), 6.74 (d, J=8.2 Hz, 1H), 6.66 (d, J=7.5 Hz, 1H), 5.89 (tt, J=53.1, 2.8 Hz, 1H), 4.90 (t, J=4.5 Hz, 1H), 4.42 (m, 1H), 3.92 (d, J=15.5 Hz, 1H), 3.31 (dd, J=15.6, 9.7 Hz, 1H), 2.49-2.31 (m, 3H), 2.19-2.09 (m, 1H), 2.00-1.91 (m, 1H); MS (ES) m/z: 582 (M+H$^+$).

Example 4

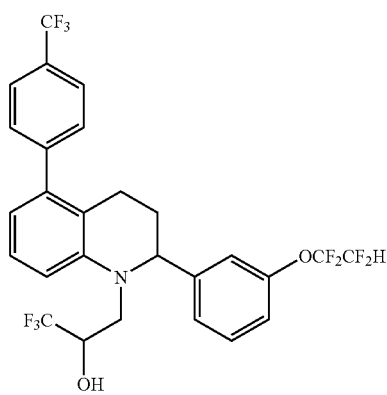

Lower Rf compound
1,1,1-Trifluoro-3-[2-[3-(1,1,2,2-tetrafluoro-ethoxy)-phenyl]-5-(4-trifluoromethyl-phenyl)-3,4-dihydro-2H-quinolin-1-yl]-propan-2-ol $^1$H NMR (400 MHz, CDCl$_3$) δ 7.61 (d, J=8.0 Hz, 2H), 7.41-7.32 (m, 3H), 7.29-7.25 (m, 1H), 7.18-7.09 (m, 2H), 7.02 (s, 1H), 6.91 (d, J=8.3 Hz, 1H), 6.68 (d, J=7.5 Hz, 1H), 5.89 (tt, J=53.1, 2.8 Hz, 1H), 4.62 (t, J=4.2 Hz, 1H), 4.34 (m, 1H), 3.81 (dd, J=15.6, 6.5 Hz, 1H), 3.52 (dd, J=15.7, 5.4 Hz, 1H), 2.41-2.36 (m, 2H), 2.26 (d, J=5.0 Hz, 1H), 2.15-2.05 (m, 1H), 2.00-1.90 (m, 1H); MS (ES) m/z: 582 (M+H$^+$).

Example 5

Cmpd 5

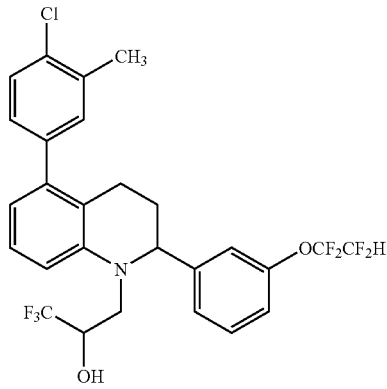

(Higher Rf compound)
3-{5-(4-Chloro-3-methyl-phenyl)-2-[3-(1,1,2,2-tetrafluoro-ethoxy)-phenyl]-3,4-dihydro-2H-quinolin-1-yl}-1,1,1-trifluoro-propan-2-ol Scheme C

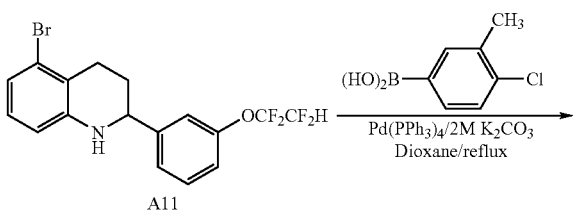

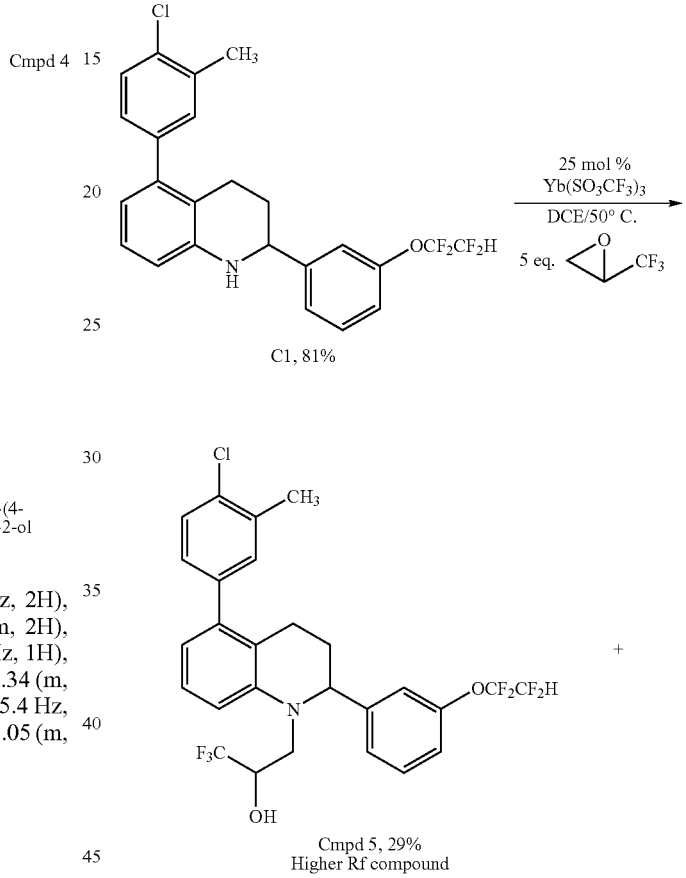

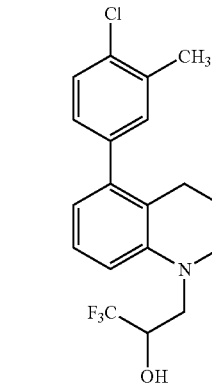

Cmpd 6, 42%
Lower Rf compound

J=16.2, 4.6 Hz, 1H), 2.42-2.31 (m, 5H), 2.18-2.09 (m, 1H), 1.99-1.91 (m, 1H); MS (ES) m/z: 562 (M+H⁺).

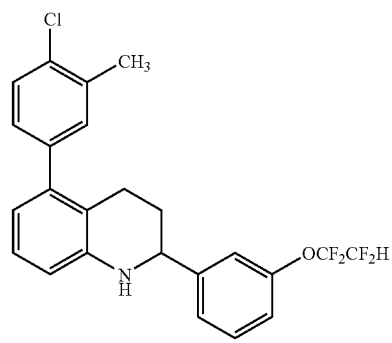

5-(4-Chloro-3-methyl-phenyl)-2-[3-(1,1,2,2-tetrafluoro-ethoxy)-phenyl]-1,2,3,4-tetrahydro-quinoline Replacing 3-trifluoromethoxy-phenyl-boronic acid with 4-chloro-3-methyl-phenyl-boronic acid and following the same procedure as in the preparation of A12 gave C1: ¹H NMR (400 MHz, CDCl₃) δ 7.38-7.29 (m, 4 H), 7.20-7.12 (m, 2H), 7.09-7.05 (m, 2H), 6.59 (m, 2H), 5.90 (tt, J=53.1, 2.8 Hz, 1H), 4.49 (dd, J=8.9, 3.4 Hz, 1H), 4.17 (brs, 1H), 2.79-2.70 (m, 1H), 2.53 (dt, J=15.6, 5.0 Hz, 1H), 2.39 (s, 3H), 2.09-2.01 (m, 1H), 1.91-1.81 (m, 1H); MS (ES) m/z: 450 (M+H⁺).

Example 6

Cmpd 6

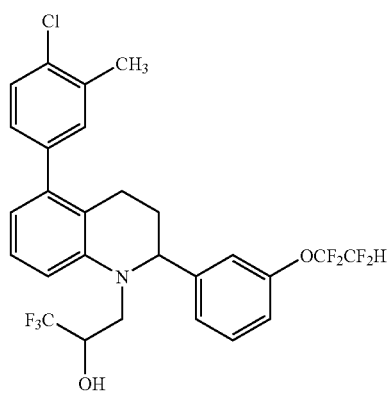

Lower Rf compound
3-{5-(4-Chloro-3-methyl-phenyl)-2-[3-(1,1,2,2-tetrafluoro-ethoxy)-phenyl]-3,4-dihydro-2H-quinolin-1-yl}-1,1,1-trifluoro-propan-2-ol ¹H NMR (400 MHz, CDCl₃) δ 7.38-7.30 (m, 2H), 7.21 (t, J=7.9 Hz, 1H), 7.15-7.09 (m, 3H), 7.05-6.99 (m, 2H), 6.86 (d, J=8.3 Hz, 1 H), 6.66 (d, J=7.0 Hz, 1H), 5.89 (tt, J=53.1, 2.8 Hz, 1H), 4.60 (t, J=4.3 Hz, 1H), 4.32 (m, 1H), 3.79 (dd, J=15.6, 6.6 Hz, 1H), 3.51 (dd, J=15.7, 5.4 Hz, 1H), 2.48-2.32 (m, 5H), 2.24 (d, J=5.0 Hz, 1H), 2.15-2.04 (m, 1H), 1.99-1.90 (m, 1H); MS (ES) m/z: 562 (M+H⁺).

Example 7

Cmpd 5

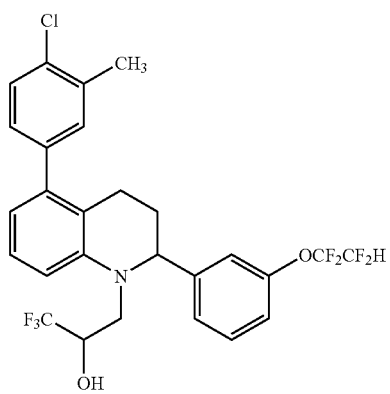

Higher Rf compound
3-{5-(4-Chloro-3-methyl-phenyl)-2-[3-(1,1,2,2-tetrafluoro-ethoxy)-phenyl]-3,4-dihydro-2H-quinolin-1-yl}-1,1,1-trifluoro-propan-2-ol Replacing A12 with C1 and following the same procedure as in the preparation of compounds 1 and 2 gave compounds 5 and 6. ¹H NMR (400 MHz, CDCl₃) δ 7.38-7.30 (m, 2H), 7.20 (t, J=7.9 Hz, 1H), 7.15-7.10 (m, 3H), 7.06-7.00 (m, 2H), 6.70 (d, J=8.3 Hz, 1H), 6.64 (d, J=7.5 Hz, 1H), 5.89 (tt, J=53.1, 2.6 Hz, 1H), 4.88 (t, J=4.5 Hz, 1H), 4.43 (m, 1H), 3.91 (d, J=15.5 Hz, 1H), 3.29 (dd, J=15.6, 9.7 Hz, 1H), 2.48 (dt, Cmpd 7

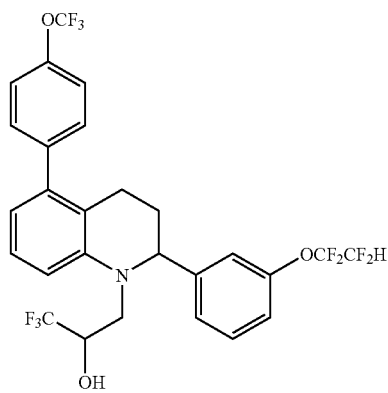

(Higher Rf compound)
1,1,1-Trifluoro-3-[2-[3-(1,1,2,2-tetrafluoro-ethoxy)-phenyl]-5-(4-trifluoromethoxy-phenyl)-3,4-dihydro-2H-quinolin-1-yl]-propan-2-ol

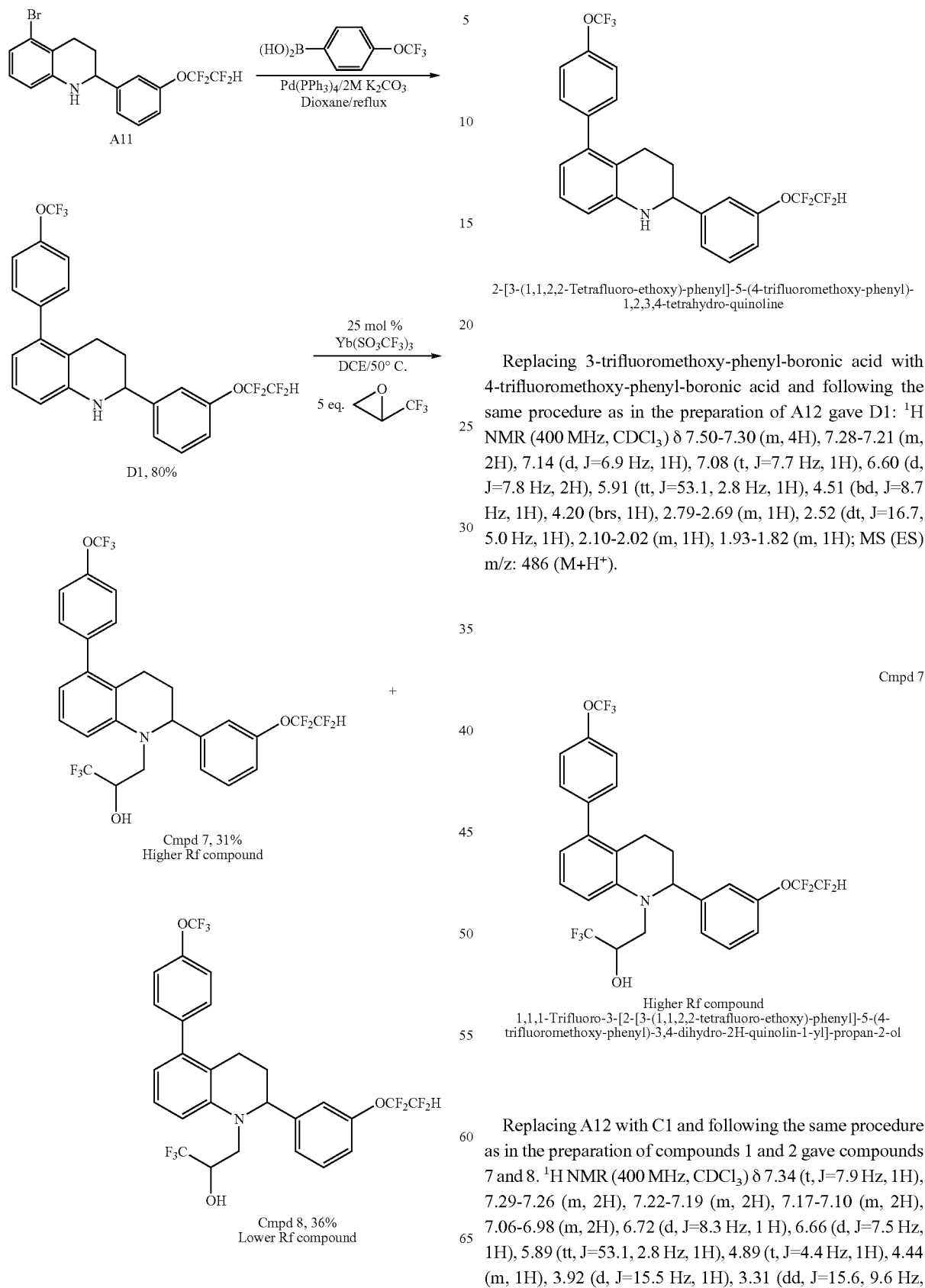

2-[3-(1,1,2,2-Tetrafluoro-ethoxy)-phenyl]-5-(4-trifluoromethoxy-phenyl)-1,2,3,4-tetrahydro-quinoline Replacing 3-trifluoromethoxy-phenyl-boronic acid with 4-trifluoromethoxy-phenyl-boronic acid and following the same procedure as in the preparation of A12 gave D1: $^1$H NMR (400 MHz, CDCl$_3$) δ 7.50-7.30 (m, 4H), 7.28-7.21 (m, 2H), 7.14 (d, J=6.9 Hz, 1H), 7.08 (t, J=7.7 Hz, 1H), 6.60 (d, J=7.8 Hz, 2H), 5.91 (tt, J=53.1, 2.8 Hz, 1H), 4.51 (bd, J=8.7 Hz, 1H), 4.20 (brs, 1H), 2.79-2.69 (m, 1H), 2.52 (dt, J=16.7, 5.0 Hz, 1H), 2.10-2.02 (m, 1H), 1.93-1.82 (m, 1H); MS (ES) m/z: 486 (M+H$^+$).

Higher Rf compound
1,1,1-Trifluoro-3-[2-[3-(1,1,2,2-tetrafluoro-ethoxy)-phenyl]-5-(4-trifluoromethoxy-phenyl)-3,4-dihydro-2H-quinolin-1-yl]-propan-2-ol Replacing A12 with C1 and following the same procedure as in the preparation of compounds 1 and 2 gave compounds 7 and 8. $^1$H NMR (400 MHz, CDCl$_3$) δ 7.34 (t, J=7.9 Hz, 1H), 7.29-7.26 (m, 2H), 7.22-7.19 (m, 2H), 7.17-7.10 (m, 2H), 7.06-6.98 (m, 2H), 6.72 (d, J=8.3 Hz, 1H), 6.66 (d, J=7.5 Hz, 1H), 5.89 (tt, J=53.1, 2.8 Hz, 1H), 4.89 (t, J=4.4 Hz, 1H), 4.44 (m, 1H), 3.92 (d, J=15.5 Hz, 1H), 3.31 (dd, J=15.6, 9.6 Hz, 1H), 2.46 (dt, J=16.2 Hz, 1H), 2.41-2.31 (m, 2H), 2.18-2.09 (m, 1 H), 2.00-1.92 (m, 1H); MS (ES) m/z: 598 (M+H⁺).

Example 8

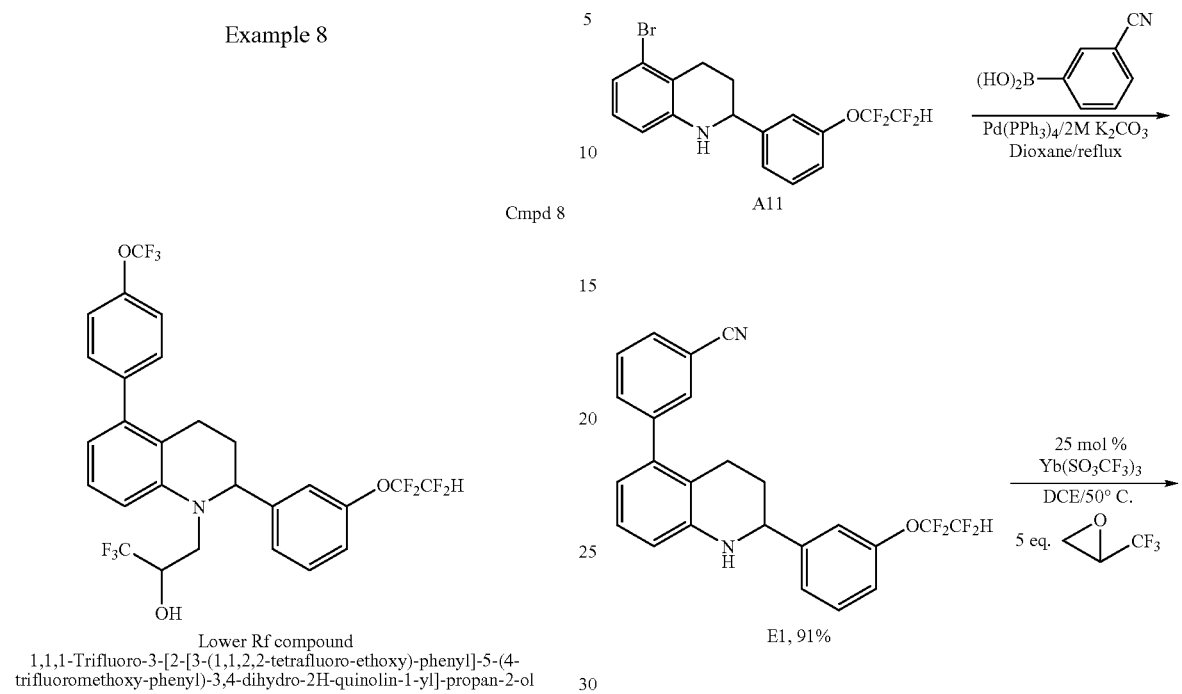

Cmpd 8

Lower Rf compound
1,1,1-Trifluoro-3-[2-[3-(1,1,2,2-tetrafluoro-ethoxy)-phenyl]-5-(4-trifluoromethoxy-phenyl)-3,4-dihydro-2H-quinolin-1-yl]-propan-2-ol ¹H NMR (400 MHz, CDCl₃) δ 7.35 (t, J=7.9 Hz, 1H), 7.29-7.26 (m, 2H), 7.22-7.19 (m, 2H), 7.17-7.10 (m, 2H), 7.06-6.98 (m, 2H), 6.72 (d, J=8.3 Hz, 1H), 6.66 (d, J=7.5 Hz, 1H), 5.89 (tt, J=53.1, 2.8 Hz, 1H), 4.89 (t, J=4.4 Hz, 1H), 4.44 (m, 1H), 3.92 (d, J=15.5 Hz, 1H), 3.31 (dd, J=15.6, 9.6 Hz, 1H), 2.46 (dt, J=16.2 Hz, 1H), 2.41-2.31 (m, 2H), 2.18-2.09 (m, 1H), 2.00-1.92 (m, 1H); MS (ES) m/z: 598 (M+H⁺).

Example 9

Cmpd 9

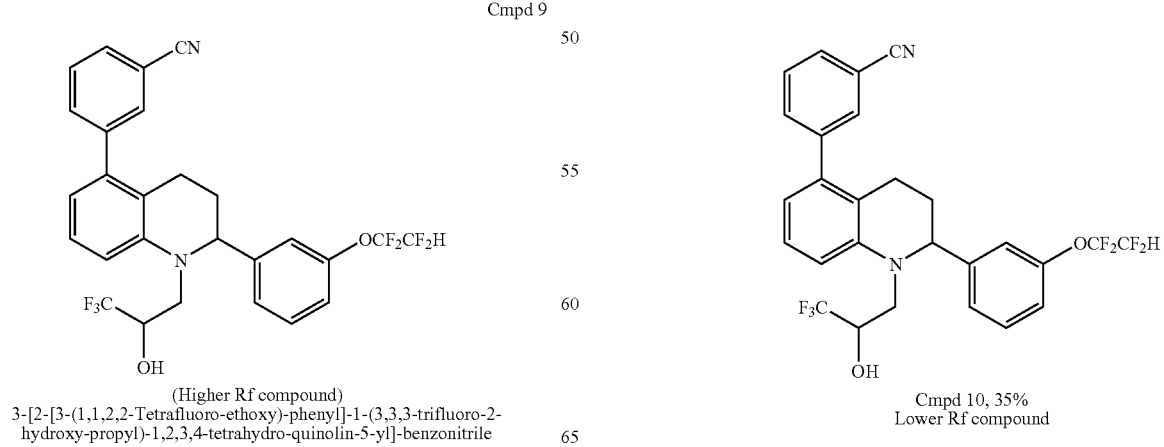

(Higher Rf compound)
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzonitrile 1H), 3.31 (dd, J=15.6, 9.7 Hz, 1H), 2.41-2.31 (m, 3H), 2.19-2.08 (m, 1H), 2.00-1.93 (m, 1H); MS (ES) m/z: 539 (M+H⁺).

Example 10

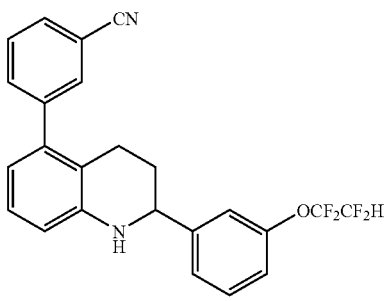

E1

3-{2-[3-(1,1,2,2-Tetrafluoro-ethoxy)-phenyl]-1,2,3,4-tetrahydro-quinolin-5-yl}-benzonitrile

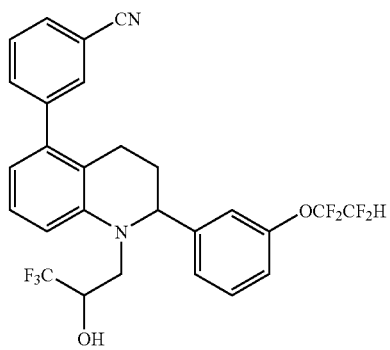

Cmpd 10

Lower Rf compound
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzonitrile Replacing 3-trifluoromethoxy-phenyl-boronic acid with 3-cyano-phenyl-boronic acid and following the same procedure as in the preparation of A12 gave E1: ¹H NMR (400 MHz, CDCl₃) δ 7.64-7.53 (m, 2H), 7.52-7.47 (m, 1H), 7.51 (m, 1H), 7.37 (t, J=7.9 Hz, 1H), 7.33 (d, J=15.6 Hz, 1 H), 7.25 (s, 1H), 7.18-7.08 (m, 2H), 6.63 (d, J=8.1 Hz, 1H), 6.57 (d, J=7.5 Hz, 1H), 5.91 (tt, J=53.1, 2.8 Hz, 1H), 4.50 (dd, J=8.8, 3.4 Hz, 1H), 4.19 (brs, 1H), 2.81-2.69 (m, 1H), 2.54 (dt, J=16.7, 5.0 Hz, 1H), 2.11-2.01 (m, 1H), 1.95-1.81 (m, 1H); MS (ES) m/z: 420 (M+H⁺).

¹H NMR (400 MHz, CDCl₃) δ 7.61-7.58 (m, 1H), 7.55 (s, 1H), 7.50-7.47 (m, 2H), 7.36 (t, J=7.9 Hz, 1H), 7.26-7.22 (m, 1H), 7.15 (d, J=6.8 Hz, 1H), 7.08 (d, J=7.6 Hz, 1H), 7.01 (s, 1H), 6.92 (d, J=8.2 Hz, 1 H), 6.64 (d, J=7.5 Hz, 1H), 5.90 (tt, J=53.1, 2.8 Hz, 1H), 4.62 (t, J=4.3 Hz, 1H), 4.33 (m, 1H), 3.81 (dd, J=15.8 Hz, 1H), 3.52 (dd, J=15.7, 5.4 Hz, 1H), 2.39-2.37 (m, 2H), 2.25 (brs, 1H), 2.16-2.05 (m, 1H), 2.00-1.93 (m, 1H); MS (ES) m/z: 539 (M+H⁺).

Example 11

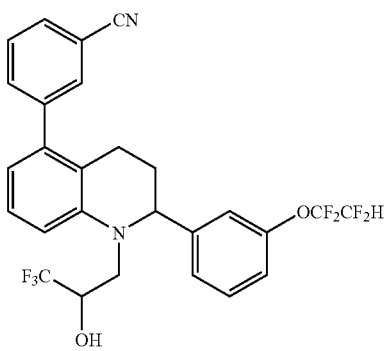

Cmpd 9

Higher Rf compound
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzonitrile

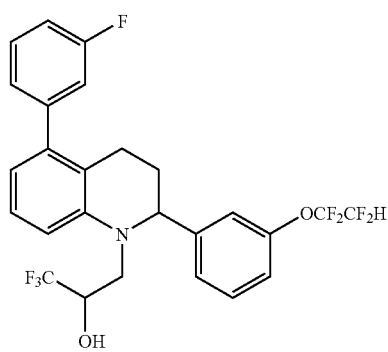

Cmpd 11

(Higher Rf compound)
1,1,1-Trifluoro-3-{5-(3-fluoro-phenyl)-2-[3-(1,1,2,2-tetrafluoro-ethoxy)-phenyl]-3,4-dihydro-2H-quinolin-1-yl}-propan-2-ol Replacing A12 with E1 and following the same procedure as in the preparation of compound 1 and 2 gave compound 9 and 10. ¹H NMR (400 MHz, CDCl₃) δ 7.61-7.58 (m, 1H), 7.55 (s, 1H), 7.51-7.48 (m, 2H), 7.49-7.33 (m, 1H), 7.23 (t, J=8.0 Hz, 1H), 7.18-7.09 (m, 2H), 7.02 (s, 1H), 6.75 (d, J=8.2 Hz, 1H), 6.62 (d, J=7.5 Hz, 1H), 5.89 (tt, J=53.1, 2.8 Hz, 1H), 4.91 (t, J=4.5 Hz, 1H), 4.43 (m, 1H), 3.92 (bd, J=15.6 Hz, Scheme E

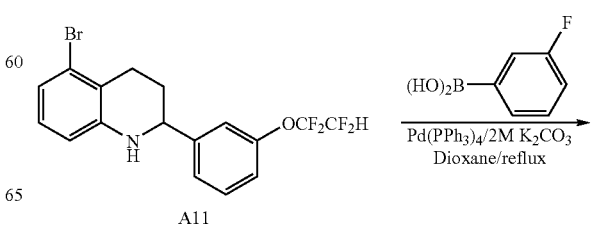

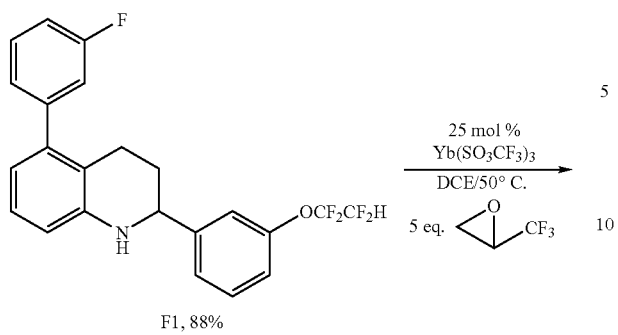

F1, 88%

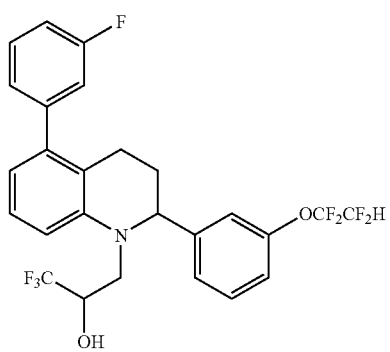

Cmpd 11, 22%
Higher Rf compound

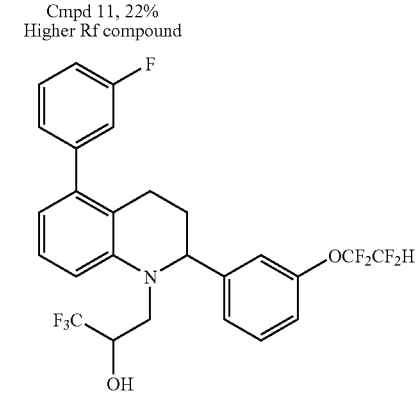

Cmpd 12, 26%
Lower Rf compound

F1

5-(3-Fluoro-phenyl)-2-[3-(1,1,2,2-tetrafluoro-ethoxy)-phenyl]-1,2,3,4-tetrahydro-quinoline Replacing 3-trifluoromethoxy-phenyl-boronic acid with 3-fluoro-phenyl-boronic acid and following the same procedure as in the preparation of A12 gave F1: $^1$H NMR (300 MHz, CDCl$_3$) δ 7.39-7.29 (m, 4H), 7.15-6.98 (m, 5H), 6.60 (dd, J=7.5, 1.6 Hz, 2H), 5.90 (tt, J=53.1, 2.8 Hz, 1H), 4.50 (dd, J=8.8, 3.4 Hz, 1H), 4.19 (broad s, 1H), 2.80-2.70 (m, 1H), 2.54 dt, J=16.5, 4.9 Hz 1H), 2.11-2.01 (m, 1H), 1.95-1.80 (m, 1H); MS (ES) m/z: 420 (M+H$^+$).

Cmpd 11

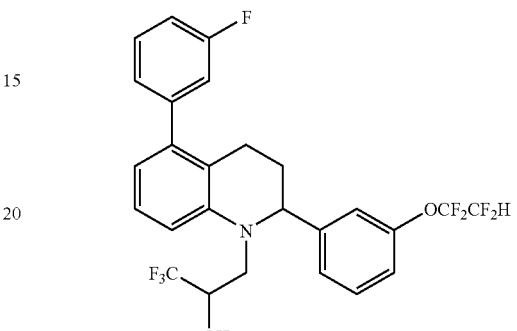

Higher Rf compound
1,1,1-Trifluoro-3-{5-(3-fluoro-phenyl)-2-[3-(1,1,2,2-tetrafluoro-ethoxy)-phenyl]-3,4-dihydro-2H-quinolin-1-yl}-propan-2-ol Replacing A12 with F1 and following the same procedure as in the preparation of compound 1 and 2 gave compound 11 and 12. $^1$H NMR (400 MHz, CDCl$_3$) δ 7.39-7.20 (m, 3H), 7.18-7.09 (m, 2H), 7.07-6.95 (m, 4H), 6.72 (d, J=8.3 Hz, 1H), 6.69 (d, J=7.5 Hz, 1H), 5.89 (tt, J=53.1, 2.8 Hz, 1H), 4.89 (t, J=4.3 Hz, 1H), 4.43 (m, 1H), 3.91 (d, J=15.4 Hz, 1H), 3.30 (dd, J=15.6, 9.7 Hz, 1H), 2.52-2.31 (m, 2H), 2.19-2.08 (m, 1H), 2.01-1.92 (m, 1H), 1.61 (brs, 1H); MS (ES) m/z: 532 (M+H$^+$).

Example 12

Cmpd 12

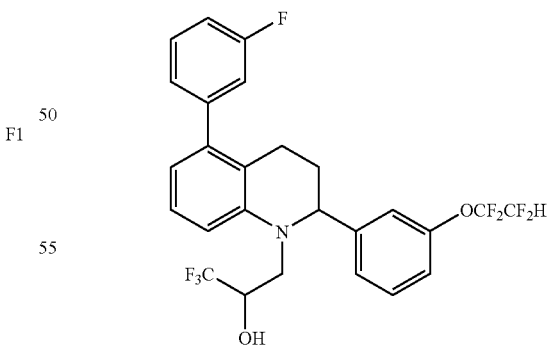

Lower Rf compound
1,1,1-Trifluoro-3-{5-(3-fluoro-phenyl)-2-[3-(1,1,2,2-tetrafluoro-ethoxy)-phenyl]-3,4-dihydro-2H-quinolin-1-yl}-propan-2-ol $^1$H NMR (400 MHz, CDCl$_3$) δ 7.39-7.20 (m, 3H), 7.18-7.08 (m, 2 H), 7.05-6.94 (m, 4H), 6.88 (d, J=7.9 Hz, 1H), 6.68 (d, J=7.5 Hz, 1H), 5.89 (tt, J=53.1, 2.8 Hz, 1H), 4.61 (t, J=4.3 Hz, 1H), 3.34 (m, 1H), 3.80 (dd, J=15.4 Hz, 1H), 3.30 (dd, J=15.6, 6.5 Hz, 1H), 2.49-2.32 (m, 2H), 2.15-2.04 (m, 1H), 2.00-1.92 (m, 1H), 1.70 (brs, 1H); MS (ES) m/z: 532 (M+H⁺).

Example 13

Cmpd 13

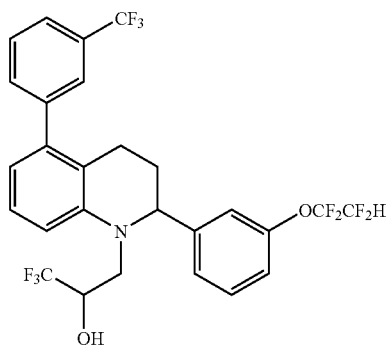

(Higher Rf compound)
1,1,1-Trifluoro-3-[2-[3-(1,1,2,2-tetrafluoro-ethoxy)-phenyl]-5-(3-trifluoromethyl-phenyl)-]3,4-dihydro-2H-quinolin-1-yl]-propan-2-ol Scheme G

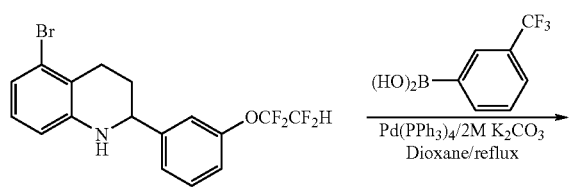

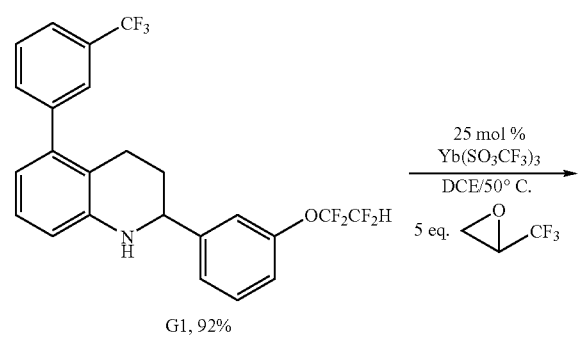

G1, 92%

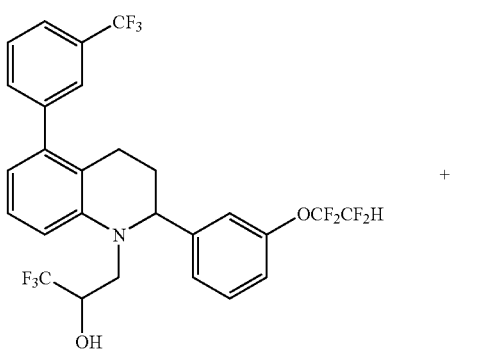

Cmpd 13, 28%
Higher Rf compound

+

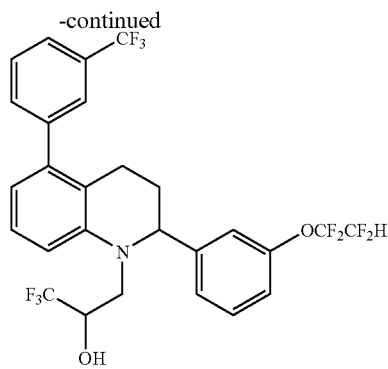

Cmpd 14, 30%
Lower Rf compound

G1

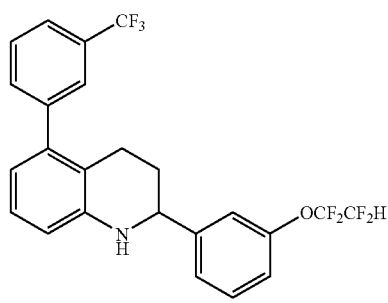

2-[3-(1,1,2,2-Tetrafluoro-ethoxy)-phenyl]-5-(3-trifluoromethyl-phenyl)-1,2,3,4-tetrahydro-quinoline Replacing 3-trifluoromethoxy-phenyl-boronic acid with 3-trifluoro-phenyl-boronic acid and following the same procedure as in the preparation of A12 gave G1: ¹H NMR (400 MHz, CDCl₃) δ 7.59 (m, 2H), 7.51 (m, 2H), 7.37 (t, J=7.6 Hz, 1H), 7.31 (d, J=6.6 Hz, 1H), 7.18-7.08 (m, 2H), 6.65-6.60 (m, 2H), 5.91 (tt, J=53.1, 2.8 Hz, 1H), 4.51 (dd, J=8.9, 3.4 Hz, 1 H), 4.22 (brs, 1H), 2.81-2.71 (m, 1H), 2.51 (dt, J=16.6, 5.0 Hz, 1H), 2.11-2.03 (m, 1H), 1.93-1.82 (m, 1H); MS (ES) m/z: 470 (M+H⁺).

Cmpd 13

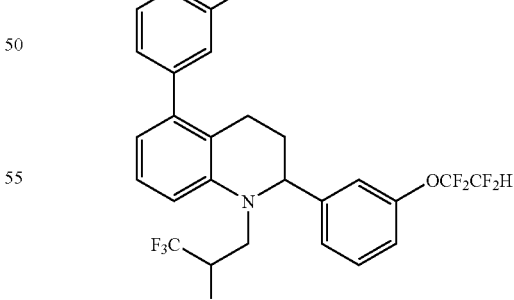

Higher Rf compound
1,1,1-Trifluoro-3-[2-[3-(1,1,2,2-tetrafluoro-ethoxy)-phenyl]-5-(3-trifluoromethyl-phenyl)-3,4-dihydro-2H-quinolin-1-yl]-propan-2-ol Replacing A12 with G1 and following the same procedure as in the preparation of compound 1 and 2 gave compound 13 and 14. ¹H NMR (400 MHz, CDCl₃) δ 7.59-7.52 (m, 2H), 7.50-7.42 (m, 2H), 7.35 (t, J=7.9 Hz, 1H), 7.23 (t, J=7.9 Hz, 1H), 7.17-7.10 (m, 2H), 7.04 (s, 1H), 6.74 (d, J=8.2 Hz, 1H), 6.67 (d, J=7.5 Hz, 1H), 5.89 (tt, J=53.1, 2.8 Hz, 1H), 4.90 (t, J=4.5 Hz, 1H), 4.43 (m, 1H), 3.91 (dd, J=15.5, 1.8 Hz, 1 H), 3.31 (dd, J=15.7, 9.7 Hz, 1H), 2.45 (dt, J=16.2, 4.6 Hz, 1H), 2.41-2.31 (m, 1H), 2.19-2.09 (m, 1H), 2.00-1.92 (m, 1H); MS (ES) m/z: 582 (M+H$^+$).

Example 14

Cmpd 14

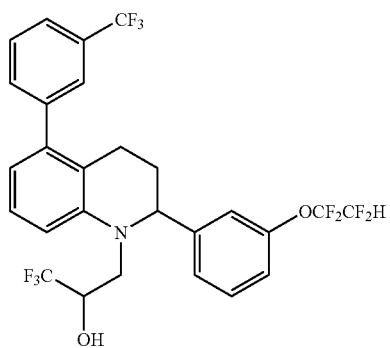

Lower Rf compound
1,1,1-Trifluoro-3-[2-[3-(1,1,2,2-tetrafluoro-ethoxy)-phenyl]-5-(3-trifluoromethyl-phenyl)-3,4-dihydro-2H-quinolin-1-yl]-propan-2-ol $^1$H NMR (400 MHz, CDCl$_3$) δ 7.59-7.52 (m, 2H), 7.50-7.41 (m, 2 H), 7.36 (t, J=7.9 Hz, 1H), 7.24 (t, J=7.9 Hz, 1H), 7.18-7.09 (m, 2H), 7.03 (s, 1H), 6.90 (d, J=8.2 Hz, 1H), 6.68 (d, J=7.5 Hz, 1H), 5.89 (tt, J=53.1, 2.8 Hz, 1H), 4.62 (t, J=4.4 Hz, 1H), 4.37-4.15 (m, 1H), 3.80 (dd, J=15.7, 6.6 Hz, 1H), 3.51 (dd, J=15.7, 5.4 Hz, 1H), 2.76 (brs, 1H), 2.42-2.37 (m, 2H), 2.17-2.08 (m, 1H), 1.99-1.91 (m, 1H); MS (ES) m/z: 582 (M+H$^+$).

Example 15

Cmpd 15

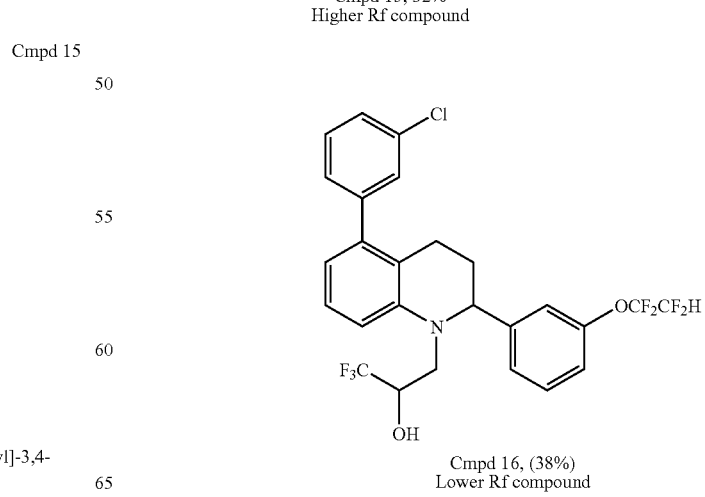

(Higher Rf compound)
3-{5-(3-Chloro-phenyl)-2-[3-(1,1,2,2-tetrafluoro-ethoxy)-phenyl]-3,4-dihydro-2H-quinolin-1-yl}-1,1,1-trifluoro-propan-2-ol Scheme H

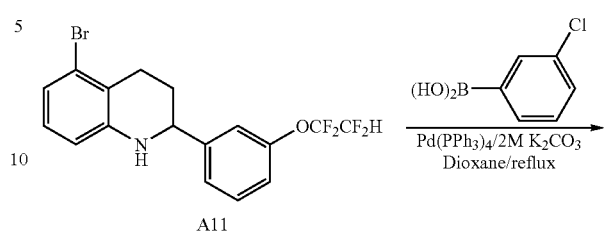

A11

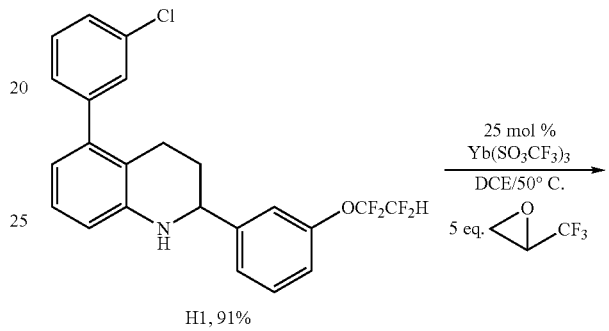

H1, 91%

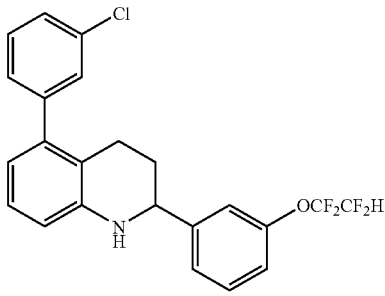

5-(3-Chloro-phenyl)-2-[3-(1,1,2,2-tetrafluoro-ethoxy)-phenyl]-1,2,3,4-tetrahydro-quinoline Replacing 3-trifluoromethoxy-phenyl-boronic acid with 3-chloro-phenyl-boronic acid and following the same procedure as in the preparation of A12 gave H1: $^1$H NMR (400 MHz, CDCl$_3$) δ 7.49-7.28 (m, 6H), 7.20 (m, 1H), 7.14 (d, J=7.8 Hz, 1H), 7.07 (t, J=7.7 Hz, 1H), 6.59 (t, J=8.4 Hz, 2 H), 5.90 (tt, J=53.3, 2.8 Hz, 1H), 4.49 (dd, J=9.0, 3.4 Hz, 1H), 4.19 (brs, 1H), 2.80-2.70 (m, 1H), 2.53 (dt, J=16.7, 4.9 Hz, 1H), 2.10-2.02 (m, 1 H), 1.92-1.82 (m, 1H); MS (ES) m/z: 436 (M+H$^+$).

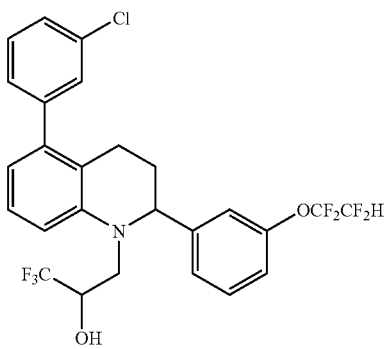

Higher Rf compound
3-{5-(3-Chloro-phenyl-2-[3-(1,1,2,2-tetrafluoro-ethoxy)-phenyl]-3,4-dihydro-2H-quinolin-1-yl}-1,1,1-trifluoro-propan-2-ol Replacing A12 with H1 and following the same procedure as in the preparation of compound 1 and 2 gave compound 15 and 16. $^1$H NMR (400 MHz, CDCl$_3$) δ 7.34 (t, J=7.9 Hz, 1H), 7.30-7.25 (m, 3H), 7.21 (t, J=7.9 Hz, 1H), 7.18-7.09 (m, 3H), 7.03 (s, 1H), 6.72 (d, J=8.3 Hz, 1H), 6.65 (d, J=7.5 Hz, 1H), 5.89 (tt, J=53.1, 2.8 Hz, 1H), 4.89 (t, J=4.5 Hz, 1H), 4.42 (m, 1H), 3.91 (d, J=15.5 Hz, 1H), 3.30 (dd, J=15.6, 9.7 Hz, 1 H), 2.48 (dt, J=16.3, 4.5 Hz, 1H), 2.42-2.31 (m, 2H), 2.18-2.08 (m, 1 H), 2.00-1.91 (m, 1H); MS (ES) m/z: 548 (M+H$^+$).

Example 16

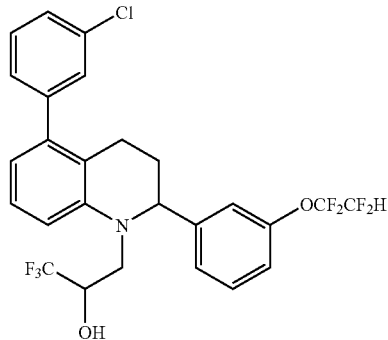

Lower Rf compound
3-{5-(3-Chloro-phenyl-2-[3-(1,1,2,2-tetrafluoro-ethoxy)-phenyl]-3,4-dihydro-2H-quinolin-1-yl}-1,1,1-trifluoro-propan-2-ol $^1$H NMR (400 MHz, CDCl$_3$) δ 7.35 (t, J=7.9 Hz, 1H), 7.30-7.19 (m, 4H), 7.17-7.09 (m, 3H), 7.02 (s, 1H), 6.88 (d, J=8.3 Hz, 1H), 6.67 (d, J=7.5 Hz, 1H), 5.89 (tt, J=53.1, 2.8 Hz, 1H), 4.61 (t, J=4.3 Hz, 1H), 4.33 (m, 1H), 3.79 (dd, J=15.7, 6.6 Hz, 1H), 3.51 (dd, J=15.7, 5.4 Hz, 1 H), 2.49-2.21 (m, 2H), 2.25 (d, J=5.0 Hz, 1H), 2.13-2.05 (m, 1H), 2.00-1.90 (m, 1H); MS (ES) m/z: 548 (M+H$^+$).

Example 17

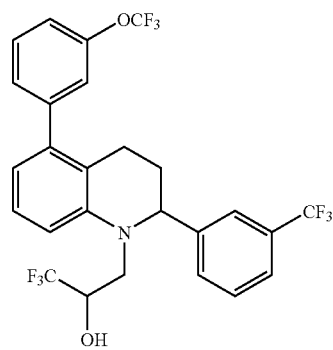

(Higher Rf Compound)
1,1,1-Trifluoro-3-[5-(3-trifluoromethoxy-phenyl)-2-(3-trifluoromethyl-phenyl)-3,4-dihydro-2H-quinolin-1-yl]-propan-2-ol Scheme I

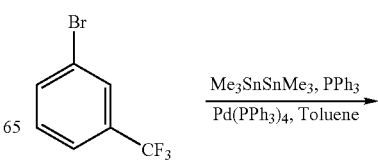

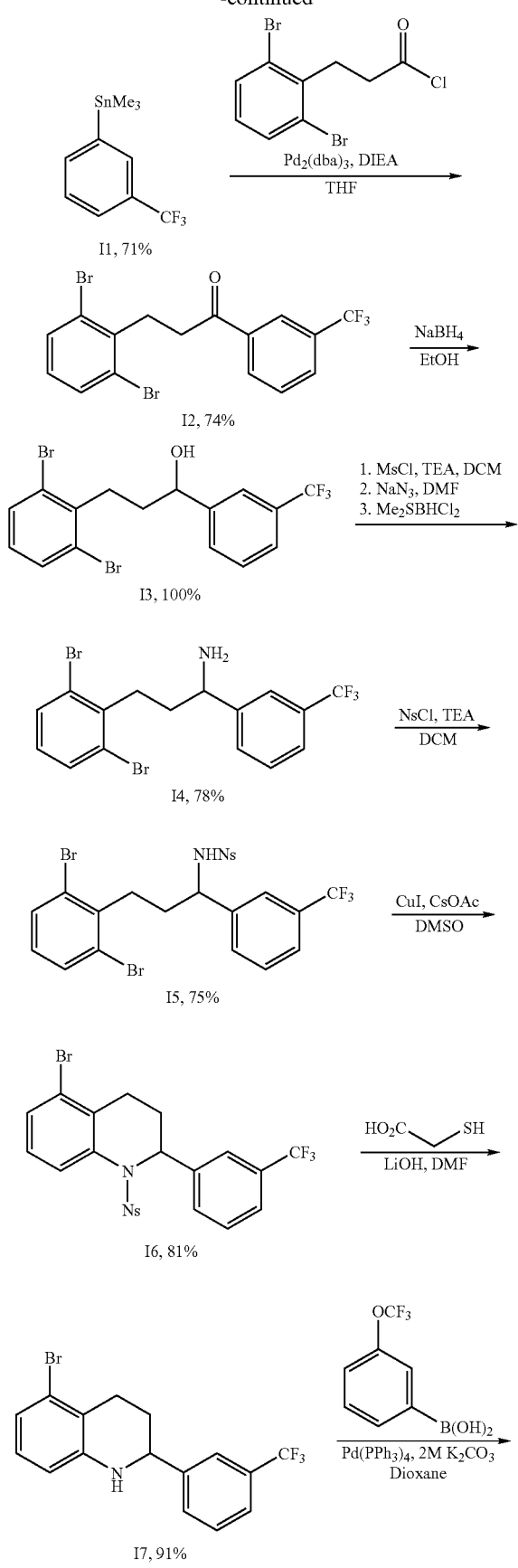
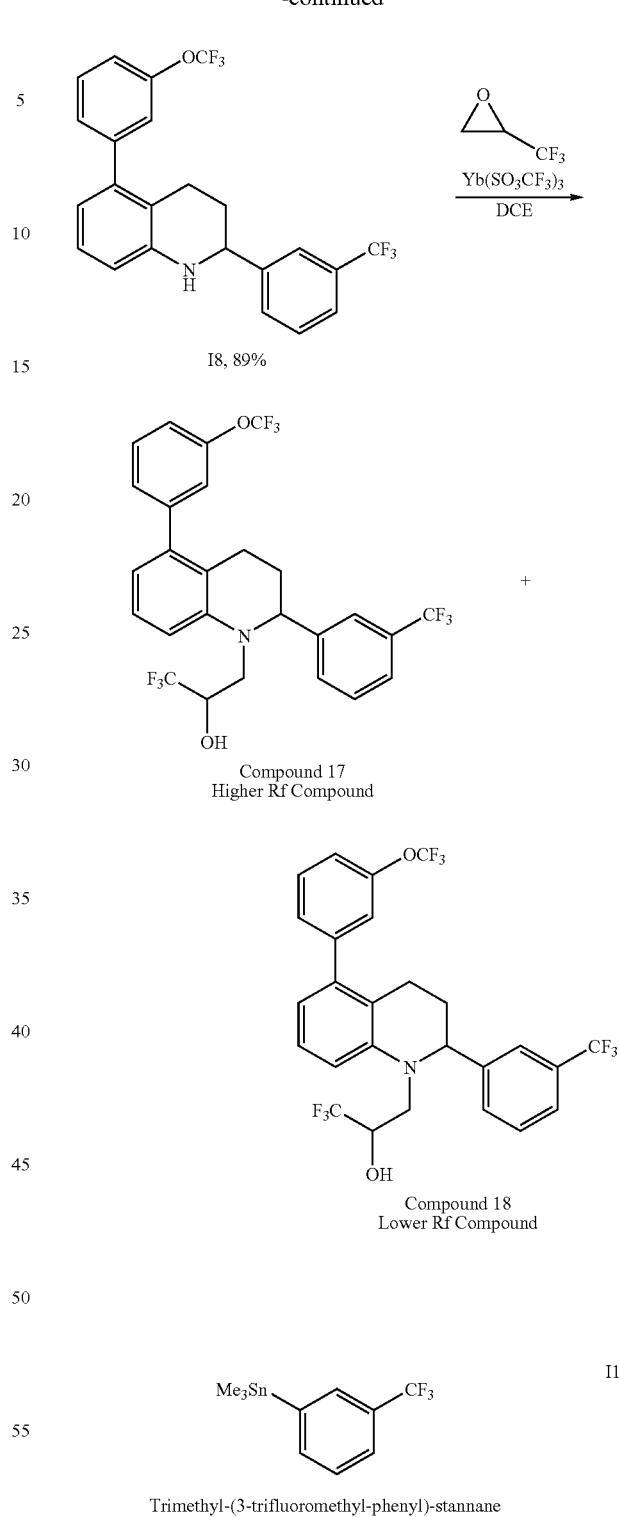
Replacing 1-bromo-3-(1,1,2,2-tetrafluoro-ethoxy)-benzene with 1-bromo-3-trifluoromethylbenzene and following the same procedure as in the preparation of A4 gave I1 (71%): $^1$H NMR (300 MHz, CDCl$_3$) δ 7.71 (s, 1H), 7.66 (d, J=7.2 Hz, 1H), 7.59-7.53 (m, 1H), 7.48-7.40 (m, 1H), 0.33 (s, 9H).

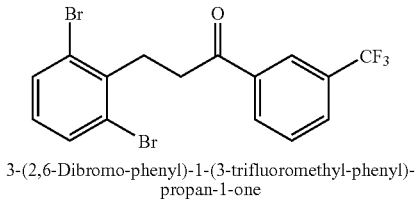

3-(2,6-Dibromo-phenyl)-1-(3-trifluoromethyl-phenyl)-propan-1-one

Replacing A4 with I1 and following the same procedure as in the preparation of A5 gave I2 (74%): $^1$H NMR (300 MHz, CDCl$_3$) δ 8.25 (s, 1H), 8.18 (d, J=7.8 Hz, 1H), 7.83 (d, J=7.7 Hz, 1H), 7.61 (t, J=7.8 Hz, 1H), 7.54 (d, J=8.0 Hz, 2H), 6.94 (t, J=7.9 Hz, 1H), 3.49-3.41 (m, 2H), 3.31-3.22 (m, 2H); MS (ES) m/z: 459 (M+Na$^+$).

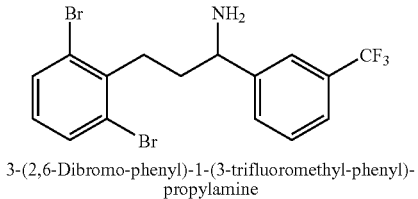

3-(2,6-Dibromo-phenyl)-1-(3-trifluoromethyl-phenyl)-propan-1-ol

Replacing A5 with I2 and following the same procedure as in the preparation of A6 gave I3 (100%): $^1$H NMR (300 MHz, CDCl$_3$) δ 7.70 (s, 1 H), 7.62-7.44 (m, 5H), 6.90 (t, J=8.0 Hz, 1H), 4.91 (t, J=6.3 Hz, 1H), 3.19-3.09 (m, 1H), 3.03-2.91 (m, 1H), 2.09-1.99 (m, 3H); MS (ES) m/z: 461.0 (M+Na$^+$).

I4

3-(2,6-Dibromo-phenyl)-1-(3-trifluoromethyl-phenyl)-propylamine

Replacing A6 with I3 and following the same procedure as in the preparation of A7 gave the crude azide intermediate.

Replacing A7 with the above azide intermediate and following the same procedure as in the preparation of A8 gave I4 (78% for 3 steps): $^1$H NMR (300 MHz, CDCl$_3$) δ 7.69 (s, 1H), 7.61 (d, J=7.4 Hz, 1H), 7.55-7.41 (m, 4H), 6.88 (t, J=8.0 Hz, 1H), 4.16 (t, J=6.8 Hz, 1H), 3.09-2.96 (m, 1H), 2.88-2.75 (m, 1H), 2.03-1.92 (m, 2H); MS (ES) m/z: 438 (M+H$^+$).

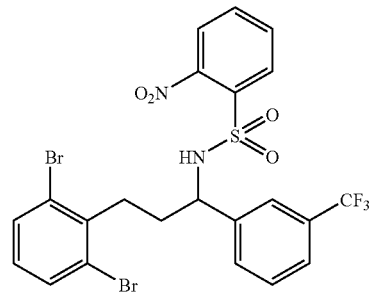

N-[3-(2,6-Dibromo-phenyl)-1-(3-trifluoromethyl-phenyl)-propyl]-2-nitro-benzenesulfonamide Replacing A8 with I4 and following the same procedure as in the preparation of A9 gave I5 (75%): $^1$H NMR (400 MHz, CDCl$_3$) δ 7.71 (d, J=8.0 Hz, 1H), 7.61 (d, J=7.8 Hz, 1H), 7.59-7.29 (m, 8H), 6.90 (t, J=8.0 Hz, 1H), 5.97 (d, J=8.9 Hz, 1H), 4.74 (dd, J=15.4, 8.2 Hz, 1H), 3.17 (td, J=12.6, 4.8 Hz, 1H), 2.84 (td, J=12.7, 5.1 Hz, 1H), 2.18-1.97 (m, 2H); MS (ES) m/z: 645 (M+Na$^+$).

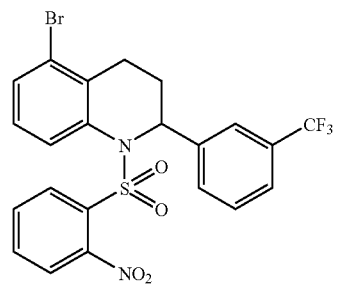

5-Bromo-1-(2-nitro-benzenesulfonyl)-2-(3-trifluoromethyl-phenyl)-1,2,3,4-tetrahydro-quinoline Replacing A9 with I5 and following the same procedure as in the preparation of A10 gave I6 (81%): $^1$H NMR (400 MHz, CDCl$_3$) δ 7.84 (d, J=8.5 Hz, 1H), 7.70 (m, 1H), 7.65-7.40 (m, 8H), 7.18 (t, J=8.1 Hz, 1H), 5.66 (t, J=8.9 Hz, 1H), 2.76-2.68 (m, 1H), 2.50-2.42 (m, 1H), 2.35-2.27 (m, 1H), 2.04-1.95 (m, 1H); MS (ES) m/z: 541 (M).

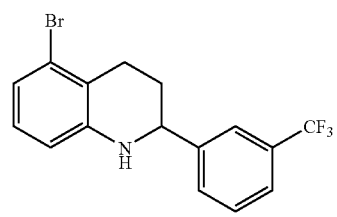

5-Bromo-2-(3-trifluoromethyl-phenyl)-1,2,3,4-tetrahydro-quinoline

Replacing A10 with I6 and following the same procedure as in the preparation of A11 gave I7 (91%): $^1$H NMR (300 MHz, CDCl$_3$) δ 7.64 (s, 1 H), 7.56 (d, J=7.7 Hz, 2H), 7.50-7.44 (m, 1H), 6.98-6.85 (m, 2H), 6.56-6.50 (m, 1H), 4.45 (d, J=9.4 Hz, 1H), 4.12 (brs, 1H), 2.89-2.81 (m, 2H), 2.23-2.11 (m, 1H), 2.08-1.92 (m, 1H); MS (ES) m/z: 356 (M).

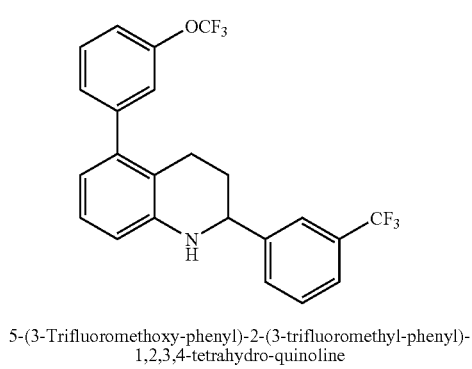

5-(3-Trifluoromethoxy-phenyl)-2-(3-trifluoromethyl-phenyl)-1,2,3,4-tetrahydro-quinoline Replacing A11 with I7 and following the same procedure as in the preparation of A12 gave I8 (89%): $^1$H NMR (400 MHz, CDCl$_3$) δ 7.67 (s, 1H), 7.61-7.54 (m, 2H), 7.50 (t, J=7.8 Hz, 1H), 7.41 (t, J=7.8 Hz, 1H), 7.27 (s, 1H), 7.18 (d, J=9.2 Hz, 2H), 7.10 (t, J=7.7 Hz, 1H), 6.63 (d, J=7.7 Hz, 2H), 4.55 (dd, J=9.2, 3.3 Hz, 1H), 4.20 (brs, 1H), 2.85-2.74 (m, 1H), 2.54 (dt, J=16.6, 4.7 Hz, 1H), 2.11-2.05 (m, 1H), 1.96-1.84 (m, 1H); MS (ES) m/z: 438 (M+H$^+$).

Example 18

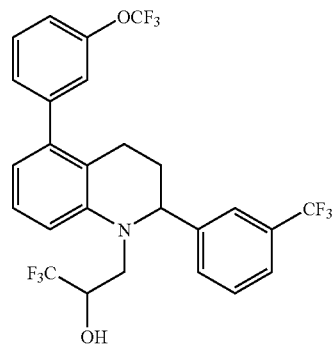

Compound 18

(Lower Rf Compound)
1,1,1-Trifluoro-3-[5-(3-trifluoromethoxy-phenyl)-2-(3-trifluoromethyl-phenyl)-3,4-dihydro-2H-quinolin-1-yl]-propan-2-ol The spectra of compound 18 are as follows: $^1$H NMR (300 MHz, CDCl$_3$) δ 7.54 (d, J=7.5 Hz, 1H), 7.49-7.42 (m, 2H), 7.41-7.34 (m, 2H), 7.24-7.10 (m, 4H), 6.91 (d, J=8.3 Hz, 1H), 6.69 (d, J=7.6 Hz, 1H), 4.66 (t, J=4.0 Hz, 1H), 4.34 (m, 1H), 3.81 (dd, J=15.5, 6.6 Hz, 1H), 3.47 (dd, J=15.5, 5.7 Hz, 1H), 2.49-2.28 (m, 2H), 2.23 (d, J=5.0 Hz, 1H), 2.19-2.08 (m, 1H), 2.00-1.91 (m, 1H); MS (ES) m/z: 550 (M+H$^+$).

Example 19

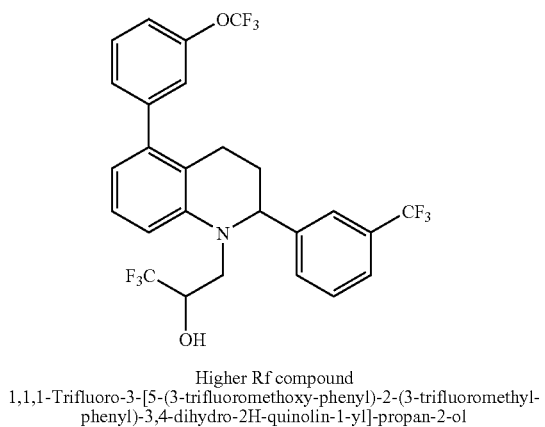

Cmpd 17

Higher Rf compound
1,1,1-Trifluoro-3-[5-(3-trifluoromethoxy-phenyl)-2-(3-trifluoromethyl-phenyl)-3,4-dihydro-2H-quinolin-1-yl]-propan-2-ol Replacing A12 with I8 and following the same procedure as in the preparation of compound 1 and 2 gave compound 17 and 18. The spectra of compound 17 are as follows: $^1$H NMR (300 MHz, CDCl$_3$) δ 7.54 (d, J=7.6 Hz, 1H), 7.48-7.33 (m, 4H), 7.23-7.10 (m, 4H), 6.74 (d, J=8.3 Hz, 1H), 6.68 (d, J=8.5 Hz, 1H), 4.96 (t, J=4.5 Hz, 1H), 4.45 (m, 1H), 3.93 (d, J=15.6 Hz, 1H), 3.26 (dd, J=15.6, 9.7 Hz, 1H), 2.49 (dt, J=16.3, 4.7 Hz, 1H), 2.42-2.28 (m, 2H), 2.21-2.10 (m, 1H), 2.02-1.92 (m, 1H); MS (ES) m/z: 550 (M+H$^+$).

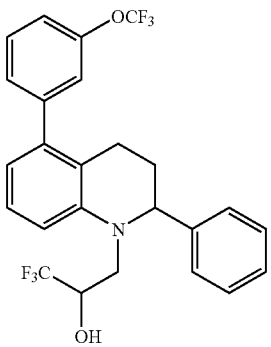

Compound 19

(Higher Rf Compound)
1,1,1-Trifluoro-3-[2-phenyl-5-(3-trifluoromethoxy-phenyl)-3,4-dihydro-2H-quinolin-1-yl]-propan-2-ol Scheme J

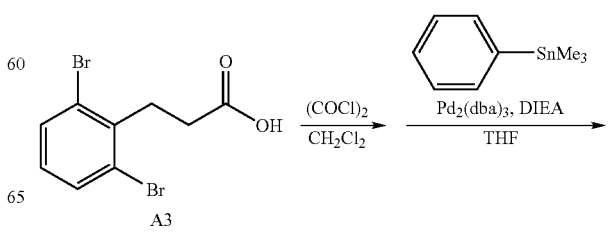

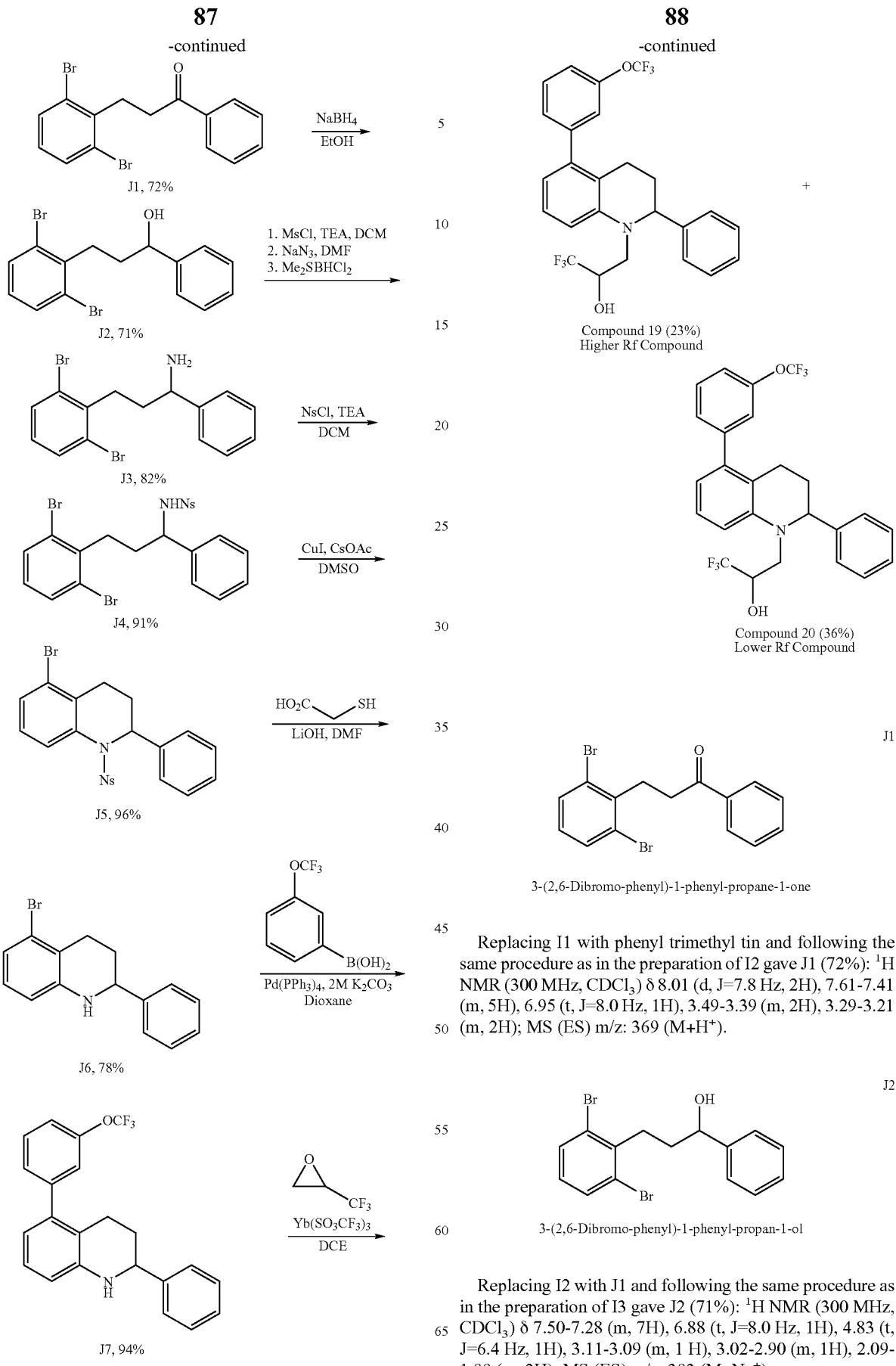

3-(2,6-Dibromo-phenyl)-1-phenyl-propane-1-one

Replacing I1 with phenyl trimethyl tin and following the same procedure as in the preparation of I2 gave J1 (72%): $^1$H NMR (300 MHz, CDCl$_3$) δ 8.01 (d, J=7.8 Hz, 2H), 7.61-7.41 (m, 5H), 6.95 (t, J=8.0 Hz, 1H), 3.49-3.39 (m, 2H), 3.29-3.21 (m, 2H); MS (ES) m/z: 369 (M+H$^+$).

3-(2,6-Dibromo-phenyl)-1-phenyl-propan-1-ol

Replacing I2 with J1 and following the same procedure as in the preparation of I3 gave J2 (71%): $^1$H NMR (300 MHz, CDCl$_3$) δ 7.50-7.28 (m, 7H), 6.88 (t, J=8.0 Hz, 1H), 4.83 (t, J=6.4 Hz, 1H), 3.11-3.09 (m, 1H), 3.02-2.90 (m, 1H), 2.09-1.99 (m, 2H); MS (ES) m/z: 393 (M+Na$^+$).

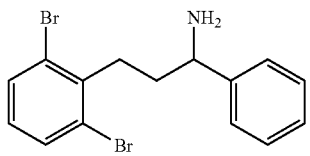

3-(2,6-Dibromo-phenyl)-1-phenyl-propylamine

Replacing I3 with J2 and following the same procedure as in the preparation of I4 gave J3 (82%): $^1$H NMR (300 MHz, CDCl$_3$) δ 7.46 (d, J=8.0 Hz, 2H), 7.41-7.23 (m, 5H), 6.87 (t, J=8.0 Hz, 1H), 4.05 (t, J=6.0 Hz, 1H), 3.11-3.00 (m, 1H), 2.90-2.79 (m, 1H), 1.99-1.89 (m, 2H), 1.73 (brs, 2H); MS (ES) m/z: 370 (M+H$^+$).

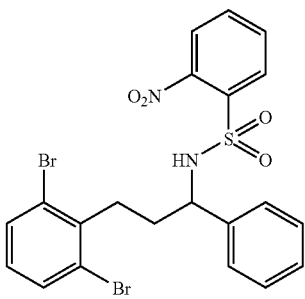

N-[3-(2,6-Dibromo-phenyl)-1-phenyl-propyl]-2-nitro-benzene sulfonamide

Replacing I4 with J3 and following the same procedure as in the preparation of I5 gave J4 (91%): $^1$H NMR (400 MHz, CDCl$_3$) δ 7.72-7.63 (m, 2H), 7.57-7.33 (m, 4H), 7.18-7.03 (m, 5H), 6.89 (t, J=8.0 Hz, 1H), 5.93 (d, J=9.0 Hz, 1H), 4.66 (dd, J=15.8, 8.1 Hz, 1H), 3.15 (td, J=12.6, 4.7 Hz, 1H), 2.84 (td, J=12.5, 5.1 Hz, 1H), 2.12-1.95 (m, 2H); MS (ES) m/z: 553 (M−H$^+$).

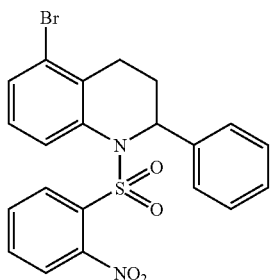

5-Bromo-1-(2-nitro-benzenesulfonyl)-2-phenyl-1,2,3,4-tetrahydro-quinoline

Replacing I5 with J4 and following the same procedure as in the preparation of I6 gave J5 (96%): $^1$H NMR (400 MHz, CDCl$_3$) δ 7.82 (d, J=8.2 Hz, 1H), 7.68 (m, 1H), 7.61 (m, 2H), 7.53 (m, 1H), 7.41 (d, J=8.1 Hz, 1H), 7.30-7.20 (m, 5H), 7.15 (t, J=8.1 Hz, 1H), 5.62 (t, J=6.6 Hz, 1H), 2.72-2.65 (m, 1H), 2.42-2.28 (m, 2H), 2.09-2.01 (m, 1H); MS (ES) m/z: 473 (M).

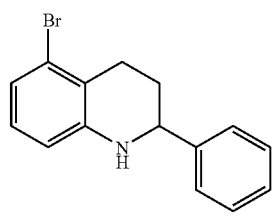

5-Bromo-2-phenyl-1,2,3,4-tetrahydro-quinoline

Replacing I6 with J5 and following the same procedure as in the preparation of I7 gave J6 (78%): $^1$H NMR (300 MHz, CDCl$_3$) δ 7.49-7.29 (m, 5H), 6.95-6.82 (m, 2H), 6.48 (d, J=7.6 Hz, 1H), 4.38 (dd, J=9.2, 3.2 Hz, 1H), 4.13 (brs, 1H), 2.89-2.80 (m, 2H), 2.21-2.11 (m, 1H), 2.05-1.94 (m, 1H); MS (ES) m/z: 288 (M).

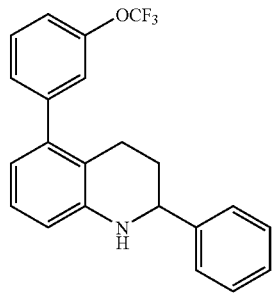

2-Phenyl-5-(3-trifluoromethoxy-phenyl)-1,2,3,4-tetrahydro-quinoline

Replacing I7 with J6 and following the same procedure as in the preparation of I8 gave J7 (94%): $^1$H NMR (300 MHz, CDCl$_3$) δ 7.45-7.30 (m, 7H), 7.22-7.15 (m, 2H), 7.08 (t, J=7.7 Hz, 1H), 6.62 (t, J=7.7 Hz, 2H), 4.48 (dd, J=9.2, 3.3 Hz, 1H), 2.83-2.71 (m, 1H), 2.56 (dt, J=16.6, 4.8 Hz, 1H), 2.13-2.03 (m, 1H), 2.00-1.88 (m, 1H), 1.53 (brs, 1H); MS (ES) m/z: 370 (M+H$^+$).

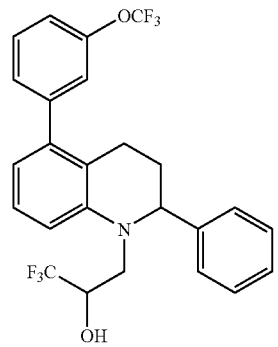

Higher Rf compound
1,1,1-Trifluoro-3-[2-phenyl-5-(3-trifluoromethoxy-phenyl)-3,4-dihydro-2H-quinolin-1-yl]-propan-2-ol Replacing I8 with J7 and following the same procedure as in the preparation of compound 17 and 18 gave compound 19 and 20. Spectra of compound 19 are as follows: $^1$H NMR (300 MHz, CDCl$_3$) δ 7.38-7.11 (m, 10H), 6.76 (d, J=8.3 Hz, 1H), 6.67 (d, J=7.5 Hz, 1H), 4.84 (t, J=4.6 Hz 1H), 4.38 (m, 1H), 3.87 (d, J=15.5 Hz, 1H), 3.35 (dd, J=15.5, 9.6 Hz, 1 H), 2.54-2.35 (m, 3H), 2.20-2.09 (m, 1H), 2.05-1.95 (m, 1H); MS (ES) m/z: 482 (M+H$^+$).

Example 20

Compound 20

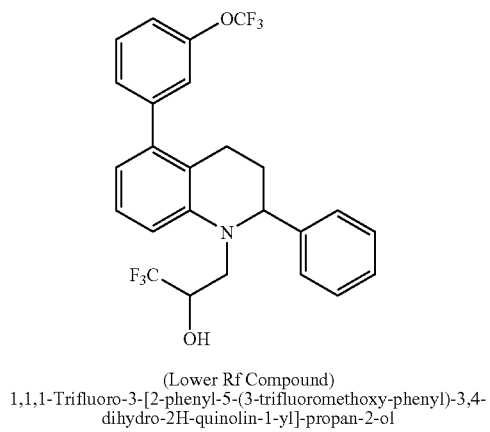

(Lower Rf Compound)
1,1,1-Trifluoro-3-[2-phenyl-5-(3-trifluoromethoxy-phenyl)-3,4-dihydro-2H-quinolin-1-yl]-propan-2-ol Spectra of compound 20 are as follows: $^1$H NMR (300 MHz, CDCl$_3$) δ 7.39-7.12 (m, 10H), 6.91 (d, J=9.4 Hz, 1H), 6.68 (d, J=7.5 Hz, 1H), 4.61 (t, J=4.4 Hz, 1H), 4.31 (m, 1H), 3.77 (dd, J=15.5, 6.9 Hz, 1H), 3.56 (dd, J=15.6, 5.1 Hz, 1H), 2.47-2.40 (m, 2H), 2.19-2.06 (m, 1H), 2.02-1.92 (m, 1H); MS (ES) m/z: 482 (M+H$^+$).

Example 21

Cmpd 21

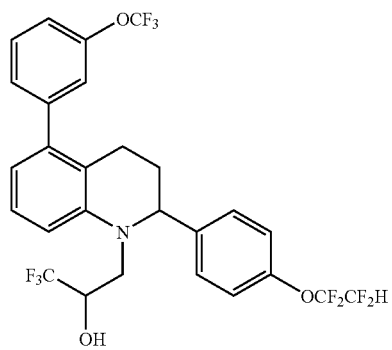

(Higher Rf Compound)
1,1,1-Trifluoro-3-[2-[4-(1,1,2,2-tetrafluoro-ethoxy)-phenyl]-5-(3-trifluoromethoxy-phenyl)-3,4-dihydro-2H-quinolin-1-yl]-propan-2-ol

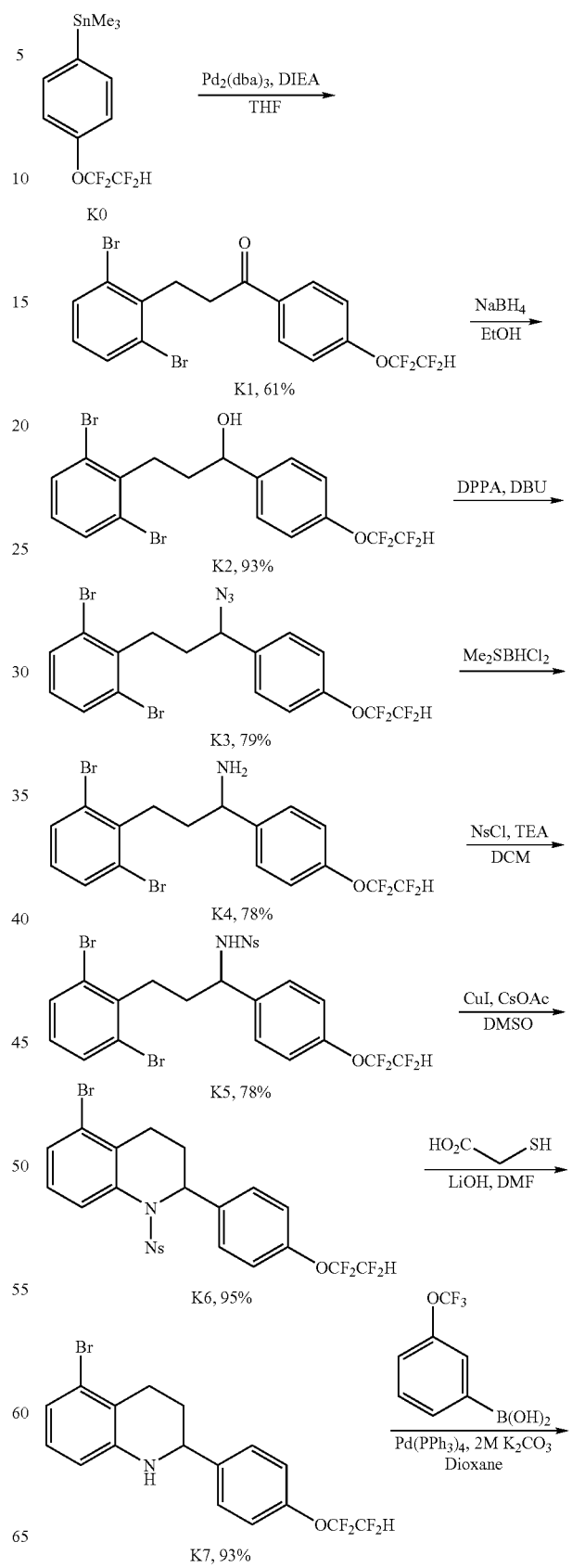

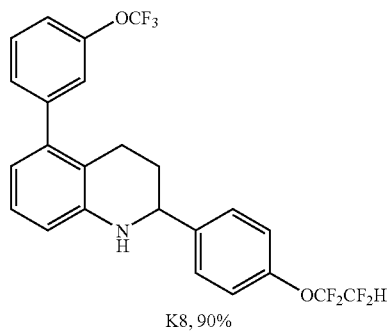

K8, 90%

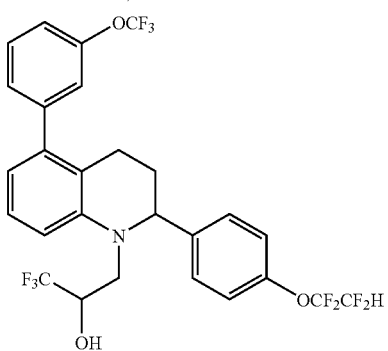

Compound 21 (20%)
Higher Rf Compound

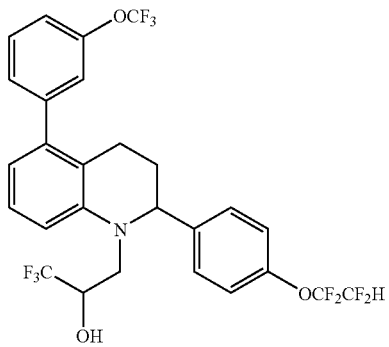

Compound 22
Lower Rf Compound

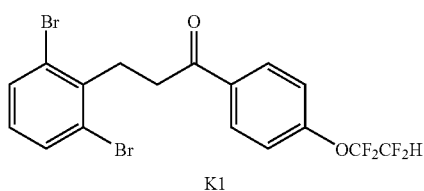

K1

3-(2,6-Dibromo-phenyl)-1-[4-(1,1,2,2-tetrafluoro-ethoxy)-phenyl]-propan-1-one

Replacing I1 with K0 and following the same procedure as in the preparation of I2 gave K1 (61%): $^1$H NMR (300 MHz, CDCl$_3$) δ 8.04 (d, J=8.8 Hz, 2H), 7.53 (d, J=8.0 Hz, 2H), 7.30 (d, J=8.2 Hz, 2H), 6.96 (t, J=8.0 Hz, 1H), 5.93 (tt, J=53.0, 2.7 Hz, 1H), 3.48-3.40 (m, 2H), 3.28-3.20 (m, 2H); MS (ES) m/z: 485 (M+H$^+$).

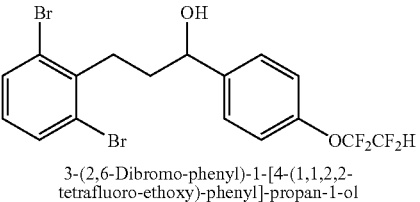

3-(2,6-Dibromo-phenyl)-1-[4-(1,1,2,2-tetrafluoro-ethoxy)-phenyl]-propan-1-ol

Replacing J1 with K1 and following the same procedure as in the preparation of J2 gave K2 (93%): $^1$H NMR (300 MHz, CDCl$_3$) δ 7.51-7.41 (m, 4H), 7.21 (d, J=8.2 Hz, 2H), 6.89 (t, J=8.0 Hz, 1H), 5.90 (tt, J=53.1, 2.8 Hz, 1H), 4.85 (t, J=6.4 Hz, 1H), 3.20-3.09 (m, 1H), 3.02-2.91 (m, 1H), 2.08-1.95 (m, 3H); MS (ES) m/z: 509 (M+Na$^+$).

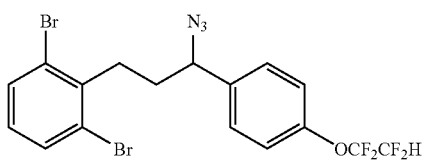

To a solution of K2 and Diphenylphosphorylazide in toluene at 0° C., was added 1,8-diazabicyclo[5.4.0]undec-7-ene. The reaction was allowed to wrm to room temperature while stirring overnight. The following day, the reaction mixture was poured into EtOAc, and washed with H$_2$O and brine. The organic layer was dried (MgSO$_4$), concentrated, and purified by silica gel chromatography 5%, 10% EtOAc/hexanes to provide 805 mg (79%) as an oil: $^1$H NMR (300 MHz, CDCl$_3$) δ 7.48 (d, J=8.0 Hz, 2H), 7.40 (d, J=8.6 Hz, 2H), 7.24 (t, J=8.9 Hz, 2H), 6.90 (t, J=8.0 Hz, 1H), 5.99 (tt, J=53.1, 2.69 Hz, 1H), 4.59 (t, J=6.9 Hz, 1H), 3.16-3.06 (m, 1H), 2.98-2.88 (m, 1H), 2.15-1.94 (m, 2H); MS (ES) m/z: 469 (M−H$_2$O+H$^+$).

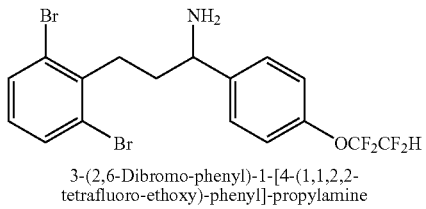

3-(2,6-Dibromo-phenyl)-1-[4-(1,1,2,2-tetrafluoro-ethoxy)-phenyl]-propylamine

To a solution of K3 (0.8 g, 1.57 mmol) in 1,2-dichloroethane (10 mL) was added Me$_2$SBHCl$_2$ (0.45 mL, 3.9 mmol) dropwise. The solution stirred at room temperature for 0.5 h and then was heated at 50° C. for 1.5 h. 6 N HCl (3.2 mL), H$_2$O (3.2 ml) and 1,2-dichloroethane (3.2 ml) were added. The reaction mixture was heated at reflux for 1 h. Upon cooling to 0° C., the solution was basified with 3 N NaOH and extracted with CHCl$_3$. The combined organic phases were dried (MgSO$_4$), and then concentrated to provide 0.739 g (97%) K4 as an oil:

$^1$H NMR (300 MHz, CDCl$_3$) δ 7.49-7.40 (m, 4H), 7.19 (d, J=8.2 Hz, 2H), 6.88 (t, J=8.0 Hz, 1H), 5.90 (tt, J=53.1, 2.5 Hz, 1H), 4.10 (t, J=6.7 Hz, 1H), 3.10-2.99 (m, 1H), 2.90-2.79 (m, 1H), 2.28-1.70 (m, 4 H); MS (ES) m/z: 469 (M−H$_2$O+H$^+$).

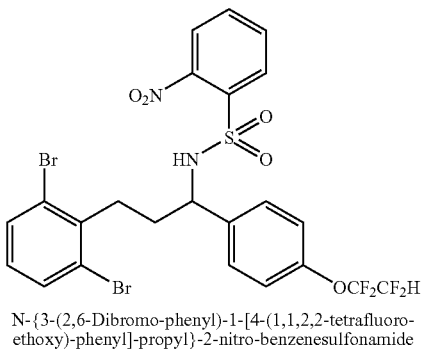

N-{3-(2,6-Dibromo-phenyl)-1-[4-(1,1,2,2-tetrafluoro-ethoxy)-phenyl]-propyl}-2-nitro-benzenesulfonamide Replacing J3 with K4 and following the same procedure as in the preparation of J4 gave K5 (78%): $^1$H NMR (300 MHz, CDCl$_3$) δ 7.71 (d, J=8.0 Hz, 1H), 7.61 (d, J=7.8 Hz, 1H), 7.52 (t, J=7.9 Hz, 1H), 7.46 (d, J=8.0 Hz, 2H), 7.38 (t, J=7.7 Hz, 1H), 7.17 (d, J=8.5 Hz, 2H), 6.93-6.87 (m, 3H), 5.95 (d, J=8.6 Hz, 1H), 5.86 (tt, J=53.1, 2.7 Hz, 1H), 4.69 (dd, J=5.8 Hz, 1H), 3.15 (td, J=12.7, 4.6 Hz, 1H), 2.84 (td, J=12.5, 5.0 Hz, 1 H), 2.15-1.90 (m, 2H); MS (ES) m/z: 669 (M−H$^−$).

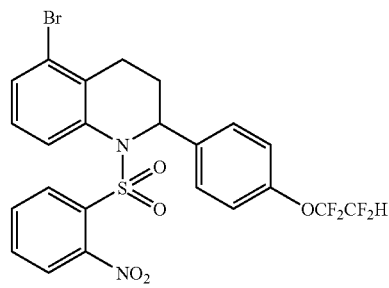

5-Bromo-1-(2-nitro-benzenesulfonyl)-2-[4-(1,1,2,2-tetrafluoro-ethoxy)-phenyl]-1,2,3,4-tetrahydro-quinoline Replacing J4 with K5 and following the same procedure as in the preparation of J5 gave K6 (95%): $^1$H NMR (300 MHz, CDCl$_3$) δ 7.82 (d, J=8.2 Hz, 1H), 7.73-7.50 (m, 4H), 7.44 (d, J=8.0 Hz, 1H), 7.29 (d, J=8.5 Hz, 2H), 7.19-7.11 (m, 3H), 5.88 (tt, J=53.1, 2.8 Hz, 1H), 5.62 (t, J=6.9 Hz, 1H), 2.78-2.65 (m, 1H), 2.49-2.38 (m, 1H), 2.36-2.24 (m, 1 H), 2.06-1.92 (m, 1H); MS (ES) m/z: 591 (M+2).

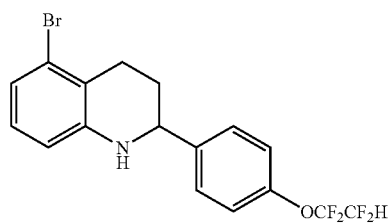

5-Bromo-2-[4-(1,1,2,2-tetrafluoro-ethoxy)-phenyl]-1,2,3,4-tetrahydro-quinoline

Replacing J5 with K6 and following the same procedure as in the preparation of J6 gave K7 (93%): $^1$H NMR (300 MHz, CDCl$_3$) δ 7.37 (d, J=8.4 Hz, 1H), 7.19 (d, J=8.4 Hz, 2H), 6.95-6.80 (m, 2H), 6.48 (d, J=7.8 Hz, 2H), 5.90 (tt, J=53.1, 2.8 Hz, 1H), 4.38 (dd, J=9.3, 3.0 Hz, 1H), 4.10 (brs, 1H), 2.86-2.71 (m, 2H), 2.20-2.09 (m, 1H), 2.01-1.89 (m, 1H).

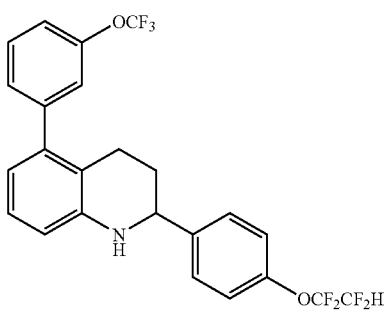

2-[4-(1,1,2,2-Tetrafluoro-ethoxy)-phenyl]-5-(3-trifluoromethoxy-phenyl)-1,2,3,4-tetrahydro-quinoline Replacing J6 with K7 and following the same procedure as in the preparation of J7 gave K8 (90%): $^1$H NMR (300 MHz, CDCl$_3$) δ 7.47-7.38 (m, 3H), 7.29-7.15 (m, 5H), 7.09 (t, J=7.8 Hz, 1H), 6.63 (m, 2H), 5.91 (tt, J=53.1, 2.4 Hz, 1H), 4.49 (dd, J=9.0, 3.2 Hz, 1H), 2.83-2.70 (m, 1 H), 2.54 (dt, J=16.7, 4.7 Hz, 1H), 2.11-2.02 (m, 1H), 1.98-1.83 (m, 1 H), 1.53 (brs, 1H); MS (ES) m/z: 486 (M+H$^+$).

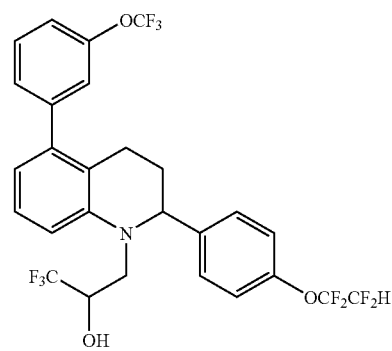

Higher Rf compound 1,1,1-Trifluoro-3-[2-[4-(1,1,2,2-tetrafluoro-ethoxy)-phenyl]-5-(3-trifluoromethoxy-phenyl)-3,4-dihydro-2H-quinolin-1-yl]-propan-2-ol Replacing I8 with K8 and following the same procedure as in the preparation of compound 17 and 18 gave compounds 21 and 22. Spectra of compound 21 are as follows: $^1$H NMR (300 MHz, CDCl$_3$) δ 7.37 (t, J=7.8 Hz, 1H), 7.28-7.10 (m, 8H), 6.72 (d, J=8.3 Hz, 1H), 6.66 (d, J=7.5 Hz, 1H), 5.90 (tt, J=53.1, 2.8 Hz, 1H), 4.89 (t, J=4.5 Hz, 1H), 4.42 (m, 1 H), 3.90 (d, J=15.5 Hz, 1H), 3.29 (dd, J=15.6, 9.7 Hz, 1H), 2.55-2.30 (m, 3H), 2.20-2.08 (m, 1H), 2.00-1.90 (m, 1H); MS (ES) m/z: 598 (M+H⁺).

Example 22

Compound 22

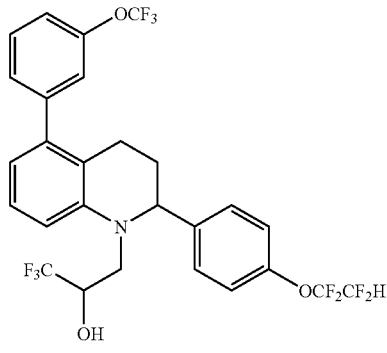

(Lower Rf Compound)

1,1,1-Trifluoro-3-[2-[4-(1,1,2,2-tetrafluoro-ethoxy)-phenyl]-5-(3-trifluoromethoxy-phenyl)-3,4-dihydro-2H-quinolin-1-yl]-propan-2-ol Spectra of compound 22 are as follows: ¹H NMR (300 MHz, CDCl₃) δ 7.37 (t, J=7.8 Hz, 1H), 7.28-7.10 (m, 8H), 6.90 (d, J=8.3 Hz, 1H), 68 (d, J=7.5 Hz, 1H), 5.90 (tt, J=53.1, 2.8 Hz, 1H), 4.61 (t, J=4.3 Hz, 1H), 4.33 (m, 1H), 3.80 (dd, J=15.7, 6.5 Hz, 1H), 3.49 (dd, J=15.6, 5.5 Hz, 1H), 2.49-2.25 (m, 3H), 2.18-2.05 (m, 1H), 1.99-1.90 (m, 1H).

Example 23

Cmpd 23

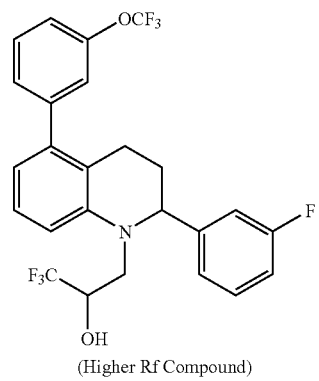

(Higher Rf Compound)

1,1,1-Trifluoro-3-[2-(3-fluoro-phenyl)-5-(3-trifluoromethoxy-phenyl)-3,4-dihydro-2H-quinolin-1-yl]-propan-2-ol Scheme L

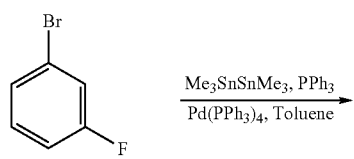

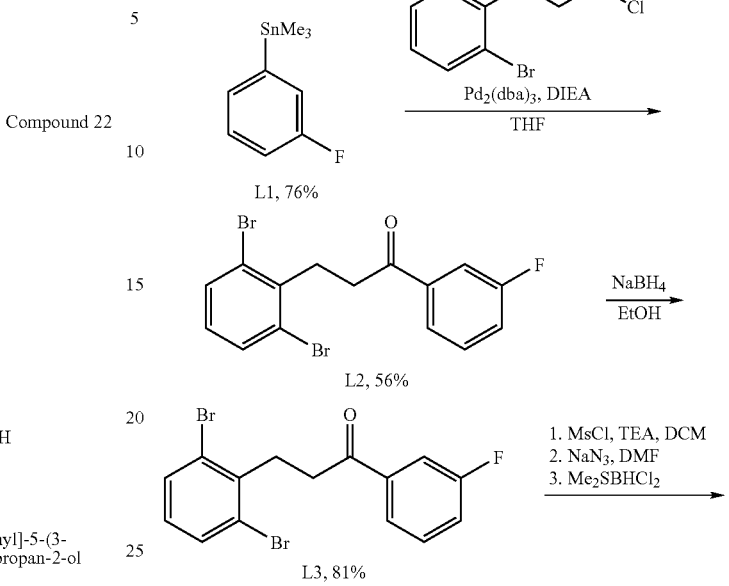

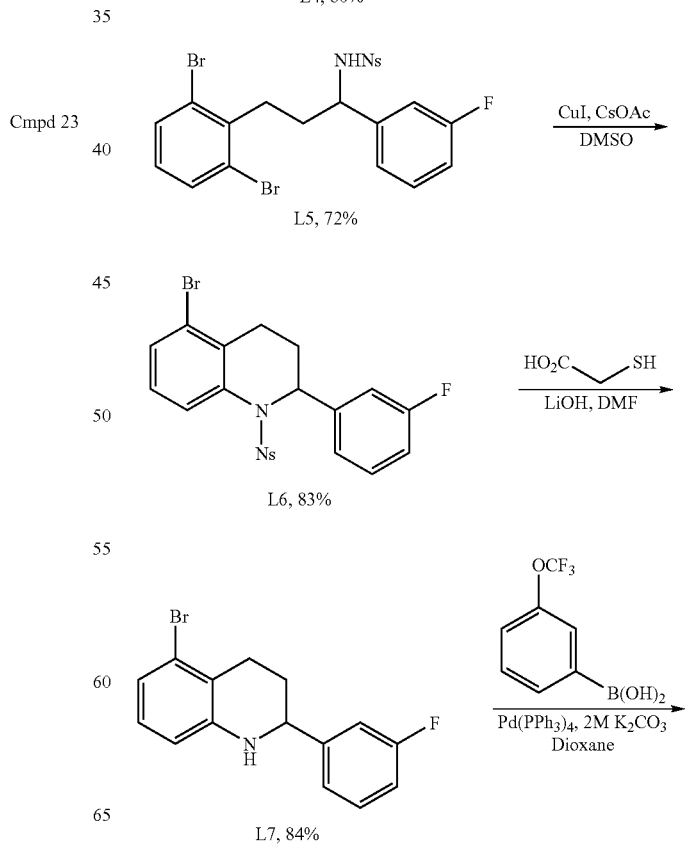

-continued

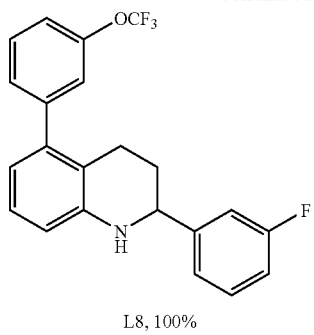

L8, 100%

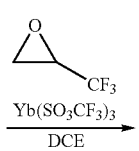

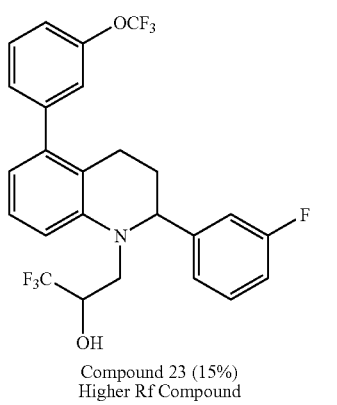

Compound 23 (15%)
Higher Rf Compound

+

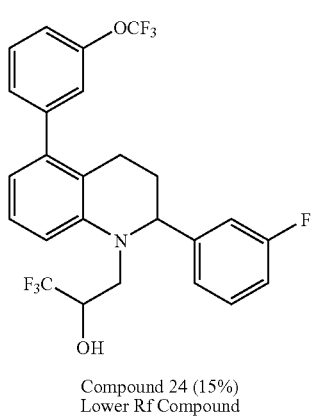

Compound 24 (15%)
Lower Rf Compound

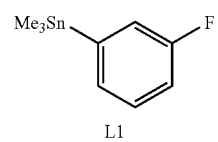

L1
(3-Fluoro-phenyl)-trimethyl-stannane

Replacing 1-bromo-3-(1,1,2,2-tetrafluoro-ethoxy)-benzene with 1-bromo-3-fluoro-benzene and following the same procedure as in the preparation of A4 gave L1 (76%): $^1$H NMR (300 MHz, CDCl$_3$) δ 7.35-7.15 (m, 3H), 7.02-6.95 (m, 1H), 0.30 (s, 9H).

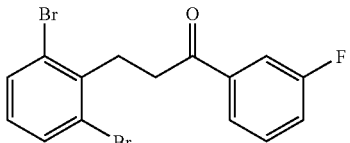

3-(2,6-Dibromo-phenyl)-1-(3-fluoro-phenyl)-propan-1-one

Replacing I1 with L1 and following the same procedure as in the preparation of I2 gave L2 (56%): $^1$H NMR (300 MHz, CDCl$_3$) δ 7.78 (d, J=7.7 Hz, 1H), 7.69 (d, J=9.5 Hz, 1H), 7.54 (d, J=8.0 Hz, 2H), 7.50-7.40 (m, 1H), 7.31-7.22 (m, 1H), 6.96 (t, J=8.1 Hz, 1H), 3.48-3.40 (m, 2H), 3.28-3.19 (m, 2H); MS (ES) m/z: 409 (M+Na$^+$).

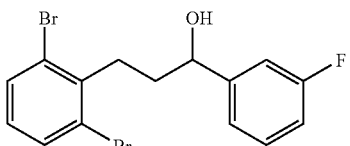

3-(2,6-Dibromo-phenyl)-1-(3-fluoro-phenyl)-propan-1-ol

Replacing I2 with L2 and following the same procedure as in the preparation of I3 gave L3 (81%): $^1$H NMR (300 MHz, CDCl$_3$) δ 7.48 (d, J=8.0 Hz, 2H), 7.38-7.29 (m, 1H), 7.21-7.11 (m, 2H), 7.01-7.88 (m, 2H), 4.84 (t, J=6.3 Hz, 1H), 3.20-3.09 (m, 1H), 3.05-2.91 (m, 1H), 2.08-1.95 (m, 3H); MS (ES) m/z: 369 (M−H$_2$O+H$^+$).

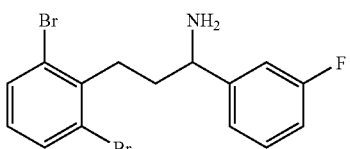

3-(2,6-Dibromo-phenyl)-1-(3-fluoro-phenyl)-propylamine

Replacing I3 with L3 and following the same procedure as in the preparation of I4 gave L4 (80%): $^1$H NMR (300 MHz, CDCl$_3$) δ 7.46 (d, J=8.0 Hz, 2H), 7.33-7.27 (m, 1H), 7.21-7.10 (m, 2H), 6.98-6.85 (m, 2H), 4.10 (t, J=7.0 Hz, 1H), 3.09-2.96 (m, 1H), 2.89-2.79 (m, 1H), 1.97 (dd, J=16.4, 7.3 Hz, 2H); MS (ES) m/z: 388 (M+H$^+$).

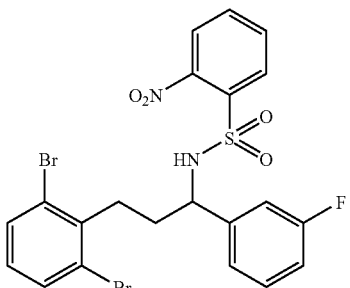

N-[3-(2,6-Dibromo-phenyl)-1-(3-fluoro-phenyl)-propyl]-2-nitro-benzenesulfonamide Replacing I4 with L4 and following the same procedure as in the preparation of I5 gave L5 (72%): $^1$H NMR (300 MHz, CDCl$_3$) δ 7.72 (t, J=8.4 Hz, 2H), 7.57 (t, J=7.7 Hz, 2H), 7.45 (t, J=8.0 Hz, 2H), 7.11-6.72 (m, 5H), 5.94 (t, J=8.4 Hz, 2H), 4.66 (dd, J=15.5, 7.8 Hz, 1H), 3.19-3.05 (m, 1H), 2.89-2.76 (m, 1H), 2.12-1.91 (m, 2H); MS (ES) m/z: 571 (M–H+).

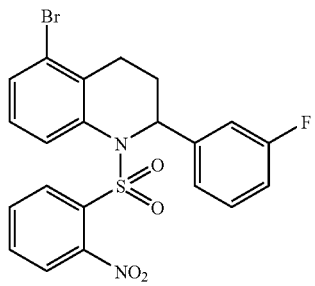

L6

5-Bromo-2-(3-fluoro-phenyl)-1-(2-nitro-benzenesulfonyl)-1,2,3,4-tetrahydro-quinoline Replacing I5 with L5 and following the same procedure as in the preparation of I6 gave L6 (83%): ¹H NMR (400 MHz, CDCl₃) δ 7.83 (d, J=8.2 Hz, 1H), 7.70 (m, 1H), 7.63-7.51 (m, 3H), 7.42 (d, J=7.9 Hz, 1H), 7.28-7.26 (m, 1H), 7.16 (d, J=8.1 Hz, 1H), 7.07 (d, J=7.7 Hz, 1H), 7.01-6.88 (m, 2H), 5.61 (t, J=6.9 Hz, 1H), 2.72-2.65 (m, 1H), 2.47-2.25 (m, 2H), 2.07-1.95 (m, 1H); MS (ES) m/z: 491 (M).

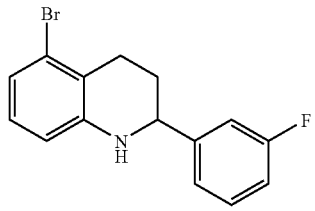

L7

5-Bromo-2-(3-fluoro-phenyl)-1,2,3,4-tetrahydro-quinoline

Replacing I6 with L6 and following the same procedure as in the preparation of I7 gave L7 (84%): ¹H NMR (300 MHz, CDCl₃) δ7.38-7.28 (m, 1H), 7.18-7.06 (m, 2H), 7.02-7.62 (m, 3H), 6.53 (d, J=8.5 Hz, 1 H), 4.39 (d, J=8.8 Hz, 1H), 4.13 (brs, 1H), 4.41-4.07 (m, 2H), 2.21-2.11 (m, 1H), 2.05-1.90 (m, 1H); MS (ES) m/z: 306 (M).

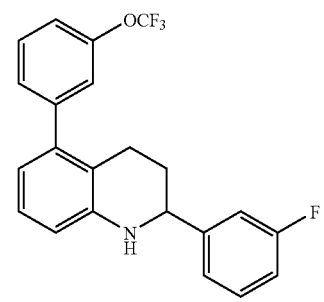

L8

2-(3-Fluoro-phenyl)-5-(3-trifluoromethoxy-phenyl)-1,2,3,4-tetrahydro-quinoline

Replacing I7 with L7 and following the same procedure as in the preparation of I8 gave L8 (100%): ¹H NMR (300 MHz, CDCl₃) δ 7.42-7.22 (m, 4H), 7.20-7.05 (m, 4H), 6.99 (m, 1H), 6.61 (d, J=7.7 Hz, 2H), 4.49 (dd, J=8.8, 3.5 Hz, 1H), 4.19 (brs, 1H), 2.86-2.19 (m, 1H), 2.52 (dt, J=6.7, 5.0 Hz, 1H), 2.10-2.01 (m, 1H), 1.95-1.80 (m, 1H); MS (ES) m/z: 388 (M+H+).

Cmpd 23

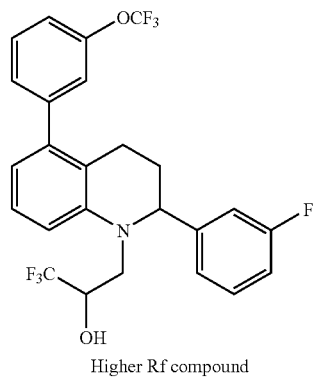

Higher Rf compound 1,1,1-Trifluoro-3-[2-(3-fluoro-phenyl)-5-(3-trifluoromethoxy-phenyl)-3,4-dihydro-2H-quinolin-1-yl]-propan-2-ol Replacing I8 with L8 and following the same procedure as in the preparation of compound 17 and 18 gave compound 23 and 24. Spectra of compound 23 are as follows: ¹H NMR (300 MHz, CDCl₃) δ 7.41-7.11 (m, 6 H), 7.02-6.88 (m, 3H), 6.73 (d, J=8.4 Hz, 1H), 6.67 (d, J=7.7 Hz, 1H), 4.88 (t, J=4.6 Hz, 1H), 4.43 (m, 1H), 3.92 (d, J=15.6 Hz, 1H), 3.30 (dd, J=15.5, 9.6 Hz, 1H), 2.53-2.30 (m, 3H), 2.19-2.07 (m, 1H), 2.02-1.91 (m, 1H); MS (ES) m/z: 500 (M+H+).

Example 24

Compound 24

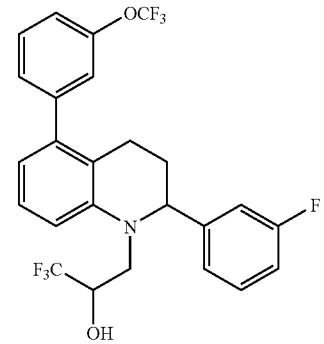

(Lower Rf Compound)

1,1,1-Trifluoro-3-[2-(3-fluoro-phenyl)-5-(3-trifluoromethoxy-phenyl)-3,4-dihydro-2H-quinolin-1-yl]-propan-2-ol Spectra of compound 24 are as follows: ¹H NMR (300 MHz, CDCl₃) δ 7.40-7.10 (m, 6H), 7.02-6.86 (m, 4H), 6.69 (d, J=7.5 Hz, 1H), 4.61 (t, J=4.4 Hz, 1H), 4.3 (m, 1H), 3.80

(dd, J=15.5 Hz, 1H), 3.52 (dd, J=15.5 Hz, 1H), 2.47-2.38 (m, 2H), 2.19-2.04 (m, 1H), 2.02-1.91 (m, 1H); MS (ES) m/z: 500 (M+H⁺).
Example 25
Cmpd 25
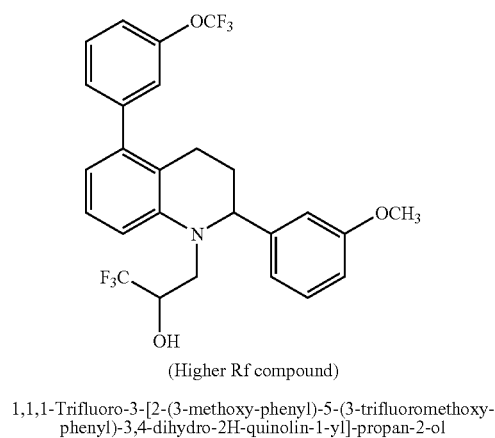
(Higher Rf compound)
1,1,1-Trifluoro-3-[2-(3-methoxy-phenyl)-5-(3-trifluoromethoxy-phenyl)-3,4-dihydro-2H-quinolin-1-yl]-propan-2-ol
Scheme M
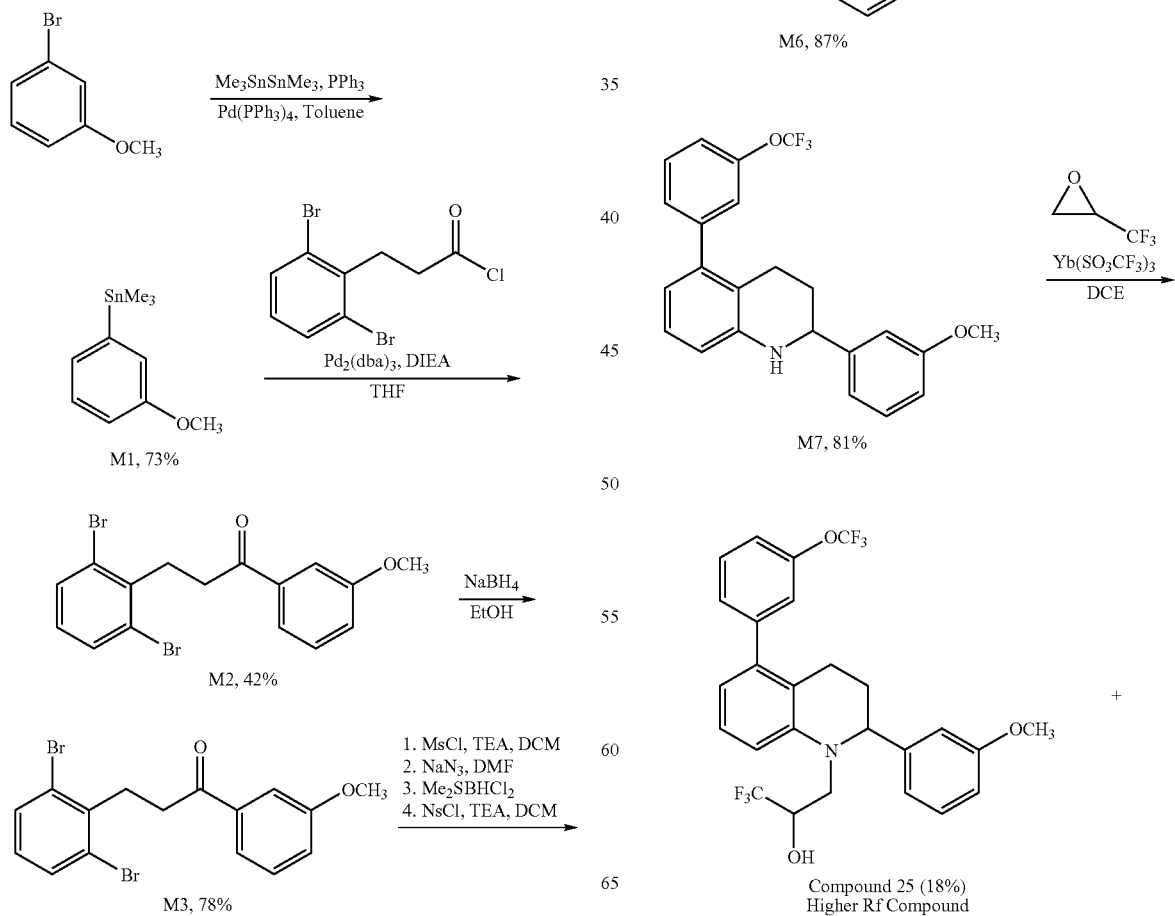
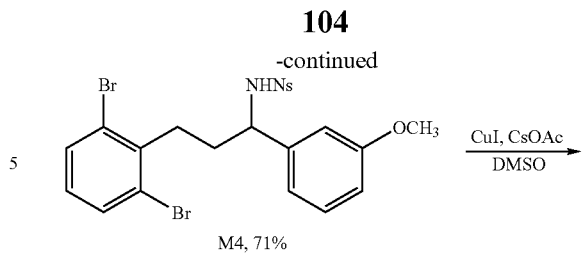

-continued

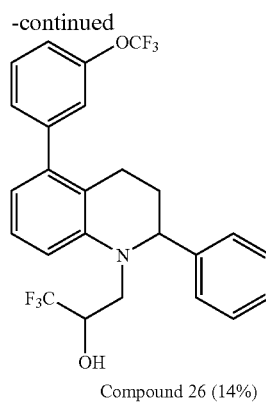

Compound 26 (14%)
Lower Rf Compound

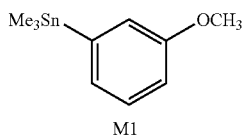

M1

(3-Methoxy-phenyl)-trimethyl-stannane

Replacing 1-bromo-3-(1,1,2,2-tetrafluoro-ethoxy)-benzene with 1-bromo-3-methoxy-benzene and following the same procedure as in the preparation of A4 gave M1 (73%): $^1$H NMR (300 MHz, CDCl$_3$) δ 7.35-7.28 (m, 2H), 7.10-7.02 (m, 1H), 6.89-6.82 (m, 1H), 3.82 (s, 3H), 0.29 (s, 9 H).

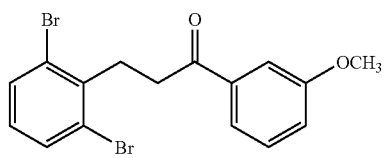

M2

3-(2,6-Dibromo-phenyl)-1-(3-methoxy-phenyl)-propan-1-one

Replacing I1 with M1 and following the same procedure as in the preparation of I2 gave M2 (42%): $^1$H NMR (300 MHz, CDCl$_3$) δ 7.61-7.50 (m, 4H), 7.37 (t, J=7.9 Hz, 1H), 7.12 (dd, J=8.0, 2.3 Hz, 1H), 6.95 (t, J=7.9 Hz, 1H), 3.86 (s, 3H), 3.48-3.39 (m, 2H), 3.29-3.20 (m, 2H); MS (ES) m/z: 421 (M+Na$^+$).

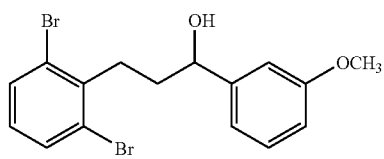

M3

3-(2,6-Dibromo-phenyl)-1-(3-methoxy-phenyl)-propan-1-ol

Replacing I2 with M2 and following the same procedure as in the preparation of I3 gave M3 (78%): $^1$H NMR (300 MHz, CDCl$_3$) δ 7.48 (d, J=8.0 Hz, 2H), 7.27-7.24 (m, 1H), 7.00-6.97 (m, 2H), 6.92-6.81 (m, 2 H), 4.85-4.78 (m, 1H), 3.83 (s, 3H), 3.21-3.10 (m, 1H), 3.04-2.91 (m, 1H), 2.09-1.98 (m, 2H), 1.94 (d, J=3.8 Hz, 1H); MS (ES) m/z: 423 (M+Na$^+$).

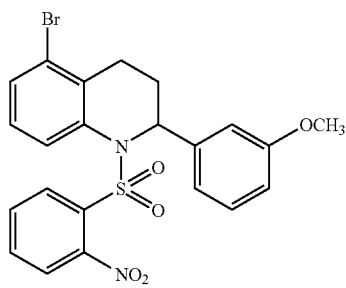

M4

N-[3-(2,6-Dibromo-phenyl)-1-(3-methoxy-phenyl)-propyl]-2-nitro-benzenesulfonamide Replacing I3 with M3 and following the same procedure as in the preparation of I4 gave the crude amine intermediate.

Replacing I4 with the above amine intermediate and following the same procedure as in the preparation of I5 gave M4 (71%): $^1$H NMR (300 MHz, CDCl$_3$) δ 7.23-7.18 (m, 2H), 7.57-7.38 (m, 4H), 6.99 (t, J=7.9 Hz, 1H), 6.89 (t, J=8.0 Hz, 1H), 6.73 (d, J=7.7 Hz, 1H), 6.64 (s, 1H), 6.59 (dd, J=8.0, 2.3 Hz, 1H), 5.90 (d, J=7.9 Hz, 1H), 4.61 (m, 1H), 3.66 (s, 3H), 3.21-3.09 (m, 1H), 2.91-2.79 (m, 1H), 2.11-1.93 (m, 2H); MS (ES) m/z: 607 (M+Na$^+$).

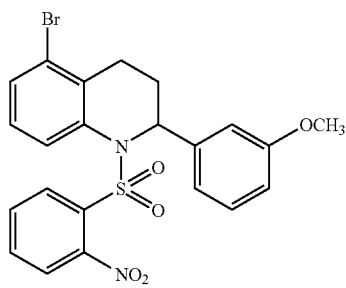

M5

5-Bromo-2-(3-methoxy-phenyl)-1-(2-nitro-benzenesulfonyl)-1,2,3,4-tetrahydro-quinoline Replacing I5 with the M4 and following the same procedure as in the preparation of I6 gave M5 (77%): $^1$H NMR (300 MHz, CDCl$_3$) δ 7.82 (d, J=8.0 Hz, 1H), 7.72-7.50 (m, 4H), 7.41 (d, J=8.1 Hz, 1H), 7.22-7.09 (m, 2H), 6.89-6.80 (m, 2H), 6.75 (d, J=8.2 Hz, 1H), 5.59 (t, J=6.5 Hz, 1 H), 3.74 (s, 3H), 2.78-2.62 (m, 1H), 2.44-2.27 (m, 2H), 2.11-1.98 (m, 1H); MS (ES) m/z: 503 (M).

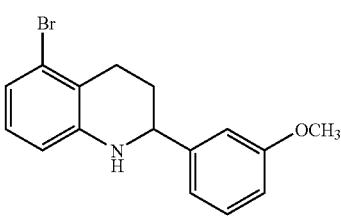

M6

5-Bromo-2-(3-methoxy-phenyl)-1,2,3,4-tetrahydro-quinoline

Replacing I6 with the M5 and following the same procedure as in the preparation of I7 gave M6 (87%): $^1$H NMR (300 MHz, CDCl$_3$) δ 7.30-7.22 (m, 1H), 6.99-6.71 (m, 5H), 6.48 (d, J=7.6 Hz, 1H), 4.36 (d, J=8.2 Hz, 1H), 4.13 (s, 1H), 3.81 (s, 3H), 2.89-2.74 (m, 2H), 2.12-2.11 (m, 1H), 2.05-1.94 (m, 1H); MS (ES) m/z: 318 (M).

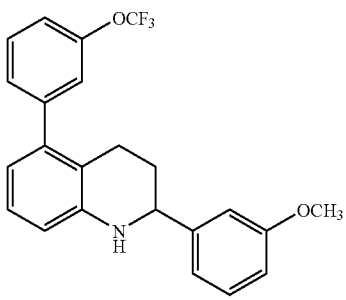

M7

2-(3-Methoxy-phenyl)-5-(3-trifluoromethoxy-phenyl)-1,2,3,4-tetrahydro-quinoline

Replacing I7 with the M6 and following the same procedure as in the preparation of I8 gave M7 (81%): $^1$H NMR (300 MHz, CDCl$_3$) δ 7.40 (t, J=7.8 Hz, 1H), 7.34-7.26 (m, 2H), 7.21-7.13 (m, 2H), 7.07 (t, J=7.7 Hz, 1H), 7.00-6.95 (m, 2H), 6.83 (dd, J=8.1 Hz, 1H), 6.59 (d, J=7.8 Hz, 2 H), 4.45 (d, J=9.2, 3.3 Hz, 1H), 4.19 (brs, 1H), 3.81 (s, 3H), 2.83-2.70 (m, 1H), 2.55 (dt, J=16.6, 4.7 Hz, 1H), 2.12-2.01 (m, 1H), 1.98-1.81 (m, 1H); MS (ES) m/z: 400 (M+H$^+$).

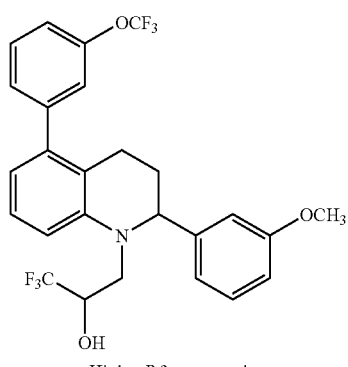

Cmpd 25

Higher Rf compound 1,1,1-Trifluoro-3-[2-(3-methoxy-phenyl)-5-(3-trifluoromethoxy-phenyl)-3,4-dihydro-2H-quinolin-1-yl]-propan-2-ol Replacing I8 with M7 and following the same procedure as in the preparation of compound 17 and 18 gave compound 25 and 26. Spectra of compound 25 are as follows: $^1$H NMR (300 MHz, CDCl$_3$) δ 7.41-7.31 (m, 1 H), 7.26-7.11 (m, 5H), 6.85-6.70 (m, 4H), 6.65 (d, J=7.4 Hz, 1H), 4.81 (t, J=4.3 Hz, 1H), 4.40 (m, 1H), 3.88 (d, J=16.4 Hz, 1H), 3.78 (s, 3 H), 3.34 (dd, J=15.5, 9.8 Hz, 1H), 2.50-2.40 (m, 3H), 2.20-1.91 (m, 2 H); MS (ES) m/z: 512 (M+H$^+$).

Example 26

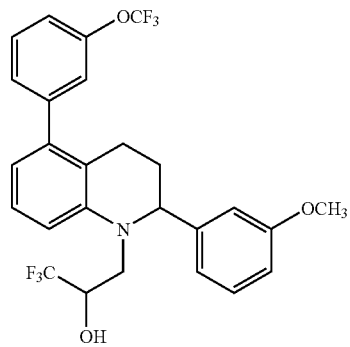

Compound 26

(Lower Rf Compound)

1,1,1-Trifluoro-3-[2-(3-methoxy-phenyl)-5-(3-trifluoromethoxy-phenyl)-3,4-dihydro-2H-quinolin-1-yl]-propan-2-ol Spectra of compound 26 are as follows: $^1$H NMR (400 MHz, CDCl$_3$) δ 7.36 (t, J=7.8 Hz, 1H), 7.29-7.11 (m, 5H), 6.87 (d, J=8.4 Hz, 1H), 6.84-6.78 (m, 2H), 6.72 (s, 1H), 6.66 (d, J=7.5 Hz, 1H), 4.56 (t, J=4.3 Hz, 1 H), 4.33 (m, 1H), 3.78-3.73 (m, 4H), 3.58 (dd, J=15.6, 5.0 Hz, 1H), 2.43 (t, J=4.6 Hz, 1H), 2.25 (d, J=4.6 Hz, 1H), 2.32-2.04 (m, 1H), 2.00-1.92 (m, 1H); MS (ES) m/z: 512 (M+H$^+$).

Example 27

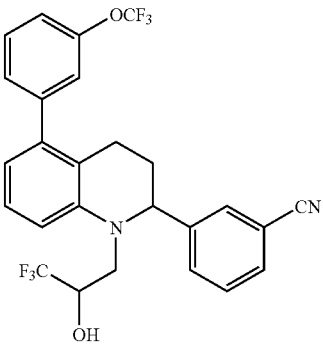

Cmpd 27

(Higher Rf compound)

3-[1-(3,3,3-Trifluoro-2-hydroxy-propyl)-5-(3-trifluoromethoxy-phenyl)-1,2,3,4-tetrahydro-quinolin-2-yl]-benzonitrile

Scheme N
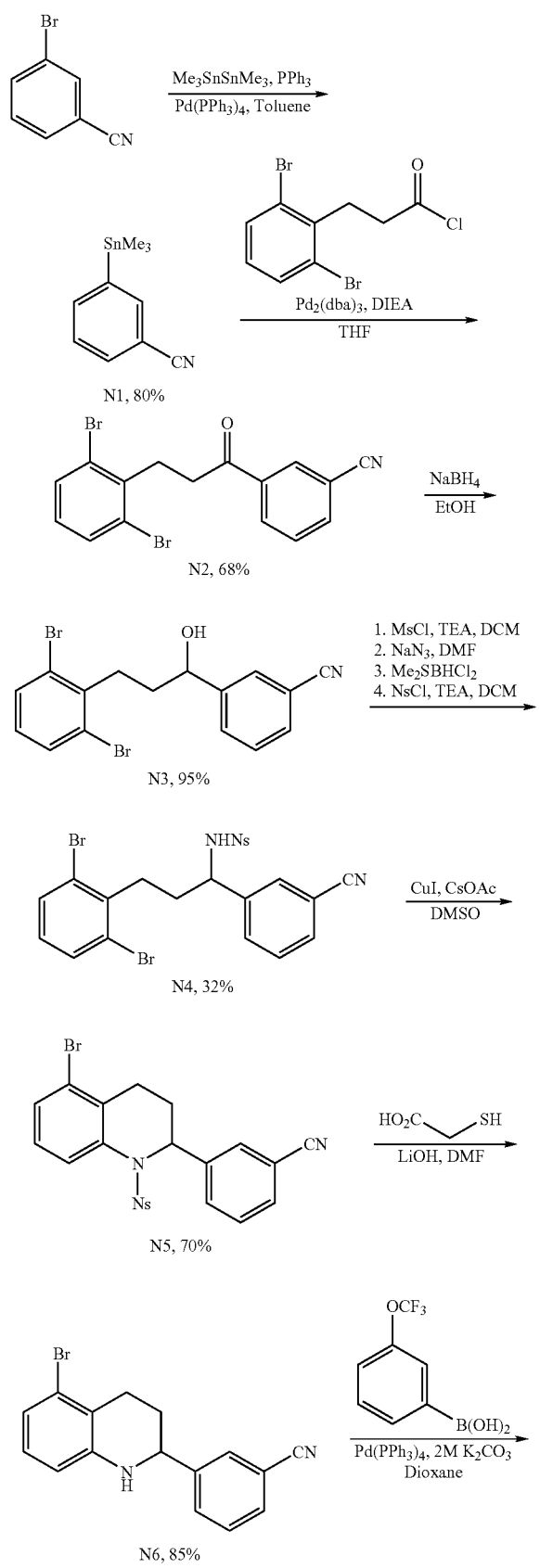
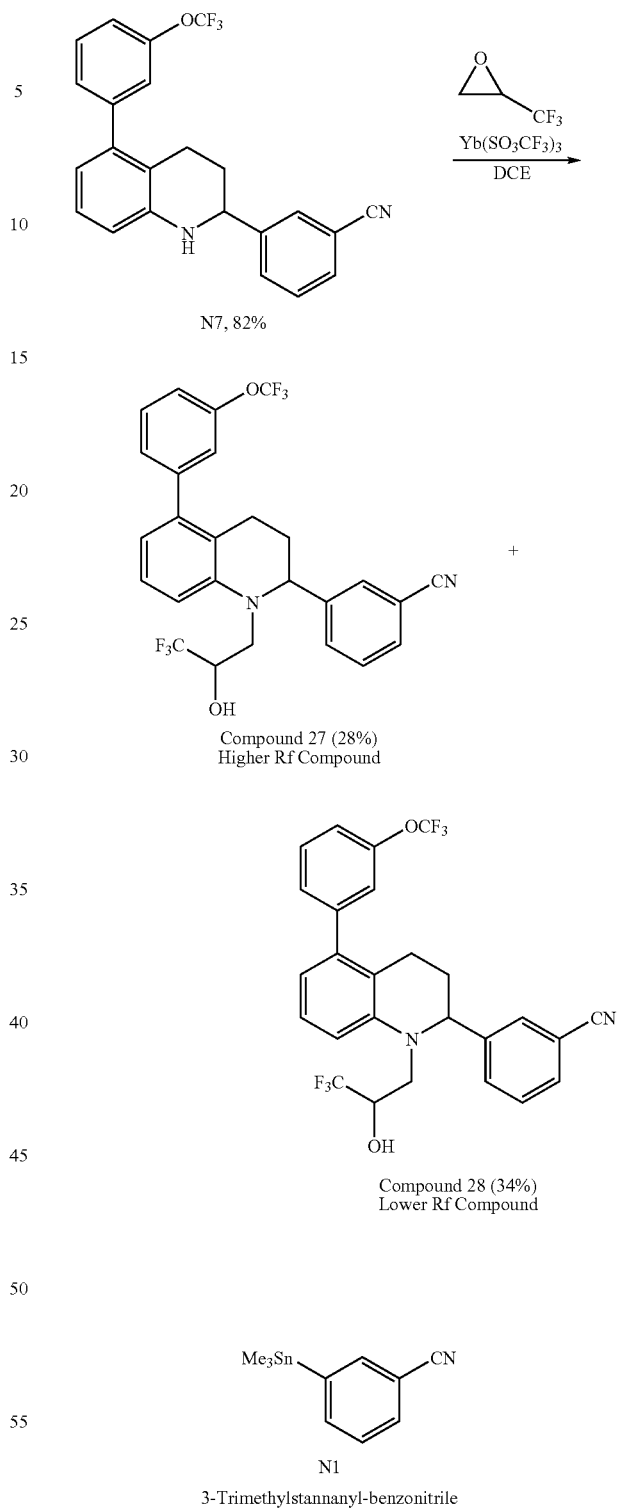
Replacing 1-bromo-3-(1,1,2,2-tetrafluoro-ethoxy)-benzene with 1-bromo-3-cyano-benzene and following the same procedure as in the preparation of A4 gave N1 (80%): $^1$H NMR (300 MHz, CDCl$_3$) δ 7.75 (s, 1 H), 7.70 (d, J=7.3 Hz, 1H), 7.58 (bd, J=7.0 Hz, 1H), 7.41 (t, J=7.6 Hz, 1 H), 0.34 (s, 9H).

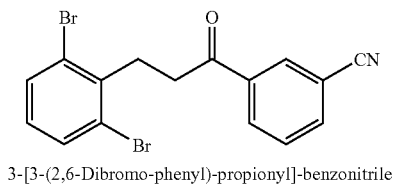

3-[3-(2,6-Dibromo-phenyl)-propionyl]-benzonitrile

Replacing I1 with N1 and following the same procedure as in the preparation of I2 gave N2 (68%): $^1$H NMR (300 MHz, CDCl$_3$) δ 8.27 (s, 1H), 8.22 (d, J=8.0 Hz, 1H), 7.85 (d, J=7.7 Hz, 1H), 7.61 (d, J=7.8 Hz, 1H), 7.54 (d, J=8.0 Hz, 2H), 6.97 (t, J=8.0 Hz, 1H), 3.49-3.40 (m, 2H), 3.29-3.21 (m, 2H); MS (ES) m/z: 416 (M+H$^+$).

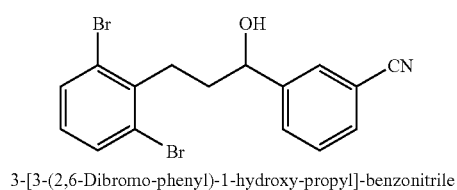

3-[3-(2,6-Dibromo-phenyl)-1-hydroxy-propyl]-benzonitrile

Replacing I2 with N2 and following the same procedure as in the preparation of I3 gave N3 (95%): $^1$H NMR (300 MHz, CDCl$_3$) δ 7.73 (s, 1H), 7.66 (d, J=7.7 Hz, 1H), 7.58 (d, J=7.7 Hz, 1H), 7.48 (bd, J=7.9 Hz, 3H), 6.91 (t, J=8.0 Hz, 1H), 4.89 (dd, J=10.2, 6.4 Hz, 1H), 3.19-2.93 (m, 2H), 2.08 (d, J=3.9 Hz, 1H), 2.08-1.98 (m, 2H).

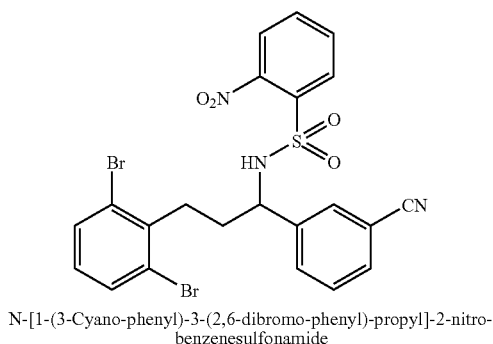

N-[1-(3-Cyano-phenyl)-3-(2,6-dibromo-phenyl)-propyl]-2-nitro-benzenesulfonamide

Replacing M3 with N3 and following the same procedure as in the preparation of M4 gave N4 (32% for 4 steps): $^1$H NMR (300 MHz, CDCl$_3$) δ 7.79 (d, J=8.3 Hz, 1H), 7.71 (d, J=7.8 Hz, 1H), 7.68-7.61 (m, 1H), 7.55-7.40 (m, 6H), 7.34-7.28 (m, 1H), 6.91 (t, J=8.0 Hz, 1H), 5.95 (d, J=7.7 Hz, 1H), 4.70 (dd, J=14.9, 7.9 Hz, 1H), 3.11 (td, J=12.4, 4.9 Hz, 1H), 2.82 (td, J=12.4, 5.6 Hz, 1H), 2.14-1.94 (m, 2H); MS (ES) m/z: 578 (M−H$^+$).

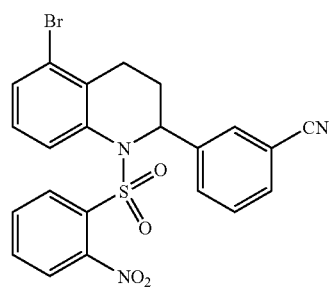

3-[5-Bromo-1-(2-nitro-benzenesulfonyl)-1,2,3,4-tetrahydro-quinolin-2-yl]-benzonitrile Replacing M4 with N4 and following the same procedure as in the preparation of M5 gave N5 (70%): $^1$H NMR (300 MHz, CDCl$_3$) δ 7.85 (d, J=8.6 Hz, 1H), 7.77-7.69 (m, 1H), 7.56-7.50 (m, 6H), 7.48-7.40 (m, 2H), 7.22-7.15 (m, 1H), 5.64 (t, J=6.5 Hz, 1H), 2.79-2.68 (m, 1H), 2.55-2.41 (m, 1H), 2.37-2.21 (m, 2H), 2.02-1.89 (m, 1H); MS (ES) m/z: 520 (M+Na$^+$).

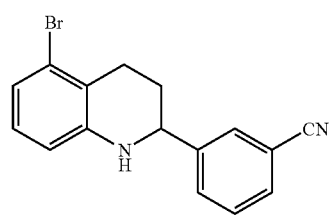

3-(5-Bromo-1,2,3,4-tetrahydro-quinolin-2-yl)-benzonitrile

Replacing M5 with N5 and following the same procedure as in the preparation of M6 gave N6 (85%): $^1$H NMR (300 MHz, CDCl$_3$) δ 7.67 (s, 1 H), 7.63-7.57 (m, 2H), 7.46 (t, J=7.7 Hz, 1H), 6.99-6.86 (m, 2H), 6.52 (d, J=7.6 Hz, 1H), 4.45 (bd, J=6.7 Hz, 1H), 4.13 (brs, 1H), 2.88-2.79 (m, 2H), 2.22-2.12 (m, 1H), 2.05-1.82 (m, 1H); MS (ES) m/z: 315 (M+2)

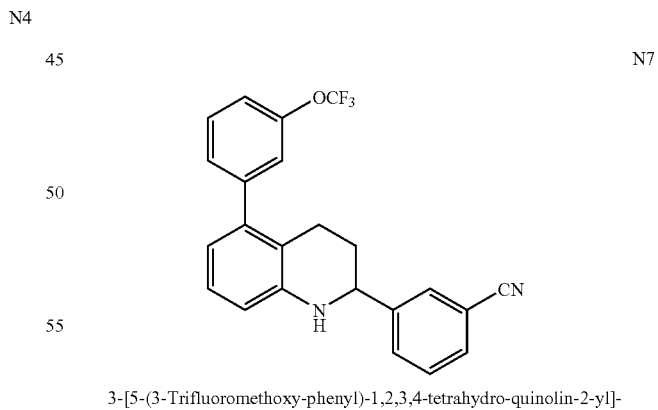

3-[5-(3-Trifluoromethoxy-phenyl)-1,2,3,4-tetrahydro-quinolin-2-yl]-benzonitrile

Replacing M6 with N6 and following the same procedure as in the preparation of M7 gave N7 (82%): $^1$H NMR (300 MHz, CDCl$_3$) δ 7.71 (s, 1 H), 7.69-7.58 (m, 2H), 7.50-7.39 (m, 2H), 7.28-7.22 (m, 1H), 7.20-7.08 (m, 3H), 6.63 (bd, J=7.4 Hz, 2H), 4.54 (bd, J=6.3 Hz, 1H), 4.19 (brs, 1H), 2.81-2.69 (m, 1H), 2.50 (dt, J=16.7, 5.2 Hz, 1H), 2.11-2.01 (m, 1H), 1.95-1.81 (m, 1H); MS (ES) m/z: 395 (M+H$^+$).

Cmpd 27

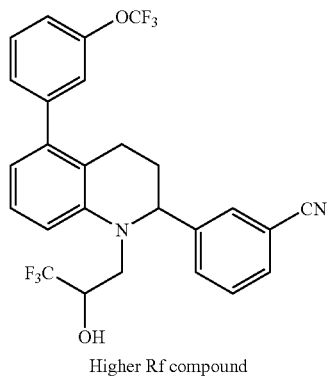

Higher Rf compound

3-[1-(3,3,3-Trifluoro-2-hydroxy-propyl)-5-(3-trifluoromethoxy-phenyl)-1,2,3,4-tetrahydro-quinolin-2-yl]-benzonitrile Replacing I8 with N7 and following the same procedure as in the preparation of compound 17 and 18 gave compound 27 and 28. Spectra of compound 27 are as follows: $^1$H NMR (300 MHz, CDCl$_3$) δ 7.61-7.56 (m, 1 H), 7.50-7.43 (m, 3H), 7.38 (t, J=7.9 Hz, 1H), 7.25-7.11 (m, 4H), 6.73 (d, J=8.4 Hz, 1H), 6.69 (d, J=7.5 Hz, 1H), 4.96 (t, J=4.3 Hz, 1H), 4.47 (m, 1H), 3.96 (d, J=15.5 Hz, 1H), 3.21 (dd, J=15.7, 9.8 Hz, 1H), 2.55-2.45 (m, 1H), 2.41 (d, J=4.0 Hz, 1H), 2.36-2.10 (m, 2H), 2.00-1.90 (m, 1H); MS (ES) m/z: 507 (M+H$^+$).

Example 28

Compound 28

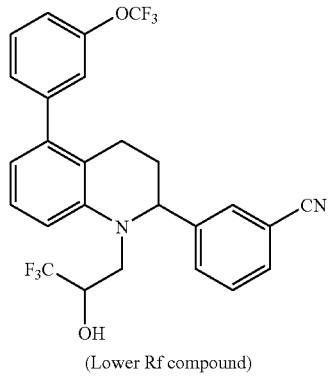

(Lower Rf compound)

3-[1-(3,3,3-Trifluoro-2-hydroxy-propyl)-5-(3-trifluoromethoxy-phenyl)-1,2,3,4-tetrahydro-quinolin-2-yl]-benzonitrile Spectra of compound 28 are as follows: $^1$H NMR (300 MHz, CDCl$_3$) δ 7.61-7.58 (m, 1H), 7.49-7.35 (m, 4H), 7.23-7.10 (m, 4H), 6.91 (d, J=8.3 Hz, 1H), 6.70 (d, J=7.2 Hz, 1H), 4.64 (t, J=4.0 Hz, 1H), 4.35 (m, 1 H), 3.83 (dd, J=15.7, 6.6 Hz, 1H), 3.45 (dd, J=15.8, 5.7 Hz, 1H), 2.50-2.40 (m, 1H), 2.36-2.21 (m, 2H), 2.20-2.06 (m, 1H), 1.99-1.90 (m, 1 H); MS (ES) m/z: 507 (M+H$^+$).

Example 29

Cmpd 29

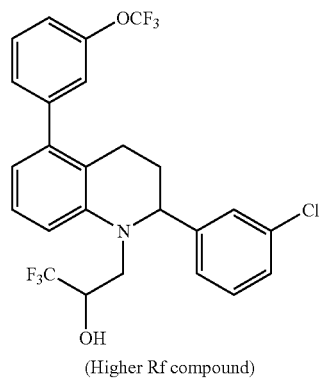

(Higher Rf compound)

3-[2-(3-Chloro-phenyl)-5-(3-trifluoromethoxy-phenyl)-3,4-dihydro-2H-quinolin-1-yl]-1,1,1-trifluoro-propan-2-ol Scheme O

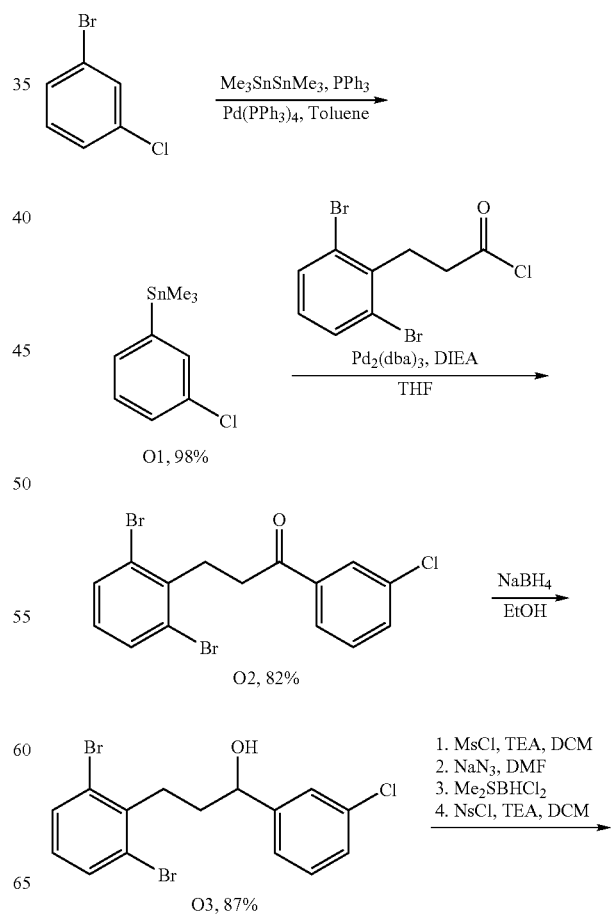

-continued

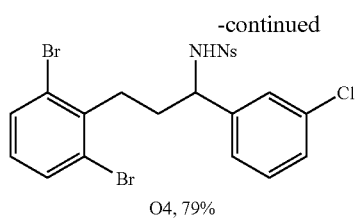

O4, 79%

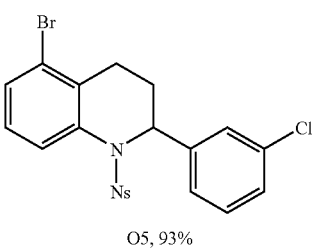

O5, 93%

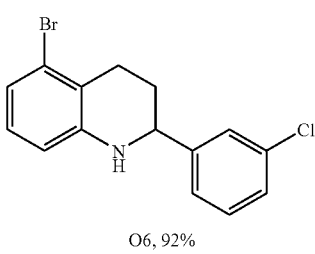

O6, 92%

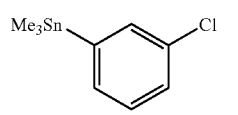

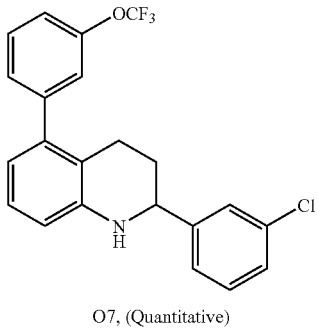

O7, (Quantitative)

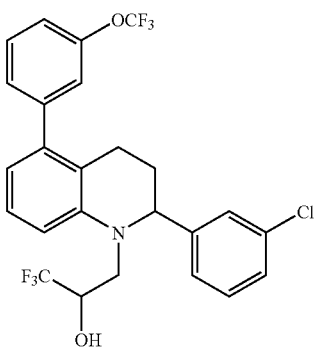

Compound 29 (21%)
Higher Rf Compound

-continued

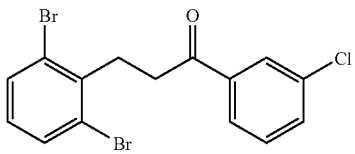

Compound 30 (9%)
Lower Rf Compound

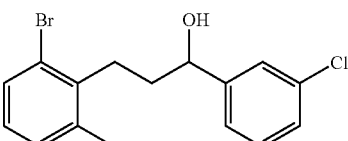

O1

(3-Chloro-phenyl)-trimethyl-stannane

Replacing 1-bromo-3-(1,1,2,2-tetrafluoro-ethoxy)-benzene with 1-bromo-3-chloro-benzene and following the same procedure as in the preparation of A4 gave O1 (98%): $^1$H NMR (300 MHz, CDCl$_3$) δ 7.43 (s, 1 H), 7.35-7.33 (m, 1H), 7.29-7.25 (m, 2H), 0.30 (s, 9H).

O2

1-(3-Chloro-phenyl)-3-(2,6-dibromo-phenyl)-propan-1-one

Replacing N1 with O1 and following the same procedure as in the preparation of N2 gave O2 (82%): $^1$H NMR (300 MHz, CDCl$_3$) δ 7.97 (s, 1 H), 7.88 (d, J=9.0 Hz, 1H), 7.54 (bd, J=8.0 Hz, 3H), 7.41 (t, J=7.8 Hz, 1 H), 6.96 (t, J=8.0 Hz, 1H), 3.48-3.39 (m, 2H), 3.26-3.19 (m, 2H); MS (ES) m/z: 425 (M+Na$^+$).

O3

1-(3-Chloro-phenyl)-3-(2,6-dibromo-phenyl)-propan-1-ol

Replacing N2 with O2 and following the same procedure as in the preparation of N3 gave O3 (87%): $^1$H NMR (300 MHz, CDCl$_3$) δ 7.49 (d, J=8.0 Hz, 1H), 7.42 (s, 1H), 7.31-7.25 (m, 3H), 6.89 (t, J=8.0 Hz, 1H), 4.82 (dd, J=10.8, 5.8 Hz, 1H), 3.20-3.09 (m, 1H), 3.03-2.91 (m, 1H), 2.08-1.95 (m, 3H); MS (ES) m/z: 427 (M+Na$^+$).

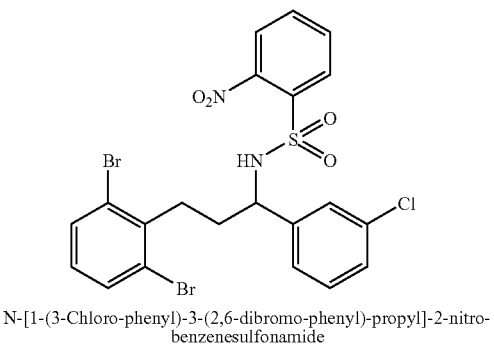

N-[1-(3-Chloro-phenyl)-3-(2,6-dibromo-phenyl)-propyl]-2-nitro-benzenesulfonamide Replacing N3 with O3 and following the same procedure as in the preparation of N4 gave O4 (79% for 4 steps): $^1$H NMR (300 MHz, CDCl$_3$) δ 7.75 (d, J=7.8 Hz, 1H), 7.68 (d, J=7.8 Hz, 1H), 7.57 (t, J=7.8 Hz, 1H), 7.50-7.43 (m, 3H), 7.11-7.02 (m, 4H), 6.90 (t, J=8.0 Hz, 1H), 5.92 (d, J=8.7 Hz, 1H), 4.64 (dd, J=15.3, 8.5 Hz, 1H), 3.15 (td, J=12.5, 4.8 Hz, 1H), 2.85 (td, J=12.5, 5.2 Hz, 1H), 2.12-1.92 (m, 2H); MS (ES) m/z: 587 (M−H$^+$).

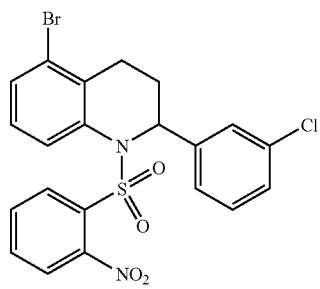

5-Bromo-2-(3-chloro-phenyl)-1-(2-nitro-benzenesulfonyl)-1,2,3,4-tetrahydro-quinoline Replacing N4 with O4 and following the same procedure as in the preparation of N5 gave O5 (93%): $^1$H NMR (300 MHz, CDCl$_3$) δ 7.84 (d, J=8.0 Hz, 1H), 7.70 (bt, J=7.3 Hz, 1H), 7.64-7.49 (m, 3H), 7.43 (d, J=8.1 Hz, 1H), 7.24-7.52 (m, 5H), 5.58 (t, J=6.8 Hz, 1H), 2.78-2.65 (m, 1 H), 2.48-2.22 (m, 2H), 2.06-1.90 (m, 1H); MS (ES) m/z: 509 (M+H$^+$).

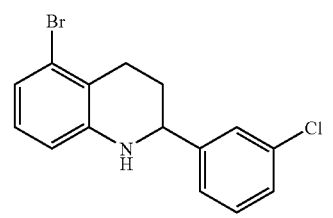

5-Bromo-2-(3-chloro-phenyl)-1,2,3,4-tetrahydro-quinoline

Replacing N5 with O5 and following the same procedure as in the preparation of N6 gave O6 (92%): $^1$H NMR (300 MHz, CDCl$_3$) δ 7.37 (s, 1 H), 7.30-7.20 (m, 3H), 6.95-6.82 (m, 2H), 6.53 (d, J=8.8 Hz, 1H), 4.37 (d, J=6.4 Hz, 1H), 4.11 (s, 1H), 2.86-2.79 (m, 2H), 2.20-2.10 (m, 1H), 2.03-1.89 (m, 1H); MS (ES) m/z: 324 (M+H$^+$).

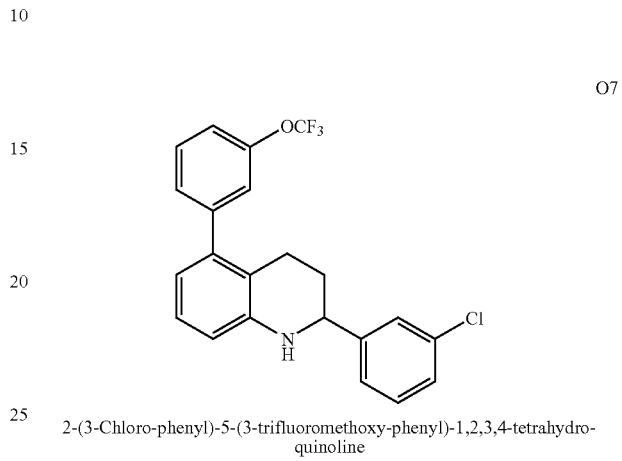

2-(3-Chloro-phenyl)-5-(3-trifluoromethoxy-phenyl)-1,2,3,4-tetrahydro-quinoline

Replacing N6 with O6 and following the same procedure as in the preparation of N7 gave O7 (Quantitative): $^1$H NMR (400 MHz, CDCl$_3$) δ 7.44-7.38 (s, 2H), 7.37-7.24 (m, 4H), 7.21-7.16 (m, 2H), 7.09 (t, J=7.8 Hz, 1H), 6.61 (d, J=7.7 Hz, 2H), 4.47 (dd, J=8.4, 3.4 Hz, 1H), 4.18 (s, 1 H), 2.80-2.71 (m, 1H), 2.53 (dt, J=16.4, 4.9 Hz, 1H), 2.10-2.01 (m, 1 H), 1.93-1.81 (m, 1H); MS (ES) m/z: 404 (M+H$^+$).

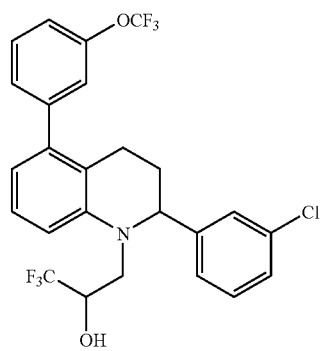

Higher Rf compound

3-[2-(3-Chloro-phenyl)-5-(3-trifluoromethoxy-phenyl)-3,4-dihydro-2H-quinolin-1-yl]-1,1,1-trifluoro-propan-2-ol Replacing I8 with O7 and following the same procedure as in the preparation of compound 17 and 18 gave compound 29 and 30. Spectra of compound 29 are as follows: $^1$H NMR (300 MHz, CDCl$_3$) δ 7.37 (t, J=7.8 Hz, 1H), 7.27-7.05 (m, 8H), 6.72 (d, J=8.2 Hz, 1H), 6.66 (d, J=7.5 Hz, 1H), 4.87 (t, J=4.6 Hz, 1H), 4.43 (m, 1H), 3.92 (d, J=15.5 Hz, 1H), 3.28 (dd, J=15.6, 9.7 Hz, 1H), 2.54-2.30 (m, 3H), 2.19-2.07 (m, 1H), 2.01-1.90 (m, 1H); MS (ES) m/z: 516 (M+H⁺).

Example 30

Compound 30

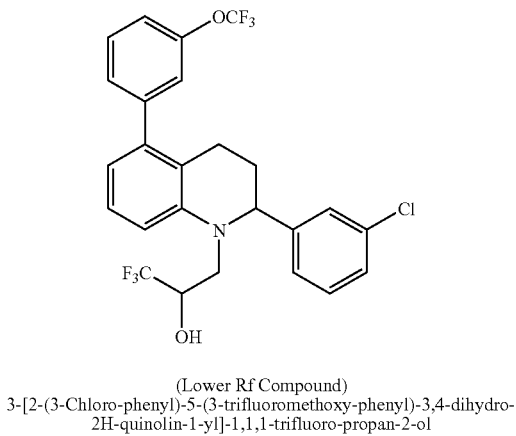

(Lower Rf Compound)
3-[2-(3-Chloro-phenyl)-5-(3-trifluoromethoxy-phenyl)-3,4-dihydro-2H-quinolin-1-yl]-1,1,1-trifluoro-propan-2-ol Spectra of compound 30 are as follows: ¹H NMR (300 MHz, CDCl₃) δ 7.37 (t, J=7.8 Hz, 1H), 7.29-7.02 (m, 8H), 6.90 (d, J=8.2 Hz, 1H), 6.68 (d, J=7.5 Hz, 1H), 4.57 (t, J=4.5 Hz, 1H), 4.33 (m, 1H), 3.81 (dd, J=15.8, 6.6 Hz, 1H), 3.49 (dd, J=15.7, 5.5 Hz, 1H), 2.45-2.36 (m, 2H), 2.24 (d, J=5.0 Hz, 1H), 2.18-2.03 (m, 1H), 2.00-1.90 (m, 1H); MS (ES) m/z: 516 (M+H⁺).

Example 31

Cmpd 31

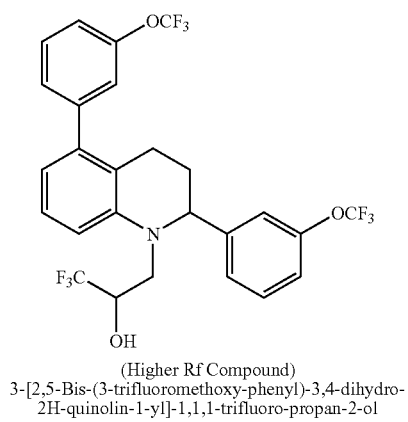

(Higher Rf Compound)
3-[2,5-Bis-(3-trifluoromethoxy-phenyl)-3,4-dihydro-2H-quinolin-1-yl]-1,1,1-trifluoro-propan-2-ol Scheme P

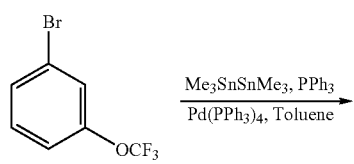

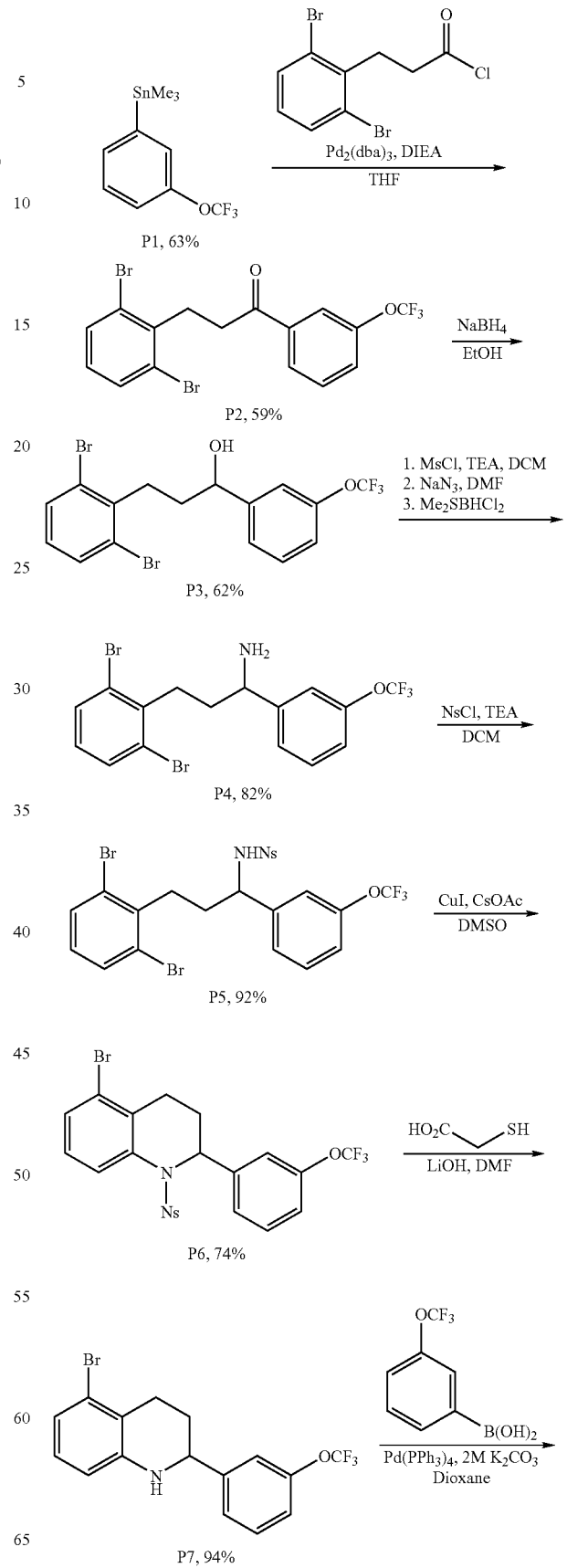

-continued

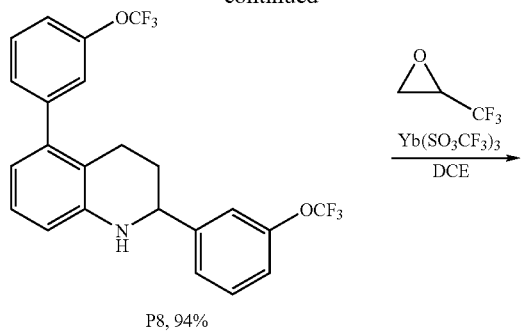

P8, 94%

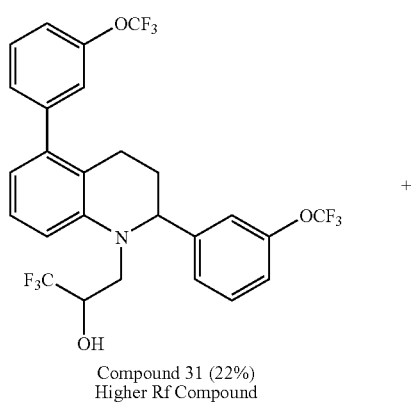

Compound 31 (22%)
Higher Rf Compound

+

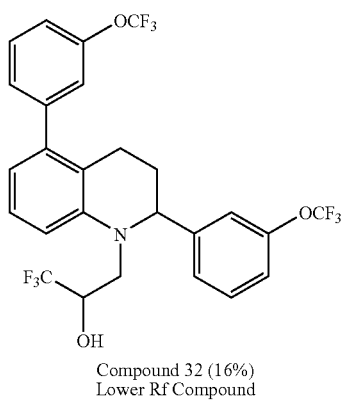

Compound 32 (16%)
Lower Rf Compound

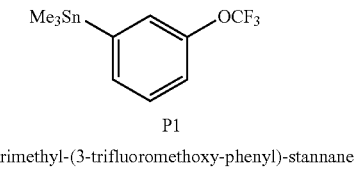

P1
Trimethyl-(3-trifluoromethoxy-phenyl)-stannane

Replacing 1-bromo-3-(1,1,2,2-tetrafluoro-ethoxy)-benzene with 1-bromo-3-trifluoromethoxy-benzene and following the same procedure as in the preparation of A4 gave P1 (63%): $^1$H NMR (300 MHz, CDCl$_3$) δ 7.42-7.29 (m, 1H), 7.19-7.11 (m, 1H), 0.31 (s, 9H).

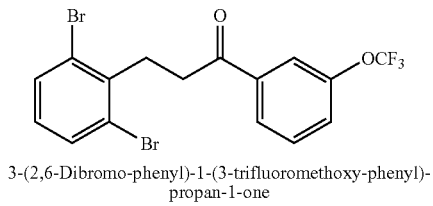

3-(2,6-Dibromo-phenyl)-1-(3-trifluoromethoxy-phenyl)-propan-1-one

Replacing I1 with P1 and following the same procedure as in the preparation of I2 gave P2 (59%): $^1$H NMR (300 MHz, CDCl$_3$) δ 7.93 (d, J=7.7 Hz, 1H), 7.85 (s, 1H), 7.58-7.49 (m, 3H), 7.43 (d, J=8.9 Hz, 1H), 6.96 (t, J=8.0 Hz, 1H), 3.48-3.39 (m, 2H), 3.29-3.20 (m, 2H); MS (ES) m/z: 453 (M+H$^+$).

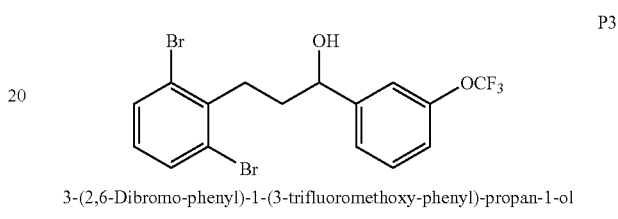

3-(2,6-Dibromo-phenyl)-1-(3-trifluoromethoxy-phenyl)-propan-1-ol

Replacing I2 with P2 and following the same procedure as in the preparation of I3 gave P3 (62%): $^1$H NMR (300 MHz, CDCl$_3$) δ 7.48 (d, J=8.0 Hz, 2H), 7.41-7.29 (m, 3H), 7.18-7.05 (m, 1H), 6.89 (t, J=8.3 Hz, 1H), 4.87 (t, J=6.3 Hz, 1H), 3.19-3.08 (m, 1H), 3.01-2.90 (m, 1H), 2.09-1.98 (m, 2H); MS (ES) m/z: 477 (M+Na$^+$).

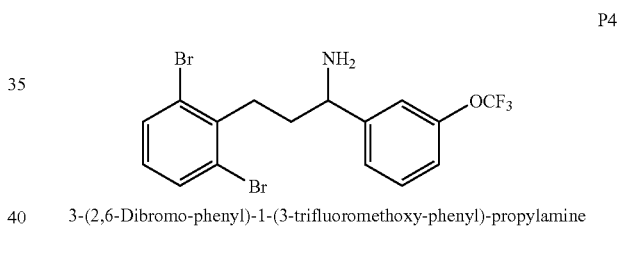

3-(2,6-Dibromo-phenyl)-1-(3-trifluoromethoxy-phenyl)-propylamine

Replacing I3 with P3 and following the same procedure as in the preparation of I4 gave P4 (82%): $^1$H NMR (300 MHz, CDCl$_3$) δ 7.47 (d, J=8.0 Hz, 2H), 7.41-7.28 (m, 3H), 7.15-7.08 (m, 2H), 6.88 (t, J=8.0 Hz, 1H), 4.09 (t, J=6.6 Hz, 1H), 3.09-2.98 (m, 1H), 2.90-2.79 (m, 1H), 1.98-1.88 (m, 2H); MS (ES) m/z: 454 (M+H$^+$).

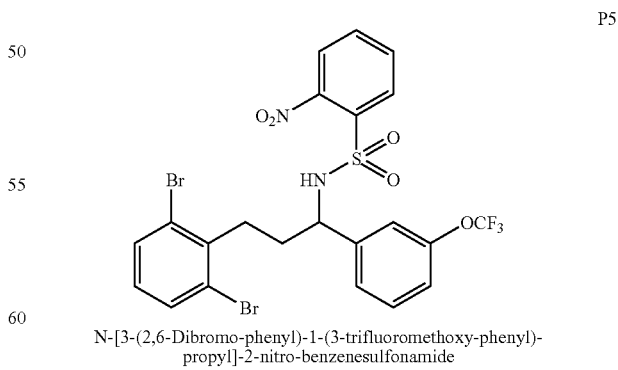

N-[3-(2,6-Dibromo-phenyl)-1-(3-trifluoromethoxy-phenyl)-propyl]-2-nitro-benzenesulfonamide Replacing I4 with P4 and following the same procedure as in the preparation of I5 gave P5 (92%): $^1$H NMR (300 MHz, CDCl$_3$) δ 7.73 (d, J=8.0 Hz, 1H), 7.66 (d, J=7.8 Hz, 1H), 7.54 (bt, J=8.4 Hz, 1H), 7.50-7.38 (m, 3H), 7.14 (m, 2H), 7.01 (m, 1H), 6.98-6.88 (m, 2H), 5.95 (d, J=8.9 Hz, 1H), 4.69 (dd, J=15.8, 7.7 Hz, 1H), 3.14 (td, J=12.4, 4.5 Hz, 1H), 2.83 (td, J=12.7, 5.2 Hz, 1H), 2.16-1.92 (m, 2H); MS (ES) m/z: 637 (M−H$^+$).

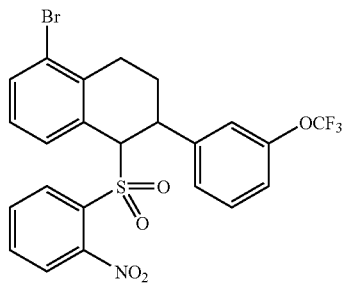

P6

5-Bromo-1-(2-nitro-benzenesulfonyl)-2-(3-trifluoromethoxy-phenyl)-1,2,3,4-tetrahydro-quinoline Replacing I5 with P5 and following the same procedure as in the preparation of I6 gave P6 (74%): $^1$H NMR (400 MHz, CDCl$_3$) δ 7.81 (d, J=8.1 Hz, 1H), 7.72-7.68 (m, 1H), 7.63-7.52 ((m, 3H), 7.43 (d, 8.0 Hz, 1H), 7.32 (t, 7.9 Hz, 1H), 7.25-7.22 (m, 1H), 7.19-7.07 (m, 3H), 5.63 (t, 7.0 Hz, 1H), 2.74-2.66 (m, 1H), 2.47-2.40, (m, 1H), 2.35-2.27 (m, 1H), 2.05-1.95 (m, 1H); MS (ES) m/z: 557 (M).

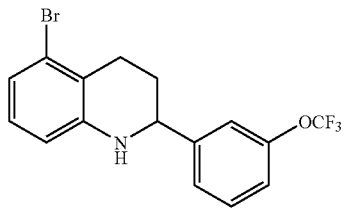

P7

5-Bromo-2-(3-trifluoromethoxy-phenyl)-1,2,3,4-tetrahydro-quinoline

Replacing I6 with P6 and following the same procedure as in the preparation of I7 gave P7 (88%): $^1$H NMR (300 MHz, CDCl$_3$) δ 7.41-7.10 (m, 4H), 6.98-6.82 (m, 2H), 6.51 (d, J=7.8 Hz, 1H), 4.41 (dd, J=9.4, 3.0 Hz, 1H), 4.13 (brs, 1H), 2.89-2.71 (m, 2H), 2.21-2.10 (m, 1H), 2.05-1.90 (m, 1H); MS (ES) m/z: 372 (M).

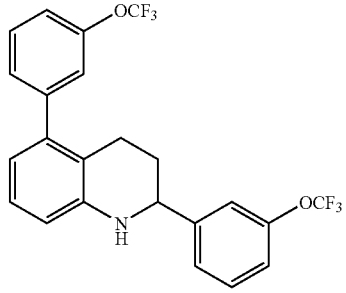

P8

2,5-Bis-(3-trifluoromethoxy-phenyl)-1,2,3,4-tetrahydro-quinoline

Replacing I7 with P7 and following the same procedure as in the preparation of I8 gave P8 (94%): $^1$H NMR (300 MHz, CDCl$_3$) δ 7.43-7.21 (m, 5H), 7.20-7.08 (m, 4H), 6.62 (d, J=7.7 Hz, 2H), 4.51 (dd, J=8.9, 3.4 Hz, 1H), 4.20 (brs, 1H), 2.82-2.70 (m, 1H), 2.52 (dt, J=16.3, 4.9 Hz, 1H), 2.11-2.01 (m, 1H), 1.96-1.80 (m, 1H); MS (ES) m/z: 454 (M+H$^+$).

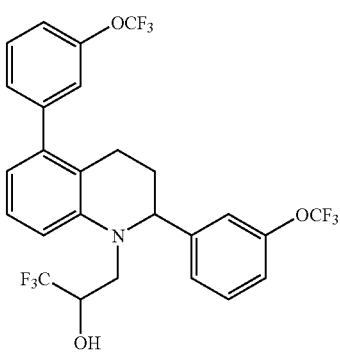

Cmpd 31

Higher Rf compound
3-[2,5-Bis-(3-trifluoromethoxy-phenyl)-3,4-dihydro-2H-quinolin-1-yl]-1,1,1-trifluoro-propan-2-ol Replacing I8 with P7 and following the same procedure as in the preparation of compound 17 and 18 gave compound 31 and 32. Spectra of compound 31 are as follows: $^1$H NMR (300 MHz, CDCl$_3$) δ 7.37 (m, 2H), 7.24-7.10 (m, 6H), 7.04 (s, 1H), 6.73 (d, J=8.3 Hz, 1H), 6.67 (d, J=7.5 Hz, 1H), 4.90 (t, J=4.3 Hz, 1H), 4.43 (m, 1H), 3.91 (d, J=15.2 Hz, 1H), 3.29 (dd, J=15.6, 9.6 Hz, 1H), 2.53-2.29 (m, 3H), 2.21-2.08 (m, 1H), 2.01-1.90 (m, 1H); MS (ES) m/z: 566 (M+H$^+$).

Example 32

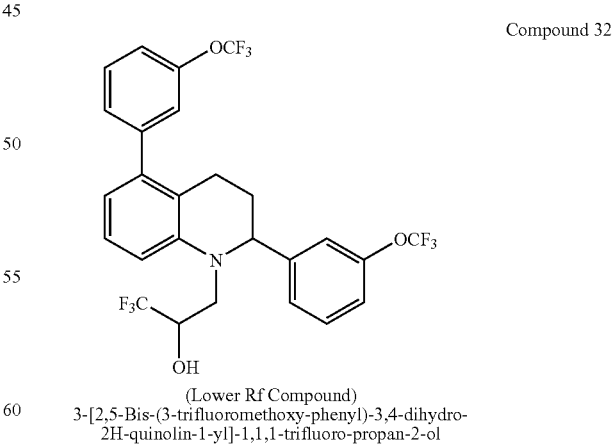

Compound 32

(Lower Rf Compound)
3-[2,5-Bis-(3-trifluoromethoxy-phenyl)-3,4-dihydro-2H-quinolin-1-yl]-1,1,1-trifluoro-propan-2-ol Spectra of compound 32 are as follows: $^1$H NMR (300 MHz, CDCl$_3$) δ 7.37 (bt, J=7.9 Hz, 2H), 7.26-7.10 (m, 6H), 7.03 (s, 1H), 6.92 (d, J=8.5 Hz, 1H), 6.70 (d, J=7.5 Hz, 1H), 4.63 (t, J=4.3 Hz, 1H), 4.32 (m, 1 H), 3.79 (dd, J=15.8, 6.5 Hz, 1H), 3.51 (dd, J=15.6, 5.3 Hz, 1H), 2.50-2.30 (m, 2H), 2.19-2.05 (m, 1H), 2.00-1.90 (m, 1H); MS (ES) m/z: 566 (M+H⁺).
Example 33
Cmpd 33
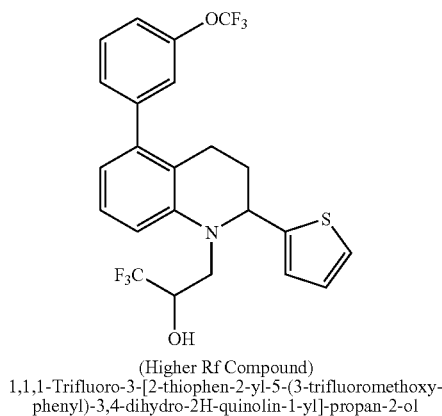
(Higher Rf Compound)
1,1,1-Trifluoro-3-[2-thiophen-2-yl-5-(3-trifluoromethoxy-phenyl)-3,4-dihydro-2H-quinolin-1-yl]-propan-2-ol
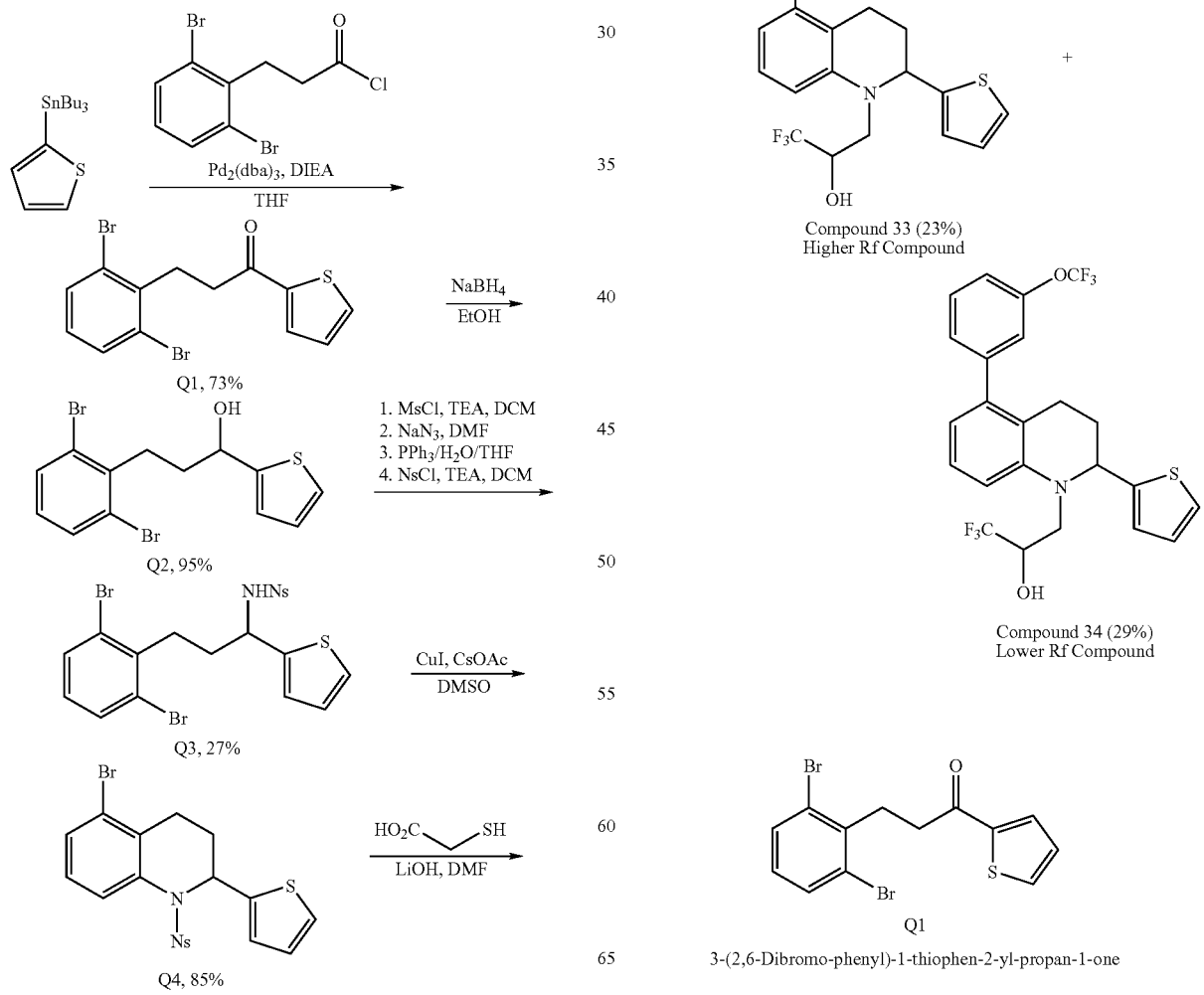
Q1
3-(2,6-Dibromo-phenyl)-1-thiophen-2-yl-propan-1-one Replacing I1 with tributyl-thiophen-2-yl-stannane and following the same procedure as in the preparation of I2 gave Q1 (73%): $^1$H NMR (400 MHz, CDCl$_3$) δ 7.75 (d, J=3.8 Hz, 1H), 7.65 (d, J=5.0 Hz, 1H), 7.53 (d, J=8.0 Hz, 2H), 7.13 (dd, J=4.9, 3.8 Hz, 1H), 6.95 (t, J=8.0 Hz, 1H), 3.49-3.40 (m, 2H), 3.21-3.15 (m, 2H); MS (ES) m/z: 375 (M+H$^+$).

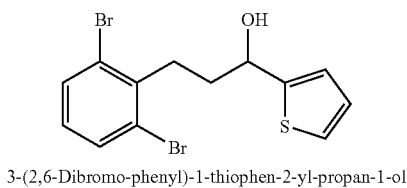

3-(2,6-Dibromo-phenyl)-1-thiophen-2-yl-propan-1-ol

Replacing I2 with Q1 and following the same procedure as in the preparation of I3 gave Q2 (95%): $^1$H NMR (300 MHz, CDCl$_3$) δ 7.49 (d, J=8.0 Hz, 2H), 7.27 (m, 1H), 7.05 (m, 1H), 6.98 (dd, J=5.0, 3.5 Hz, 1H), 6.90 (t, J=8.0 Hz, 1H), 5.07 (dd, J=11.2, 6.5 Hz, 1H), 3.27-3.13 (m, 1H), 3.09-2.98 (m, 1H), 2.19-2.05 (m, 3H); MS (ES) m/z: 399 (M+Na$^+$).

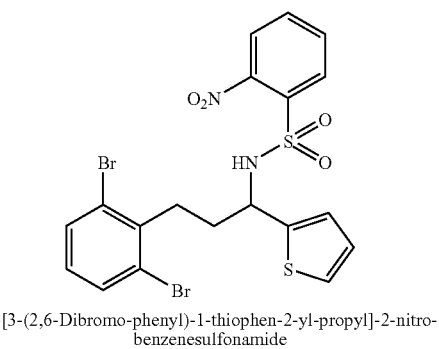

N-[3-(2,6-Dibromo-phenyl)-1-thiophen-2-yl-propyl]-2-nitro-benzenesulfonamide

Replacing O3 with Q2 and follows the same procedure as in the preparation of O4 except for step 3. The reduction of the azide was carried out by dissolving the azide (0.123 mmol) in THF (0.65 ml), adding PPh$_3$ (0.048 g, 0.184 mmol) and H$_2$O (48 ul), then refluxing for 4 hours. The amine intermediate was then taken on directly to give Q3 (27% for 4 steps): $^1$H NMR (300 MHz, CDCl$_3$) δ 7.89 (d, J=7.6 Hz, 1H), 7.79 (d, J=7.7 Hz, 1 H), 7.65-7.51 (m, 2H), 7.48 (d, J=8.0 Hz, 2H), 6.99 (d, J=5.1 Hz, 1H), 6.95-6.86 (m, 2H), 6.72 (dd, J=5.1, 3.6 Hz, 1H), 5.86 (d, J=8.8 Hz, 1H), 4.97 (d, J=7.4 Hz, 1H), 3.22-3.11 (m, 1H), 3.00-2.89 (m, 1H), 2.19-2.09 (m, 2H); MS (ES) m/z: 583 (M+Na$^+$).

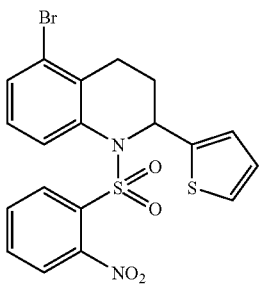

5-Bromo-1-(2-nitro-benzenesulfonyl)-2-thiophen-2-yl-1,2,3,4-tetrahydro-quinoline Replacing P5 with Q3 and following the same procedure as in the preparation of P6 gave Q4 (85%): $^1$H NMR (300 MHz, CDCl$_3$) δ 7.72-7.68 (m, 2H), 7.62 (d, J=7.7 Hz, 2H), 7.56 (d, J=6.8 Hz, 1H), 7.42 (d, J=8.0 Hz, 1H), 7.19-7.09 (m, 2H), 6.95-6.86 (m, 2H), 5.92 (m, 1H), 2.85-2.70 (m, 1H), 2.50-2.32 (m, 2H), 2.25-2.10 (m, 1H); MS (ES) m/z: 502 (M+Na$^+$).

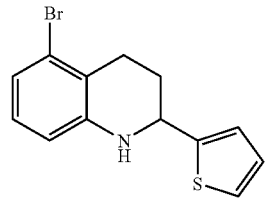

5-Bromo-2-thiophen-2-yl-1,2,3,4-tetrahydro-quinoline

Replacing P6 with Q4 and following the same procedure as in the preparation of P7 gave Q5 (83%): $^1$H NMR (300 MHz, CDCl$_3$) δ 7.28-7.20 (m, 1H), 7.01-7.81 (m, 4H), 6.48 (d, J=7.8 Hz, 1H), 4.70 (d, J=9.0 Hz, 1H), 4.25 (brs, 1H), 2.90-2.79 (m, 2H), 2.31-2.20 (m, 1H), 2.15-2.01 (m, 1H); MS (ES) m/z: 296 (M+2).

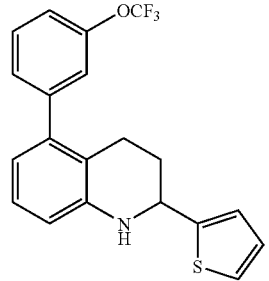

2-Thiophen-2-yl-5-(3-trifluoromethoxy-phenyl)-1,2,3,4-tetrahydro-quinoline

Replacing P7 with Q5 and following the same procedure as in the preparation of P8 gave Q6 (97%): $^1$H NMR (300 MHz, CDCl$_3$) δ 7.43-7.31 (m, 2H), 7.29-7.13 (m, 3H), 7.11-6.96 (m, 3H), 6.62-6.57 (m, 2H), 4.79 (dd, J=8.9, 3.3 Hz, 1H), 4.30 (brs, 1H), 2.82-2.70 (m, 1H), 2.65-2.52 (m, 1H), 2.10-1.90 (m, 2H); MS (ES) m/z: 376 (M+H$^+$).

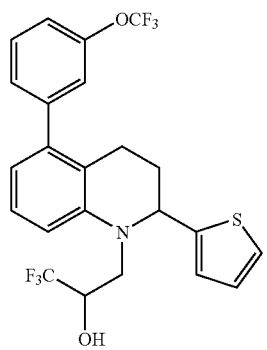

Cmpd 33
Higher Rf compound
1,1,1-Trifluoro-3-[2-thiophen-2-yl-5-(3-trifluoromethoxy-phenyl)-3,4-dihydro-2H-quinolin-1-yl]-propan-2-ol Replacing I8 with Q6 and following the same procedure as in the preparation of compound I7 and I8 gave compound 33 and 34. Spectra of compound 33 are as follows: ¹H NMR (300 MHz, CDCl₃) δ 7.38 (t, J=7.8 Hz, 1H), 7.25-7.12 (m, 5H), 6.96 (dd, J=4.7, 3.7 Hz, 1H), 6.86 (d, J=3.2 Hz, 1H), 6.73 (d, J=8.3 Hz, 1H), 6.66 (d, J=7.5 Hz, 1H), 5.04 (t, J=4.4 Hz, 1H), 4.33 (m, 1H), 3.87 (d, J=15.5 Hz, 1H), 3.48 (dd, J=15.5, 9.8 Hz, 1H), 2.60-2.51 (m, 2H), 2.44 (d, J=4.6 Hz, 1H), 2.22-2.02 (m, 2H); MS (ES) m/z: 488 (M+H⁺).

Example 34

Compound 34

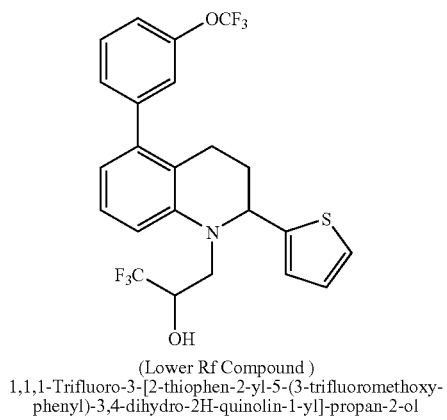

(Lower Rf Compound)
1,1,1-Trifluoro-3-[2-thiophen-2-yl-5-(3-trifluoromethoxy-phenyl)-3,4-dihydro-2H-quinolin-1-yl]-propan-2-ol Spectra of compound 34 are as follows: ¹H NMR (400 MHz, CDCl₃) δ 7.38 (t, J=7.9 Hz, 1H), 7.29-7.12 (m, 5H), 7.00-6.95 (m, 1H), 6.89-6.81 (m, 2H), 6.68 (d, J=7.5 Hz, 1H), 4.81 (t, J=4.0 Hz, 1H), 4.33 (m, 1 H), 3.79-3.64 (m, 2H), 2.68-2.58 (m, 1H), 2.48 (dt, J=16.5, 4.0 Hz, 1 H), 2.31 (d, J=4.7 Hz, 1H), 2.16-2.02 (m, 2H); MS (ES) m/z: 488 (M+H⁺).

Example 35

Cmpd 35

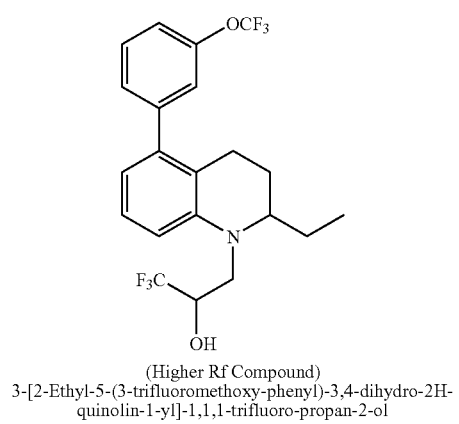

(Higher Rf Compound)
3-[2-Ethyl-5-(3-trifluoromethoxy-phenyl)-3,4-dihydro-2H-quinolin-1-yl]-1,1,1-trifluoro-propan-2-ol Scheme R

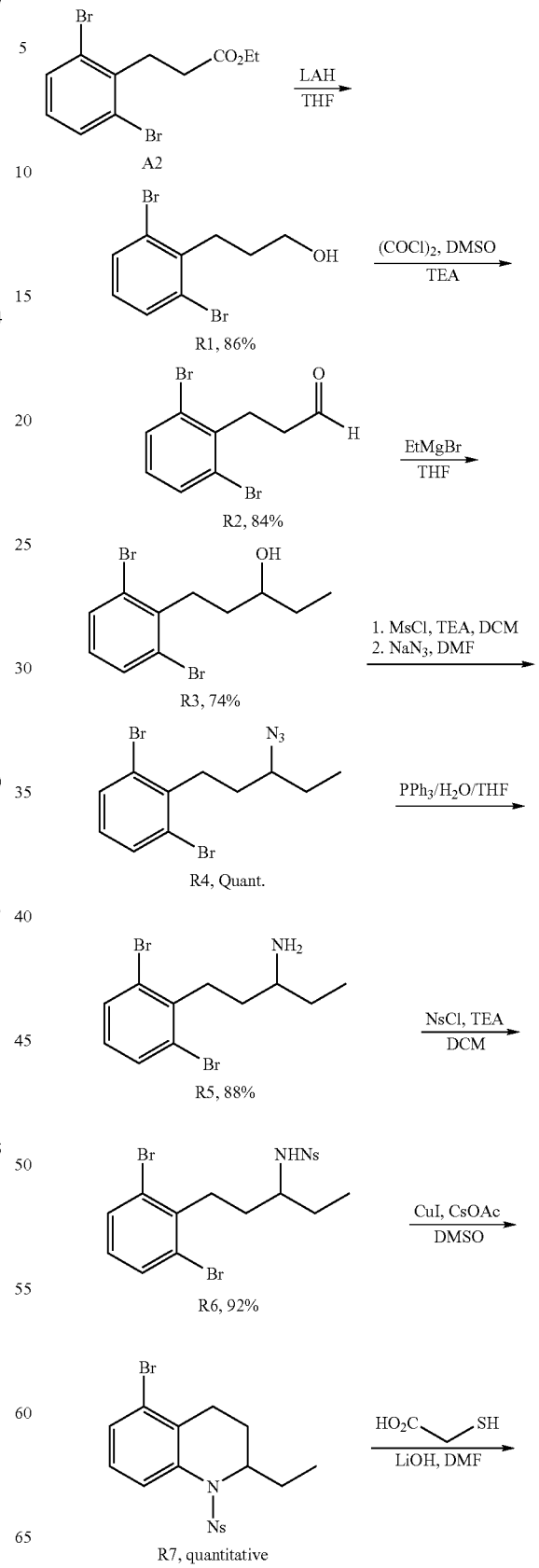

-continued

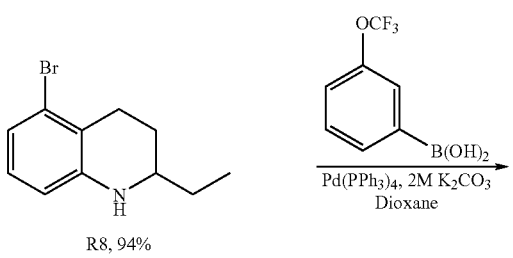

R8, 94%

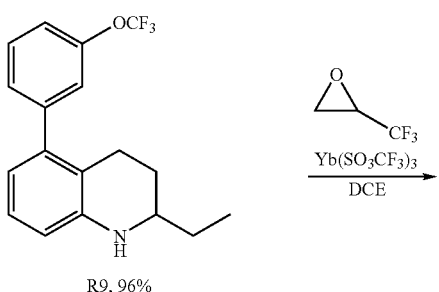

R9, 96%

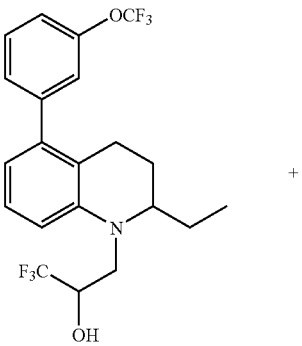

Compound 35 (15%)
Higher Rf Compound

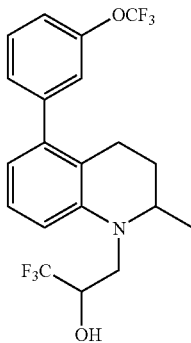

Compound 36 (21%)
Lower Rf Compound

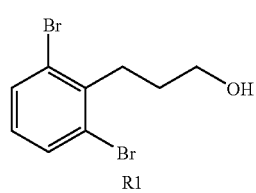

R1
3-(2,6-Dibromo-phenyl)-propan-1-ol

To the solution of A2 (1.14 g, 3.39 mmol) in THF (28 mL) at 0° C. was added 1.0 M LiAlH$_4$ (1.86 mL, 1.86 mmol) in THF dropwise. After stirring at room temperature for 20 min, upon cooling to 0° C. the reaction was slowly quenched with water and then 1 N HCl. The solution was extracted with EtOAc. The combined organic phases were dried (Na$_2$SO$_4$), concentrated and purified through column chromatography to afford 0.864 g (86%) of R1 as a white solid: $^1$H NMR (400 MHz, CDCl$_3$) δ 7.50 (d, J=8.0 Hz, 2H), 6.91 (t, J=8.0 Hz, 1H), 3.76 (t, J=6.4 Hz, 2H), 3.08 (m, 2H), 1.89 (m, 2H).

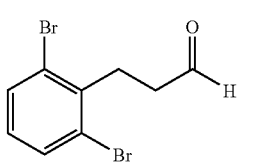

R2

3-(2,6-Dibromo-phenyl)-propionaldehyde

To the solution of oxalyl chloride (3.2 mL, 6.36 mmol) in THF (28 mL) at −60° C. was added DMSO (0.90 mL, 12.7 mmol) in CH$_2$Cl$_2$ (5 mL) dropwise. After stirring at −60° C. for 2 min, R1 (0.85 g, 2.89 mmol) in CH$_2$Cl$_2$ (7 mL) was added and the reaction mixture was stirred for 15 min at −60° C. Triethylamine (2.92 g, 28.9 mmol) was added and the reaction mixture was stirred for another 5 min at −60° C. The reaction was then allowed to warm to the room temperature and kept stirring at room temperature for 1 h. Water was added and the solution was extracted with ether. The combined organic phases were back washed with water and brine, dried (Na$_2$SO$_4$), concentrated and purified through column chromatography to afford 0.707 g (84%) of R2 as a yellow oil: $^1$H NMR (400 MHz, CDCl$_3$) δ 9.88 (s, 1H), 7.51 (d, J=8.0 Hz, 2H), 6.94 (t, J=8.0 Hz, 1 H), 3.32 (m, 2H), 2.74 (m, 2H).

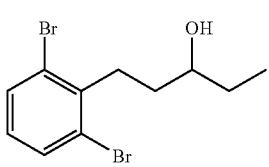

R3

1-(2,6-Dibromo-phenyl)-pentan-3-ol

To the solution of R2 (265 mg, 0.908 mmol) in THF (3.6 mL) at −60° C. under N$_2$ was added 1 M ethyl magnesium bromide in THF (1.18 mL, 1.18 mmol). After stirring at −60° C. for 15 min, the solution was allowed to warm slowly to room temperature and stirred at room temperature for 45 min. 1 N HCl was added and the solution was extracted with EtOAc. The combined organic phases were back washed with brine, dried (Na$_2$SO$_4$), concentrated and purified through column chromatography to afford 216 mg (74%) of R3 as clear oil: $^1$H NMR (400 MHz, CDCl$_3$) δ 7.50 (d, J=8.3 Hz, 2 H), 6.90 (t, J=8.1 Hz, 1H), 3.67 (m, 1H), 3.23-3.13 (m, 1H), 3.08-2.98 (m, 1H), 1.83-1.48 (m, 5H), 0.99 (t, J=7.5 Hz, 3H).

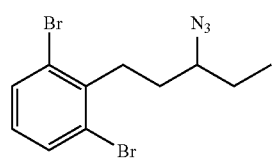

2-(3-Azido-pentyl)-1,3-dibromo-benzene

To a solution of R3 (203 mg, 0.630 mmol) in DCM (5.8 mL) cooled to 0° C. was added TEA (234 uL, 1.68 mmol) followed by MsCl (97 uL, 1.26 mmol). After 1.5 hours at room temperature, the reaction was poured into EtOAc, washed with 1 N HCl, water, saturated NaHCO$_3$ solution, water and brine. Filtration and removal of the solvent in vacuo provided 259 mg of crude mesylate. To a solution of the crude mesylate (249 mg, 0.623 mmol) in DMF (7.5 ml) was added sodium azide (202 mg, 3.11 mmol). The mixture was heated at 50° C. for 2 hours, after which the reaction was cooled to room temperature. The reaction was poured in EtOAc, washed with H$_2$O, NaHCO$_3$, H$_2$O, and brine, dried MgSO$_4$ and concentrated to give 216 mg (Quant.) of R4: $^1$H NMR (400 MHz, CDCl$_3$) δ 7.50 (d, J=7.96 Hz, 2H), 6.91 (t, J=8.0 Hz, 1H), 3.37-3.31 (m, 1H), 3.21-3.14 (m, 1H), 3.07-2.98 (m, 1H), 1.84-1.61 (m, 4H), 1.04 (t, J=7.3 Hz, 3H).

R5

3-(2,6-Dibromo-phenyl)-1-ethyl-propylamine

To a solution of the R4 (184 mg, 0.530 mmol) in THF (2.8 ml), was added triphenylphosphine (209 mg, 0.795 mmol), and water (0.21 ml). After stirring overnight, the solution was heated 3 hours at reflux. The reaction was cooled to RT and concentrated in vacuo. Purification by column chromatography (10% MeOH/CH$_2$Cl$_2$ afforded 150 mg (88%) R5 as an oil: $^1$H NMR (400 MHz, CDCl$_3$) δ 7.49 (d, J=8.3 Hz, 2H), 6.89 (t, J=7.9 Hz, 1H), 3.11 (td, J=12.4, 5.1 Hz, 1H), 2.99 (td, J=12.3, 4.9 Hz, 1H), 2.83 (m, 1H), 1.89 (brs, 2H), 1.78-1.68 (m, 1H), 1.62-1.52 (m, 2H), 1.49-1.38 (m, 1H), 0.99 (t, J=7.4 Hz, 3H); MS (ES) m/z: 322 (M+H$^+$).

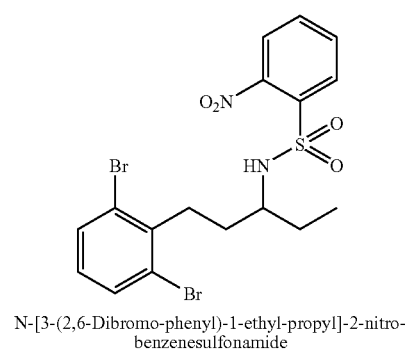

N-[3-(2,6-Dibromo-phenyl)-1-ethyl-propyl]-2-nitro-benzenesulfonamide

Replacing P4 with R4 and following the same procedure as in the preparation of P5 gave R6 (92%): $^1$H NMR (300 MHz, CDCl$_3$) δ 8.18-8.15 (m, 1H), 7.88-7.85 (m, 1H), 7.77-7.69 (m, 2H), 7.45 (d, J=8.0 Hz, 2H), 6.88 (t, J=8.0 Hz, 1H), 5.25 (d, J=8.4 Hz, 1H), 3.55 (m, 1H), 3.00-2.80 (m, 2H), 1.82-1.48 (m, 4H), 0.91 (t, J=7.4 Hz, 3H); MS (ES) m/z: 507 (M+H$^+$).

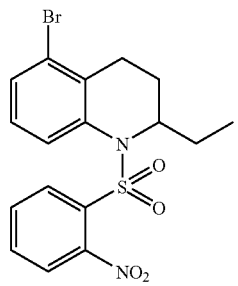

5-Bromo-2-ethyl-1-(2-nitro-benzenesulfonyl)-1,2,3,4-tetrahydro-quinoline

Replacing P5 with R6 and following the same procedure as in the preparation of P6 gave R7 (quant.): $^1$H NMR (300 MHz, CDCl$_3$) δ 7.73-7.62 (m, 2H), 7.59-7.42 (m, 4H), 7.12 (t, J=8.1 Hz, 1H), 4.39 (m, 1H), 2.72-2.60 (m, 1H), 2.27 (dt, J=17.2, 6.1 Hz, 1H), 2.00-1.86 (m, 1H), 1.69-1.38 (m, 3H), 0.96 (t, J=7.4 Hz, 3H); MS (ES) m/z: 427 (M+2).

R8

5-Bromo-2-ethyl-1,2,3,4-tetrahydro-quinoline

Replacing P6 with R7 and following the same procedure as in the preparation of P7 gave R8 (94%): $^1$H NMR (400 MHz, CDCl$_3$) δ 6.89-6.29 (m, 2H), 6.43 (d, J=7.6 Hz, 1H), 3.18-3.09 (m, 1H), 2.91-2.83 (m, 1 H), 2.72-2.61 (m, 1H), 2.06-1.98 (m, 1H), 1.65-1.49 (m, 4H), 0.99 (t, J=7.5 Hz, 3H); MS (ES) m/z: 240 (M).

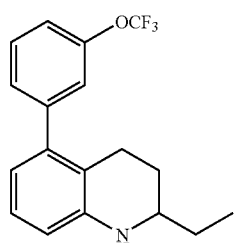

2-Ethyl-5-(3-trifluoromethoxy-phenyl)-1,2,3,4-tetrahydro-quinoline

Replacing P7 with R8 and following the same procedure as in the preparation of P8 gave R9 (96%): $^1$H NMR (300 MHz, CDCl$_3$) δ 7.38 (t, J=7.8 Hz, 1H), 7.28-7.13 (m, 3H), 7.02 (t, J=7.7 Hz, 1H), 6.53 (dd, J=7.8, 2.0 Hz, 2H), 4.00 (brs, 1H), 2.72-2.49 (m, 2H), 1.98-1.87 (m, 1H), 1.60-1.43 (m, 3H), 0.99 (t, J=7.5 Hz, 3H); MS (ES) m/z: 322 (M+H$^+$).

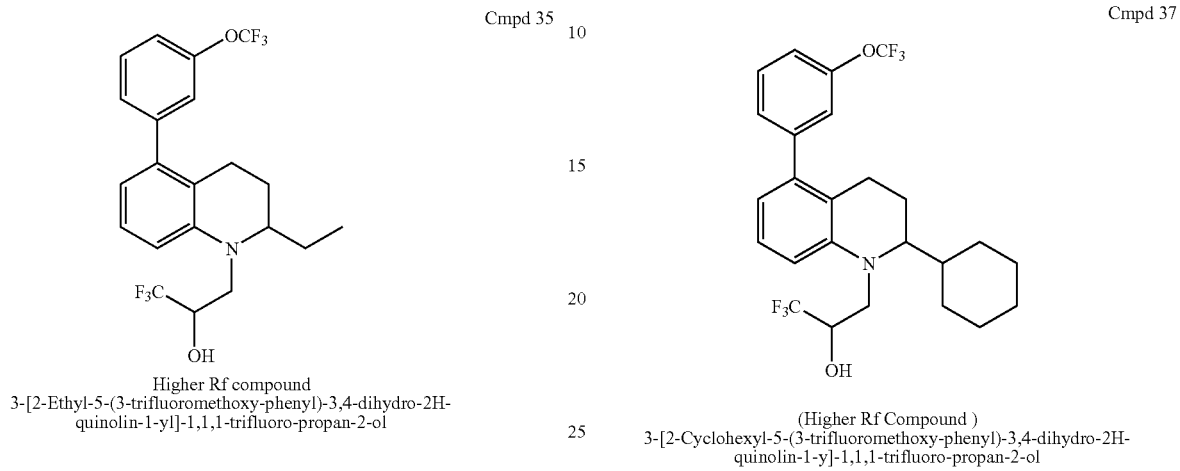

Cmpd 35

Higher Rf compound
3-[2-Ethyl-5-(3-trifluoromethoxy-phenyl)-3,4-dihydro-2H-quinolin-1-yl]-1,1,1-trifluoro-propan-2-ol Replacing I8 with R9 and following the same procedure as in the preparation of compound 17 and 18 gave compound 35 and 36. Spectra of compound 35 are as follows: $^1$H NMR (400 MHz, CDCl$_3$) δ 7.41 (t, J=7.6 Hz, 1H), 7.28-7.21 (m, 4H), 6.73 (d, J=8.0 Hz, 1H), 6.63 (d, J=7.4 Hz, 1H), 6.61 (d, J=7.5 Hz, 1H), 4.31 (m, 1H), 3.70 (dd, J=15.3, 6.4 Hz, 1 H), 3.62 (dd, J=15.3, 5.7 Hz, 1H), 3.17 (m, 1H), 2.68-2.39 (m, 2H), 1.92-1.85 (m, 1H), 1.79-1.68 (m, 2H), 1.59-1.42 (m, 1H), 0.91 (t, J=7.4 Hz, 3H); MS (ES) m/z: 434 (M+H$^+$).

Example 36

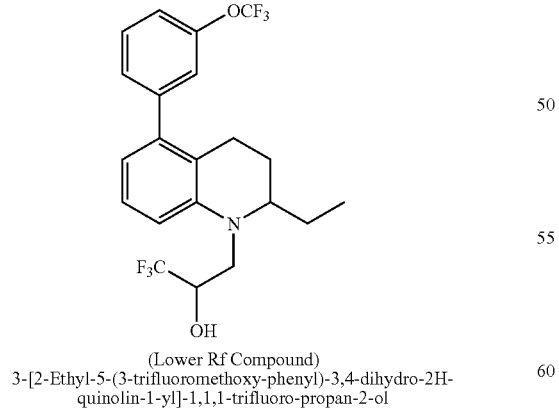

Compound 36

(Lower Rf Compound)
3-[2-Ethyl-5-(3-trifluoromethoxy-phenyl)-3,4-dihydro-2H-quinolin-1-yl]-1,1,1-trifluoro-propan-2-ol Spectra of compound 36 are as follows: $^1$H NMR (400 MHz, CDCl$_3$) δ 7.42 (t, J=7.9 Hz, 1H), 7.25-7.13 (m, 4H), 6.70 (d, J=8.1 Hz, 1H), 6.66 (d, J=7.5 Hz, 1H), 4.40-4.32 (m, 1H), 3.84 (dd, J=15.0, 2.3 Hz, 1H), 3.45-3.33 (m, 2H), 2.71-2.41 (m, 3H), 1.91-1.81 (m, 2H), 1.72-1.61 (m, 1H), 1.55-1.42 (m, 1H), 0.93 (t, J=7.5 Hz, 3H); MS (ES) m/z: 434 (M+H$^+$).

Example 37

Cmpd 37

(Higher Rf Compound)
3-[2-Cyclohexyl-5-(3-trifluoromethoxy-phenyl)-3,4-dihydro-2H-quinolin-1-y]-1,1,1-trifluoro-propan-2-ol Scheme S

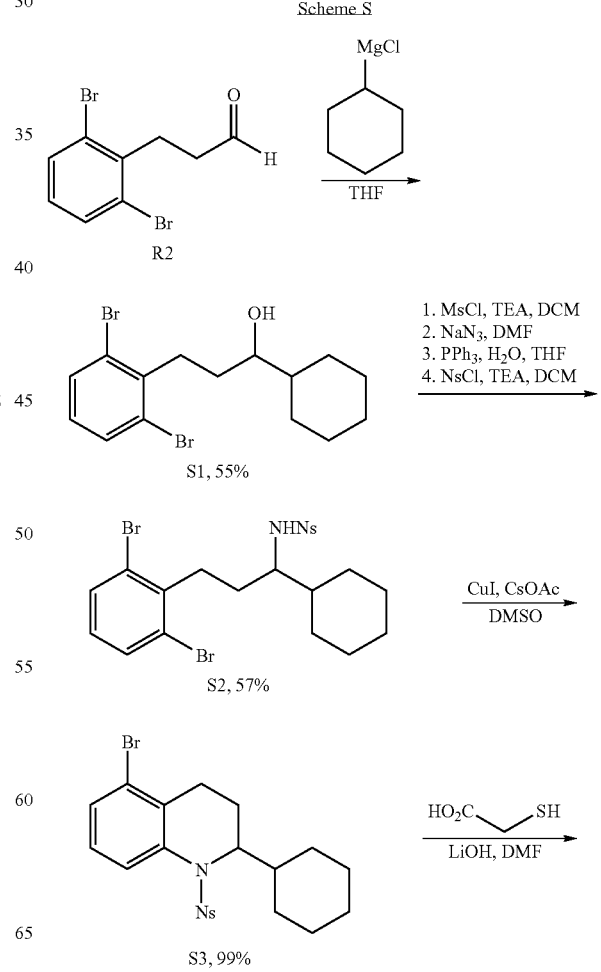

-continued

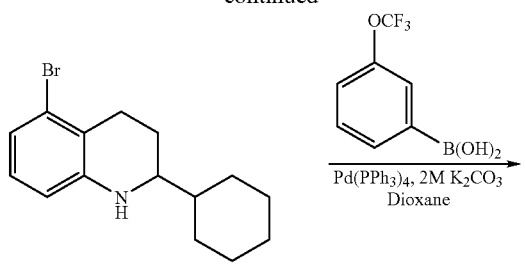

S4, 93%

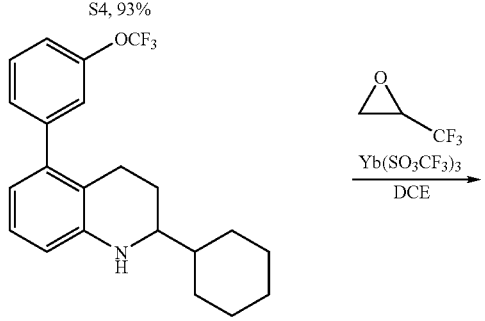

S5, 89%

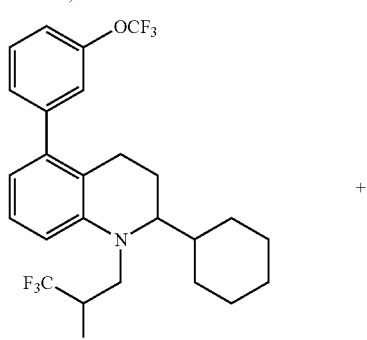

Compound 37 (36%)
Higher Rf Compound

+

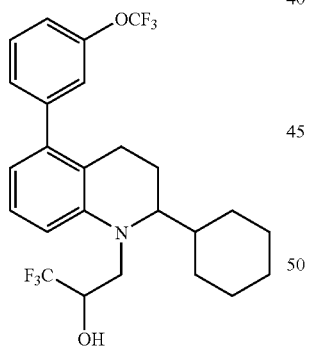

Compound 38 (36%)
Lower Rf Compound

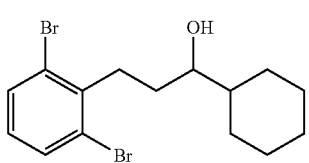

S1
1-Cyclohexyl-3-(2,6-dibromo-phenyl)-propan-1-ol

Replacing ethyl magnesium bromide with cyclohexyl magnesium chloride and following the same procedure as in the preparation of R3 gave S1 (55%): $^1$H NMR (300 MHz, CDCl$_3$) δ 7.50 (d, J=8.0 Hz, 2H), 6.90 (t, J=8.0Hz, 1H), 3.53-3.44 (m, 1H), 3.21 (td, J=12.0, 5.2Hz, 1H), 2.99 (td, J=12.0, 5.2 Hz, 1H), 1.91-1.61 (m, 7H), 1.47-1.34 (m, 1H), 1.30-0.99 (m, 5H).

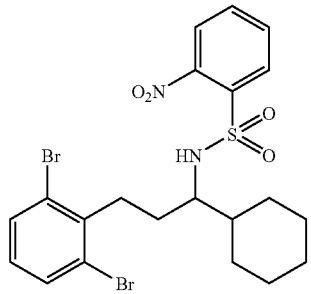

N-[1-Cyclohexyl-3-(2,6-dibromo-phenyl)-propyl]-2-nitro-benzenesulfonamide

Replacing A6 with S1 and following the same procedure as in the preparation of A7 gave the azide intermediate.

To a solution of the above intermediate (0.809 mmol) in THF (4.3 mL) was added PPh$_3$ (0.32 g, 1.21 mmol) and H$_2$O (0.32 mL). After stirring at room temperature for 20 h and 70° C. for 4 h, the solution was cooled, concentrated and purified through column chromatography to afford 364 mg of the amine as a clear oil which also contained a small amount of an unidentified impurity.

Replacing A8 with the above amine intermediate and following the same procedure as in the preparation of A9 gave S2 (57%): $^1$H NMR (300 MHz, CDCl$_3$) δ 8.16 (dd, J=6.8, 1.8 Hz, 1H), 7.86 (dd, J=6.7, 1.9 Hz, 1 H), 7.79-7.68 (m, 2H), 7.43 (d, J=8.1 Hz, 2H), 6.87 (t, J=7.6 Hz, 1H), 5.27 (d, J=9.2 Hz, 1H), 3.55-3.45 (m, 1H), 2.92-2.70 (m, 2H), 1.80-1.45 (m, 8H), 1.21-0.92 (m, 4H); MS (ES) m/z: 561 (M+H$^+$).

S3

5-Bromo-2-cyclohexyl-1-(2-nitro-benzenesulfonyl)-1,2,3,4-tetrahydro-quinoline

Replacing R6 with S2 and following the same procedure as in the preparation of R7 gave S3 (99%): $^1$H NMR (300 MHz, CDCl$_3$) δ 7.79-7.71 (m, 1H), 7.69-7.61 (m, 1H), 7.55-7.41 (m, 4H), 7.14 (t, J=8.1 Hz, 1 H), 4.19-4.09 (m, 1H), 2.69-2.53 (m, 1H), 2.25-2.12 (m, 1H), 1.92-1.58 (m, 8H), 1.41-0.95 (m, 5H); MS (ES) m/z: 481 (M+2).

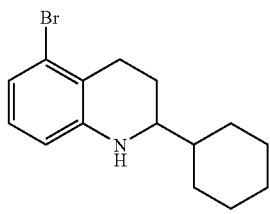

5-Bromo-2-cyclohexyl-1,2,3,4-tetrahydro-quinoline

Replacing R7 with S3 and following the same procedure as in the preparation of R8 gave S4 (93%): $^1$H NMR (300 MHz, CDCl$_3$) δ 6.89-6.78 (m, 2H), 6.49-6.40 (m, 1H), 3.02-2.95 (m, 1H), 2.97 (dt, J=9.2, 3.0 Hz, 1H), 2.78-2.57 (m, 1H), 2.00-1.90 (m, 1H), 1.88-1.62 (m, 6H), 1.48-0.93 (m, 6H); MS (ES) m/z: 296 (M+2).

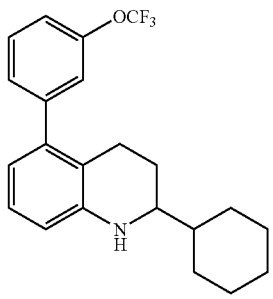

2-Cyclohexyl-5-(3-trifluoromethoxy-phenyl)-1,2,3,4-tetrahydro-quinoline

Replacing R8 with S4 and following the same procedure as in the preparation of R9 gave S5 (89%): $^1$H NMR (400 MHz, CDCl$_3$) δ 7.40 (t, J=7.9 Hz, 1H), 7.38-7.15 (m, 3H), 7.03 (t, J=7.6 Hz, 1H), 6.57 (m, 2H), 3.09 (m, 1H), 2.19-2.50 (m, 2H), 1.91-0.99 (m, 13H); MS (ES) m/z: 376 (M+H$^+$).

Replacing I8 with S5 and following the same procedure as in the preparation of compound 17 and 18 gave compound 37 and 38. Spectra of compound 37 are as follows: $^1$H NMR (300 MHz, CDCl$_3$) δ 7.42 (t, J=7.8 Hz, 1H), 7.25-7.13 (m, 4H), 6.89-6.80 (m, 1H), 6.67 (d, J=7.5 Hz, 1 H), 4.39-4.29 (m, 1H), 3.96 (d, J=15.1 Hz, 1H), 3.39 (dd, J=15.1, 10.4 Hz, 1H), 3.13-3.06 (m, 1H), 2.70-2.55 (m, 1H), 2.46-2.35 (m, 1H), 2.08-1.96 (m, 1H), 1.91-1.48 (m, 7H), 1.24-0.84 (m, 5H); MS (ES) m/z: 488 (M+H$^+$).

Example 38

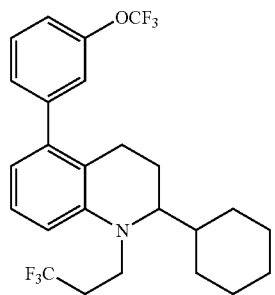

Compound 38

(Lower Rf Compound)
3-[2-Cyclohexyl-5-(3-trifluoromethoxy-phenyl)-3,4-dihydro-2H-quinolin-1-yl]-1,1,1-trifluoro-propan-2-ol Spectra of compound 38 are as follows: $^1$H NMR (300 MHz, CDCl$_3$) δ 7.43 (t, J=7.8 Hz, 1H), 7.24-7.16 (m, 4H), 6.99-6.89 (m, 1H), 6.69 (d, J=7.3 Hz, 1H), 4.35-4.25 (m, 1H), 3.88 (dd, J=14.8, 5.5 Hz, 1H), 3.53 (dd, J=15.1, 6.1 Hz, 1H), 3.09-3.00 (m, 1H), 2.69-2.55 (m, 1H), 2.48-2.35 (m, 1H), 2.00-1.90 (m, 1H), 1.81-1.48 (m, 8H), 1.29-0.83 (m, 5H); MS (ES) m/z: 488 (M+H$^+$).

Example 39

Cmpd 37

Higher Rf compound
3-[2-Cyclohexyl-5-(3-trifluoromethoxy-phenyl)-3,4-dihydro-2H-quinolin-1-yl]-1,1,1-trifluoro-propan-2-ol

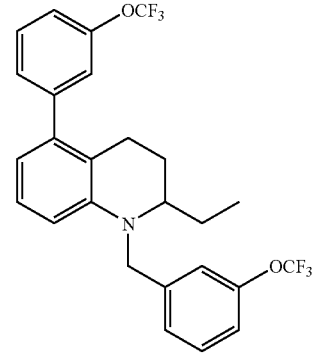

Cmpd 39

2-Ethyl-1-(3-trifluoromethoxy-benzyl)-5-(3-trifluoromethoxy-phenyl)-1,2,3,4-tetrahydro-quinoline Scheme T

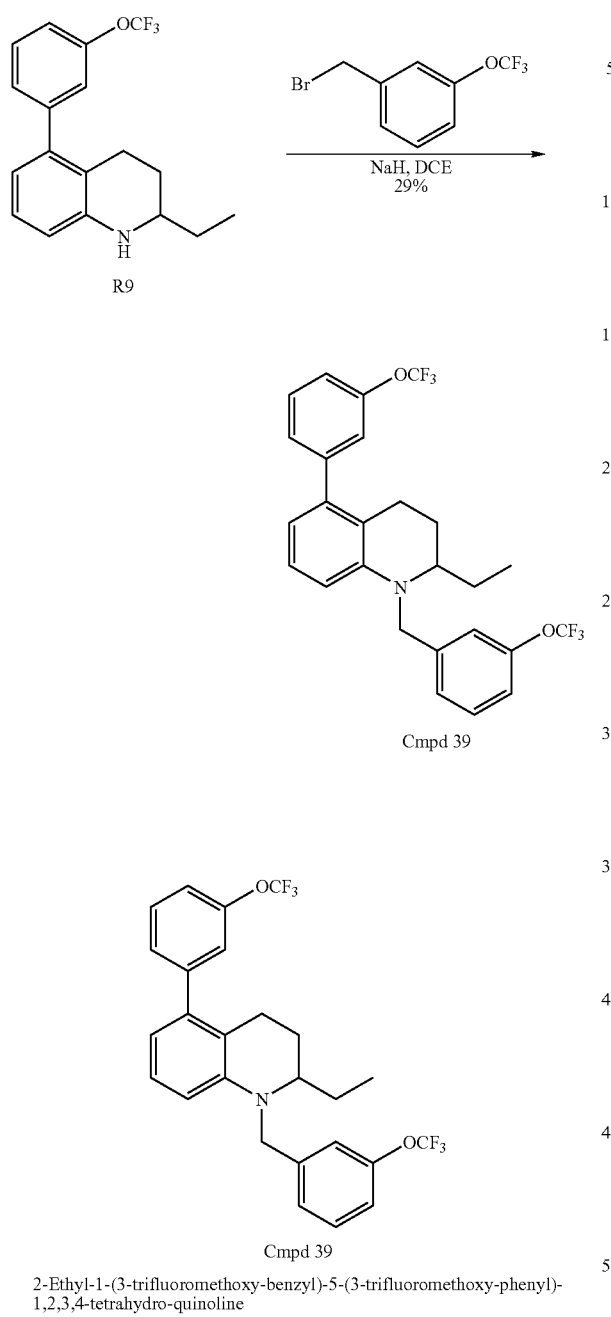

Cmpd 39
2-Ethyl-1-(3-trifluoromethoxy-benzyl)-5-(3-trifluoromethoxy-phenyl)-1,2,3,4-tetrahydro-quinoline To a mixture of R9 (25.7 mg, 0.0799 mmol), 3-trifluoromethoxy-benzylbromide (30.6 mg, 0.12 mmol) and 2,6-ditertbutyl-4-methyl diamino pyridine (32.9 mg, 0.160 mmol) in THF (4.3 mL) was added excess NaH (~60 mg). After stirring at 50° C. for 2 days and 75° C. for 7 h, the solution was cooled, quenched with $H_2O$ and extracted with EtOAc. The combined organic phases were dried ($Na_2SO_4$), concentrated and purified through column chromatography to afford compound 39: $^1$H NMR (300 MHz, CDCl$_3$) δ 7.45-7.07 (m, 8H), 7.00 (t, J=7.9 Hz, 1H), 6.53 (d, J=7.4 Hz, 1H), 6.40 (d, J=8.3 Hz, 1H), 4.63 (d, J=17.5 Hz, 1H), 4.54 (d, J=7.5 Hz, 1 H), 3.31-3.22 (m, 1H), 2.79-2.62 (m, 1H), 2.52 (dt, J=16.6, 4.2 Hz, 1 H), 2.00-1.48 (m, 4H), 0.89 (t, J=7.5 Hz, 3H); MS (ES) m/z: 496 (M+H$^+$).

Example 40

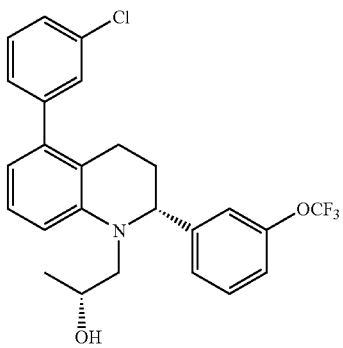

(Higher Rf compound)
(αR,2R)-5-(3-Chlorophenyl)-3,4-dihydro-α-methyl-2-[3-(trifluoromethoxy)phenyl]-1(2H)-quinolineethanol Scheme U

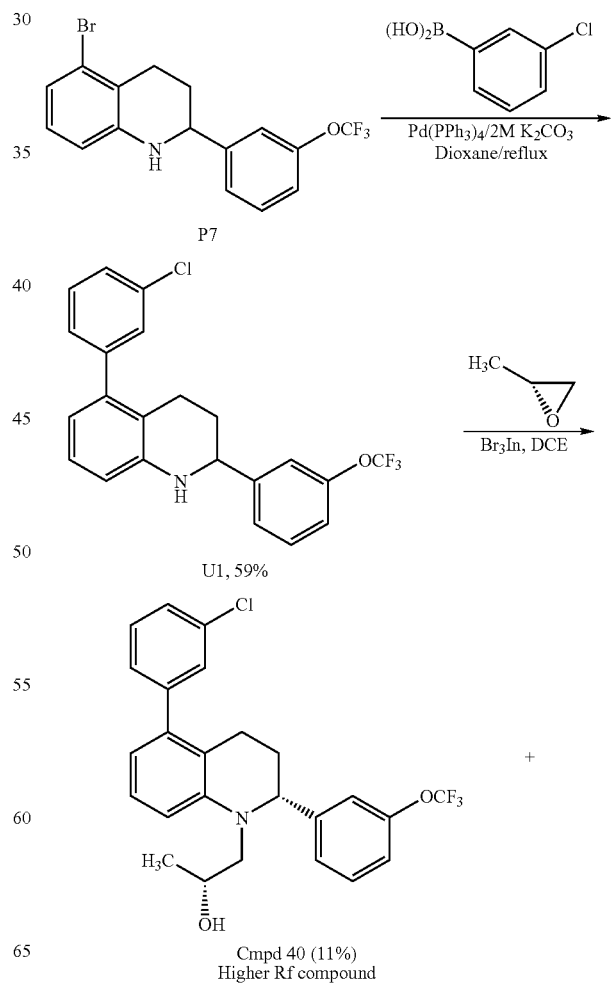

Cmpd 40 (11%)
Higher Rf compound

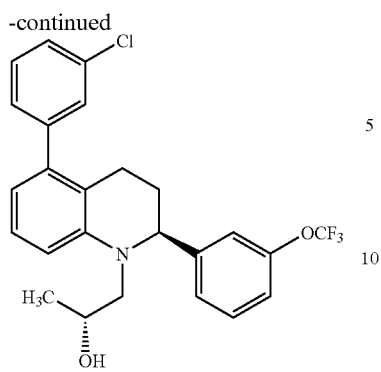

Cmpd 41 (9%)
Lower Rf compound

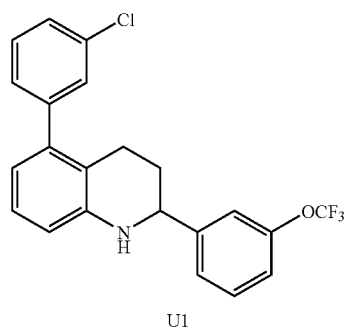

U1
5-(3-Chloro-phenyl)-2-(3-trifluoromethoxy-phenyl)-1,2,3,4-tetrahydroquinoline Replacing 3-trifluoromethoxy-benzene boronic acid with 3-chloro-benzene boronic acid and following the same procedure as in the preparation of P8 gave U1 (59%): $^1$H NMR (300 MHz, CDCl$_3$) δ 7.33-7.20 (m, 5H), 7.18 (s, 1H), 7.13-7.10 (m, 1H), 7.07 (d, J=7.9 Hz, 1H), 7.01 (t, J=7.8 Hz, 1H), 6.53 (d, J=7.7 Hz, 2H), 4.43 (dd, J=8.8, 3.4 Hz, 1H), 4.12 (brs, 1H), 2.72-2.62 (m, 1H), 2.45 (dt, J=16.6, 5.0 Hz, 1H), 2.03-1.95 (m, 1H), 1.86-1.75 (m, 1H); MS (ES) m/z: 404 (M+H$^+$).

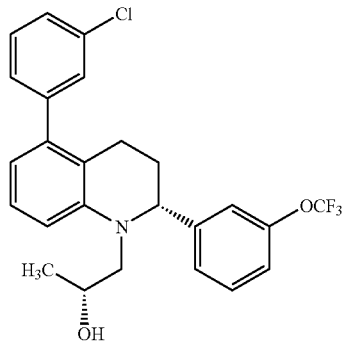

Cmpd 40
Higher Rf compound
(αR,2R)-5-(3-Chlorophenyl)-3,4-dihydro-α-methyl-2-[3-(trifluoromethoxy)phenyl]-1(2H)-quinolineethanol To a solution of U1 (41.8 mg, 0.103 mmol) in DCE (0.9 mL) was added InBr$_3$ (55 mg, 0.155 mmol). The reaction mixture was stirred for 3 h and poured into EtOAc. The organic layer was washed with NaHCO$_3$, H$_2$O, brine, dried (MgSO$_4$), concentrated and purified by HPLC to afford compounds 40 and 41. Spectra of compound 40 are as follows: $^1$H NMR (400 MHz, CDCl$_3$) δ 7.34 (t, J=7.9 Hz, 1H), 7.29-7.23 (m, 4H), 7.21-7.09 (m, 3H), 7.01 (s, 1H), 6.74 (d, J=8.3 Hz, 1H), 6.61 (d, J=7.5 Hz, 1H), 4.85 (t, J=4.2 Hz, 1H), 4.24 (m, 1H), 3.57 (dd, J=15.1, 2.4 Hz, 1H), 2.96 (dd, J=15.1, 9.8 Hz, 1H), 2.49-2.29 (m, 2H), 2.21-2.11 (m, 1H), 2.04-1.88 (m, 2H), 1.20 (d, J=6.3 Hz, 3H); MS (ES) m/z: 462 (M+H$^+$).

Example 41

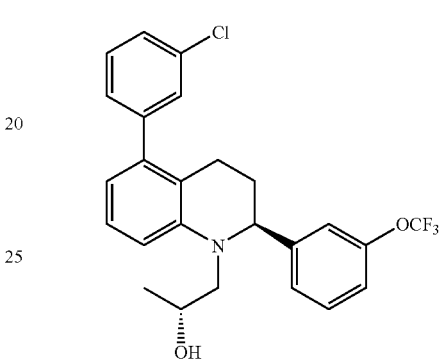

Compound 41
(Lower Rf Compound)
(αR,2S)-5-(3-Chlorophenyl)-3,4-dihydro-α-methyl-2-[3-(trifluoromethoxy)phenyl]-1(2H)-quinolineethanol Spectra of compound 41 are as follows: $^1$H NMR (400 MHz, CDCl$_3$) δ 7.35 (t, J=7.9 Hz, 1H), 7.29-7.23 (m, 4H), 7.18 (t, J=8.0 Hz, 1H), 7.12 (m, 2H), 7.02 (s, 1H), 6.94 (d, J=8.3 Hz, 1H), 6.61 (d, J=7.5 Hz, 1H), 4.69 (t, J=4.0 Hz, 1H), 4.22 (m, 1H), 3.62 (dd, J=15.0, 7.5 Hz, 1H), 3.05 (dd, J=15.1, 5.3 Hz, 1H), 2.45-2.29 (m, 2H), 2.19-2.08 (m, 1H), 2.01-1.91 (m, 1H), 1.71 (brs, 1H), 1.25 (d, J=6.1 Hz, 3H); MS (ES) m/z: 462 (M+H$^+$).

Example 42

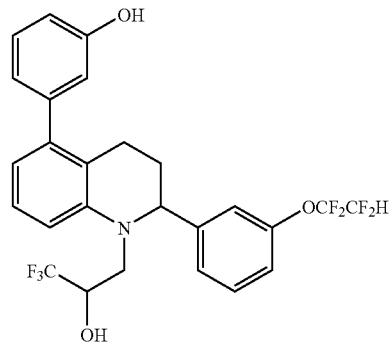

Cmpd 42
(Higher Rf Cmpd)
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-phenol Scheme V

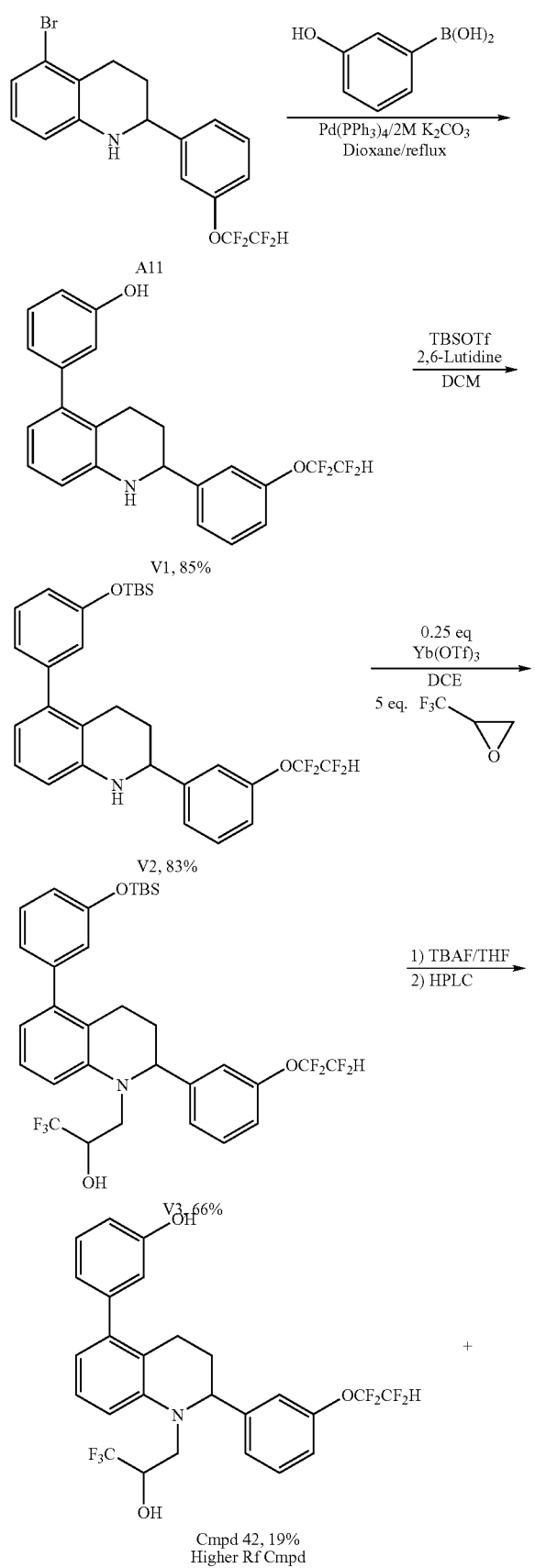

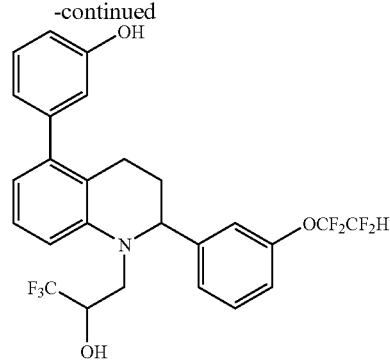

Cmpd 43, 30%
Lower Rf Cmpd

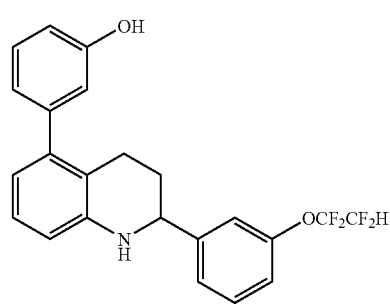

V1

3-{2-[3-(1,1,2,2-Tetrafluoro-ethoxy)-phenyl]-1,2,3,4-tetrahydro-quinolin-5-yl}-phenol Replacing 3-trifluoromethoxy-benzene-boronic acid with 3-hydroxy-benzene-boronic acid and following the same procedure as in the preparation of compound A12 gave compound V1 (85%): $^1$H NMR (400 MHz, CDCl$_3$) δ 7.41-7.21 (m, 4H), 7.13 (d, J=7.9 Hz, 1H), 7.07 (t, J=7.7 Hz, 1H), 6.87 (d, J=7.6 Hz, 1H), 6.80-6.77 (m, 2H), 6.63-6.57 (m, 2H), 5.89 (tt, J=53.1, 2.8 Hz, 1H), 4.91 (brs, 1H), 4.49 (dd, J=8.8, 3.2 Hz, 1H), 4.18 (brs, 1H), 2.79-2.71 (m, 1H), 2.56 (dt, J=16.7, 5.0 Hz, 1 H), 2.09-2.00 (m, 1H), 1.92-1.91 (m, 1H); MS (ES) m/z: 418 (M+H$^+$).

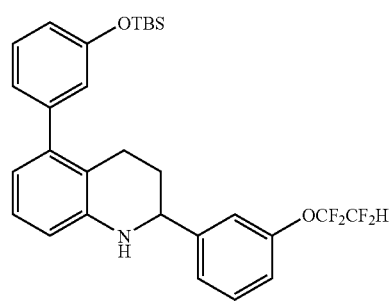

5-[3-(tert-Butyl-dimethyl-silanyloxy)-phenyl]-2-[3-(1,1,2,2-tetrafluoro-ethoxy)-phenyl]-1,2,3,4-tetrahydro-quinoline To a stirred solution of V1 (37 mg; 0.0886 mmol) in 1 mL of anhydrous DCM at ambient temperature was added 2,6-lutidine (20 uL; 2 equiv) followed by TBSOTf (24.4 uL; 1.2 equiv). After 2 hours the reaction contents were poured into EtOAc and washed with saturated NaHCO₃ solution, water and brine. The organic layer was dried (MgSO₄), concentrated and purified by column chromatography (5% EtOAc/Hex) to provide 39 mg (83%) of V2: $^1$H NMR (400 MHz, CDCl₃) δ 7.19-7.10 (m, 2 H), 7.09-7.00 (m, 2H), 6.94 (d, J=7.8 Hz, 1H), 6.88 (t, J=7.7 Hz, 1H), 6.70 (d, J=7.5 Hz, 1H), 6.60 (m, 2H), 6.42 (d, J=7.4 Hz, 1H), 6.38 (d, J=8.0 Hz, 1H), 5.69 (bt, J=53.0 Hz, 1H), 4.29 (d, J=6.7 Hz, 1H), 3.96 (s, 1H), 2.61-2.52 (m, 1H), 2.42-2.33 (m, 1H), 1.90-1.81 (m, 1H), 1.73-1.61 (m, 1H), 0.78 (s, 9H), 0.00 (s, 6H); MS (ES) m/z: 532 (M+H⁺).

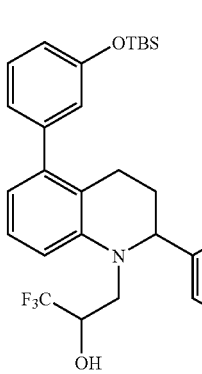

V3

3-{5-[3-(tert-Butyl-dimethyl-silanyloxy)-phenyl]-2-[3-(1,1,2,2-tetrafluoro-ethoxy)-phenyl]-3,4-dihydro-2H-quinolin-1-yl}-1,1,1-trifluoro-propan-2-ol Replacing A12 with V2 and following the same procedure as in the preparation of compound 1 provided V3 as an inseparable mixture: MS (ES) m/z: 644 (M+H⁺).

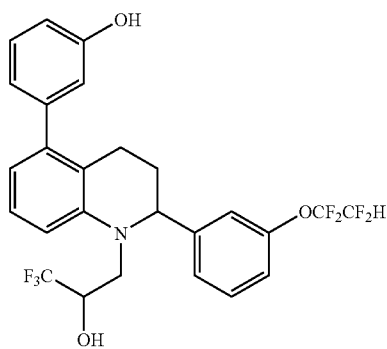

Cmpd 42

Higher Rf compound
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-phenol To a stirred solution of V3 (28 mg; 0.0435 mmol) in 500 uL of anhydrous THF at ambient temperature under a nitrogen atmosphere was added TBAF (52 uL; 1.2 equivalents). After TLC indicated consumption of the starting material, the reaction mixture was poured into EtOAc and washed with 0.5N HCl, water, saturated NaHCO₃ solution and brine. The organic layer was dried (MgSO₄), concentrated and purified by HPLC to provide 4.4 mg (19%) of compound 42 and 7.0 mg (30%) of compound 43. $^1$H NMR (400 MHz, CDCl₃) δ 7.34 (t, J=7.9 Hz, 1H), 7.25-7.18 (m, 2H), 7.15-7.09 (m, 2H), 7.03 (s, 1H), 6.83 (d, J=7.6 Hz, 1H), 6.77 (dd, J=8.1, 1.9 Hz, 1H), 6.74-6.67 (m, 3H), 5.85 (tt, J=53.1, 2.8 Hz, 1H), 4.88 (t, J=4.4 Hz, 1H), 4.68 (brs, 1H), 4.43 (m, 1H), 3.90 (d, J=15.9 Hz, 1H), 3.30 (dd, J=15.6, 9.7 Hz, 1H), 2.51 (dt, J=16.3, 4.3 Hz, 1H), 2.44-2.33 (m, 2H), 2.19-2.08 (m, 1H), 1.99-1.91 (m, 1H); MS (ES) m/z: 530 (M+H⁺).

Example 43

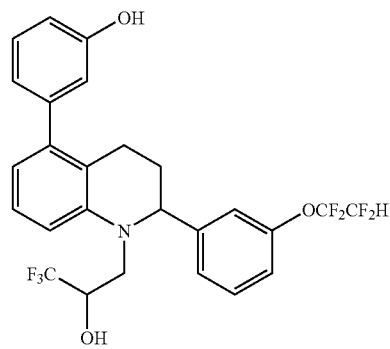

Cmpd 43

Lower Rf compound
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-phenol $^1$H NMR (400 MHz, CDCl₃) δ 7.34 (t, J=7.9 Hz, 1H), 7.24-7.19 (m, 2H), 7.14-7.08 (m, 2H), 7.02 (s, 1H), 6.87 (d, J=8.2 Hz, 1H), 6.82 (d, J=7.7 Hz, 1H), 6.78 (d, J=8.1 Hz, 1H), 6.72-6.68 (m, 2H), 5.89 (tt, J=53.1, 2.8 Hz, 1H), 4.67 (brs, 1H), 4.60 (t, J=4.2 Hz, 1H), 4.34 (m, 1 H), 3.79 (dd, J=15.7, 6.6 Hz, 1H), 3.51 (dd, J=15.6, 5.4 Hz, 1H), 2.52-2.33 (m, 2H), 2.25 (d, J=4.9 Hz, 1H), 2.16-2.04 (m, 1H), 1.99-1.91 (m, 1H); MS (ES) m/z: 530 (M+H⁺).

Example 44

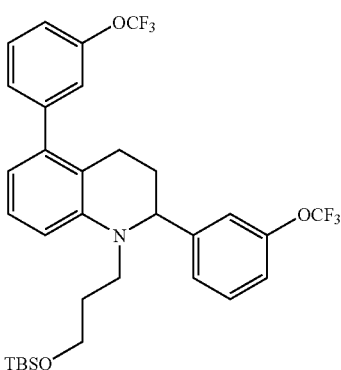

Cmpd 44

1-[3-(tert-Butyl-dimethyl-silanyloxy)-propyl]-2,5-bis-(3-trifluoromethoxy-phenyl)-1,2,3,4-tetrahydro-quinoline

Scheme W

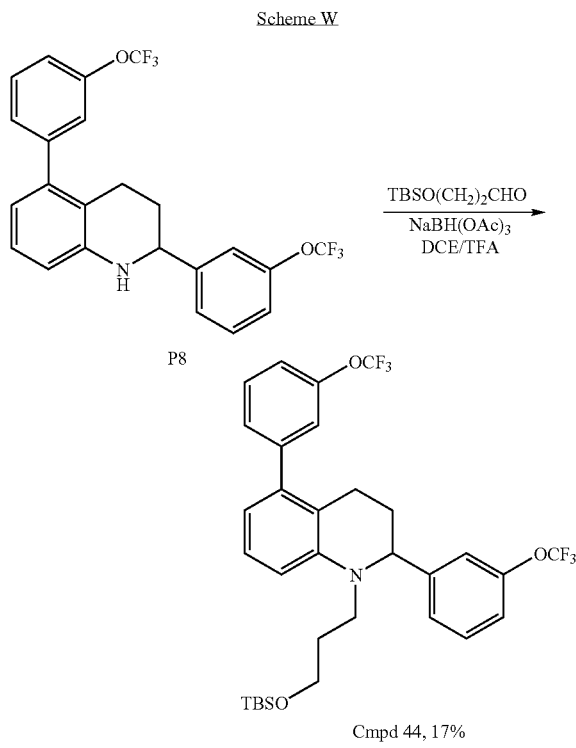

To a solution of P8 (54 mg, 0.119 mmol) and TBSO(CH)$_2$CHO (67 mg, 0.357 mmol) in CH$_2$Cl$_2$ (1 mL) was added NaBH(OAc)$_3$ (50 mg, 0.238 mmol) and TFA (0.009 mL, 0.119 mmol). After the reaction mixture was stirred at room temperature for 3 h, EtOAc was added and the solution was washed with 1 N HCl, H$_2$O, NaHCO$_3$ and brine, dried (MgSO$_4$) and concentrated to give 13 mg (17%) of compound 44: $^1$H NMR (400 MHz, CDCl$_3$) δ 7.33-7.25 (m, 2H), 7.22-7.16 (m, 3H), 7.15-7.05 (m, 4H), 6.89 (d, J=5.6 Hz, 1H), 6.45 (dd, J=7.65, 2.2 Hz, 1H), 4.35 (brs, 1H), 3.69-3.62 (m, 1H), 3.20-3.07 (m, 2H), 2.83-2.77 (m 2H), 2.46-2.26 (m, 2 H), 2.04-1.83 (m, 4H), 0.84 (s, 9H), 0.01 (s, 6H), 1.02-0.82 (s, 6H).

Example 45

Cmpd 45

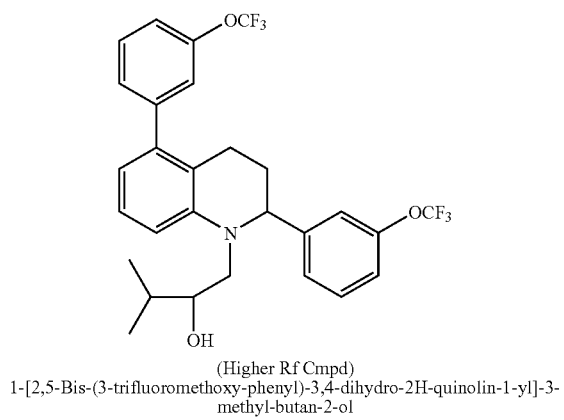

(Higher Rf Cmpd)
1-[2,5-Bis-(3-trifluoromethoxy-phenyl)-3,4-dihydro-2H-quinolin-1-yl]-3-methyl-butan-2-ol

Scheme X

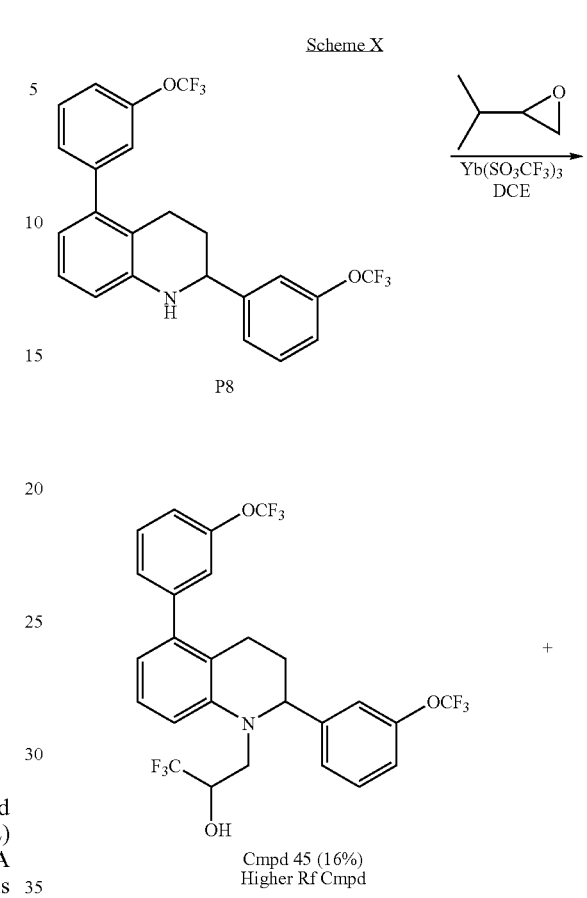

Replacing 2-trifluoromethyl-oxirane with 2-isopropyl-oxirane and following the same procedure as in the preparation of compound 31 and 32 gave compounds 45 (16%) and 46 (26%). Spectra of compound 45 are as follows: $^1$H NMR (400 MHz, CDCl$_3$) δ 7.39-7.31 (m, 2H), 7.22-7.09 (m, 6 H), 7.02 (s, 1H), 6.73 (d, J=8.2 Hz, 1H), 6.61 (d, J=7.4 Hz, 1H), 4.87 (brs, 1H), 3.82 (t, J=7.9 Hz, 1H), 3.68 (d, J=15.0 Hz, 1H), 2.98 (dd, J=15.1, 10.2 Hz, 1H), 2.49-2.29 (m, 2H), 2.21-2.10 (m, 1H), 2.00-1.85 (m, 2H), 1.78-1.68 (m, 1H), 1.02-0.82 (m, 6H); MS (ES) m/z: 540 (M+H$^+$).

Example 46

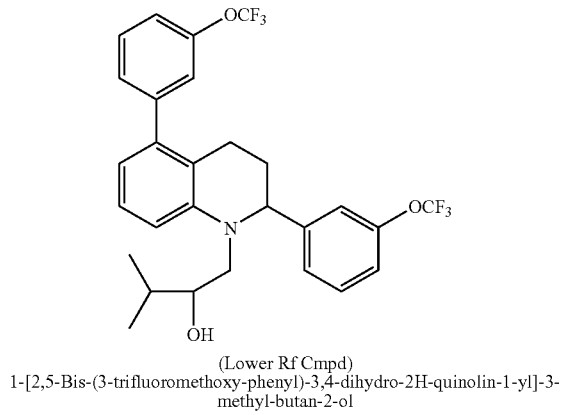

(Lower Rf Cmpd)
1-[2,5-Bis-(3-trifluoromethoxy-phenyl)-3,4-dihydro-2H-quinolin-1-yl]-3-methyl-butan-2-ol Spectra of compound 46 are as follows: $^1$H NMR (400 MHz, CDCl$_3$) δ 7.36 (t, J=7.9 Hz, 2H), 7.22-7.10 (m, 6H), 7.03 (s, 1H), 6.98 (d, J=8.3 Hz, 1H), 6.62 (d, J=7.0 Hz, 1H), 4.65 (t, J=4.0 Hz, 1H), 3.81-3.77 (m, 1H), 3.60 (dd, J=14.9, 8.6 Hz, 1H), 3.17 (dd, J=15.0, 4.1 Hz, 1H), 2.45-2.31 (m, 2H), 2.19-2.06 (m, 1H), 1.99-1.91 (m, 1H), 1.80-1.70 (m, 2H), 1.00-0.92 (m, 6H); MS (ES) m/z: 540 (M+H$^+$).

Example 47

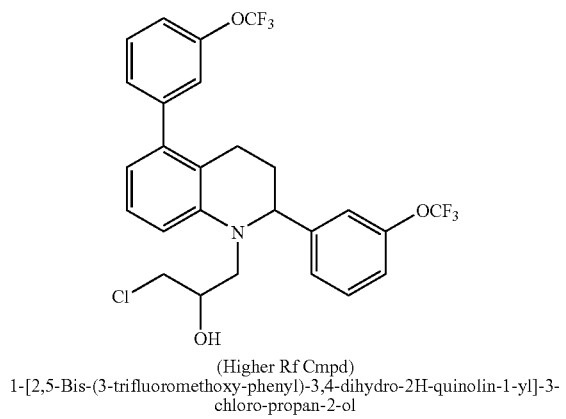

(Higher Rf Cmpd)
1-[2,5-Bis-(3-trifluoromethoxy-phenyl)-3,4-dihydro-2H-quinolin-1-yl]-3-chloro-propan-2-ol Scheme Z

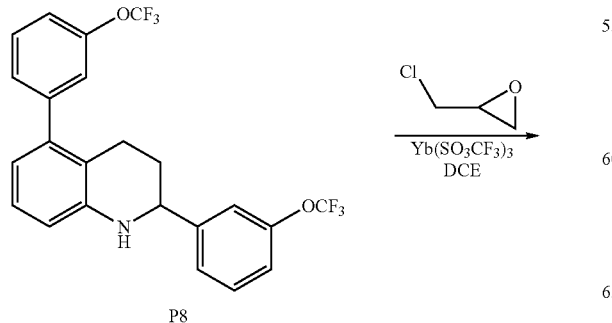

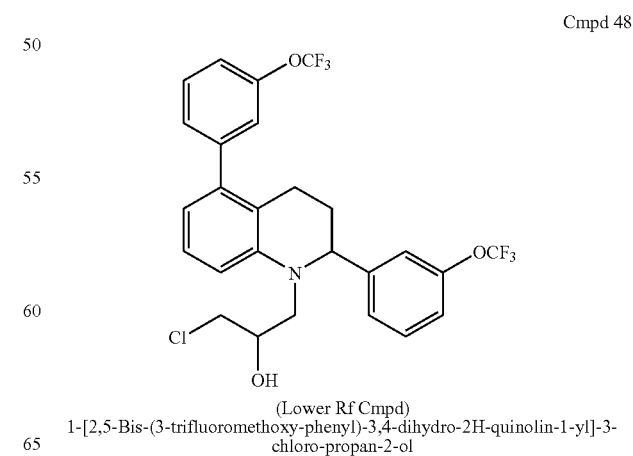

Cmpd 47 (20%)
Higher Rf Cmpd

Cmpd 48 (34%)
Lower Rf Cmpd

Replacing 2-trifluoromethyl-oxirane with 2-chloromethyl-oxirane and following the same procedure as in the preparation of compound 31 and 32 gave compound 47 (20%) and 48 (34%). Spectra of compound 47 are as follows: $^1$H NMR (400 MHz, CDCl$_3$) δ 7.40-7.22 (m, 2H), 7.24-7.10 (m, 6 H), 7.04 (s, 1H), 6.77 (d, J=8.3 Hz, 1H), 6.64 (d, J=7.4 Hz, 1H), 4.87 (t, J=4.2 Hz, 1H), 4.27 (m, 1H), 3.76 (dd, J=15.3, 3.0 Hz, 1H), 3.61 (dd, J=11.2, 4.6 Hz, 1H), 3.51 (dd, J=16.4, 6.4 Hz, 1H), 3.15 (dd, J=15.3, 8.8 Hz, 1H), 2.45 (dt, J=16.3, 4.2 Hz, 1H), 2.39-2.29 (m, 2H), 2.19-2.09 (m, 1H), 1.99-1.90 (m, 1H); MS (ES) m/z: 540 (M+H$^+$).

Example 48

Cmpd 48

(Lower Rf Cmpd)
1-[2,5-Bis-(3-trifluoromethoxy-phenyl)-3,4-dihydro-2H-quinolin-1-yl]-3-chloro-propan-2-ol Spectra of compound 48 are as follows: $^1$H NMR (400 MHz, CDCl$_3$) δ 7.45-7.22 (m, 2H), 7.24-7.10 (m, 6H), 7.01 (s, 1H), 6.90 (d, J=8.2 Hz, 1H), 6.65 (d, J=7.4 Hz, 1H), 4.68 (m, 1H), 4.29 (m, 1H), 3.85-3.65 (m, 3H), 3.22 (dd, J=15.1, 7.9 Hz, 1H), 2.50-2.31 (m, 2H), 2.23-2.09 (m, 2H), 1.96 (m, 1H); MS (ES) m/z: 546 (M+H$^+$).

Example 49

Cmpd 49

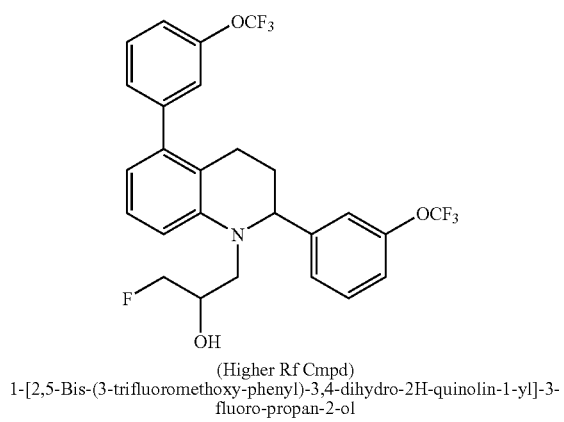

(Higher Rf Cmpd)
1-[2,5-Bis-(3-trifluoromethoxy-phenyl)-3,4-dihydro-2H-quinolin-1-yl]-3-fluoro-propan-2-ol

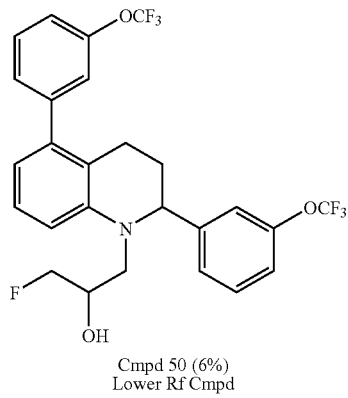

Cmpd 50 (6%)
Lower Rf Cmpd

Replacing 2-trifluoromethyl-oxirane with 2-fluoromethyl-oxirane and following the same procedure as in the preparation of compound 31 and 32 gave compound 49 (12%) and 50 (6%). Spectra of compound 49 are as follows: $^1$H NMR (400 MHz, CDCl$_3$) δ 7.40-7.32 (m, 2H), 7.23-7.10 (m, 6 H), 7.03 (s, 1H), 6.77 (d, J=8.3 Hz, 1H), 6.64 (d, J=6.9 Hz, 1H), 4.84 (t, J=4.0 Hz, 1H), 4.57-4.28 (m, 3H), 3.70 (dd, J=15.3, 3.3 Hz, 1H), 3.17 (dd, J=15.3, 2.8 Hz, 1H), 2.45 (dt, J=16.4, 4.2 Hz, 1H), 2.40-2.30 (m, 1 H), 2.20-2.09 (m, 2H), 2.00-1.91 (m, 1H); MS (ES) m/z: 530 (M+H$^+$).

Example 50

Scheme AA

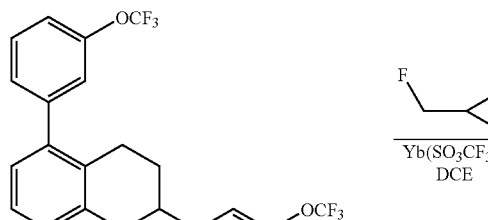

P8

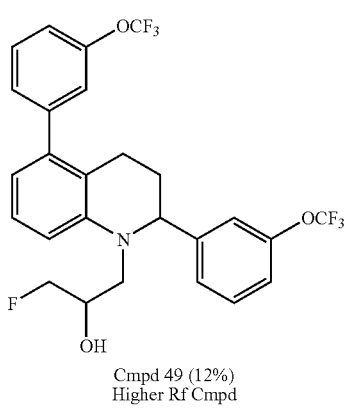

Cmpd 49 (12%)
Higher Rf Cmpd

+

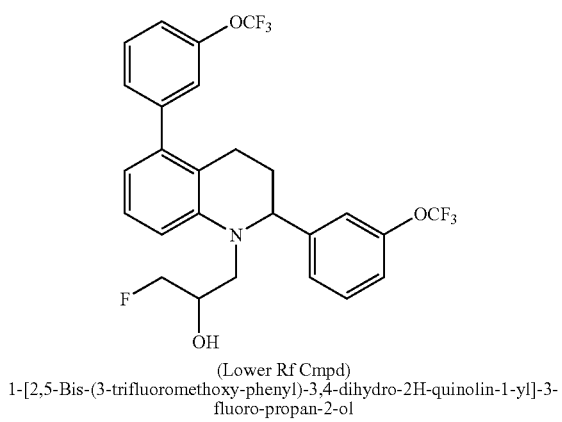

Cmpd 50

(Lower Rf Cmpd)
1-[2,5-Bis-(3-trifluoromethoxy-phenyl)-3,4-dihydro-2H-quinolin-1-yl]-3-fluoro-propan-2-ol Spectra of compound 50 are as follows: $^1$H NMR (400 MHz, CDCl$_3$) δ 7.40-7.32 (m, 2H), 7.26-7.09 (m, 6H), 7.01 (s, 1H), 6.89 (d, J=8.3 Hz, 1H), 6.64 (d, J=7.4 Hz, 1H), 4.66-4.41 (m, 3H), 4.22 (d, J=21.4 Hz, 1 H), 3.75-3.69 (m, 1H), 3.22 (dd, J=15.1, 8.1 Hz, 1H), 2.48-2.29 (m, 2 H), 2.19-1.91 (m, 3H); MS (ES) m/z: 530 (M+H$^+$).

Example 51

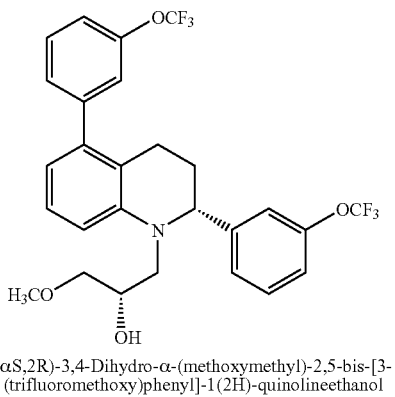

(αS,2R)-3,4-Dihydro-α-(methoxymethyl)-2,5-bis-[3-(trifluoromethoxy)phenyl]-1(2H)-quinolineethanol Scheme BB

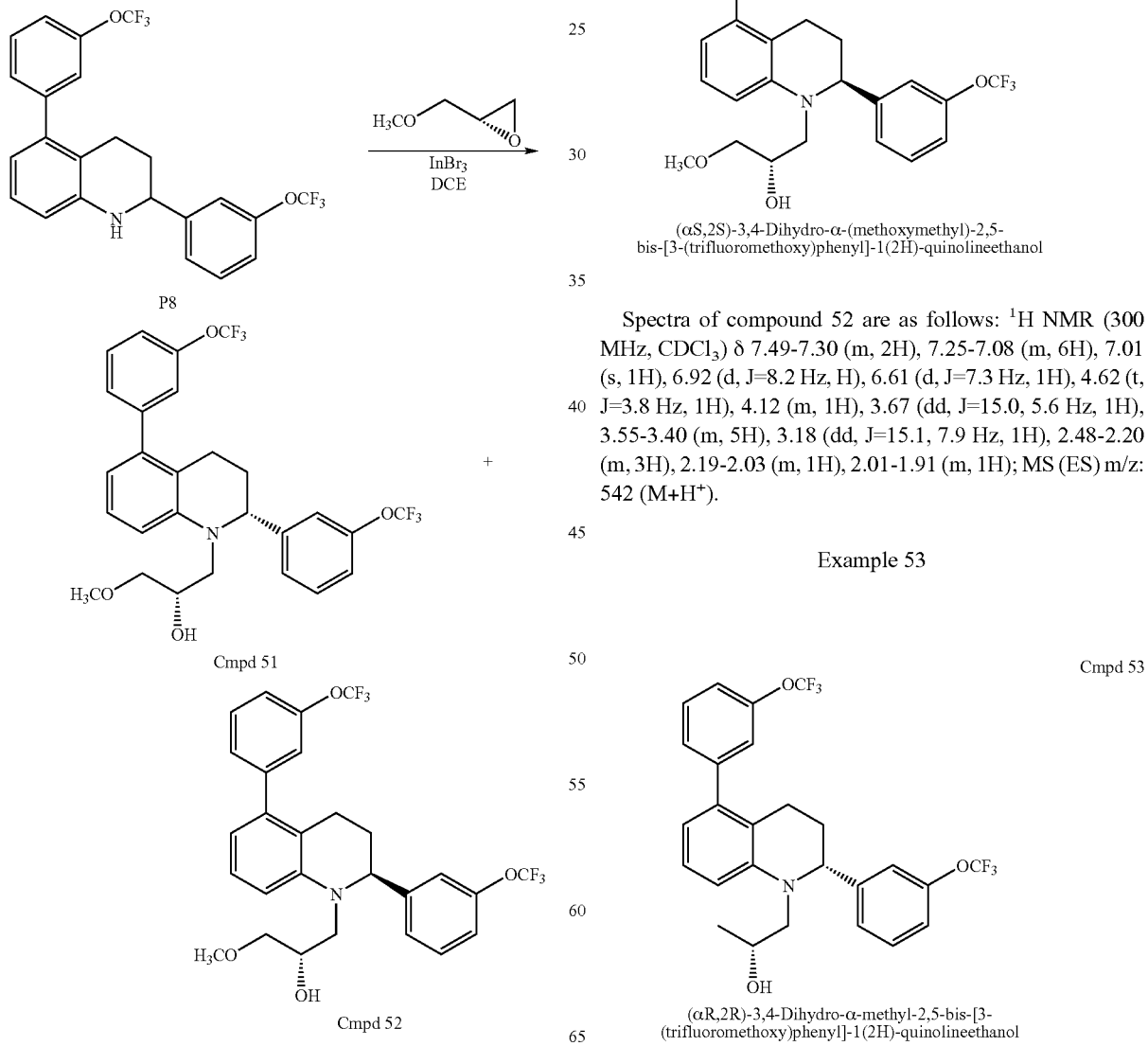

Replacing 2-methyl-oxirane with (S)-(+)-glycidyl methyl ether and following the same procedure as in the preparation of compound 40 and 41 gave compound 51 and 52. Spectra of compound 51 are as follows: $^1$H NMR (300 MHz, CDCl$_3$) δ 7.40-7.30 (m, 2H), 7.23-7.09 (m, 6H), 7.03 (s, 1H), 6.78 (d, J=8.2 Hz, 1H), 6.60 (d, J=7.2 Hz, 1H), 4.88 (t, J=3.9 Hz, 1H), 4.20 (m, 1H), 3.66 (dd, J=15.2, 3.4 Hz, 1H), 3.44 (dd, J=19.5, 4.0 Hz, 1H), 3.37-3.31 (m, 4H), 3.11 (dd, J=15.4, 8.6 Hz, 1H), 2.50-2.25 (m, 3H), 2.20-2.07 (m, 1H), 2.00-1.90 (m, 1H); MS (ES) m/z: 542 (M+H$^+$).

Example 52

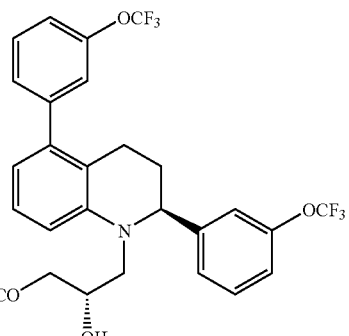

(αS,2S)-3,4-Dihydro-α-(methoxymethyl)-2,5-bis-[3-(trifluoromethoxy)phenyl]-1(2H)-quinolineethanol Spectra of compound 52 are as follows: $^1$H NMR (300 MHz, CDCl$_3$) δ 7.49-7.30 (m, 2H), 7.25-7.08 (m, 6H), 7.01 (s, 1H), 6.92 (d, J=8.2 Hz, H), 6.61 (d, J=7.3 Hz, 1H), 4.62 (t, J=3.8 Hz, 1H), 4.12 (m, 1H), 3.67 (dd, J=15.0, 5.6 Hz, 1H), 3.55-3.40 (m, 5H), 3.18 (dd, J=15.1, 7.9 Hz, 1H), 2.48-2.20 (m, 3H), 2.19-2.03 (m, 1H), 2.01-1.91 (m, 1H); MS (ES) m/z: 542 (M+H$^+$).

Example 53

(αR,2R)-3,4-Dihydro-α-methyl-2,5-bis-[3-(trifluoromethoxy)phenyl]-1(2H)-quinolineethanol

Scheme CC

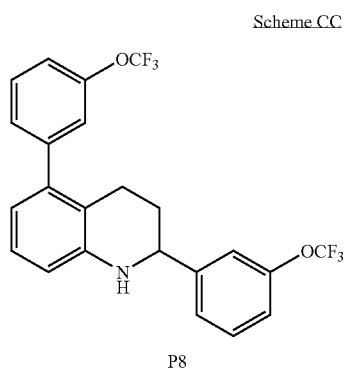

P8

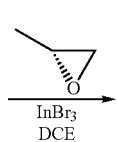
InBr₃
DCE

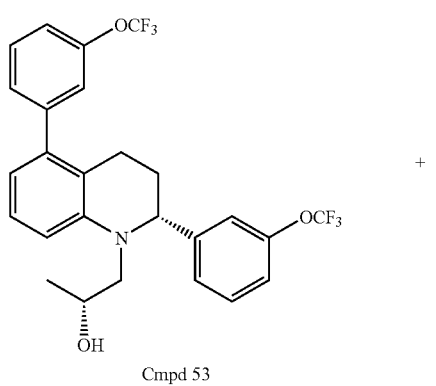

Cmpd 53

+

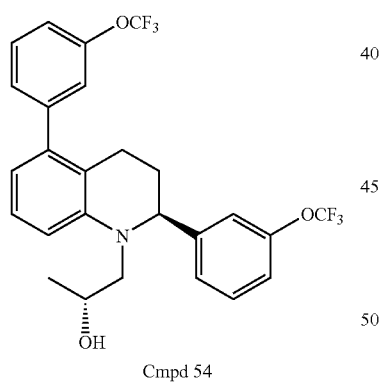

Cmpd 54

Replacing 2-methyl-oxirane with (R)-(+)-propylene oxide and following the same procedure as in the preparation of compound 40 and 41 gave compound 53 and 54. Spectra of compound 53 are as follows: ¹H NMR (400 MHz, CDCl₃) δ 7.40-7.31 (m, 2H), 7.22-7.09 (m, 6H), 7.02 (s, 1H), 6.75 (d, J=8.3 Hz, 1H), 6.62 (d, J=7.5 Hz, 1H), 4.85 (t, J=4.0 Hz, 1H), 4.25 (m, 1H), 3.57 (dd, J=15.1, 2.4 Hz, 1H), 2.97 (dd, J=15.2, 9.8 Hz, 1H), 2.49-2.40 (m, 1H), 2.39-2.29 (m, 1H), 2.22-2.11 (m, 1H), 2.00-1.88 (m, 2H), 1.20 (d, J=6.3 Hz, 3H); MS (ES) m/z: 512 M+H⁺).

Example 54

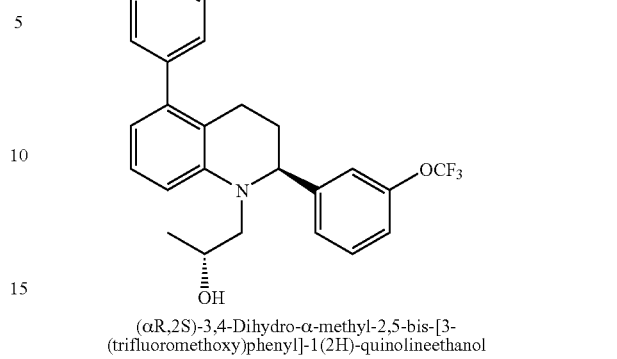

Cmpd 54

(αR,2S)-3,4-Dihydro-α-methyl-2,5-bis-[3-(trifluoromethoxy)phenyl]-1(2H)-quinolineethanol Spectra of compound 54 are as follows: ¹H NMR (400 MHz, CDCl₃) δ 7.39-7.33 (m, 2H), 7.24-7.10 (m, 6H), 7.02 (s, 1H), 6.96 (d, J=8.3 Hz, 1H), 6.62 (d, J=7.5 Hz, 1H), 4.69 (t, J=3.9 Hz, 1H), 4.21 (m, 1H), 3.62 (dd, J=15.0, 7.5 Hz, 1H), 3.05 (dd, J=15.0, 5.2 Hz, 1H), 2.46-2.29 (m, 2H), 2.19-2.09 (m, 1H), 2.00-1.92 (m, 1H), 1.71 (brs, 1H), 1.25 (d, J=6.2 Hz, 3H); MS (ES) m/z: 512 (M+H⁺).

Example 55

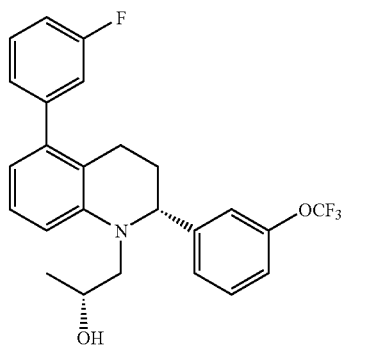

Cmpd 55

(αR,2R)-5-(3-Fluorophenyl)-3,4-dihydro-α-methyl-2-[3-(trifluoromethoxy)phenyl]-1(2H)-quinolineethanol

Scheme DD

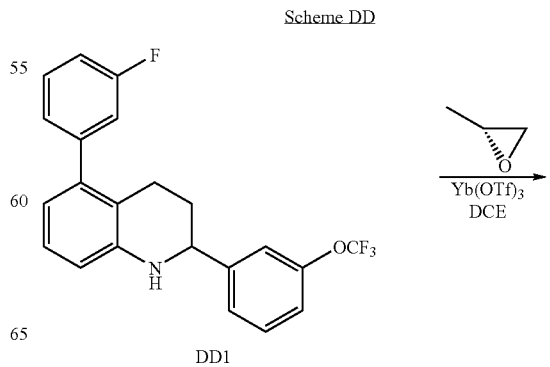

DD1

-continued

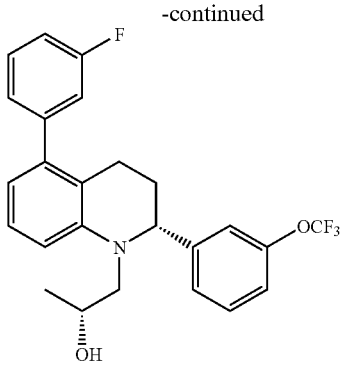
Cmpd 55

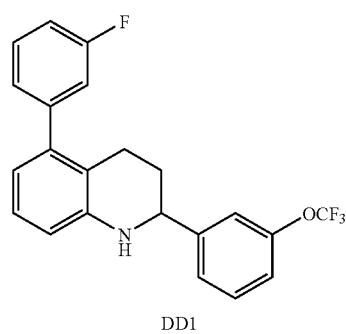
Cmpd 56

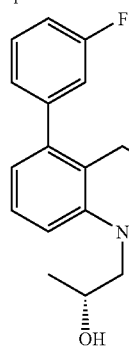
DD1
5-(3-Fluoro-phenyl)-2-(3-trifluoromethoxy-phenyl)-1,2,3,4-tetrahydro-quinoline ¹H NMR (400 MHz, CDCl₃) δ 7.40-7.30 (m, 4H), 7.19-6.99 (m, 5H), 6.65-6.59 (m, 2H), 4.51 (dd, J=8.8, 3.4 Hz, 1H), 4.19 (brs, 1H), 2.81-2.70 (m, 1H), 2.54 (dt, J=16.7, 4.9 Hz, 1H), 2.11-2.02 (m, 1H), 1.93-1.82 (m, 1H); MS (ES) m/z: 388 (M+H⁺).

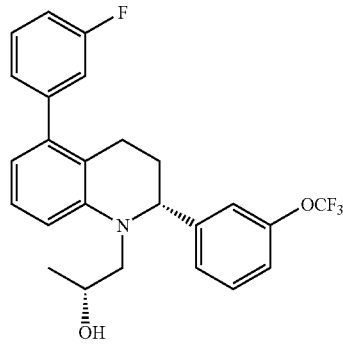
(αR,2R)-5-(3-Fluorophenyl)-3,4-dihydro-α-methyl-2-[3-(trifluoromethoxy)phenyl]-1(2H)-quinolineethanol Replacing A12 with DD1, 2-trifluoromethyl-oxirane with (R)-(+)-propylene oxide and following the same procedure as in the preparation of compound 1 and 2 gave compound 55 and 56. Spectra of compound 55 are as follows: ¹H NMR (300 MHz, CDCl₃) δ 7.39-7.29 (m, 2H), 7.22-7.09 (m, 3H), 7.06-6.82 (m, 4H), 6.74 (d, J=8.3 Hz, 1H), 6.62 (d, J=7.5 Hz, 1H), 4.84 (t, J=4.1 Hz, 1H), 4.24 (m, 1H), 3.56 (dd, J=15.1, 2.4 Hz, 1H), 2.96 (dd, J=15.2, 9.8 Hz, 1H), 2.51-2.28 (m, 2H), 2.22-2.09 (m, 1H), 2.00-1.87 (m, 2H), 1.20 (d, J=6.3 Hz, 3H); MS (ES) m/z: 446 (M+H⁺).

Example 56

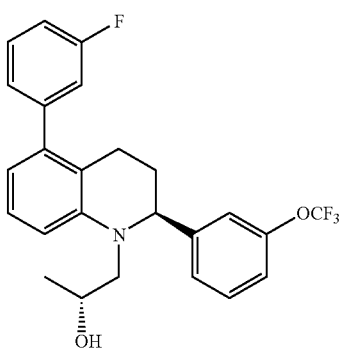
Cmpd 56
(αR,2S)-5-(3-Fluorophenyl)-3,4-dihydro-α-methyl-2-[3-(trifluoromethoxy)phenyl]-1(2H)-quinolineethanol Spectra of compound 56 are as follows: ¹H NMR (300 MHz, CDCl₃) δ 7.39-7.27 (m, 2H), 7.22-7.09 (m, 3H), 7.05-6.91 (m, 5H), 6.62 (d, J=7.5 Hz, 1H), 4.69 (t, J=3.9 Hz, 1H), 4.20 (m, 1H), 3.62 (dd, J=15.0, 7.5 Hz, 1H), 3.05 (dd, J=15.0, 5.2 Hz, 1H), 2.48-2.28 (m, 2H), 2.19-2.05 (m, 1H), 2.01-1.90 (m, 1H), 1.71 (brs, 1H), 1.25 (d, J=6.1 Hz, 3H); MS (ES) m/z: 446 (M+H⁺).

Example 57

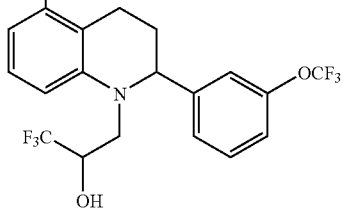
Cmpd 57
(Higher Rf Cmpd)
1,1,1-Trifluoro-3-[5-(3-fluoro-phenyl)-2-(3-trifluoromethoxy-phenyl)-3,4-dihydro-2H-quinolin-1-yl]-propan-2-ol Scheme EE

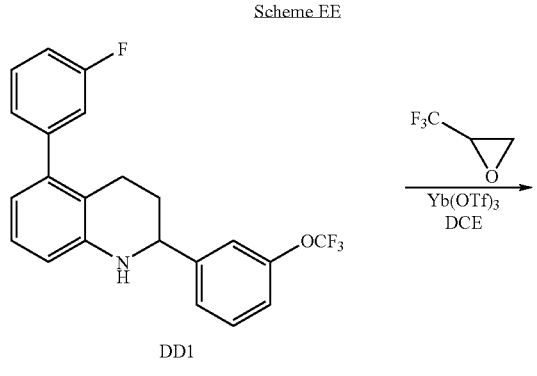

DD1

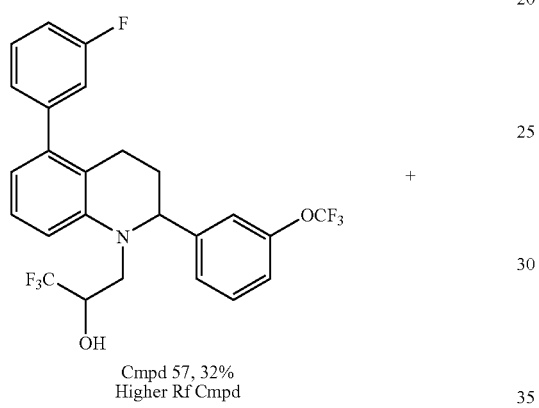

Cmpd 57, 32%
Higher Rf Cmpd

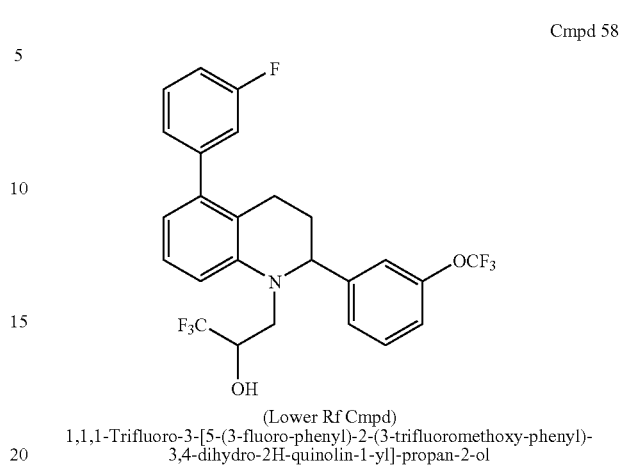

+

Cmpd 58, 23%
Lower Rf Cmpd

Replacing A12 with DD1 and following the same procedure as in the preparation of compound 1 and 2 gave compound 57 (32%) and 58 (23%). Spectra of compound 57 are as follows: $^1$H NMR (400 MHz, CDCl$_3$) δ 7.39-7.19 (m, 3H), 7.13 (d, J=7.7 Hz, 2H), 7.06-6.93 (m, 4H), 6.71 (d, J=8.2 Hz, 1H), 6.67 (d, J=7.5 Hz, 1H), 4.90 (t, J=4.4 Hz, 1H), 4.48-4.40 (m, 1H), 3.91 (dd, J=15.5 Hz, 1H), 3.29 (dd, J=15.6, 9.7 Hz, 1H), 2.48 (dt, J=11.9, 4.4 Hz, 1H), 2.41-2.31 (m, 2H), 2.19-2.09 (m, 1H), 2.00-1.91 (m, 1H); MS (ES) m/z: 500 (M+H$^+$).

Example 58

Cmpd 58

(Lower Rf Cmpd)
1,1,1-Trifluoro-3-[5-(3-fluoro-phenyl)-2-(3-trifluoromethoxy-phenyl)-3,4-dihydro-2H-quinolin-1-yl]-propan-2-ol Spectra of compound 58 are as follows: $^1$H NMR (400 MHz, CDCl$_3$) δ 7.39-7.20 (m, 3H), 7.12 (bt, J=7.8 Hz, 2H), 7.05-6.93 (m, 4H), 6.88 (d, J=8.2 Hz, 1H), 6.68 (d, J=7.5 Hz, 1H), 4.61 (t, J=4.2 Hz, 1H), 4.38-4.29 (m, 1H), 3.80 (dd, J=15.7, 6.5 Hz, 1H), 3.51 (dd, J=15.6, 5.5 Hz, 1H), 2.49-2.30 (m, 2H), 2.23 (d, J=5.0 Hz, 1H), 2.17-2.06 (m, 1H), 1.99-1.90 (m, 1H); MS (ES) m/z: 500 (M+H$^+$).

Example 59

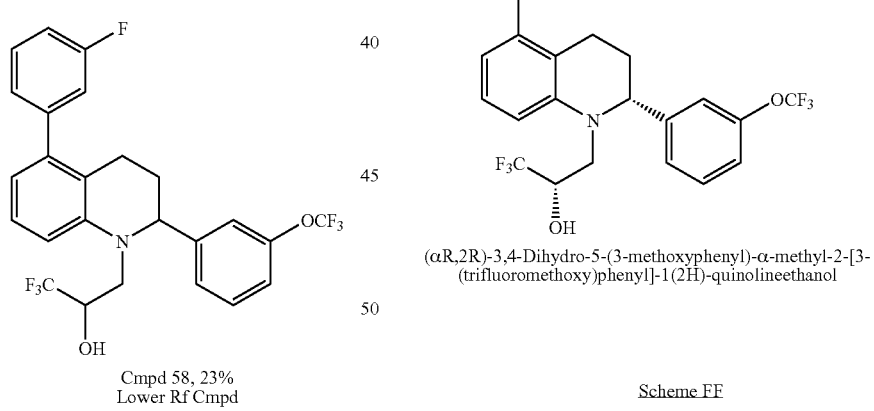

Cmpd 59

(αR,2R)-3,4-Dihydro-5-(3-methoxyphenyl)-α-methyl-2-[3-(trifluoromethoxy)phenyl]-1(2H)-quinolineethanol Scheme FF

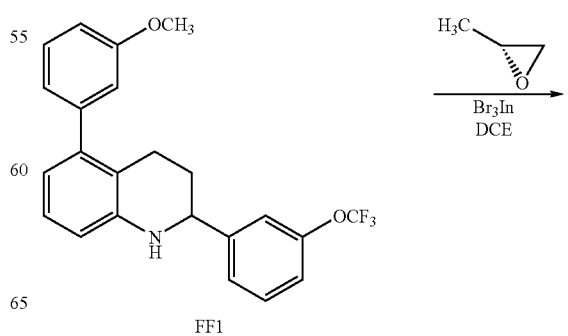

FF1

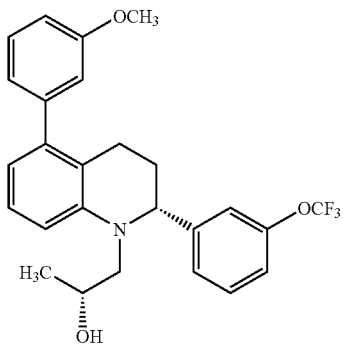

Cmpd 59, 21%

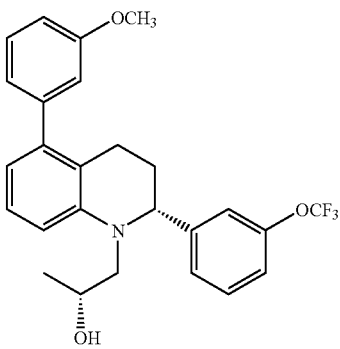

(αR,2R)-3,4-Dihydro-5-(3-methoxyphenyl)-α-methyl-2-[3-(trifluoromethoxy)phenyl]-1(2H)-quinolineethanol Replacing 2-methyl-oxirane with (R)-(+)-propylene oxide and following the same procedure as in the preparation of compound 40 and 41 gave compound 59 and 60. Spectra of compound 59 are as follows: $^1$H NMR (400 MHz, CDCl$_3$) δ 7.33 (t, J=7.9 Hz, 1H), 7.28-7.23 (m, 1H), 7.18 (t, J=7.9 Hz, 1H), 7.12-7.09 (m, 2H), 7.02 (s, 1H), 6.85-6.79 (m, 3H), 6.73 (d, J=8.2 Hz, 1H), 6.66 (d, J=7.5 Hz, 1H), 4.83 (t, J=4.2 Hz, 1H), 4.24 (m, 1H), 3.78 (s, 3H), 3.56 (dd, J=15.1, 2.5 Hz, 1H), 2.96 (dd, J=15.1, 9.8 Hz, 1H), 2.52-2.45 (m, 1H), 2.41-2.30 (m, 1H), 2.21-2.11 (m, 1H), 1.98-1.90 (m, 2H), 1.19 (d, J=6.3 Hz, 3H); MS (ES) m/z: 458 (M+H$^+$).

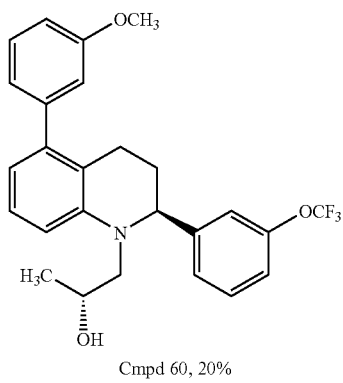

Cmpd 60, 20%

Example 60

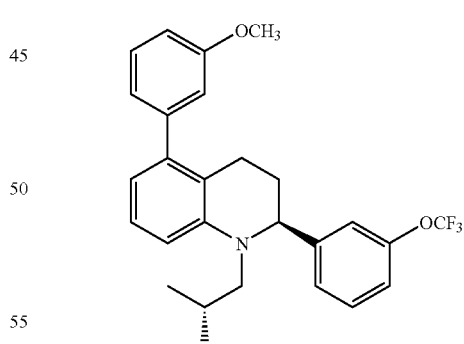

Cmpd 60

(αR,2S)-3,4-Dihydro-5-(3-methoxyphenyl)-α-methyl-2-[3-(trifluoromethoxy)phenyl]-1(2H)-quinolineethanol

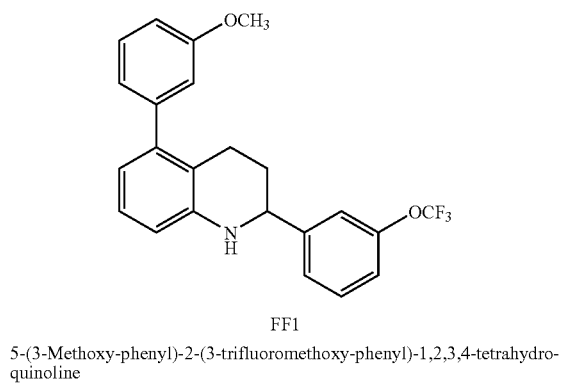

FF1
5-(3-Methoxy-phenyl)-2-(3-trifluoromethoxy-phenyl)-1,2,3,4-tetrahydro-quinoline Replacing 3-trifluoromethoxy-benzene boronic acid with 3-methoxy-benzene boronic acid and following the same procedure as in the preparation of P8 gave FF1. $^1$H NMR (400 MHz, CDCl$_3$) δ 7.50-7.21 (m, 4 H), 7.13 (d, J=7.7 Hz, 1H), 7.07 (t, J=7.7 Hz, 1H), 6.93-6.86 (m, 3H), 6.64 (d, J=7.5 Hz, 1H), 6.58 (d, J=8.0 Hz, 1H), 4.49 (dd, J=8.8, 3.2 Hz, 1H), 4.17 (brs, 1H), 3.81 (s, 3H), 2.81-2.61 (m, 1H), 2.57 (dt, J=16.7, 5.0 Hz, 1H), 2.09-2.01 (m, 1H), 1.92-1.80 (m, 1H); MS (ES) m/z: 400 (M+H$^+$).

Spectra of compound 60 are as follows: $^1$H NMR (400 MHz, CDCl$_3$) δ 7.34 (t, J=7.9 Hz, 1H), 7.27-7.23 (m, 1H), 7.18 (t, J=7.9 Hz, 1H), 7.13-7.09 (m, 2H), 7.03 (s, 1H), 6.93 (d, J=8.2 Hz, 1H), 6.88-6.79 (m, 3 H), 6.66 (d, J=7.5 Hz, 1H), 4.68 (t, J=4.0 Hz, 1H), 4.21 (m, 1H), 3.78 (s, 3H), 3.61 (dd, J=14.9, 7.6 Hz, 1H), 3.05 (dd, J=15.0, 5.2Hz, 1H), 2.49-2.30

(m, 2H), 2.18-2.07 (m, 1H), 1.99-1.90 (m, 1H), 1.74 (d, J=2.9 Hz, 1H), 1.25 (d, J=6.2 Hz, 3H); MS (ES) m/z: 458 (M+H⁺).

Example 61

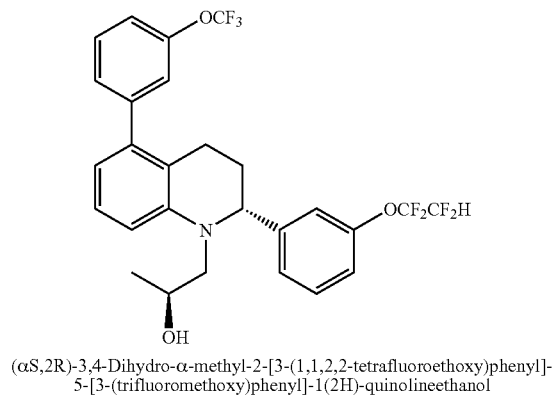

Cmpd 61

(αS,2R)-3,4-Dihydro-α-methyl-2-[3-(1,1,2,2-tetrafluoroethoxy)phenyl]-5-[3-(trifluoromethoxy)phenyl]-1(2H)-quinolineethanol

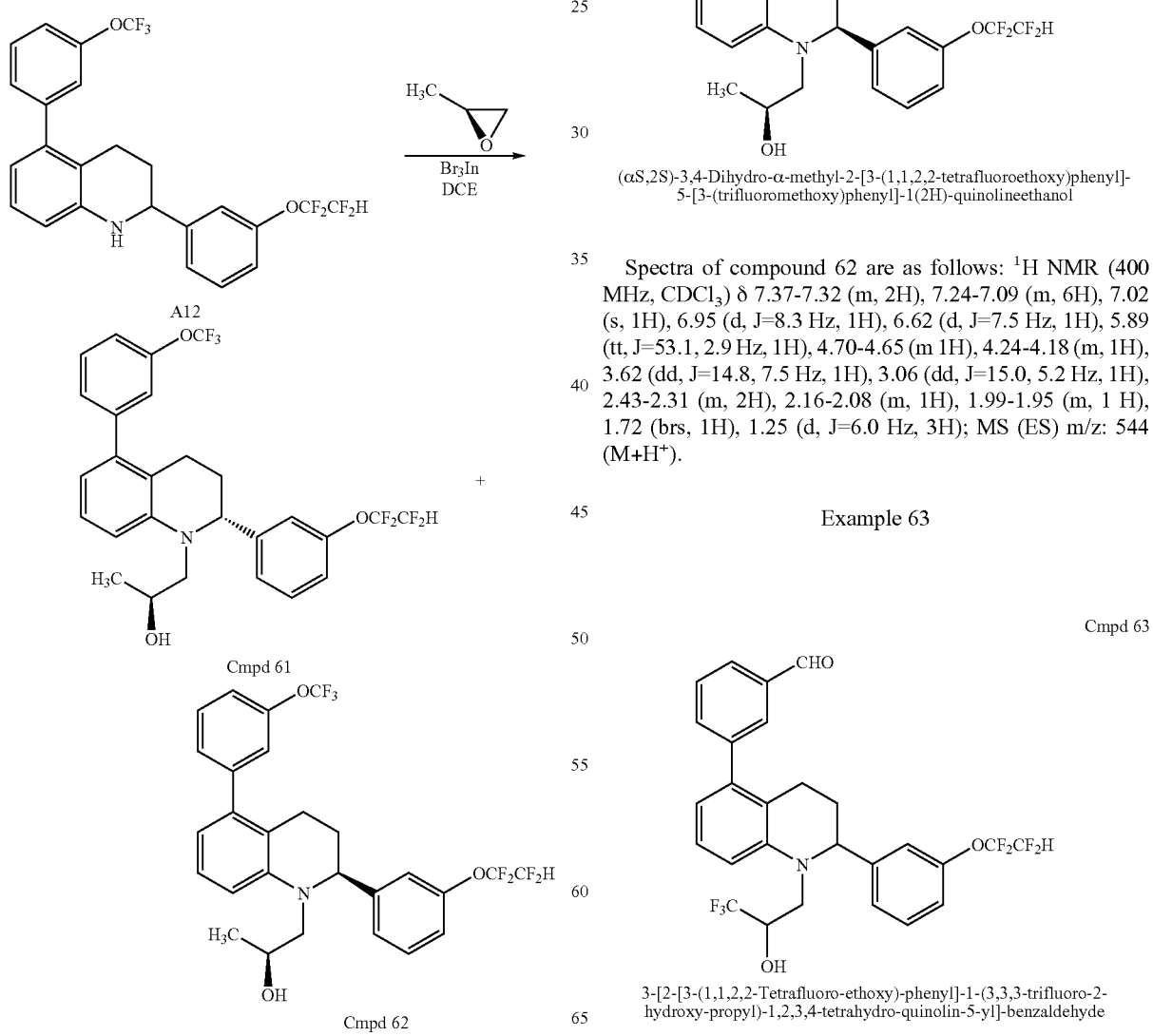

Scheme GG

Cmpd 61

Cmpd 62

Replacing 2-trifluoromethyl-oxirane with (S)-(−)-propylene oxide and following the same procedure as in the preparation of compound 40 and 41 gave compound 61 and 62. Spectra of compound 61 are as follows: $^1$H NMR (400 MHz, CDCl$_3$) δ 7.09-7.31 (m, 2H), 7.22-7.09 (m, 6H), 7.01 (s, 1H), 6.75 (t, J=8.2 Hz, 1H), 6.62 (d, J=7.5 Hz, 1H), 5.89 (tt, J=53.1, 2.9 Hz, 1H), 4.84 (t, J=4.2 Hz, 1H), 4.24 (m, 1H), 3.56 (dd, J=15.1, 2.4 Hz, 1H), 2.98 (dd, J=15.2, 9.8 Hz, 1H), 2.49-2.30 (m, 2H), 2.11-2.10 (m, 1H), 2.00-1.92 (m, 1H), 1.88 (brs, 1H), 1.20 (d, J=6.3 Hz, 3H); MS (ES) m/z: 544 (M+H⁺).

Example 62

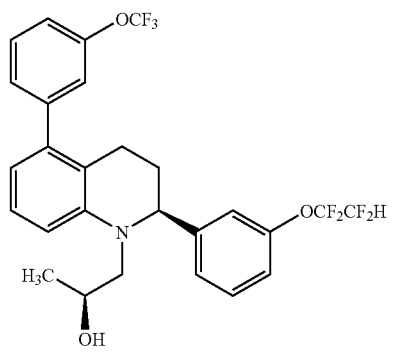

Cmpd 62

(αS,2S)-3,4-Dihydro-α-methyl-2-[3-(1,1,2,2-tetrafluoroethoxy)phenyl]-5-[3-(trifluoromethoxy)phenyl]-1(2H)-quinolineethanol Spectra of compound 62 are as follows: $^1$H NMR (400 MHz, CDCl$_3$) δ 7.37-7.32 (m, 2H), 7.24-7.09 (m, 6H), 7.02 (s, 1H), 6.95 (d, J=8.3 Hz, 1H), 6.62 (d, J=7.5 Hz, 1H), 5.89 (tt, J=53.1, 2.9 Hz, 1H), 4.70-4.65 (m 1H), 4.24-4.18 (m, 1H), 3.62 (dd, J=14.8, 7.5 Hz, 1H), 3.06 (dd, J=15.0, 5.2 Hz, 1H), 2.43-2.31 (m, 2H), 2.16-2.08 (m, 1H), 1.99-1.95 (m, 1 H), 1.72 (brs, 1H), 1.25 (d, J=6.0 Hz, 3H); MS (ES) m/z: 544 (M+H⁺).

Example 63

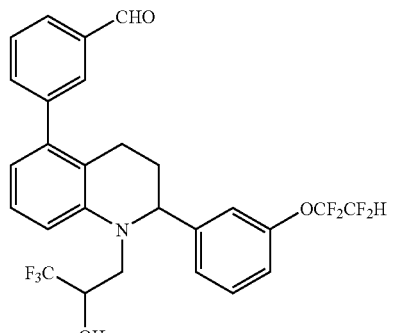

Cmpd 63

3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzaldehyde Scheme HH

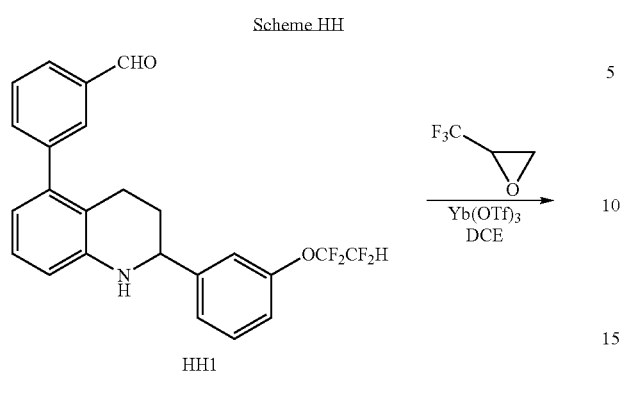

HH1

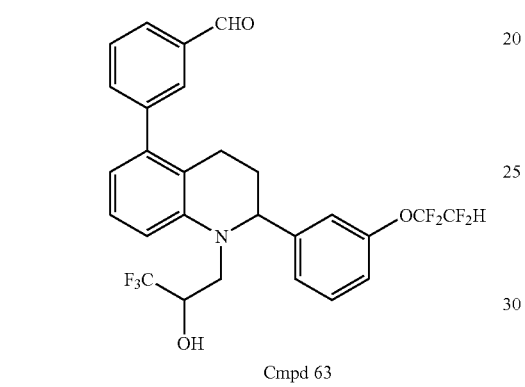

Cmpd 63

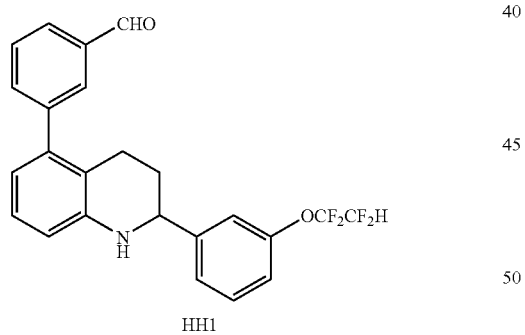

HH1

3-{2-[3-(1,1,2,2-Tetrafluoro-ethoxy)-phenyl]-1,2,3,4-tetrahydro-quinolin-5-yl}-benzaldehyde Replacing 3-trifluoromethoxy-benzene boronic acid with 3-formyl-benzene boronic acid and following the same procedure as in the preparation of A12 gave HH1. $^1$H NMR (300 MHz, CDCl$_3$) δ 10.05 (s, 1H), 7.84 (m, 2H), 7.58 (m, 2H), 7.47-7.06 (m, 5H), 6.63 (d, J=7.7 Hz, 2H), 5.90 (bt, J=53.1 Hz, 1H), 4.53 (bd, 1H), 4.22 (brs, 1H), 2.85-2.70 (m, 1 H), 2.60-2.46 (m, 1H), 2.16-1.81 (m, 2H); MS (ES) m/z: 430 (M+H$^+$).

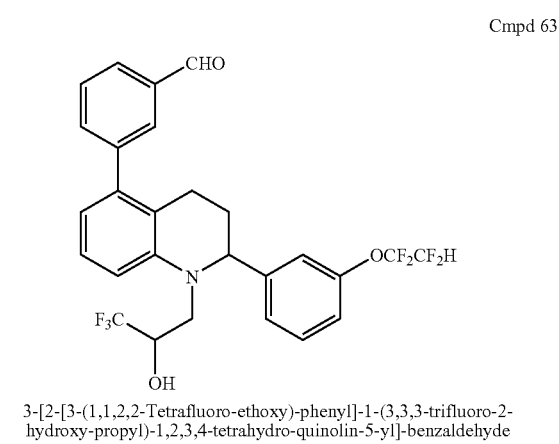

Cmpd 63

3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzaldehyde Replacing A12 with HH1 and following the same procedure as in the preparation of compound 1 and 2 gave an inseparable mixture of compound 63: MS (ES) m/z: 542 (M+H$^+$).

Example 64

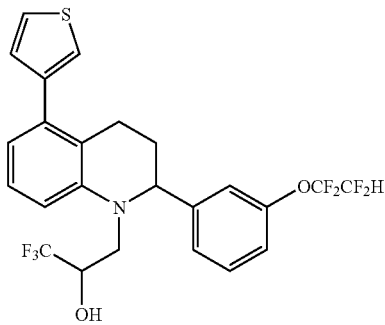

Cmpd 64

(Higher Rf Cmpd)
1,1,1-Trifluoro-3-{2-[3-(1,1,2,2-tetrafluoro-ethoxy)-phenyl]-5-thiophen-3-yl-3,4-dihydro-2H-quinolin-1-yl}-propan-2-ol Scheme II

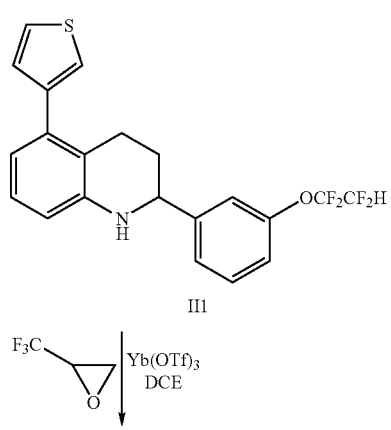

II1

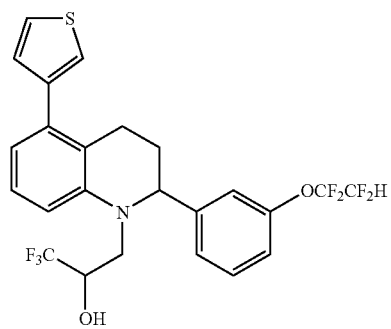

Cmpd 64, 25%
Higher Rf Cmpd

+

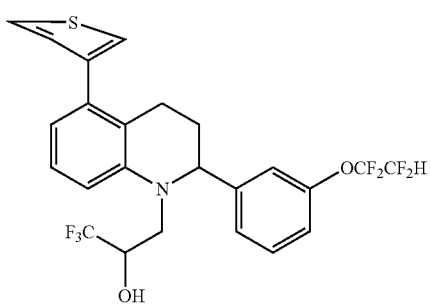

Cmpd 65, 31%
Lower Rf Cmpd

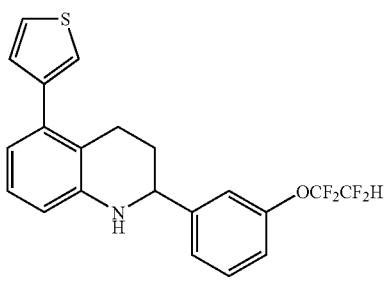

2-[3-(1,1,2,2-Tetrafluoro-ethoxy)-phenyl]-5-thiophen-3-yl-1,2,3,4-tetrahydro-quinoline Replacing 3-trifluoromethoxy-benzene boronic acid with 3-thiophene boronic acid and following the same procedure as in the preparation of A12 gave II1. $^1$H NMR (400 MHz, CDCl$_3$) δ 7.40-7.40 (m, 4H), 7.18 (d, J=3.0 Hz, 1H), 7.15-7.12 (m, 2H), 7.06 (t, J=7.7 Hz, 1H), 6.71 (d, J=7.5 Hz, 1H), 6.57 (d, J=8.0 Hz, 1H), 5.90 (tt, J=53.1, 2.8 Hz, 1H), 4.50 (dd, J=9.0, 3.4 Hz, 1H), 4.16 (brs, 1H), 2.89-2.79 (m, 1H), 2.66 (dt, J=16.6, 5.0 Hz, 1H), 2.11-2.04 (m, 1H), 1.94-1.83 (m, 1H); MS (ES) m/z: 408 (M+H$^+$).

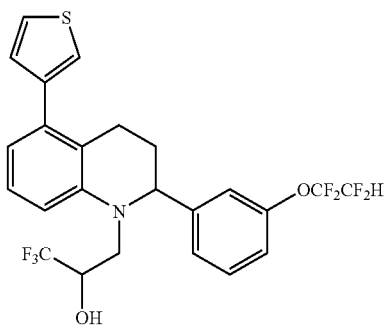

Higher Rf Cmpd
1,1,1-Trifluoro-3-{2-[3-(1,1,2,2-tetrafluoro-ethoxy)-phenyl]-5-thiophen-3-yl-3,4-dihydro-2H-quinolin-1-yl}-propan-2-ol Replacing A12 with II1 and following the same procedure as in the preparation of compound 1 and 2 gave compound 64 and 65. Spectra of compound 64 are as follows: $^1$H NMR (400 MHz, CDCl$_3$) δ 7.38-7.30 (m, 2 H), 7.22-7.01 (m, 6H), 6.76 (d, J=7.5 Hz, 1H), 6.70 (d, J=8.3 Hz, 1H), 5.89 (tt, J=53.1, 2.8 Hz, 1H), 4.89 (t, J=4.2 Hz, 1H), 4.43 (m, 1H), 3.90 (d, J=15.6 Hz, 1H), 3.30 (dd, J=15.6, 9.7 Hz, 1H), 2.68-2.59 (m, 1H), 2.50-2.35 (m, 2H), 2.20-2.09 (m, 1H), 2.03-1.93 (m, 1H); MS (ES) m/z: 520 (M+H$^+$).

Example 65

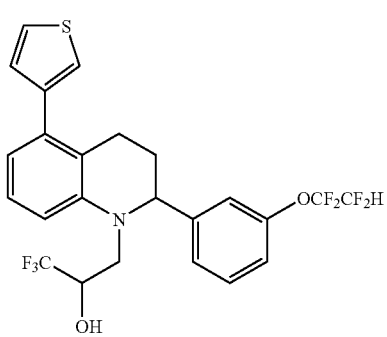

(Lower Rf Cmpd)
1,1,1-Trifluoro-3-{2-[3-(1,1,2,2-tetrafluoro-ethoxy)-phenyl]-5-thiophen-3-yl-3,4-dihydro-2H-quinolin-1-yl}-propan-2-ol Spectra of compound 65 are as follows: $^1$H NMR (400 MHz, CDCl$_3$) δ 7.38-7.29 (m, 2H), 7.20 (t, J=7.9 Hz, 1H), 7.18-7.01 (m, 5H), 6.85 (d, J=8.2 Hz, 1H), 6.78 (d, J=7.5 Hz, 1H), 5.88 (tt, J=53.1, 2.8 Hz, 1H), 4.61 (t, J=4.2 Hz, 1H), 4.33 (m, 1H), 3.79 (d, J=15.6 Hz, 1H), 3.51 (dd, J=15.7, 5.4 Hz, 1H), 2.59 (dd, J=16.3, 4.1 Hz, 1H), 2.50-2.39 (m, 1H), 2.21 (d, J=5.0 Hz, 1H), 2.19-2.08 (m, 1H), 2.01-1.92 (m, 1H); MS (ES) m/z: 520 (M+H$^+$).

Example 66

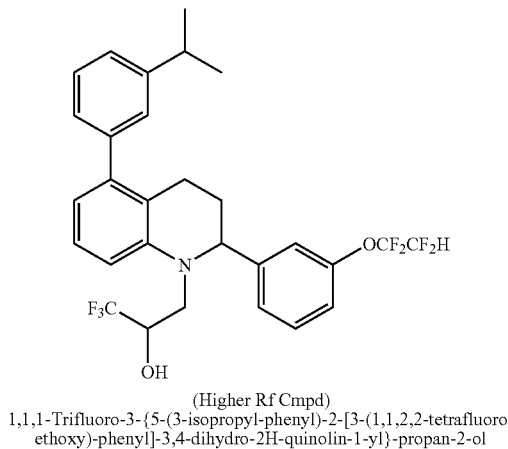

(Higher Rf Cmpd)
1,1,1-Trifluoro-3-{5-(3-isopropyl-phenyl)-2-[3-(1,1,2,2-tetrafluoro-ethoxy)-phenyl]-3,4-dihydro-2H-quinolin-1-yl}-propan-2-ol Scheme JJ

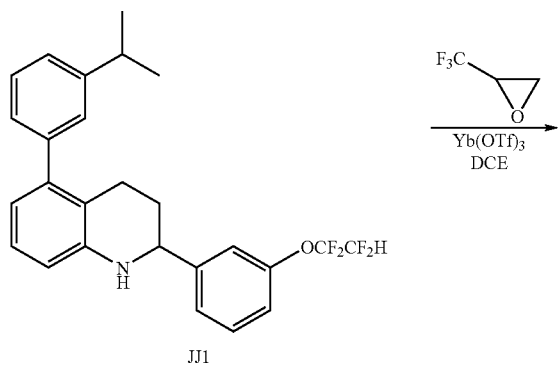

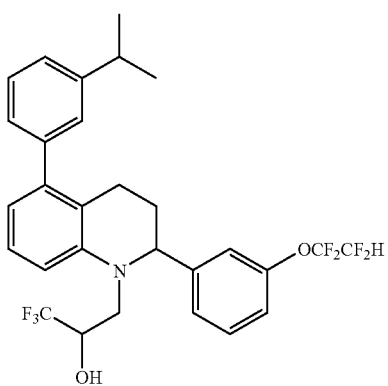

Cmpd 66
Higher Rf Cmpd

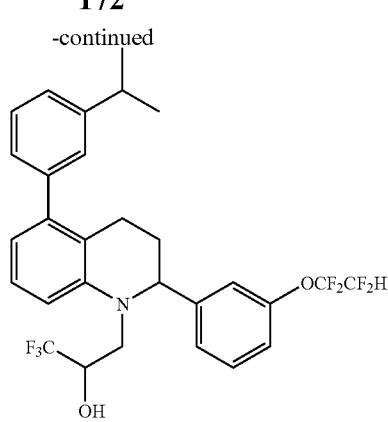

Cmpd 67
Lower Rf Cmpd

JJ1

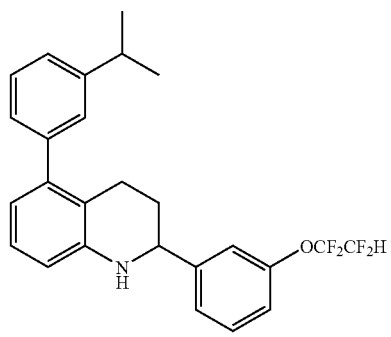

5-(3-Isopropyl-phenyl)-2-[3-(1,1,2,2-tetrafluoro-ethoxy)-phenyl]-1,2,3,4-tetrahydro-quinoline Replacing 3-trifluoromethoxy-benzene boronic acid with 3-isopropyl-benzene boronic acid and following the same procedure as in the preparation of A12 gave JJ1. $^1$H NMR (300 MHz, CDCl$_3$) δ 7.40-7.05 (m, 9H), 6.65 (d, J=7.4 Hz, 1H), 6.58 (d, J=8.0 Hz, 1H), 5.89 (tt, J=53.1, 2.7 Hz, 1H), 4.49 (dd, J=9.0, 3.3 Hz, 1H), 4.15 (brs, 1H), 2.99-2.89 (m, 1H), 2.88-2.72 (m, 1H), 2.57 (dt, J=16.6, 4.8 Hz, 1H), 2.11-2.00 (m, 1H), 1.93-1.79 (m, 1H), 1.27 (d, J=7.0 Hz, 6H); MS (ES) m/z: 444 (M+H$^+$).

Cmpd 66

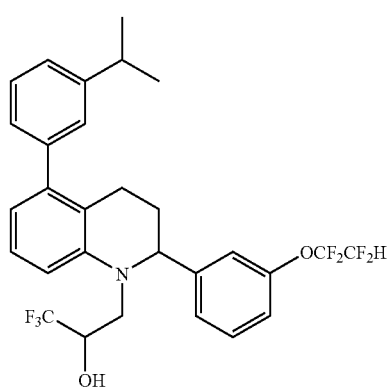

Higher Rf Cmpd
1,1,1-Trifluoro-3-{5-(3-isopropyl-phenyl)-2-[3-(1,1,2,2-tetrafluoro-ethoxy)-phenyl]-3,4-dihydro-2H-quinolin-1-yl}-propan-2-ol Replacing A12 with JJ1 and following the same procedure as in the preparation of compound 1 and 2 gave compound 66 and 67. Spectra of compound 66 are as follows: ¹H NMR (300 MHz, CDCl₃) δ 7.39-7.03 (m, 9 H), 6.71 (d, J=7.8 Hz, 2H), 5.89 (tt, J=53.1, 2.8 Hz, 1H), 4.87 (t, J=4.6 Hz, 1H), 4.43 (m, 1H), 3.90 (d, J=15.4 Hz, 1H), 3.29 (dd, J=15.6, 9.7 Hz, 1H), 2.97-2.85 (m, 1H), 2.59-2.32 (m, 3H), 2.20-2.06 (m, 1H), 1.99-1.89 (m, 1H), 1.24 (d, J=6.9 Hz, 6H); MS (ES) m/z: 556 (M+H⁺).

Example 67

Cmpd 67

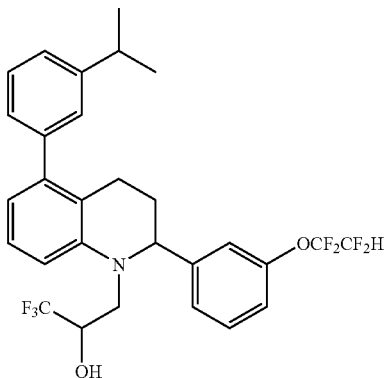

(Lower Rf Cmpd)
1,1,1-Trifluoro-3-{5-(3-isopropyl-phenyl)-2-[3-(1,1,2,2-tetrafluoro-ethoxy)-phenyl]-3,4-dihydro-2H-quinolin-1-yl}-propan-2-ol Spectra of compound 67 are as follows: ¹H NMR (300 MHz, CDCl₃) δ 7.40-7.01 (m, 9H), 6.87 (d, J=8.2 Hz, 1H), 6.73 (d, J=7.1 Hz, 1H), 5.89 (bt, J=53.0 Hz, 1H), 4.59 (m, 1H), 4.34 (m, 1H), 3.79 (dd, J=15.8, 5.2 Hz, 1H), 3.51 (dd, J=15.8, 3.6 Hz, 1H), 2.90 (m, 1H), 2.56-2.24 (m, 2H), 2.23 (d, J=2.6 Hz, 1H), 2.19-2.01 (m, 1H), 1.99-1.88 (m, 1H), 1.24 (d, J=6.0 Hz, 6H); MS (ES) m/z: 556 (M+H⁺).

Example 68

Cmpd 68

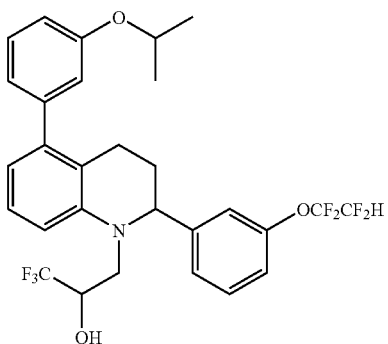

(Higher Rf Cmpd)
1,1,1-Trifluoro-3-{5-(3-isopropoxy-phenyl)-2-[3-(1,1,2,2-tetrafluoro-ethoxy)-phenyl]-3,4-dihydro-2H-quinolin-1-yl}-propan-2-ol Scheme KK

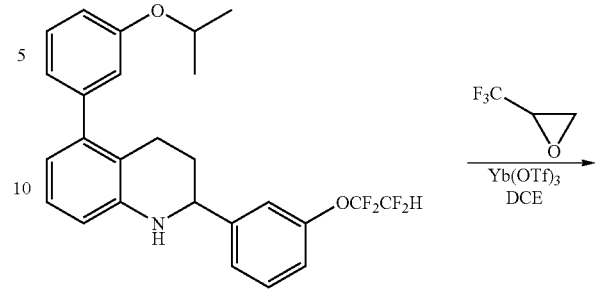

KK1

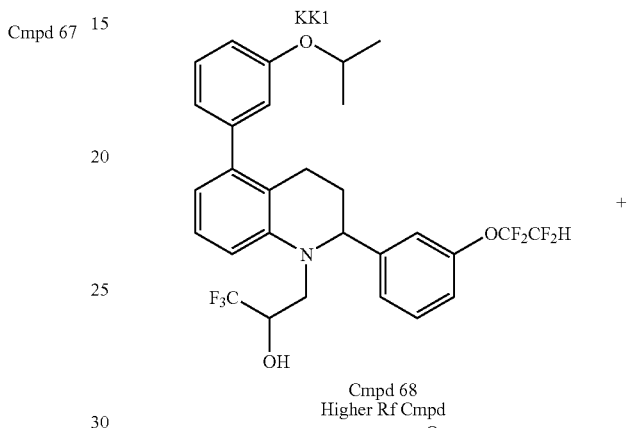

Cmpd 68
Higher Rf Cmpd

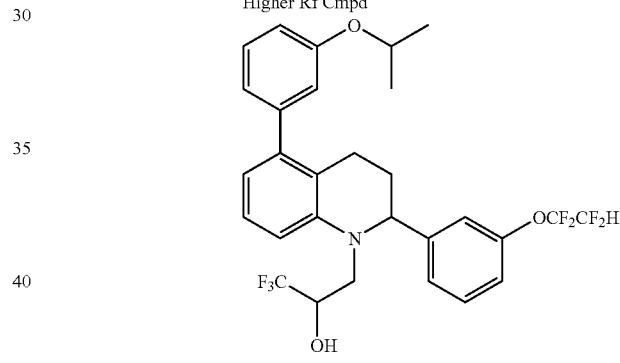

Cmpd 69
Lower Rf Cmpd

KK1

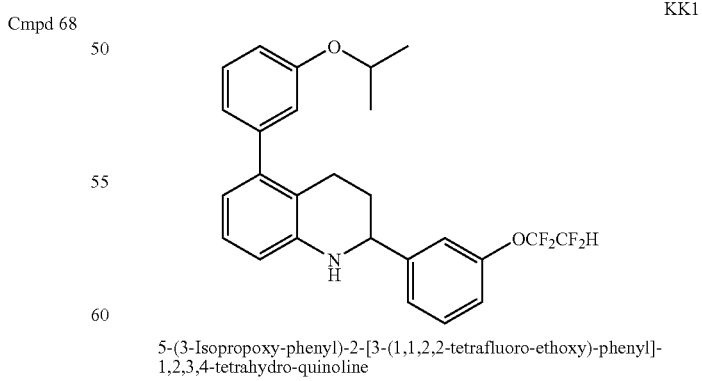

5-(3-Isopropoxy-phenyl)-2-[3-(1,1,2,2-tetrafluoro-ethoxy)-phenyl]-1,2,3,4-tetrahydro-quinoline Replacing 3-trifluoromethoxy-benzene boronic acid with 3-isopropoxy-benzene boronic acid and following the same procedure as in the preparation of A12 gave KK1. ¹H NMR (400 MHz, CDCl$_3$) δ 7.39-7.29 (m, 4H), 7.14 (d, J=7.8 Hz, 1H), 7.07 (t, J=7.7 Hz, 1H), 6.89-6.83 (m, 3H), 6.64 (d, J=7.5 Hz, 1H), 6.58 (d, J=8.0 Hz, 1H), 5.90 (tt, J=53.1, 2.8 Hz, 1H), 4.60-4.47 (m, 2H), 4.17 (brs, 1H), 2.83-2.72 (m, 1H), 2.58 (dt, J=16.7, 4.9 Hz, 1H), 2.09-2.01 (m, 1H), 1.92-1.81 (m, 1H), 1.35 (d, J=6.0 Hz, 3H), 1.34 (d, J=6.0 Hz, 3H); MS (ES) m/z: 460 (M+H$^+$).

Cmpd 68

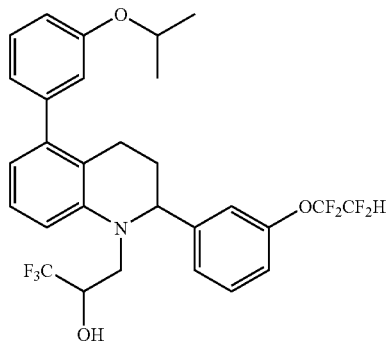

Higher Rf Cmpd
1,1,1-Trifluoro-3-{5-(3-isopropoxy-phenyl)-2-[3-(1,1,2,2-tetrafluoro-ethoxy)-phenyl]-3,4-dihydro-2H-quinolin-1-yl}-propan-2-ol Replacing A12 with KK1 and following the same procedure as in the preparation of compound 1 and 2 gave compound 68 and 69. Spectra of compound 68 are as follows: $^1$H NMR (400 MHz, CDCl$_3$) δ 7.34 (t, J=7.9 Hz, 1H), 7.27-7.17 (m, 3H), 7.15-7.10 (m, 2H), 7.04 (s, 1H), 6.87-6.79 (m, 3H), 6.70 (d, J=7.7 Hz, 1H), 5.89 (bt, J=53.1, 2.9 Hz, 1H), 4.87 (t, J=4.5 Hz, 1H), 4.58-4.39 (m, 2H), 3.91 (d, J=15.5 Hz, 1H), 3.29 (dd, J=15.6, 9.7 Hz, 1H), 2.53 (dt, J=16.3, 4.5 Hz, 1H), 2.45-2.34 (m, 2 H), 2.19-2.08 (m, 1H), 1.99-1.90 (m, 1H), 1.31 (bt, J=5.5 Hz, 6H); MS (ES) m/z: 572 (M+H$^+$).

Example 69

Cmpd 69

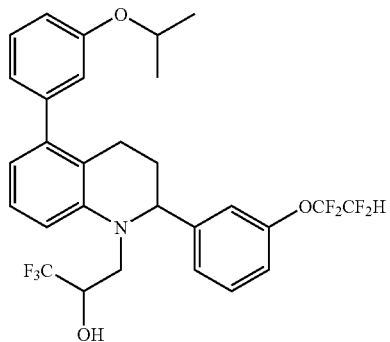

(Lower Rf Cmpd)
1,1,1-Trifluoro-3-{5-(3-isopropoxy-phenyl)-2-[3-(1,1,2,2-tetrafluoro-ethoxy)-phenyl]-3,4-dihydro-2H-quinolin-1-yl}-propan-2-ol Spectra of compound 69 are as follows: $^1$H NMR (400 MHz, CDCl$_3$) δ 7.34 (t, J=7.9 Hz, 1H), 7.24-7.19 (m, 2H), 7.11 (bt, J=8.9 Hz, 2H), 7.02 (s, 1H), 6.99-6.78 (m, 4H), 6.71 (d, J=7.5 Hz, 1H), 5.89 (bt, J=53.1, 2.9 Hz, 1H), 4.60 (t, J=4.3 Hz, 1H), 4.52 (m, 1H), 4.35 (m, 1H), 3.79 (d, J=15.6, 6.7 Hz, 1H), 3.51 (dd, J=15.6, 5.4 Hz, 1H), 2.53-2.35 (m, 2H), 2.24 (d, J=4.9 Hz, 1H), 2.15-2.04 (m, 1H), 1.98-1.89 (m, 1 H), 1.31 (bt, J=5.6 Hz, 6H); MS (ES) m/z: 572 (M+H$^+$).

Example 70-71

Cmpd 70

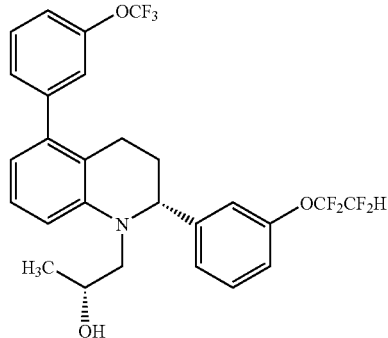

(αR,2R)-3,4-Dihydro-α-methyl-2-[3-(1,1,2,2-tetrafluoroethoxy)phenyl]-5-[3-(trifluoromethoxy)phenyl]-1(2H)-quinolineethanol Scheme LL

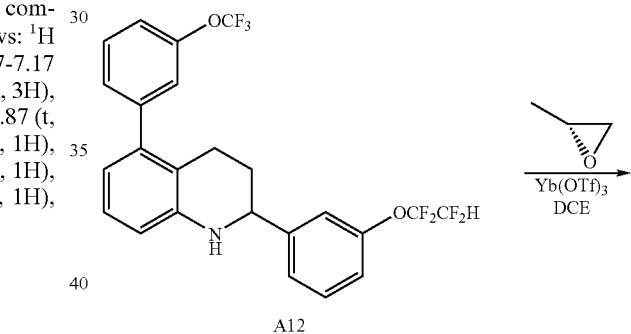

A12

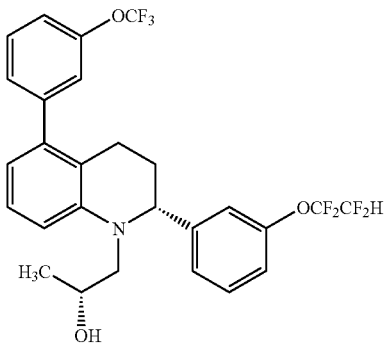

Cmpd 70

Replacing 2-trifluoromethyl-oxirane with (R)-(+)-propylene oxide and following the same procedure as in the preparation of compound 1 gave compound 70. Spectra of compound 70 are as follows: $^1$H NMR (400 MHz, CDCl$_3$) δ 7.39-7.30 (m, 2H), 7.22-7.08 (m, 6H), 7.01 (s, 1H), 6.75 (d, J=8.4 Hz, 1H), 6.63 (d, J=7.4 Hz, 1H), 5.89 (tt, J=53.1, 2.8 Hz, 1H), 4.84 (t, J=4.2 Hz, 1H), 4.24 (m, 1H), 3.57 (d, J=15.2 Hz, 1H), 2.98 (dd, J=15.1, 9.8 Hz, 1H), 2.49-2.30 (m, 2H), 2.21-

2.11 (m, 1H), 2.01-1.92 (m, 1H), 1.88 (brs, 1H), 1.20 (d, J=6.3 Hz, 3H); MS (ES) m/z: 544 (M+H⁺).

Example 72

Cmpd 72

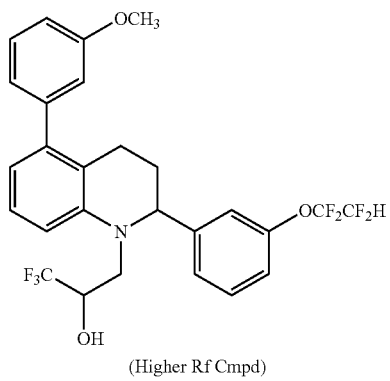

(Higher Rf Cmpd)

1,1,1-Trifluoro-3-{5-(3-methoxy-phenyl)-2-[3-(1,1,2,2-tetrafluoro-ethoxy)-phenyl]-3,4-dihydro-2H-quinolin-1-yl}-propan-2-ol Scheme MM

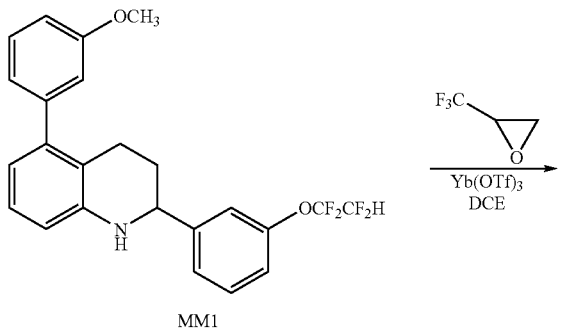

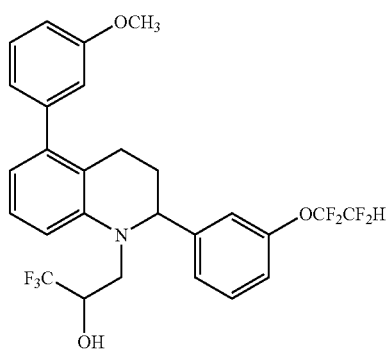

Cmpd 72
Higher Rf Cmpd

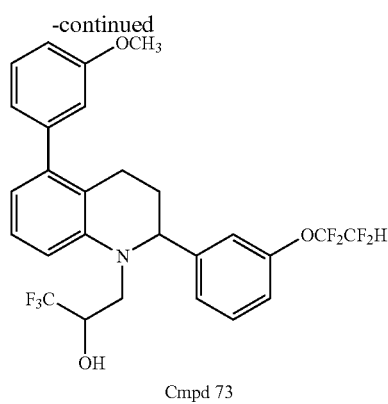

Cmpd 73
Lower Rf Cmpd

MM1

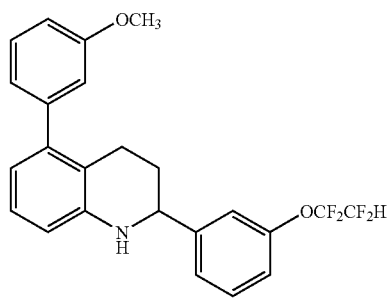

5-(3-Methoxy-phenyl)-2-[3-(1,1,2,2-tetrafluoro-ethoxy)-phenyl]-1,2,3,4-tetrahydro-quinoline Replacing 3-trifluoromethoxy-benzene boronic acid with 3-methoxy-benzene boronic acid and following the same procedure as in the preparation of A12 gave MM1. ¹H NMR (400 MHz, CDCl₃) δ 7.39-7.23 (m, 4H), 7.14 (d, J=7.9 Hz, 1H), 7.08 (t, J=7.7 Hz, 1H), 6.92-6.85 (m, 3H), 6.64 (d, J=7.4 Hz, 1H), 6.59 (d, J=8.0 Hz, 1H), 5.90 (tt, J=53.1, 2.8 Hz, 1H), 4.49 (dd, J=8.9, 4.3 Hz, 1H), 4.17 (brs, 1H), 3.81 (s, 3H), 2.82-2.71 (m, 1H), 2.57 (dd, J=16.7, 5.9 Hz, 1H), 2.10-2.01 (m, 1H), 1.82-1.81 (m, 1H); MS (ES) m/z: 432 (M+H⁺).

Cmpd 72

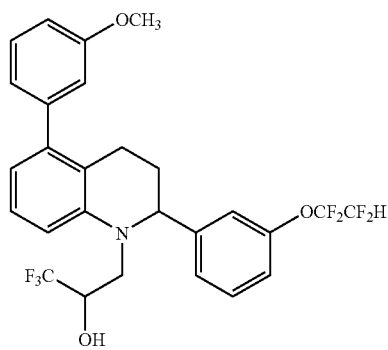

Higher Rf Cmpd 1,1,1-Trifluoro-3-{5-(3-methoxy-phenyl)-2-[3-(1,1,2,2-tetrafluoro-ethoxy)-phenyl]-3,4-dihydro-2H-quinolin-1-yl}-propan-2-ol Replacing A12 with MM1 and following the same procedure as in the preparation of compound 1 and 2 gave compound 72 and 73. Spectra of compound 72 are as follows: $^1$H NMR (400 MHz, CDCl$_3$) δ 7.34 (t, J=7.9 Hz, 1H), 7.29-7.18 (m, 2H), 7.12 (d, J=6.7 Hz, 2H), 7.04 (s, 1H), 6.86-6.79 (m, 3H), 6.70 (m, 2H), 5.89 (tt, J=53.1, 2.9 Hz, 1H), 4.88 (t, J=4.4 Hz, 1H), 4.43 (m, 1H), 3.90 (d, J=15.5 Hz, 1H), 3.79 (s, 3H), 3.30 (dd, J=15.6, 9.7 Hz, 1H), 2.58-2.48 (m, 1H), 2.44-2.34 (m, 2H), 2.19-2.09 (m, 1H), 1.99-1.90 (m, 1H); MS (ES) m/z: 544 (M+H$^+$).

Example 73

Cmpd 73

(Lower Rf Cmpd)

1,1,1-Trifluoro-3-{5-(3-methoxy-phenyl)-2-[3-(1,1,2,2-tetrafluoro-ethoxy)-phenyl]-3,4-dihydro-2H-quinolin-1-yl}-propan-2-ol Spectra of compound 73 are as follows: $^1$H NMR (400 MHz, CDCl$_3$) δ 7.34 (t, J=7.9 Hz, 1H), 7.26-7.19 (m, 2H), 7.11 (bt, J=9.2 Hz, 2H), 7.02 (s, 1H), 6.88-6.79 (m, 4H), 6.72 (t, J=7.3 Hz, 1H), 5.89 (tt, J=53.1, 2.8 Hz, 1H), 4.60 (t, J=4.2 Hz, 1H), 4.34 (m, 1H), 3.82-3.76 (m, 4 H), 3.51 (dd, J=15.6, 5.4 Hz, 1H), 2.52-2.35 (m, 2H), 2.24 (d, J=5.0 Hz, 1H), 2.18-2.05 (m, 1H), 1.99-1.89 (m, 1H); MS (ES) m/z: 544 (M+H$^+$).

Example 74

Cmpd 74

(Higher Rf Cmpd)

1,1,1-Trifluoro-3-{2-[3-(1,1,2,2-tetrafluoro-ethoxy)-phenyl]-5-thiophen-2-yl-3,4-dihydro-2H-quinolin-1-yl}-propan-2-ol

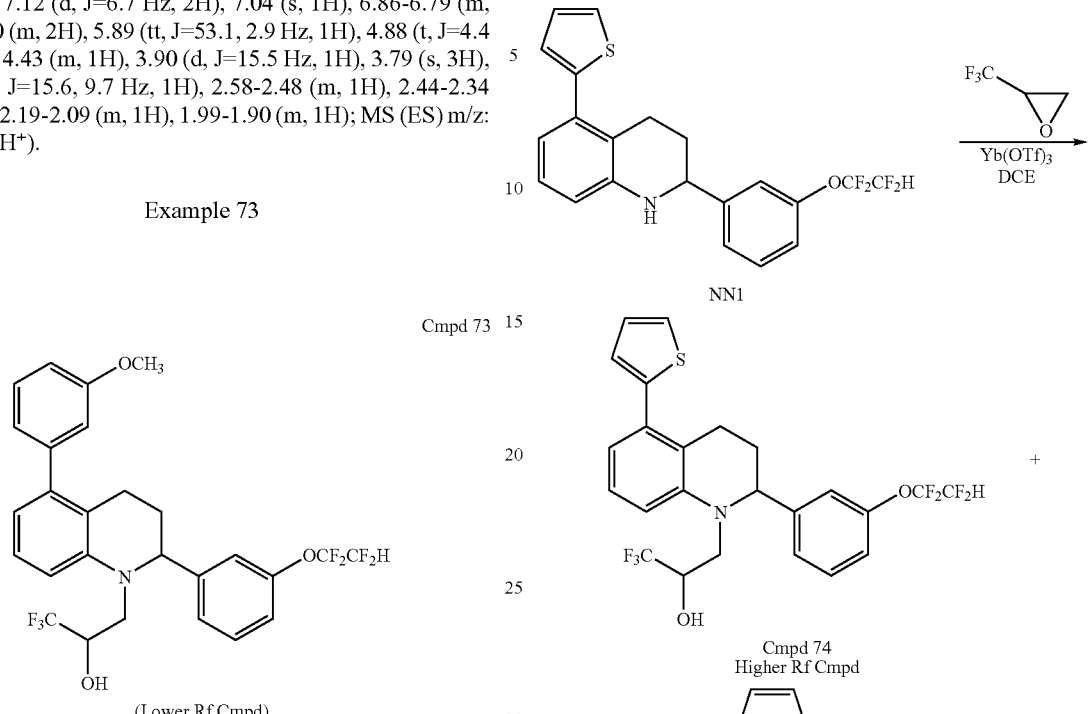

Scheme NN

NN1

Cmpd 74
Higher Rf Cmpd

Cmpd 75
Lower Rf Cmpd

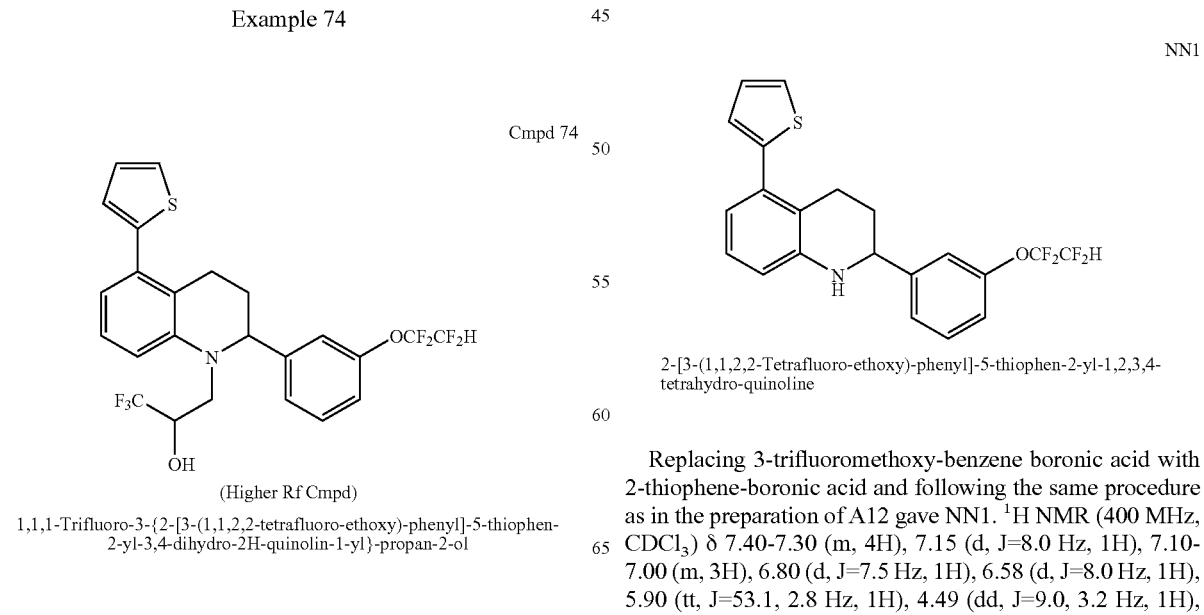

NN1

2-[3-(1,1,2,2-Tetrafluoro-ethoxy)-phenyl]-5-thiophen-2-yl-1,2,3,4-tetrahydro-quinoline Replacing 3-trifluoromethoxy-benzene boronic acid with 2-thiophene-boronic acid and following the same procedure as in the preparation of A12 gave NN1. $^1$H NMR (400 MHz, CDCl$_3$) δ 7.40-7.30 (m, 4H), 7.15 (d, J=8.0 Hz, 1H), 7.10-7.00 (m, 3H), 6.80 (d, J=7.5 Hz, 1H), 6.58 (d, J=8.0 Hz, 1H), 5.90 (tt, J=53.1, 2.8 Hz, 1H), 4.49 (dd, J=9.0, 3.2 Hz, 1H), 4.18 (brs, 1H), 2.98-2.88 (m, 1H), 2.78 (dt, J=16.6, 4.8 Hz, 1H), 2.16-2.07 (m, 1H), 1.98-1.85 (m, 1H); MS (ES) m/z: 406 (M–H⁺).

4.1 Hz, 1H), 2.56-2.45 (m, 1H), 2.26 (d, J=5.0 Hz, 1 H), 2.19-2.09 (m, 1H), 2.04-1.95 (m, 1H); MS (ES) m/z: 520 (M+H⁺).

Example 76

Cmpd 74

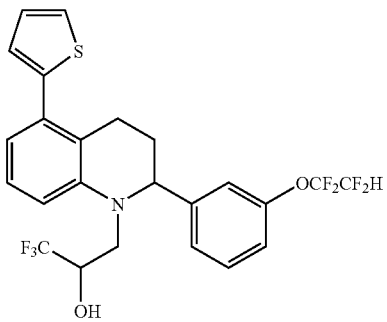

Higher Rf Cmpd 1,1,1-Trifluoro-3-{2-[3-(1,1,2,2-tetrafluoro-ethoxy)-phenyl]-5-thiophen-2-yl-3,4-dihydro-2H-quinolin-1-yl}-propan-2-ol Cmpd 76

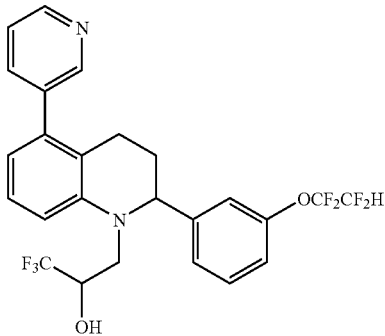

1,1,1-Trifluoro-3-{5-pyridin-3-yl-2-[3-(1,1,2,2-tetrafluoro-ethoxy)-phenyl]-3,4-dihydro-2H-quinolin-1-yl}-propan-2-ol Replacing A12 with NN1 and following the same procedure as in the preparation of compound 1 and 2 gave compound 74 and 75. Spectra of compound 74 are as follows: ¹H NMR (400 MHz, CDCl₃) δ 7.38-7.29 (m, 2 H), 7.22-7.09 (m, 3H), 7.07-7.00 (m, 2H), 6.94 (d, J=3.4 Hz, 1H), 6.85 (d, J=3.4 Hz, 1H), 6.71 (d, J=8.3 Hz, 1H), 5.89 (tt, J=53.1, 2.8 Hz, 1H), 4.89 (t, J=4.5 Hz, 1H), 4.41 (m, 1H), 3.89 (d, J=15.6 Hz, 1H), 3.30 (dd, J=15.6, 9.7 Hz, 1H), 2.75 (dt, J=16.4, 4.4 Hz, 1H), 2.56-2.41 (m, 2H), 2.20-2.10 (m, 1H), 2.05-1.96 (m, 1H); MS (ES) m/z: 520 (M+H⁺).

Scheme OO

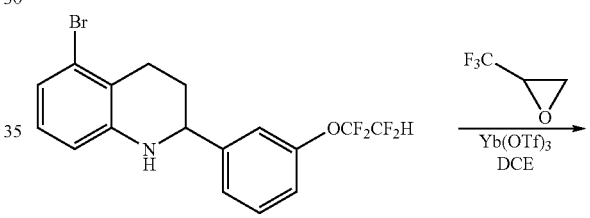

Example 75

Cmpd 75

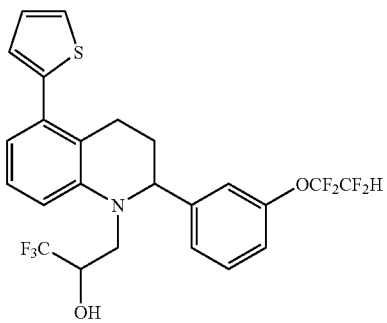

(Lower Rf Cmpd)

1,1,1-Trifluoro-3-{2-[3-(1,1,2,2-tetrafluoro-ethoxy)-phenyl]-5-thiophen-2-yl-3,4-dihydro-2H-quinolin-1-yl}-propan-2-ol Spectra of compound 75 are as follows: ¹H NMR (400 MHz, CDCl₃) δ 7.34 (t, J=7.9 Hz, 1H), 7.29 (d, J=5.1 Hz, 1H), 7.20 (t, J=8.0 Hz, 1H), 7.15-7.08 (m, 2H), 7.05-7.00 (m, 2H), 6.94 (d, J=3.5 Hz, 1H), 6.89-6.85 (m, 2H), 5.89 (tt, J=53.1, 2.8 Hz, 1H), 4.61 (t, J=4.2 Hz, 1H), 4.31 (m, 1H), 3.79 (d, J=15.7, 6.6 Hz, 1H), 3.51 (dd, J=15.7, 5.4 Hz, 1H), 2.72 (dt, J=16.5,

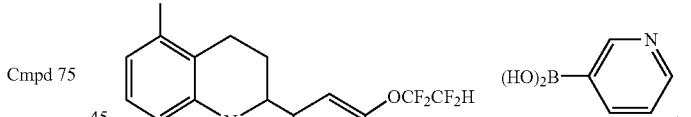

OO1
(Higher Rf Cmpd)

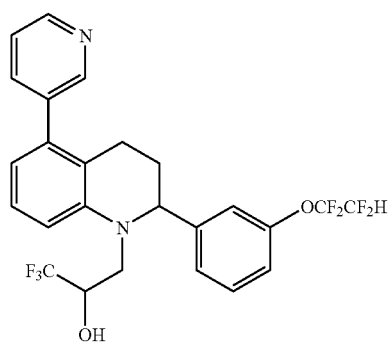

Cmpd 76, 85%

OO1

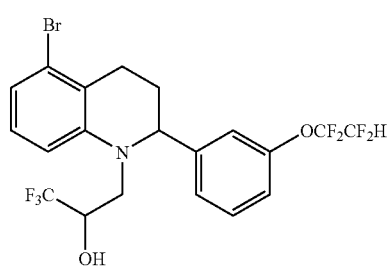

(Higher Rf Cmpd)
3-{5-Bromo-2-[3-(1,1,2,2-tetrafluoro-ethoxy)-phenyl]-3,4-dihydro-2H-quinolin-1-yl}-1,1,1-trifluoro-propan-2-ol Replacing A12 with A11 and following the procedure as in the preparation of compound 1, compound OO1 was obtained. $^1$H NMR (400 MHz, CDCl$_3$) δ 7.31 (t, J=8.0 Hz, 1H), 7.26 (s, 1H), 7.12 (d, J=8.3 Hz 1 H), 7.02-6.97 (m, 3H), 6.62 (d, J=8.0 Hz, 1H), 6.39 (d, J=7.4 Hz, 1H), 5.88 (tt, J=53.1, 2.8 Hz, 1H), 4.87-4.85 (m, 1H), 4.39-4.30 (complex m, 1 H), 3.85 (d, J=15.6, 1H), 3.29 (dd, J=15.8, 9.9 Hz, 1H), 2.90 (dt, J=16.7, 4.1 Hz, 1H), 2.42-2.35 (m, 2H), 2.27-2.18 (m, 1H), 2.13-2.06 (m, 1H).

Cmpd 76

1,1,1-Trifluoro-3-{5-pyridin-3-yl-2-[3-(1,1,2,2-tetrafluoro-ethoxy)-phenyl]-3,4-dihydro-2H-quinolin-1-yl}-propan-2-ol Replacing A11 with OO1, 3-trifluoromethoxy-benzene-boronic acid with pyridine-3-boronic acid and following the same procedure as in the preparation of compound A12 gave compound 76 (yield 85%): $^1$H NMR (400 MHz, CDCl$_3$) δ 8.40 (d, J=3.7 Hz, 1H), 7.59-7.51 (m, 1H), 7.41-7.22 (m, 4H), 7.11 (d, J=8.5 Hz, 2H), 7.03 (m, 1H), 6.80 (d, J=8.4 Hz, 1 H), 6.39 (d, J=7.4 Hz, 1H), 5.89 (tt, J=53.1, 2.8 Hz, 1H), 5.12 (m, 1H), 4.69 (t, J=7.4 Hz, 1H), 4.02 (d, J=15.1, 1H), 3.31 (dd, J=15.2, 10.7 Hz, 1H), 2.12-2.15 (m, 2H), 2.10-1.99 (m, 1H), 1.96-1.88 (m, 1H); MS (ES) m/z: 515 (M+H$^+$).

Example 77

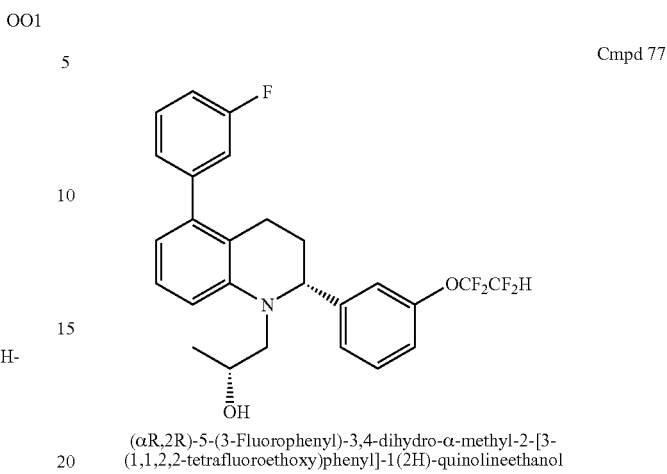

Cmpd 77

(αR,2R)-5-(3-Fluorophenyl)-3,4-dihydro-α-methyl-2-[3-(1,1,2,2-tetrafluoroethoxy)phenyl]-1(2H)-quinolineethanol

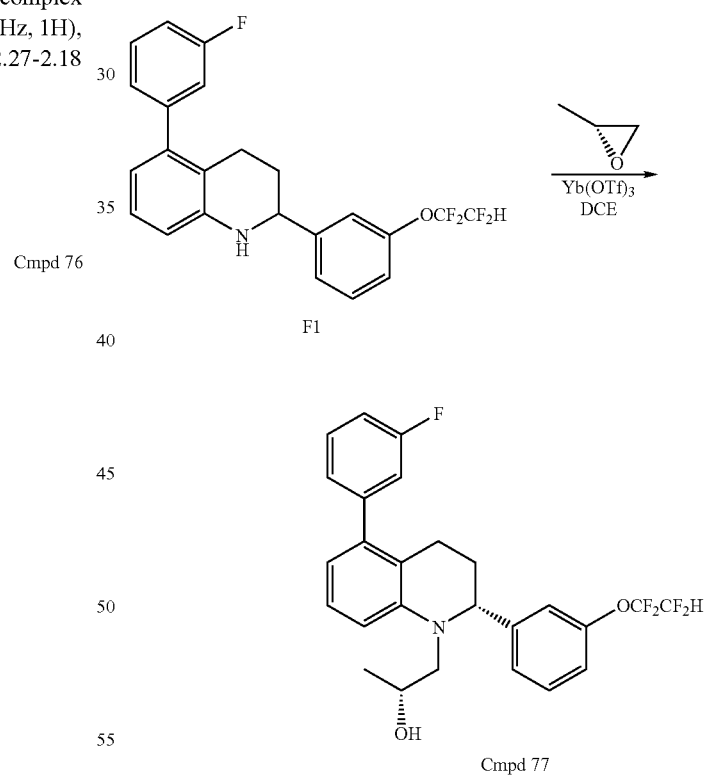

Replacing 2-trifluoromethyl-oxirane with (R)-(+)-propylene oxide and following the same procedure as in the preparation of compound 1 and 2 gave a pure compound 77: $^1$H NMR (400 MHz, CDCl$_3$) δ 7.38-7.25 (m, 2 H), 7.22-6.92 (m, 7H), 6.74 (d, J=8.3 Hz, 1H), 6.62 (d, J=7.4 Hz, 1H), 5.88 (tt, J=53.1, 2.8 Hz, 1H), 4.84 (t, J=4.2 Hz, 1H), 4.24 (m, 1H), 3.56 (dd, J=15.1, 2.4 Hz, 1H), 2.97 (dd, J=15.1, 9.8 Hz, 1H), 2.52-2.29 (m, 2H), 2.21-2.09 (m, 1H), 2.01-1.86 (m, 2H), 1.20 (d, J=6.2 Hz, 3H); MS (ES) m/z: 478 (M+H$^+$).

Example 78
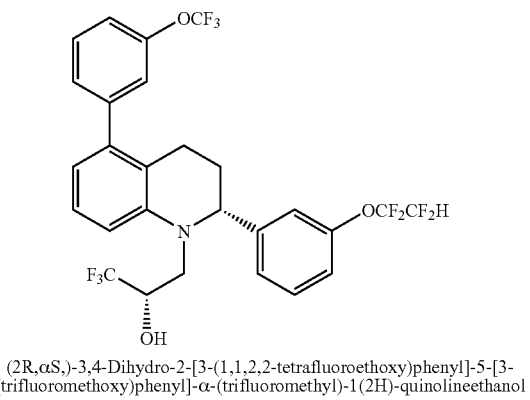
(2R,αS,)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol
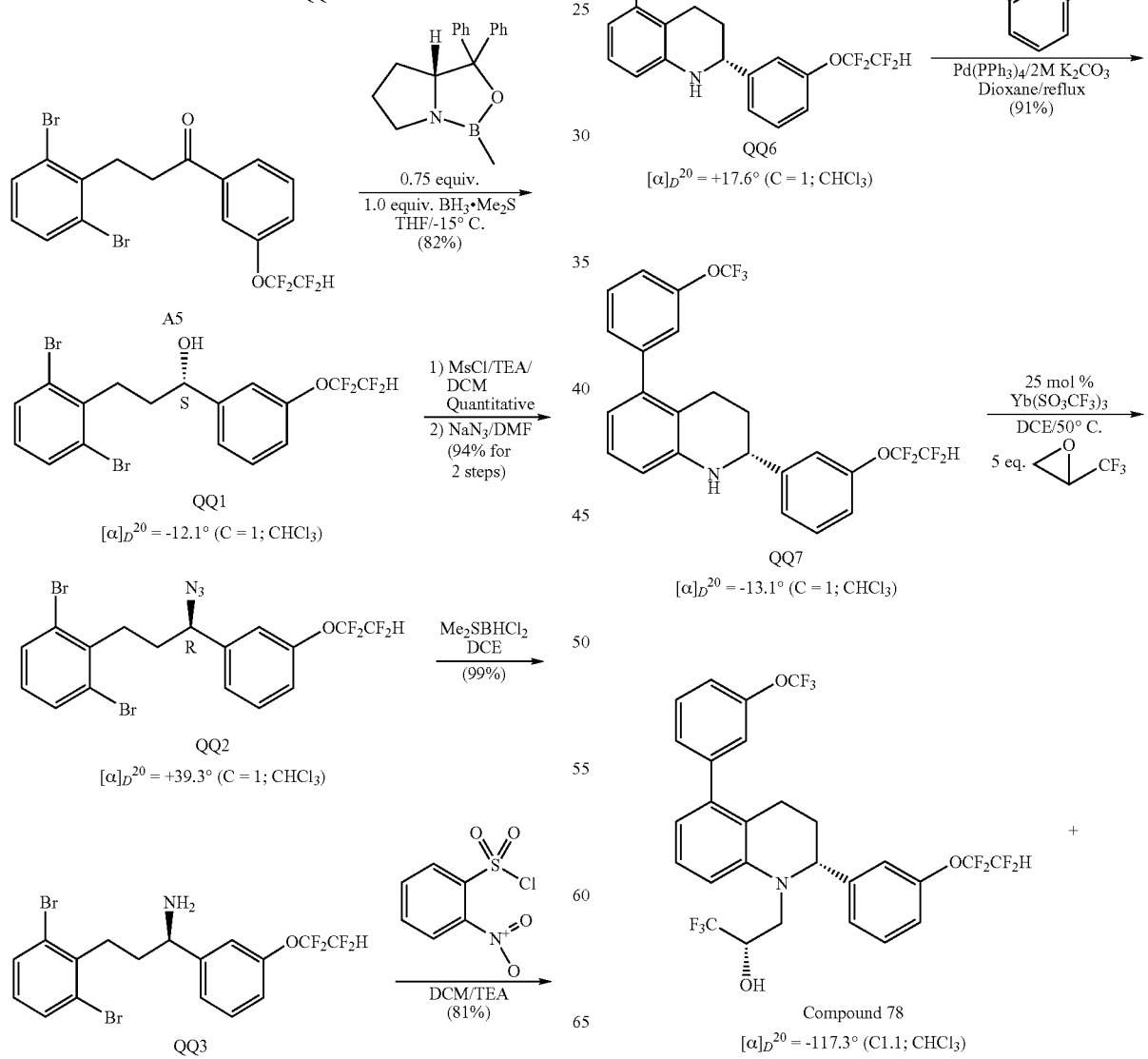

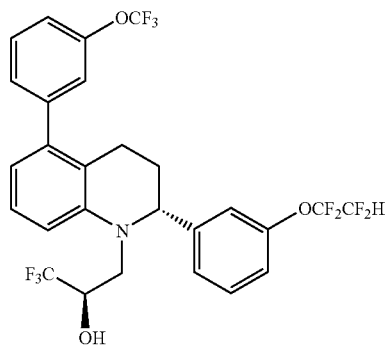

Compound 79
$[\alpha]_D^{20} = -64.9°$ (C1; CHCl$_3$)

Alternate Route to QQ7

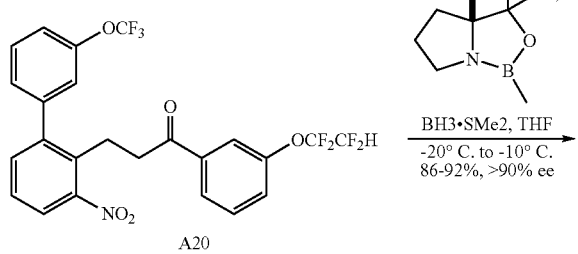

A20

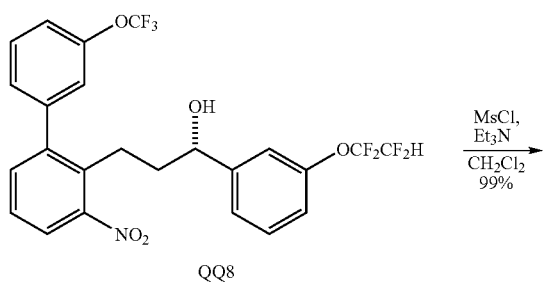

QQ8

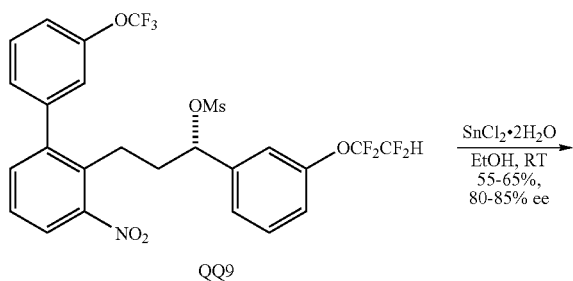

QQ9

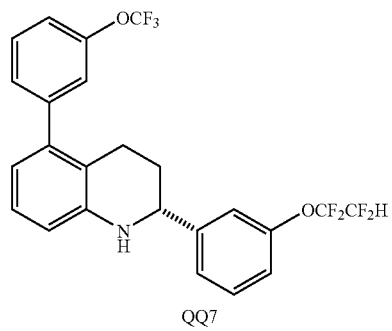

QQ7

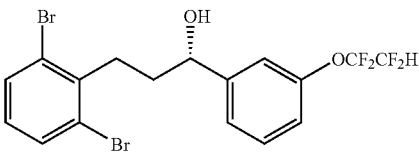

QQ1

(αS)-2,6-Dibromo-α-[3-(1,1,2,2-tetrafluoroethoxy)phenyl]benzenepropanol

To a stirred solution of ketone A5 (511 mg; 1.05 mmol) in anhydrous THF under nitrogen was added (R)-2-Methyl-CBS-oxazaborolidine (792 uL; 0.792 mmol). The reaction vessel was cooled to −15° C. followed by the addition of borane-dimethyl sulfide complex (528 uL; 1.05 mmol) slowly dropwise. The reaction was aged for 50 minutes before being quenched with MeOH at −20° C. The contents of the reaction vessel were poured into EtOAc and washed with water/2N HCl (2:1), water, saturated sodium bicarbonate solution, water and brine. The organic layer was dried over MgSO$_4$, filtered and the solvent removed in vacuo. Purification employing SiO$_2$ flash column chromatography (15% EtOAc/Hex) provided 420 mg (82%) of the desired alcohol of the S absolute configuration as an oil. Analysis by chiral HPLC (Chiralcel AS; Isocratic elution 90/10 Hexane/IPA) by area integration at 210 nm indicated the enantiomeric excess >95%. This alcohol was identical in all respects to the racemic alcohol A6, except for the optical rotation. $[\alpha]_D^{20} = -12.1°$ (c1; CHCl$_3$); $^1$H NMR (300 MHz, CDCl$_3$) δ 7.48 (d, J=8.0 Hz, 2H), 7.41-7.28 (m, 3H), 7.14 (d, J=7.7 Hz, 1H), 6.89 (t, J=8.0 Hz, 1H), 5.91 (tt, J=53.1, 2.8 Hz, 1H), 4.86 (dd, J=10.1, 6.2 Hz, 1H), 3.19-3.05 (m, 1H), 3.03-2.92 (m, 1H), 2.09-1.95 (m, 3H); MS (ES) m/z: 509 (M+Na$^+$).

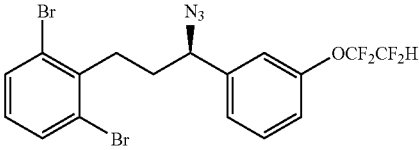

QQ2

2-[(3R)-3-Azido-3-[3-(1,1,2,2-tetrafluoroethoxy)phenyl]propyl]-1,3-dibromobenzene Substituting QQ1 for A6 and following the procedure described for the preparation of A7, QQ2 was obtained of the R absolute configuration. This azide was identical in all respects to the racemic azide A7, except for the optical rotation. $[\alpha]_D^{20} = +39.3°$ (c1; CHCl$_3$): $^1$H NMR (300 MHz, CDCl$_3$) δ 7.48 (d, J=8.0 Hz, 2H), 7.42 (t, J=7.9 Hz, 1H), 7.31-7.19 (m, 3H), 6.90 (t, J=8.0 Hz, 1H), 5.92 (tt, J=53.1, 2.8 Hz, 1H), 4.60 (t, J=6.9 Hz, 1H), 3.15-3.05 (m, 1H), 2.99-2.82 (m, 1H), 2.09-1.97 (m, 2H); MS (ES) m/z: 484 (M−N$_2$+H$^+$).

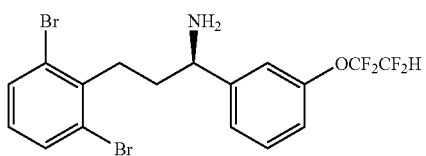

QQ3

(αR)-2,6-Dibromo-α-[3-(1,1,2,2-tetrafluoroethoxy)phenyl]benzenepropanamine

Substituting QQ2 for A7 and following the procedure described for the preparation of A8, QQ3 was obtained of the R absolute configuration. $^1$H NMR (300 MHz, CDCl$_3$) δ 7.46

(d, J=8.2 Hz, 2H), 7.39-7.26 (m, 3H), 7.14-7.10 (m, 1H), 6.88 (t, J=8.0 Hz, 1H), 5.91 (tt, J=53.1, 2.9 Hz, 1 H), 4.08 (t, J=6.6 Hz, 1H), 3.09-3.00 (m, 1H), 2.90-2.80 (m, 1H), 1.98-1.88 (m, 2H), 1.57 (brs, 2H); MS (ES) m/z: 486 (M+H⁺).

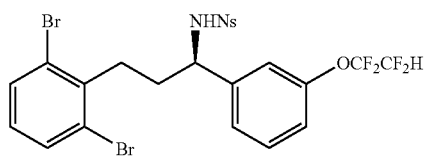

QQ4

N-[(1R)-3-(2,6-Dibromophenyl)-1-[3-(1,1,2,2-tetrafluoroethoxy)phenyl]-propyl]-2-nitrobenzenesulfonamide Substituting QQ3 for A8 and following the procedure described for the preparation of A9, QQ4 was obtained of the R absolute configuration. $[\alpha]_D^{20}$=+100.0° (c1; CHCl₃); ¹H NMR (400 MHz, CDCl₃) δ 7.72 (d, J=8.0 Hz, 1H), 7.66 (d, J=7.9 Hz, 1H), 7.55-7.33 (m, 4H), 7.13-7.08 (m, 2 H), 7.01 (s, 1H), 6.95-6.88 (m, 2H), 5.96 (d, J=8.9 Hz, 1H), 5.86 (tt, J=53.1, 2.8 Hz, 1H), 4.69 (dd, J=16.0, 7.8 Hz, 1H), 3.19-3.11 (m, 1H), 2.88-2.80 (m, 1H), 2.14-1.94 (m, 2H); MS (ES) m/z: 693 (M+Na⁺).

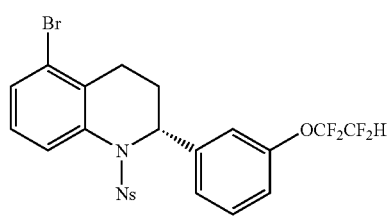

QQ5

(2R)-5-Bromo-1,2,3,4-tetrahydro-1-[(2-nitrophenyl)sulfonyl]-2-[3-(1,1,2,2-tetrafluoroethoxy)phenyl]quinoline Substituting QQ4 for A9 and following the procedure described for the preparation of A10, QQ5 was obtained of the R absolute configuration. This compound was identical in all respects to the racemic compound A10, except for the optical rotation. $[\alpha]_D^{20}$=+55.0° (c1; CHCl₃); ¹H NMR (400 MHz, CDCl₃) δ 7.81 (d, J=8.1 Hz, 1H), 7.73-7.69 (m, 1H), 7.63-7.50 (m, 3H), 7.43 (d, J=8.0 Hz, 1H), 7.39-7.09 (m, 5H), 5.88 (tt, J=53.1, 2.9 Hz, 1H), 5.62 (t, J=6.9 Hz, 1H), 2.74-2.66 (m, 1H), 2.47-2.39 (m, 1H), 2.35-2.27 (m, 1H), 2.05-1.96 (m, 1H); MS (ES) m/z: 589 (M).

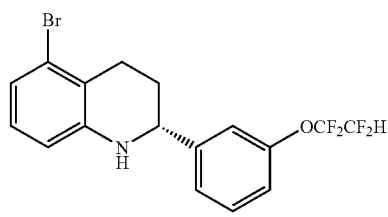

QQ6

(2R)-5-Bromo-1,2,3,4-tetrahydro-2-[3-(1,1,2,2-tetrafluoroethoxy)phenyl]quinoline Substituting QQ5 for A10 and following the procedure described for the preparation of A11, QQ6 was obtained of the R absolute configuration. This amine was identical in all respects to the racemic amine A11, except for the optical rotation. $[\alpha]_D^{20}$=+17.6° (c1; CHCl₃); ¹H NMR (300 MHz, CDCl₃) δ 7.37 (t, J=7.8 Hz, 1H), 7.30-7.21 (m, 2H), 7.15 (d, J=7.9 Hz, 1H), 6.95-6.71 (m, 2H), 6.51 (d, J=7.8 Hz, 1H), 5.90 (tt, J=53.1, 2.8 Hz, 1H), 4.40 (dd, J=9.3, 3.1 Hz, 1H), 4.13 (brs, 1H), 2.88-2.79 (m, 2 H), 2.21-2.11 (m, 1H), 2.05-1.90 (m, 1H); MS (ES) m/z: 406 (M+2).

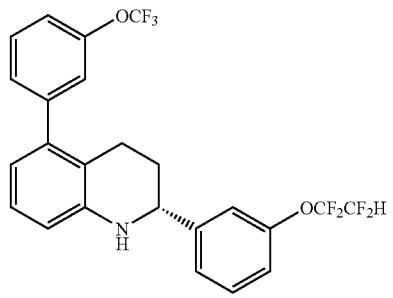

QQ7

(2R)-1,2,3,4-Tetrahydro-2-[3-(1,1,2,2-tetrafluoroethoxy)phenyl]-5-[3-trifluoromethoxy)phenyl]quinoline Substituting QQ6 for A11 and following the procedure described for the preparation of A12, QQ7 was obtained of the R absolute configuration. This bi-phenyl was identical in all respects to the racemic bi-phenyl A12, except for the optical rotation: $[\alpha]_D^{20}$=−13.1° (c1; CHCl3); ¹H NMR (400 MHz, CDCl₃) δ 7.42-7.30 (m, 4H), 7.25 (m, 1H), 7.21-7.08 (m, 4H), 6.62 (s, 1H), 6.60 (s, 1H), 5.90 (tt, J=53.1, 2.8 Hz, 1H), 4.51 (dd, J=8.9, 3.3 Hz, 1H), 4.20 (brs, 1H), 2.81-2.71 (m, 1H), 2.53 (dt, J=16.6, 4.8 Hz, 1H), 2.10-2.02 (m, 1H), 1.92-1.82 (m, 1H); MS (ES) m/z: 486 (M+H⁺).

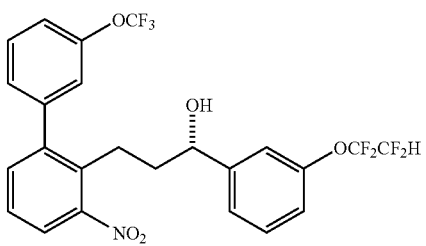

QQ8

(αS)-3-Nitro-α-[3-(1,1,2,2-tetrafluoroethoxy)phenyl]-3′-(trifluoromethoxy)-[1,1′-biphenyl]-2-propanol To a solution of THF (0.2 mL) and 1.0 M R-2-methyl-CBS-oxazaborolidine (0.186 mL, 0.186 mmol) in toluene was added 2.0 M borane-dimethylsulfide complex (0.137 mL, 0.274 mmol) in THF. After stirring at room temperature for 15 min, the mixture was cooled to −25° C. and a solution of A20 (132 mg, 0.249 mmol) in THF (2 mL) was added. The reaction mixture was stirred at −20° C. to −10° C. for 3.5 h and then quenched with a few drops of MeOH followed by a few drops of 1 N HCl. The reaction mixture was partitioned between CH₂Cl₂ and water. The organic layer was dried, concentrated, and chromatographed to provide 114 mg (86%) QQ8: ¹H NMR (300 MHz, CDCl₃) δ 7.83-7.77 (m, 1H), 7.40-7.37 (m, 3H), 7.28-7.23 (m, 2H), 7.13-6.99 (m, 5H), 5.90 (tt, J=53.1, 2.8 Hz, 1H), 4.54 (m, 1H), 2.89-2.79 (m, 1H), 2.73-2.63 (m, 1H), 1.90-1.75 (m, 2H), 1.73 (brs, 1H); MS (ES) m/z: 556 (M+Na⁺). $[\alpha]_D^{20}$=−10.6° (C=1.0, CHCl₃). >90% ee by HPLC.

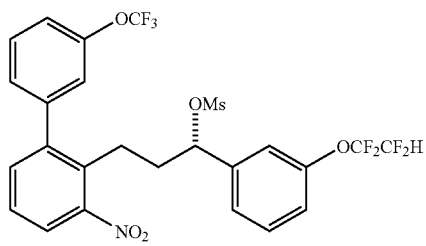

(αS)-3-Nitro-α-[3-(1,1,2,2-tetrafluoroethoxy)phenyl]-3'-(trifluoromethoxy)-[1,1'-biphenyl]-2-propanol methanesulfonate To a solution QQ8 (220 mg, 0.413 mmol) and CH$_2$Cl$_2$ (3 mL) was added methanesulfonyl chloride (0.040 mL, 0.52 mmol) and Et$_3$N (0.086 mL, 0.62 mmol). After stirring at room temperature for 2 h, water was added and the mixture was acidified with 1 N HCl until acidic by pH paper. The organic layer was separated and the aqueous layer was extracted with CH$_2$Cl$_2$. The combined organic phases were dried and concentrated to give 250 mg (99%) of QQ9: $^1$H NMR (400 MHz, CDCl$_3$) δ 7.84 (m, 1H), 7.46 (t, J=8.0 Hz, 1H), 7.41 (m, 2H), 7.33 (t, J=8.0 Hz, 1H), 7.31-7.28 (m, 1H), 7.16 (m, 2H), 7.08-7.06 (m, 2H), 7.02 (m, 1H), 5.91 (tt, J=53.0, 2.7 Hz, 1H), 5.38 (dd, J=7.3, 5.9 Hz, 1H), 2.84 (m, 1H), 2.71 (s, 3H), 2.68-2.64 (m, 1H), 2.12-2.00 (m, 2H); MS (ES) m/z: 634 (M+Na$^+$).

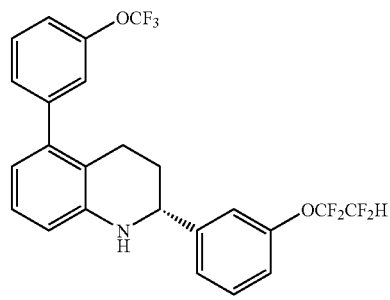

(2R)-1,2,3,4-Tetrahydro-2-[3-(1,1,2,2-tetrafluoroethoxy)phenyl]-5-[3-trifluoromethoxy)phenyl]quinoline A solution of QQ9 (105 mg, 0.172 mmol) and EtOH (2 mL) was degassed under house-vacuum and then filled with N$_2$ three times. To the solution, SnCl$_2$.2H$_2$O (244 mg, 1.08 mmol) was added and the reaction mixture stirred at room temperature under N$_2$ for 4.5 h. After removal of EtOH under vacuum, to the residue were added CH$_2$Cl$_2$ and saturated NH$_4$OH. The precipitated solid was filtered through Celite, and rinsed with CH$_2$Cl$_2$ and EtOAc. The filtrate was separated and the aqueous layer was extracted with CH$_2$Cl$_2$. The combined organic solutions were dried, concentrated in vacuo, and purified by chromatograph to give 46 mg (55%) QQ7; $[α]_D^{20}$=−12.9° (C=1.0, CHCl$_3$). 80-85% ee by HPLC.

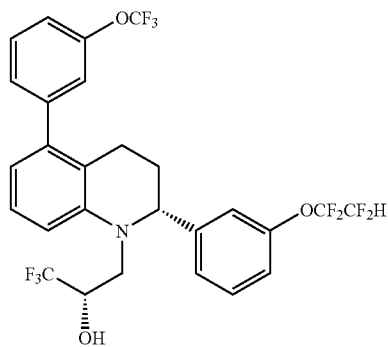

Cmpd 78

(2R,αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol Substituting QQ7 for A12 and following the procedure described for the preparation of compound 1, the pure R,S compound 78 was obtained. Compound 78 was identical in all respects to compound 1, except for the optical rotation. $[α]_D^{20}$=−117.3° (c1; CHCl3); $^1$H NMR (400 MHz, CDCl$_3$) δ 7.40-7.20 (m, 2H), 7.28-7.10 (m, 6H), 7.04 (s, 1H), 6.73 (d, J=8.3 Hz, 1H), 6.67 (d, J=7.4 Hz, 1H), 5.89 (tt, J=53.1, 2.8 Hz, 1H), 4.89 (t, J=4.4 Hz, 1H), 4.42 (m, 1H), 3.91 (d, J=15.5 Hz, 1H), 3.30 (dd, J=15.6, 9.7 Hz, 1H), 2.48 (dt, J=16.3, 4.4 Hz, 1H), 2.42-2.31 (m, 2H), 2.19-2.09 (m, 1H), 2.00-1.92 (m, 1H); MS (ES) m/z: 598 (M+H$^+$).

Alternatively, Compound 78 was made as described in the following steps:

Scheme QQ'

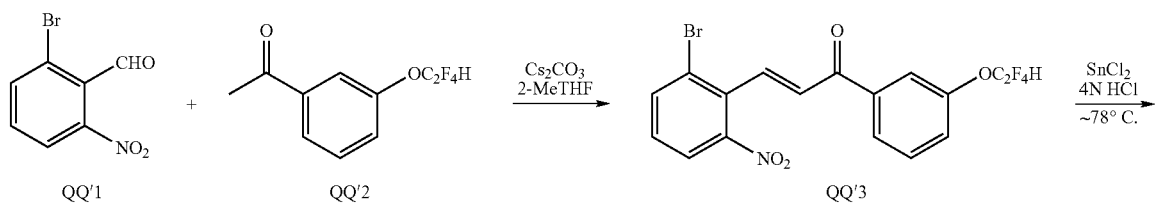

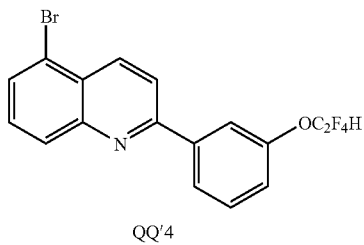

QQ'4

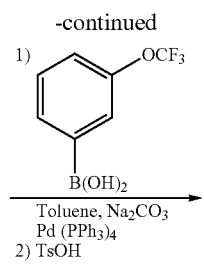

1) 
Toluene, Na₂CO₃
Pd (PPh₃)₄
2) TsOH

-continued

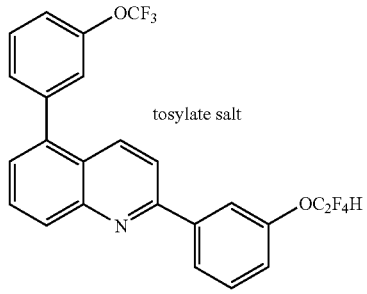

tosylate salt

QQ'5

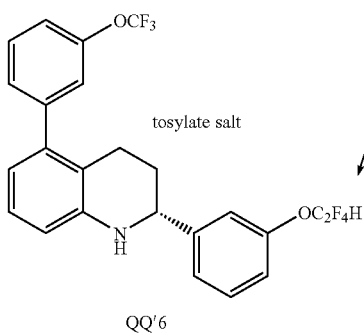

tosylate salt

QQ'6

1) EtOAc, Na₂CO₃
2) Diludine, CSA
(93%)
3) chiral separation

1) EtOAc, Na₂CO₃
2) Diludiine

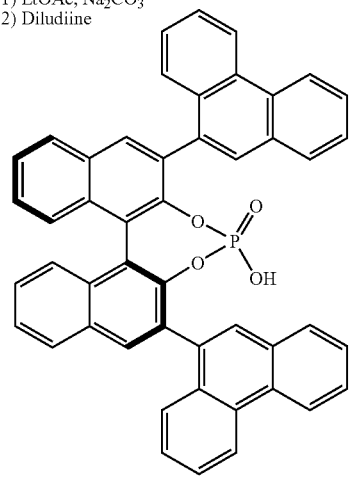

HFIPA

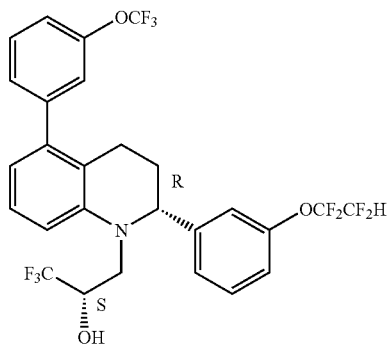

Compound 78

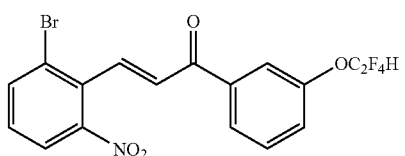

(E)-3-(2-Bromo-6-nitrophenyl)-1-[3-(1,1,2,2-tetrafluoroethoxy)phenyl]propenone

QQ'3

A 2L 4-neck flask equipped with an overhead stirrer, thermocouple, addition funnel, nitrogen purge, and condenser was charged with anhydrous 2-methyl THF (330 mL). To the flask was then added 2-bromo-6-nitrobenzaldehyde (110.0 g, 478.2 mmol) and cesium carbonate (311.6 g, 956.4 mmol) and the resulting mixture stirred under nitrogen. To the reaction mixture was then added 3-(1,1,2,2-tetrafluoroethoxyl) acetophenone (112.9 g, 478.2 mmol) slowly via an addition funnel over 40 minutes. The reaction mixture was maintained at a temperature below 45° C. and preferably below 30° C. The resultant suspension was stirred until the reaction was complete. To the reaction mixture was then added water (220 mL) at room temperature, which dissolved the cesium carbonate. The resulting mixture was allowed to cool to room temperature while agitating, then transferred to a separatory funnel. The aqueous layer was removed and the organic layer which contains the title compound (QQ'3) was used in the next step without further purification or isolation.

Note: An aliquot of the reaction mixture was purified by evaporating the solvent on a rotary evaporator to yield a dark solid, which was dissolved in CDCl$_3$, filtered to remove any undissolved solid and concentrated again on a rotary evaporator to yield the title compound as a dark solid.

$^1$H NMR (300 MHz, CDCl$_3$) d 7.93-7.82 (m, 5H), 7.55 (t, J=8.0 Hz, 1H), 7.46 (dd, J=1.2, 8.3 Hz, 1H), 7.41 (t, J=8.1 Hz, 1H), 7.05 (d, J=16.1 Hz, 1H), 5.95 (tt, J=2.8, 53.0 Hz, 1H); MH$^+$ (API-ES) calculated for C$_{17}$H$_{11}$BrF$_4$NO$_4$ 448, measured: 448.

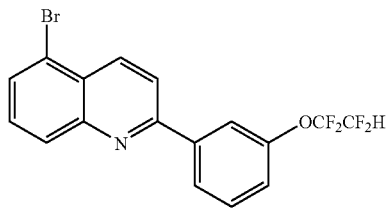

5-bromo-2-(3-(1,1,2,2-tetrafluoroethoxy)phenyl)quinoline

To a 1 L 4-neck flask equipped with agitator, thermocouple, addition funnel, and condenser was added 4N aqueous HCl (394 mL) and tin dichloride (133.2 g, 702.8 mmol). The reaction mixture was then agitated until the tin dichloride was dissolved. To the reaction mixture was then added, via addition funnel (E)-3-(2-Bromo-6-nitrophenyl)-1-[3-(1,1,2,2-tetrafluoroethoxy)phenyl]propenone (78.75 g, 175.7 mmol) as a solution in 2-methyl-THF (~197mL solution) (prepared as in Example 1 above) while maintaining the temperature of the reaction mixture at <35° C. (preferably <~30° C.). The resulting mixture was then heated to ~78° C. and stirred until the reaction was determined complete. The resulting mixture was cooled to room temperature, then transferred to a separatory funnel. The aqueous layer (TOP) was removed and discarded. The organic layer was transferred back to the flask and 4N aqueous HCl (394 mL) was added. The resulting mixture was agitated for 5 min, then transfer to a separatory funnel and the aqueous (TOP) layer discarded.

To the organic layer was added 2-methyl-THF (200 mL) and the resulting mixture was cooled using an ice water bath. To the resulting mixture was then added lithium hydroxide monohydrate (98.5 g, 2340 mmol). The resulting mixture was filtered and the filter cake washed with 2-methyl-THF (80 mL). To the filtrate was then added water (100 mL), the mixture agitated, and the aqueous (BOTTOM) layer discarded. The organic layer containing the title compound (QQ'4) was used in the next step without further purification or isolation.

Note: An aliquot of the solution was purified by flash chromatography to yield the title compound as a white solid.

$^1$H NMR (300 MHz, CDCl$_3$) δ 8.59 (d, J=8.9 Hz, 1H), 8.13 (d, J=8.5 Hz, 1H), 8.09-8.06 (m, 2H), 7.93 (d, J=8.9 Hz, 1H), 7.81 (dd, J=0.9, 7.5 Hz, 1H), 7.61-7.52 (m, 2H), 7.34 (td, J=0.8, 8.1 Hz, 1H), 5.98 (tt, J=2.8, 53.0 Hz, 1H);

MH$^+$ (API-ES) calculated for C$_{17}$H$_{11}$BrF$_4$NO 400, measured 400.

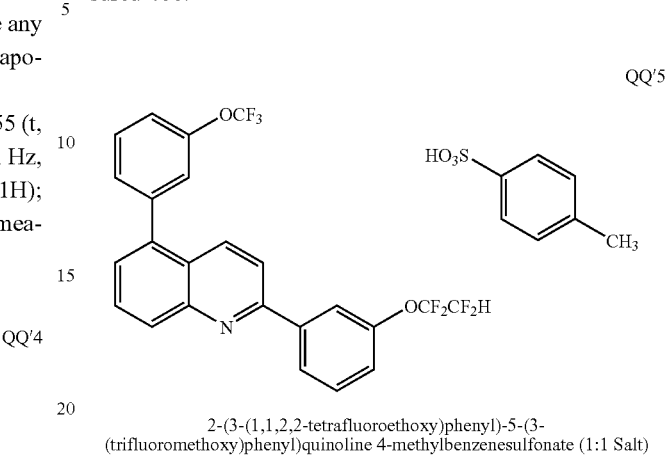

2-(3-(1,1,2,2-tetrafluoroethoxy)phenyl)-5-(3-(trifluoromethoxy)phenyl)quinoline 4-methylbenzenesulfonate (1:1 Salt)

To a 1-L four-necked round bottom flask equipped with a mechanical stirrer, thermocouple and condenser was added a solution of 5-bromo-2-(3-(1,1,2,2-tetrafluoroethoxy)phenyl) quinoline (70.3 g, 175.7 mmol) in 2-methyl-THF (as prepared in Example 2 above), and toluene (349 g, 3788 mmol). The resulting mixture was agitated and heated to 98-100° C., to distill ~325-330 mL solvent. The resulting mixture was cooled to 50-55° C. To the resulting mixture was then added aqueous sodium carbonate (~2M, 50.9 g dissolved in 240.0 g water for a total of 291 g, 480 mmol), 3-(trifluoromethoxy) phenylboronic acid (36.2 g, 175.7 mmol) and tetrakis(triphenyl-phosphine)palladium (0) (1.02 g, 0.88 mmoL). The resulting mixture was heated to reflux (82-85° C.) for 2-3 h. If the reaction was not complete, additional 3-(trifluoromethoxy)phenylboronic acid (3-5%) was added. The resulting mixture was cooled to room temperature and stirred overnight.

The aqueous (BOTTOM) layer of the resulting biphasic mixture was removed and the organic layer washed with brine (~240 mL). The aqueous (BOTTOM) layer was removed and the resulting mixture filtered into another 1-L 4-necked round bottom flask. The flask was washed with toluene (21.6 g, 235 mmol) and combined with the filtrate. The combined filtrate was heated to reflux to distill off ~125 mL of solvent, then cooled to 80-85° C. To the resulting mixture was then added p-toluenesulfonic acid monohydrate (36.8 g, 193.2 mmoL) and the resulting mixture stirred at 80-85° C. for ~1.5 hours, then cooled to room temperature and stirred overnight. To the resulting mixture was then added ethyl acetate (135.3 g, 1536 mmol) and the mixture cooled to 0-5° C. for ~2 hours. The resulting slurry was filtered, washed twice with ethyl acetate (36.1 g, 409 mmol) and then dried under vacuum at 40-45° C., 27-28" Hg overnight to yield the title compound as crude 2-(3-(1,1,2,2-tetrafluoroethoxy)phenyl)-5-(3-(trifluoromethoxy)phenyl)quinoline 4-methylbenzenesulfonate, as a pale yellow crystalline solid. The product (QQ'5) was used in the next step without further purification.

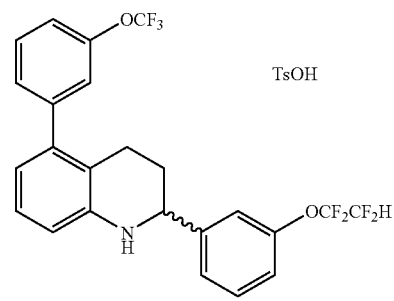

QQ'6

2-(3-(1,1,2,2-tetrafluoroethoxy)phenyl)-5-(3-(trifluoromethoxy)phenyl)-1,2,3,4-tetrahydroquinolium 4-methylbenzene sulfonate To a 50 L phase separator equipped with overhead mechanical stirring was added –(3-(1,1,2,2-tetrafluoroethoxy)phenyl)-5-(3-(trifluoromethoxy)phenyl)quinoline 4-methylbenzenesulfonate (870 g, 1.33 mol) and ethyl acetate (4592 g) and the resulting mixture agitated. To the agitated mixture was then added a 50% saturated aqueous sodium carbonate solution (2.55 L). The resulting biphasic mixture was agitated for ~15 min. and then allowed to settle. The aqueous (BOTTOM) layer was discarded. To the organic layer was added additional 50% saturated aqueous sodium carbonate solution (2.55 L). The resulting biphasic mixture was agitated for ~15 min. and then allowed to settle. The aqueous (BOTTOM) layer was discarded.

The organic layer was dried with sodium sulfate (600 g, 4.22 mol), with agitation for ~30 minutes. The resulting suspension was filtered to remove the sodium sulfate and the filtrate transferred to a 22L flask equipped with an overhead mechanical stirring. To the filtrate was then added (1S)-(+)-10-camphorsulfonic acid (92.80 g, 0.30 mol) and the resulting mixture was agitated for ~10 minutes. To the resulting mixture was then added diludine (877 g, 3.46 mol) and the resulting mixture agitated at ambient temperature for 6 hours. If the reaction was not complete, additional diludine (135 g, 0.53 mol) was added and the resulting mixture agitated at ambient temperature overnight. The resulting mixture was heated to ~40-50° C. to achieve a clear homogeneous solution (to decompose any remaining diludine), then cooled to ambient temperature. To the resulting mixture, at ambient temperature was then added 4N HCl (2.50 L) and the resulting biphasic mixture agitated for ~15-20 minutes. The layers were allowed to split, the aqueous layer was removed and discarded. The 4N HCl wash was repeated 3-5 times to remove byproduct.

To the resulting mixture was then added a 50% saturated aqueous carbonate solution (2.55 L) and the resulting biphasic mixture agitated for ~15 min. The aqueous (BOTTOM) layer was discarded, the organic layer washed a second time with a 50% saturated aqueous carbonate solution (2.55 L), the resulting biphasic mixture agitated for ~15 min and the aqueous (BOTTOM) layer discarded. The organic layer was concentrated to a thick oil. To the oil was then added toluene (4444 g) and the resulting mixture agitated at ambient temperature. To the agitating mixture was then added p-toluenesulfonic acid (279 g, 1.46 mol) and the resulting suspension agitated for ~2 hours. To the resulting mixture was then added heptane (2632 g), the mixture agitated for another ~1.5 hours, then cooled to 0-5° C. The resulting suspension was maintained at 0-5° C. for 1 hour, then filtered. The filter cake was washed with heptane (2.50 L) and allowed to air dry for ~30-40 minutes. The resulting moist solid was transferred to a drying tray and dried under vacuum with a nitrogen bleed (~27" Hg) at ~45-50° C. overnight to yield the title compound (QQ'6) as a white crystalline solid.

Compound 78

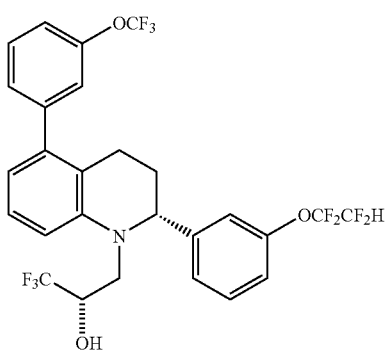

In a 2L round bottom flask equipped with a magnetic stirrer and thermocouple, and nitrogen purge was dissolved (R)-2-(3-(1,1,2,2-tetrafluoroethoxy)phenyl)-5-(3-(trifluoromethoxy)phenyl)-1,2,3,4-tetrahydroquinoline (250 g) in ethyl acetate (2500 mL). The resulting solution was transferred to a 5 L separatory flask equipped with an overhead stirrer. To the mixture was then added 4N HCl (750 mL) and the resulting mixture stirred vigorously for 5 minutes, then allowed to split into a biphasic mixture. The aqueous (BOTTOM) layer was discarded. To the organic layer was added a second portion of 4N HCl (500 mL), the resulting mixture stirred vigorously for 5 minutes, allowed to split into a biphasic mixture and the aqueous (BOTTOM) layer was discarded. To the organic layer was added a 50% saturated (aq.) $Na_2CO_3$ solution (550 mL), the resulting mixture stirred vigorously for 5 minutes, allowed to split into a biphasic mixture and the aqueous (BOTTOM) layer was discarded. The organic layer was dried with $Na_2SO_4$ (250 g), filtered to remove the desiccant and then concentrated on a rotary evaporator at <40° C. in vacuo to yield a bright yellow oil.

The oil (255.3 g) was transferred to a 2L round bottom flask, to which was then added 1,1,1,3,3,3-hexafluoroisopropanol (511 mL). The flask was then flushed with nitrogen. To the resulting mixture was then added (S)-2-(trifluoromethyl)oxirane (164 g). The flask was covered with aluminum foil, the reaction mixture cooled with a room temperature water bath and slowly stirred for 4 hours and allowed to stand at room temperature for 36 hours. When the reaction was deemed complete, the solvent and any excess (S)-2-(trifluoromethyl)oxirane was removed on a rotary evaporator at 40° C. under vacuum. To the resulting residue was added 200 proof ethanol (500 mL) and the mixture polish filtered through a M-sintered glass filtration funnel. The solvent was removed on a rotary evaporator at 50° C. under vacuum. To the residue was added a second amount of 200 proof ethanol (500 mL). The solvent in the resulting mixture was removed on a rotary evaporator at 50° C. under vacuum until dry to yield the title compound (compound 78) as a golden gel-like oil (compound 78 can also have the following nomenclature as an alternative to the nomenclature described above: (S)-1,1,1-trifluoro-3-((R)-2-(3-(1,1,2,2-tetrafluoroethoxy)phenyl)-5-(3-(trifluoromethoxy)phenyl)-3,4-dihydroquinolin-1(2H)-yl)propan-2-ol).

$^1$H NMR (300 MHz, CDCl$_3$) δ 7.38 (d, J=7.6 Hz, 1H), 7.33 (d, J=7.5 Hz, 1H), 7.23 (d, J=8.3 Hz, 1H), 7.20-7.10 (m, 5H), 7.04 (s, 1H), 6.73 (d, J=8.3 Hz, 1H), 6.67 (d, J=7.3 Hz, 1H), 5.89 (tt, J=2.8, 53.0 Hz, 1H), 4.90 (t, J=4.5 Hz, 1H), 4.45-4.36 (m, 1H), 3.91 (d, J=15.6 Hz, 1H), 3.30 (dd, J=9.7, 15.6 Hz, 1H), 2.51 (d, J=4.5 Hz, 1H), 2.47-2.31 (m, 2H), 2.18-2.09 (m, 1H), 2.00-1.91 (m, 1H);

MH+ (API-ES) calculated for $C_{27}H_{22}F_{10}NO_3$ 598, measured 598.

Asymmetric Reduction

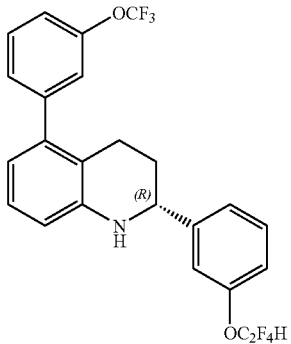

2-(R)-(3-(1,1,2,2-tetrafluoroethoxy)phenyl)-5-(3-(trifluoromethoxy)phenyl)-1,2,3,4-tetrahydroquinoline To a 25 mL carousel tube containing diludine (1.61 g, 3.0 eq., 6.36 mmoL) and the 9-phenanthrylene substituted (S)-chiral catalyst of the following structure:

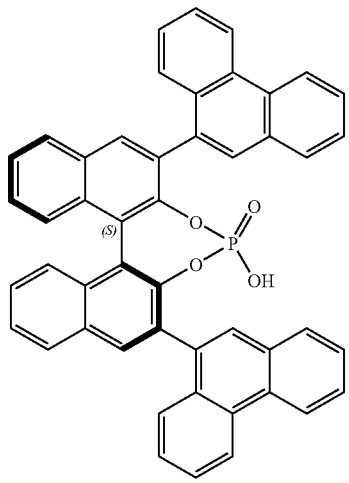

(also known as 4-oxo-2,6-di-phenanthren-9-yl-3,5-dioxa-4l5-phospha-cyclohepta[2,1-a; 3,4-a']dinaphthalen-4-ol) (44.5 mg, 0.06 mmoL, 3 mol %), was added a solution made from 2-(3-(1,1,2,2-tetrafluoroethoxy)phenyl)-5-(3-(trifluoromethoxy)phenyl)quinoline (1.02 g, 2.12 mmoL) and toluene (3.61 g). The resulting slurry was stirred, heated to 58° C. and then stirred at 58° C. for 8 hours. The resulting mixture was then cooled to room temperature. (1S)-(+)-10-camphorsulfonic acid (148 mg, 0.30 eq) and additional diludine (160 mg, 0.3 eq.) were added and the resulting slurry was stirred at room temperature for 6 hours. To the resulting reaction mixture were added ethyl acetate (4 mL) and aqueous 2N $Na_2CO_3$ (6 mL). The phases of the resulting biphasic mixture wre separated. After the clear lower aqueous layer was mostly removed, the remaining organic phase and some precipitates were filtered and the filtrate was washed with 4N HCl for (3-5 times, 6 mL each time), followed by washing with 50% saturated aqueous $Na_2CO_3$ solution (2×). The resulting mixture was concentrated to yield the title compound, (R)-2-(3-(1,1,2,2-tetrafluoroethoxy)phenyl)-5-(3-(trifluoromethoxy)phenyl)-1,2,3,4-tetrahydroquinoline, as crude product, as an oil.

Note: The crude oil may be further, optionally converted to its corresponding tosylate salt and/or further recrystallized.

Example 79

Cmpd 79

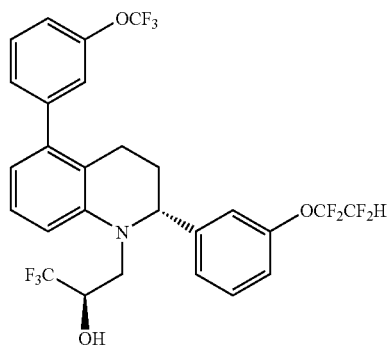

(2R,αR)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol A small amount of the lower Rf R,R diasteriomer 79 was obtained from the reaction. Compound 79 was identical in all respects to compound 2, except for the optical rotation. $[\alpha]_D^{20}$=−64.9° (c1; CHCl3); $^1$H NMR (400 MHz, CDCl$_3$) δ 7.59-7.52 (m, 2H), 7.50-7.41 (m, 2H), 7.36 (t, J=7.9 Hz, 1H), 7.24 (t, J=7.9 Hz, 1H), 7.18-7.09 (m, 2H), 7.03 (s, 1H), 6.90 (d, J=8.2 Hz, 1H), 6.68 (d, J=7.5 Hz, 1H), 5.89 (tt, J=53.1, 2.8 Hz, 1H), 4.62 (t, J=4.4 Hz, 1H), 4.37-4.15 (m, 1H), 3.80 (dd, J=15.7, 6.6 Hz, 1 H), 3.51 (dd, J=15.7, 5.4 Hz, 1H), 2.76 (brs, 1H), 2.42-2.37 (m, 2H), 2.17-2.08 (m, 1H), 1.99-1.91 (m, 1H); MS (ES) m/z: 582 (M+H+).

Example 80

Cmpd 80

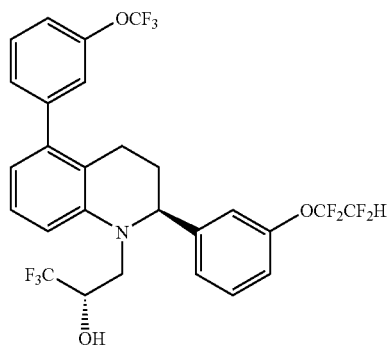

(2R,αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol Scheme RR
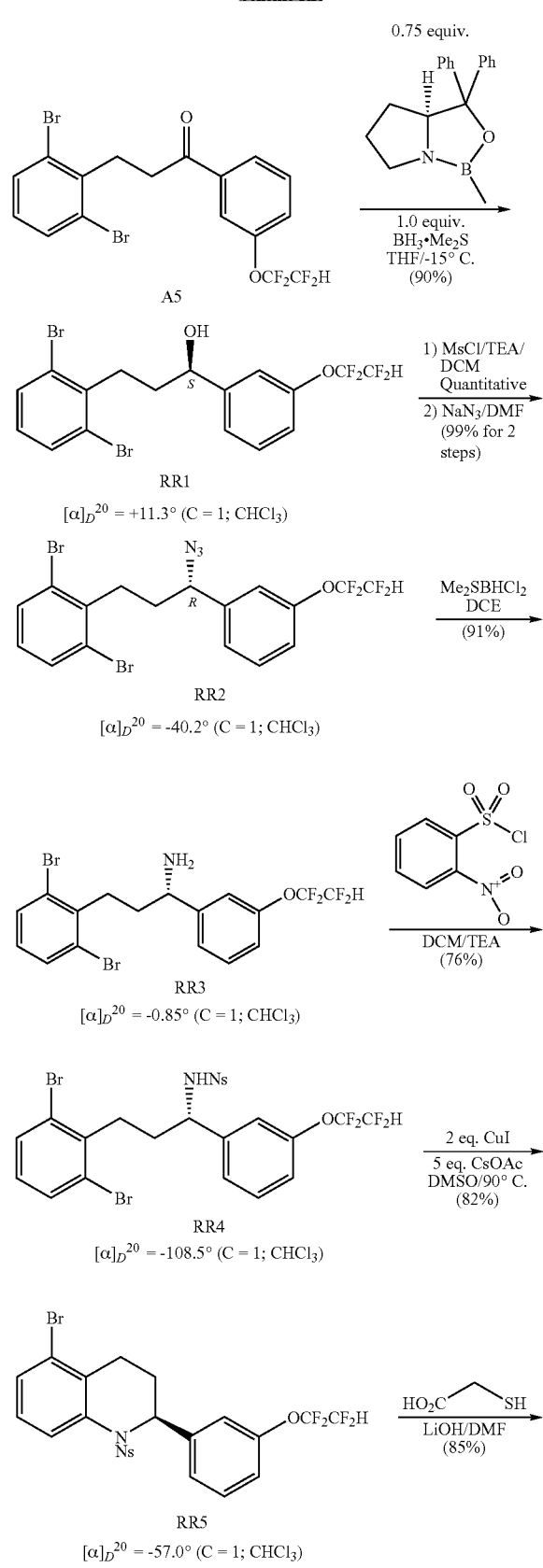
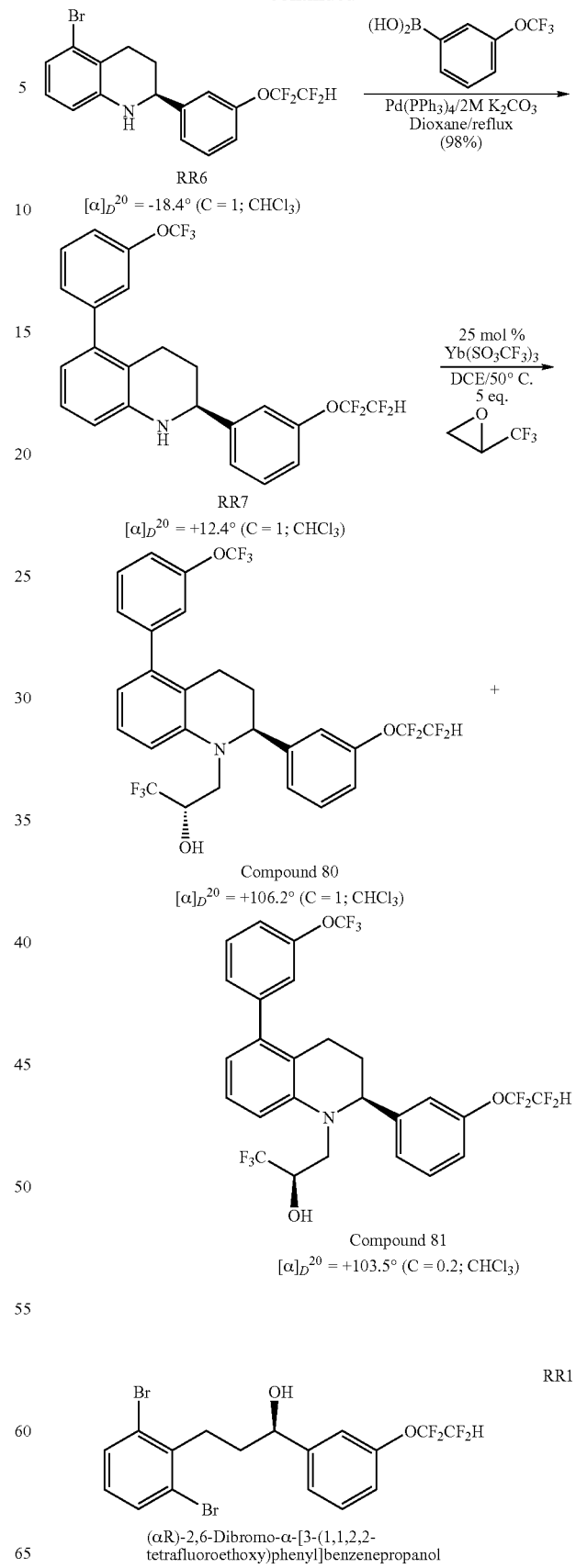

Compound RR1 was prepared exactly as compound QQ1, substituting (S)-2-Methyl-CBS-oxazaborolidine for (R)-2-Methyl-CBS-oxazaborolidine. Analysis by chiral HPLC (Chiralcel AS; Isocratic elution 90/10 Hexane/IPA) by area integration at 210 nm indicated the enantiomeric excess >95%. This alcohol was identical in all respects to the racemic alcohol A6, except for the optical rotation. $[\alpha]_D^{20}$=+11.4° (c1; CHCl3); $^1$H NMR (300 MHz, CDCl$_3$) δ 7.48 (d, J=8.0 Hz, 2H), 7.41-7.28 (m, 3H), 7.14 (d, J=7.7 Hz, 1H), 6.89 (t, J=8.0 Hz, 1H), 5.91 (tt, J=53.1, 2.8 Hz, 1H), 4.86 (dd, J=10.1, 6.2 Hz, 1H), 3.19-3.05 (m, 1H), 3.03-2.92 (m, 1H), 2.09-1.95 (m, 3H); MS (ES) m/z: 509 (M+Na$^+$).

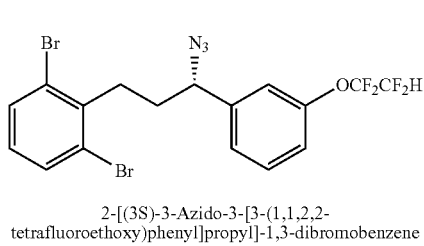

RR2

2-[(3S)-3-Azido-3-[3-(1,1,2,2-tetrafluoroethoxy)phenyl]propyl]-1,3-dibromobenzene Substituting RR1 for A6 and following the procedure described for the preparation of A7, RR2 was obtained. This azide was identical in all respects to the racemic azide A7, except for the optical rotation. $[\alpha]_D^{20}$=−40.2° (c1; CHCl3); $^1$H NMR (300 MHz, CDCl$_3$) δ 7.48 (d, J=8.0 Hz, 2H), 7.42 (t, J=7.9 Hz, 1H), 7.31-7.19 (m, 3H), 6.90 (t, J=8.0 Hz, 1H), 5.92 (tt, J=53.1, 2.8 Hz, 1H), 4.60 (t, J=6.9 Hz, 1H), 3.15-3.05 (m, 1H), 2.99-2.82 (m, 1H), 2.09-1.97 (m, 2H); MS (ES) m/z: 484 (M−N$_2$+H$^+$).

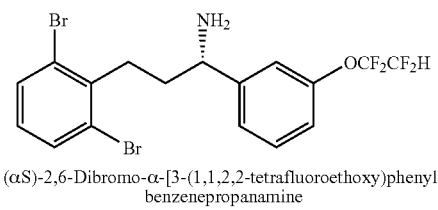

RR3

(αS)-2,6-Dibromo-α-[3-(1,1,2,2-tetrafluoroethoxy)phenyl]benzenepropanamine

Substituting RR2 for A7 and following the procedure described for the preparation of A8, RR3 was obtained. This amine was identical in all respects to the racemic amine A8, except for the optical rotation. $[\alpha]_D^{20}$=−0.88° (c1; CHCl3); $^1$H NMR (300 MHz, CDCl$_3$) δ 7.46 (d, J=8.2 Hz, 2H), 7.39-7.26 (m, 3H), 7.14-7.10 (m, 1H), 6.88 (t, J=8.0 Hz, 1H), 5.91 (tt, J=53.1, 2.9 Hz, 1H), 4.08 (t, J=6.6 Hz, 1H), 3.09-3.00 (m, 1H), 2.90-2.80 (m, 1H), 1.98-1.88 (m, 2H), 1.57 (brs, 2H); MS (ES) m/z: 486 (M+H$^+$).

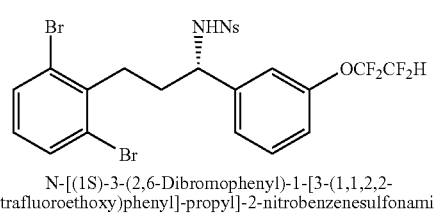

RR4

N-[(1S)-3-(2,6-Dibromophenyl)-1-[3-(1,1,2,2-tetrafluoroethoxy)phenyl]-propyl]-2-nitrobenzenesulfonamide Substituting RR3 for A8 and following the procedure described for the preparation of A9, RR4 was obtained. This sulfonamide was identical in all respects to the racemic sulfonamide A9, except for the optical rotation. $[\alpha]_D^{20}$=−108.5° (c1; CHCl3); $^1$H NMR (400 MHz, CDCl$_3$) δ 7.72 (d, J=8.0 Hz, 1H), 7.66 (d, J=7.9 Hz, 1H), 7.55-7.33 (m, 4H), 7.13-7.08 (m, 2H), 7.01 (s, 1H), 6.95-6.88 (m, 2H), 5.96 (d, J=8.9 Hz, 1H), 5.86 (tt, J=53.1, 2.8 Hz, 1H), 4.69 (dd, J=16.0, 7.8 Hz, 1H), 3.19-3.11 (m, 1H), 2.88-2.80 (m, 1H), 2.14-1.94 (m, 2H); MS (ES) m/z: 693 (M+Na$^+$).

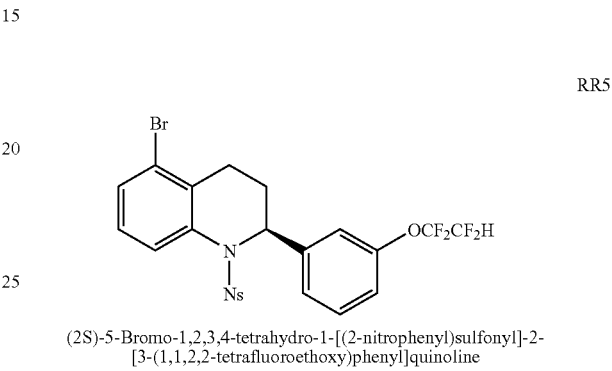

RR5

(2S)-5-Bromo-1,2,3,4-tetrahydro-1-[(2-nitrophenyl)sulfonyl]-2-[3-(1,1,2,2-tetrafluoroethoxy)phenyl]quinoline Substituting RR4 for A9 and following the procedure described for the preparation of A10, RR5 was obtained. This compound was identical in all respects to the racemic compound A10, except for the optical rotation. $[\alpha]_D^{20}$=−57.0° (c1; CHCl3); $^1$H NMR (400 MHz, CDCl$_3$) δ 7.81 (d, J=8.1 Hz, 1H), 7.73-7.69 (m, 1H), 7.63-7.50 (m, 3H), 7.43 (d, J=8.0 Hz, 1 H), 7.39-7.09 (m, 5H), 5.88 (tt, J=53.1, 2.9 Hz, 1H), 5.62 (t, J=6.9 Hz, 1H), 2.74-2.66 (m, 1H), 2.47-2.39 (m, 1H), 2.35-2.27 (m, 1H), 2.05-1.96 (m, 1H); MS (ES) m/z: 589 (M).

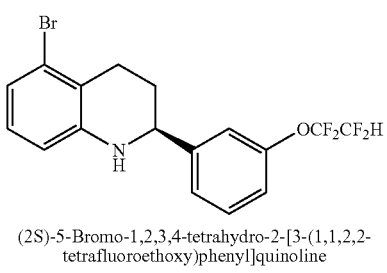

RR6

(2S)-5-Bromo-1,2,3,4-tetrahydro-2-[3-(1,1,2,2-tetrafluoroethoxy)phenyl]quinoline Substituting RR5 for A10 and following the procedure described for the preparation of A11, RR6 was obtained. This amine was identical in all respects to the racemic amine A 11, except for the optical rotation. $[\alpha]_D^{20}$=−18.2° (c1; CHCl3); $^1$H NMR (300 MHz, CDCl$_3$) δ 7.37 (t, J=7.8 Hz, 1H), 7.30-7.21 (m, 2H), 7.15 (d, J=7.9 Hz, 1H), 6.95-6.71 (m, 2H), 6.51 (d, J=7.8 Hz, 1H), 5.90 (tt, J=53.1, 2.8 Hz, 1H), 4.40 (dd, J=9.3, 3.1 Hz, 1 H), 4.13 (brs, 1H), 2.88-2.79 (m, 2H), 2.21-2.11 (m, 1H), 2.05-1.90 (m, 1H); MS (ES) m/z: 406 (M+2).

RR7

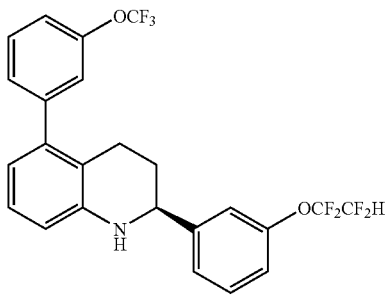

(2S)-1,2,3,4-Tetrahydro-2-[3-(1,1,2,2-tetrafluoroethoxy)phenyl]-
5-[3-(trifluoromethoxy)phenyl]quinoline Substituting RR6 for A11 and following the procedure described for the preparation of A12, RR7 was obtained. This bi-phenyl was identical in all respects to the racemic bi-phenyl A12, except for the optical rotation: $[\alpha]_D^{20} = +12.4°$ (c1; CHCl3); $^1$H NMR (400 MHz, CDCl$_3$) δ 7.42-7.30 (m, 4 H), 7.25 (m, 1H), 7.21-7.08 (m, 4H), 6.62 (s, 1H), 6.60 (s, 1H), 5.90 (tt, J=53.1, 2.8 Hz, 1H), 4.51 (dd, J=8.9, 3.3 Hz, 1H), 4.20 (brs, 1H), 2.81-2.71 (m, 1H), 2.53 (dt, J=16.6, 4.8 Hz, 1H), 2.10-2.02 (m, 1H), 1.92-1.82 (m, 1H); MS (ES) m/z: 486 (M+H$^+$).

Cmpd 80

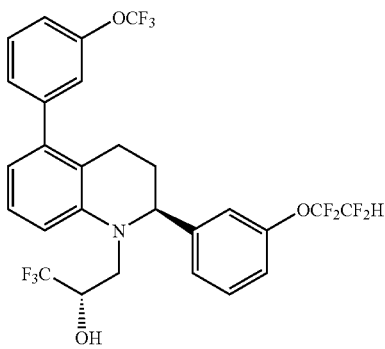

(2S,αS)-3,4-Dihydro-2-[3-(1,1,2,2-tetrafluoroethoxy)phenyl]-5-[3-
(trifluoromethoxy)phenyl]-α-(trifluoromethyl)-1(2H)-quinolineethanol Substituting RR7 for A12 and following the procedure described for the preparation of compound 1, the pure S,S compound 80 was obtained. Compound 80 was identical in all respects to compound 2, except for the optical rotation. $[\alpha]_D^{20} = +106.200$ (c1; CHCl3); $^1$H NMR (400 MHz, CDCl$_3$) δ 7.40-7.20 (m, 2H), 7.28-7.10 (m, 6H), 7.04 (s, 1H), 6.73 (d, J=8.3 Hz, 1H), 6.67 (d, J=7.4 Hz, 1H), 5.89 (tt, J=53.1, 2.8 Hz, 1H), 4.89 (t, J=4.4 Hz, 1H), 4.42 (m, 1H), 3.91 (d, J=15.5 Hz, 1H), 3.30 (dd, J=15.6, 9.7 Hz, 1H), 2.48 (dt, J=16.3, 4.4 Hz, 1H), 2.42-2.31 (m, 2H), 2.19-2.09 (m, 1H), 2.00-1.92 (m, 1H); MS (ES) m/z: 598 (M+H$^+$).

Example 81

Cmpd 81

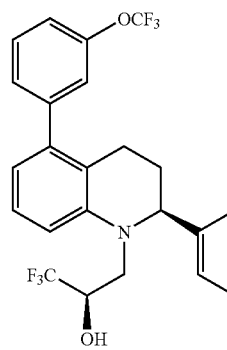

(2S,αR)-3,4-Dihydro-2-[3-(1,1,2,2-tetrafluoroethoxy)phenyl]-5-[3-
(trifluoromethoxy)phenyl]-α-(trifluoromethyl)-1(2H)-quinolineethanol A small amount of the higher Rf S,R diasteriomer 81 was obtained from the reaction. Compound 81 was identical in all respects to the compound 1 except for the optical rotation. $[\alpha]_D^{20} = +103.5°$ (c1; CHCl3); $^1$H NMR (400 MHz, CDCl$_3$) δ 7.40-7.20 (m, 2H), 7.28-7.10 (m, 6H), 7.04 (s, 1H), 6.73 (d, J=8.3 Hz, 1H), 6.67 (d, J=7.4 Hz, 1H), 5.89 (tt, J=53.1, 2.8 Hz, 1H), 4.89 (t, J=4.4 Hz, 1H), 4.42 (m, 1H), 3.91 (d, J=15.5 Hz, 1H), 3.30 (dd, J=15.6, 9.7 Hz, 1H), 2.48 (dt, J=16.3, 4.4 Hz, 1H), 2.42-2.31 (m, 2H), 2.19-2.09 (m, 1H), 2.00-1.92 (m, 1H); MS (ES) m/z: 598 (M+H$^+$).

Example 82

Cmpd 82

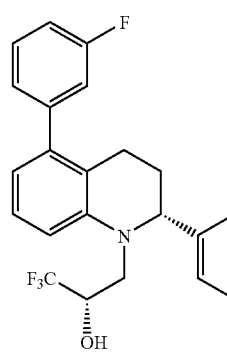

(2R,αS)-3,4-Dihydro-2-[3-(1,1,2,2-tetrafluoroethoxy)phenyl]-5-[3-
(fluoro)phenyl]-α-(trifluoromethyl)-1(2H)-quinolineethanol

Scheme SS

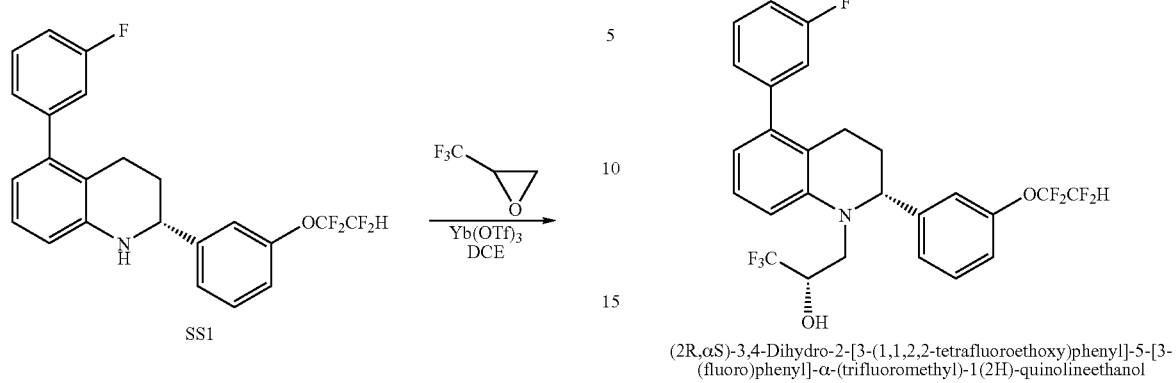

Replacing 3-trifluoromethoxy-benzene boronic acid with 3-fluoro-benzene boronic acid and replacing A11 with QQ6 and following the same procedure as in the preparation of A12 gave SS1. $^1$H NMR (300 MHz, CDCl$_3$) δ 7.39-7.29 (m, 4H), 7.15-6.98 (m, 5H), 6.60 (dd, J=7.5, 1.6 Hz, 2H), 5.90 (tt, J=53.1, 2.8 Hz, 1H), 4.50 (dd, J=8.8, 3.4 Hz, 1H), 4.19 (broad s, 1H), 2.80-2.70 (m, 1H), 2.54 dt, J=16.5, 4.9 Hz 1H), 2.11-2.01 (m, 1H), 1.95-1.80 (m, 1H); MS (ES) m/z: 420 (M+H$^+$).

Replacing A12 with SS1 and following the same procedure as in the preparation of compound 1 and 2 gave compound a pure compound 82 (yield 70%): $^1$H NMR (400 MHz, CDCl$_3$) δ 7.39-7.29 (m, 2H), 7.21 (t, J=7.9 Hz, 1H), 7.12 (bt, J=7.7 Hz, 2H), 7.04-6.94 (m, 4H), 6.72 (d, J=8.2 Hz, 1H), 6.67 (d, J=7.5 Hz, 1H), 5.89 (tt, J=53.1, 2.8 Hz, 1H), 4.89 (t, J=4.4 Hz, 1H), 4.43 (m, 1H), 3.91 (d, J=15.5 Hz, 1H), 3.30 (dd, J=15.6, 9.7 Hz, 1H), 2.49 (dt, J=16.3, 4.5 Hz, 1H), 2.42-2.31 (m, 2H), 2.19-2.09 (m, 1H), 2.00-1.91 (m, 1H); MS (ES) m/z: 532 (M+H$^+$).

Example 83

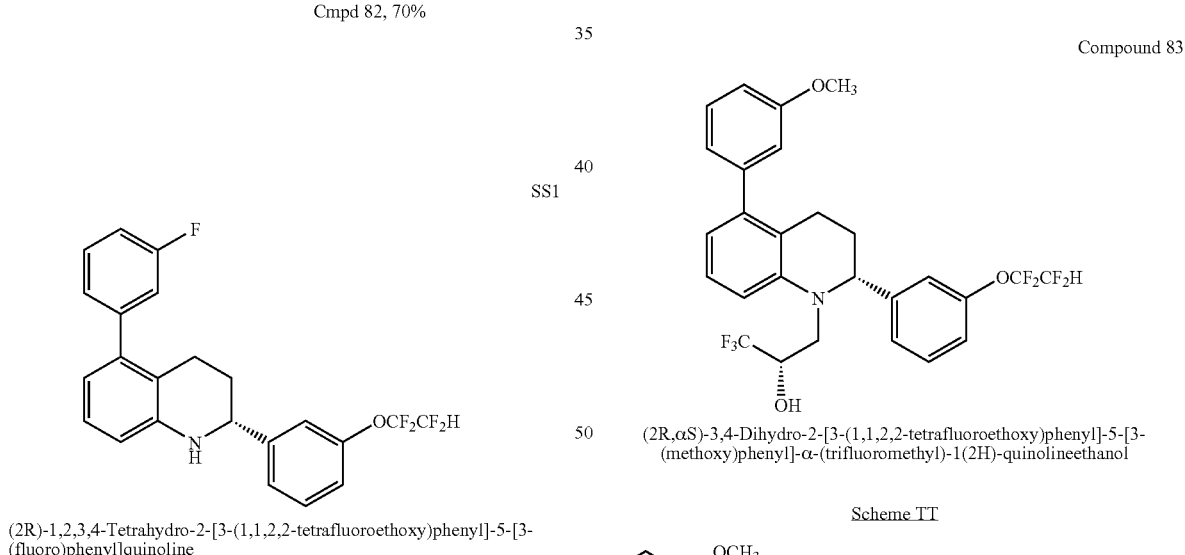

Scheme TT

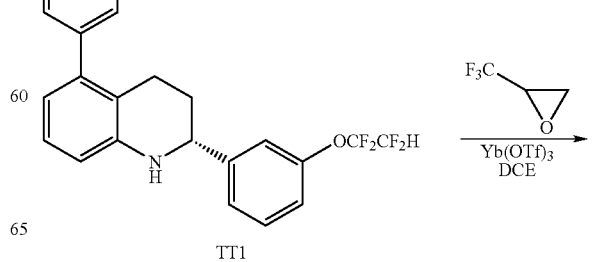

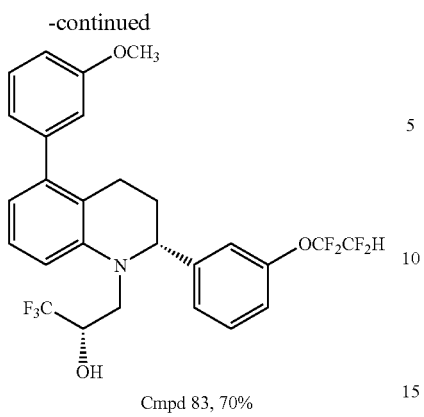

Cmpd 83, 70%

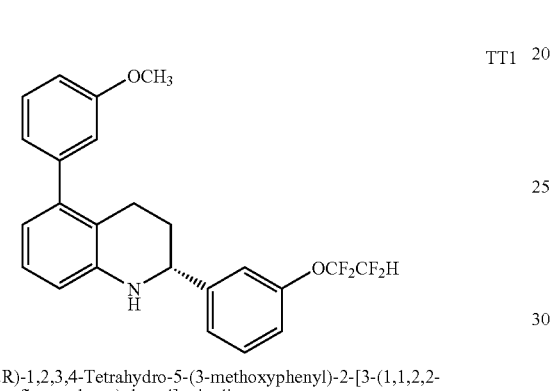

(2R)-1,2,3,4-Tetrahydro-5-(3-methoxyphenyl)-2-[3-(1,1,2,2-tetrafluoroethoxy)phenyl]quinoline Replacing 3-trifluoromethoxy-benzene boronic acid with 3-methoxy-benzene boronic acid and replacing A11 with QQ6 and following the same procedure as in the preparation of A12 gave TT1. $^1$H NMR (400 MHz, CDCl$_3$) δ 7.39-7.23 (m, 4H), 7.14 (d, J=7.9 Hz, 1H), 7.08 (t, J=7.7 Hz, 1H), 6.92-6.85 (m, 3H), 6.64 (d, J=7.4 Hz, 1H), 6.59 (d, J=8.0 Hz, 1H), 5.90 (tt, J=53.1, 2.8 Hz, 1H), 4.49 (dd, J=8.9, 4.3 Hz, 1H), 4.17 (brs, 1H), 3.81 (s, 3H), 2.82-2.71 (m, 1H), 2.57 (dd, J=16.7, 5.9 Hz, 1H), 2.10-2.01 (m, 1H), 1.82-1.81 (m, 1H); MS (ES) m/z: 432 (M+H$^+$).

Compound 83

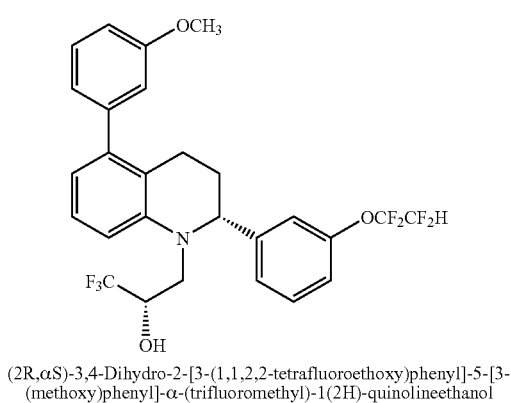

(2R,αS)-3,4-Dihydro-2-[3-(1,1,2,2-tetrafluoroethoxy)phenyl]-5-[3-(methoxy)phenyl]-α-(trifluoromethyl)-1(2H)-quinolineethanol Replacing A12 with TT1 and following the same procedure as in the preparation of compounds 1 and 2 afforded a pure compound 83 (yield 70%): $^1$H NMR (300 MHz, CDCl$_3$) δ 7.39-7.19 (m, 3H), 7.11 (d, J=8.2 Hz, 2H), 7.04 (s, 1H), 6.87-6.80 (m, 3H), 6.70 (d, J=8.0 Hz, 2H), 5.90 (tt, J=53.1, 2.8 Hz, 1H), 4.87 (t, J=4.6 Hz, 1H), 4.42 (m, 1H), 3.90 (d, J=15.6 Hz, 1H), 3.79 (s, 3H), 3.29 (dd, J=15.5, 7.7 Hz, 1H), 2.59-2.31 (m, 3H), 2.20-2.08 (m, 1H), 2.00-1.89 (m, 1H); MS (ES) m/z: 544 (M+H$^+$).

Example 84

Compound 84

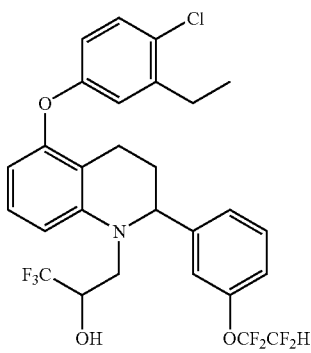

(Higher Rf Compound)

3-{5-(4-Chloro-3-ethyl-phenoxy)-2-[3-(1,1,2,2-tetrafluoro-ethoxy)-phenyl]-3,4-dihydro-2H-quinolin-1-yl}-1,1,1-trifluoro-propan-2-ol Scheme UU

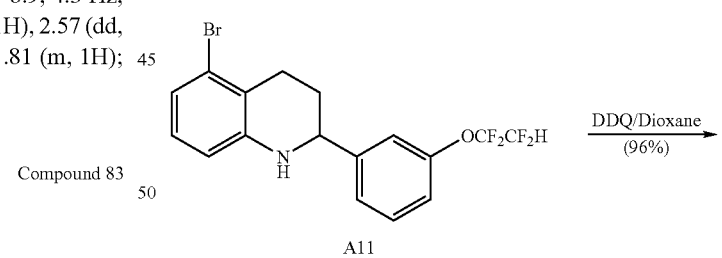

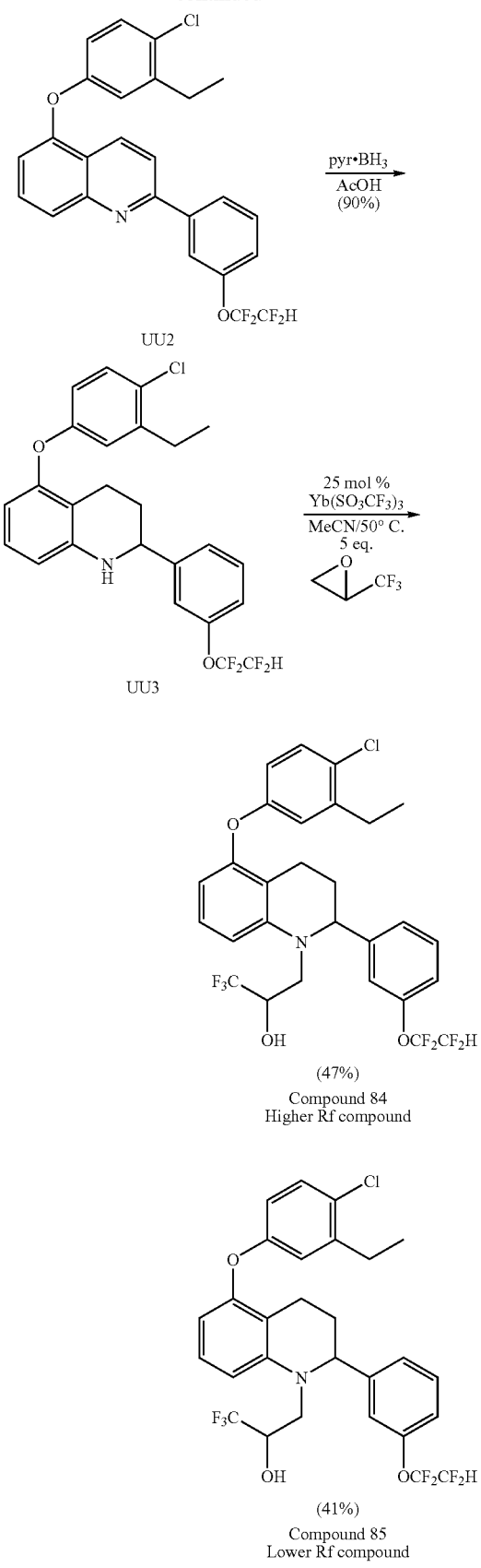

(90%)

UU2

UU3

(47%)
Compound 84
Higher Rf compound (41%)
Compound 85
Lower Rf compound

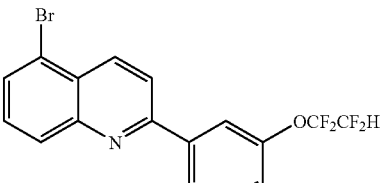

5-Bromo-2-[3-(1,1,2,2-tetrafluoro-ethoxy)-phenyl]-quinoline

To a solution of A11 (717 mg; 1.77 mmol) in anhydrous dioxane (10 ml) under an atmosphere of nitrogen was added DDQ (2.4 g; 10.6 mmol). The reaction was aged approximately 2 hours before being diluted with EtOAc. Washing with 3N NaOH (3×), water (2×) and brine was followed by drying over MgSO$_4$, filtration and removal of the solvent in vacuo. The remainder was filtered through a short plug of silica. This purified product was then lyophilized from benzene to provide 687 mg (96%) of a white solid: $^1$H NMR (400 MHz, CDCl$_3$) δ 8.61 (d, J=8.8 Hz, 1H), 8.17-8.08 (m, 3H), 7.95 (d, J=8.8 Hz, 1H), 7.82 (d, J=7.4 Hz, 1H), 7.62-7.53 (m, 2H) 7.36-7.33 (m, 1H), 5.90 (tt, J=53.1, 2.8 Hz, 1H); MS (ES) m/z: 400 (M+H$^+$).

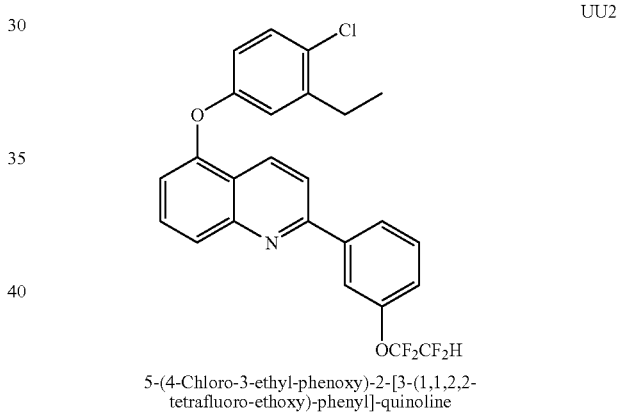

5-(4-Chloro-3-ethyl-phenoxy)-2-[3-(1,1,2,2-tetrafluoro-ethoxy)-phenyl]-quinoline The solids UU1 (687 mg, 1.72 mmol), 3-ethyl-4-chlorophenol (672 mg, 4.29 mmol) and Cs$_2$CO$_3$ (1.39 g, 4.29 mmol) were charged into a flask and purged with N$_2$ three times. 1-Methyl-2-pyrrolidinone (10 mL) was added and the N$_2$ purge repeated. 2,2,6,6-tetramethyl-heptane-3,5-dione (72 uL, 0.344 mmol) was added followed by CuCl (170 mg, 1.72 mmol) and the N$_2$ purge repeated. The flask was sealed and placed in a 125° C. oil bath for approximately 20 hours. The reaction mixture was cooled to ambient temperature, diluted with EtOAc and filtered through celite. The organic layer was then washed with saturated NaHCO$_3$ solution (2×), water and brine. The organic phase was dried (MgSO$_4$), filtered, concentrated and purified by column chromatography (3%-4%-5% EtOAc/Hex) to provide 567 mg (70%) of UU2: $^1$H NMR (400 MHz, CDCl$_3$) δ 8.62 (d, J=87 Hz, 1H), 8.07-8.10 (m, 2H), 7.94 (d, J=8.7 Hz, 1H), 7.87 (d, J=8.9 Hz, 1H), 7.65-7.61 (m, 1H), 7.57-7.53 (m, 1H), 7.32-7.35 (m, 2H), 7.0 (d, J=2.5 Hz, 1H), 6.93 (d, J=7.5 Hz, 1H), 6.84 (dd, J=8.7, 3.0 Hz, 1H), 5.90 (tt, J=53.1, 2.8 Hz, 1H) 2.74 (q, J=7.7 Hz, 2H), 1.23 (t, J=7.5 Hz, 3H); MS (ES) m/z: 476 (M+H$^+$)

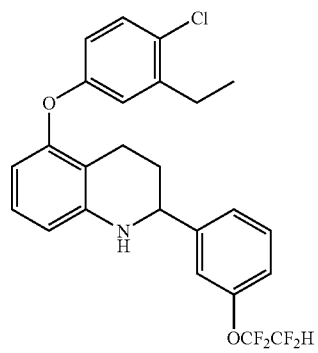

5-(4-Chloro-3-ethyl-phenoxy)-2-[3-(1,1,2,2-tetrafluoro-
ethoxy)-phenyl]-1,2,3,4-tetrahydro-quinoline To a stirred solution of UU2 (576 mg, 1.21 mmol) in ACOH (8 mL) under an atmosphere of nitrogen was added borane-pyridine complex (605 uL, 4.85 mmol). After approximately 15 hours, the reaction was poured into EtOAc and washed with 3N NaOH, (1×), water and brine. The organic phase was dried (MgSO$_4$), filtered, concentrated and purified by column chromatography (15% EtOAc/Hex) to provide 525 mg (90%) of UU3: MS (ES) m/z: 480 (M+H$^+$).

Compound 84

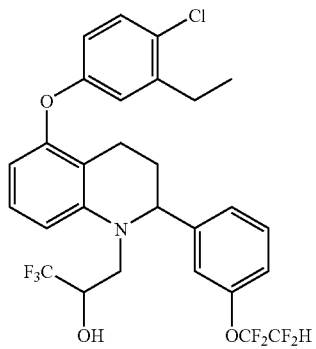

Higher Rf compound

3-{5-(4-Chloro-3-ethyl-phenoxy)-2-[3-(1,1,2,2-tetrafluoro-ethoxy)-
phenyl]-3,4-dihydro-2H-quinolin-1-yl}-1,1,1-trifluoro-propan-2-ol Replacing A12 with UU3 and following the same procedure as in the preparation of compounds 1 and 2 gave compounds 84 and 85: $^1$H NMR (400 MHz, CDCl$_3$) δ 7.32-7.28 (m, 1H), 7.18 (d, J=8.7 Hz, 1H), 7.14-7.04 (m, 2H), 6.98 (s, 1H), 6.78 (d, J=2.9 Hz, 1H), 6.61 (dd, J=8.7, 3.0 Hz, 1H), 6.50 (d, J=8.3 Hz, 1H), 6.33 (d, J=8.0 Hz, 1H), 5.87 (tt, J=53.1, 2.8 Hz, 1H), 4.87 (bs, 1H), 4.41-4.37 (m, 1H), 3.88 (dd, J=15.4, 1.6 Hz, 1H), 3.29 (dd, J=15.5, 9.6 Hz, 1H), 2.80-2.71 (m, 1H), 2.66 (q, J=7.4 Hz, 2H), 2.56 (bs, 1H), 2.23-2.13 (m, 2H), 2.09-2.02 (m, 1H), 1.17 (t, J=7.5, 3H); MS (ES) m/z: 592 (M+H$^+$).

Example 85

Compound 85

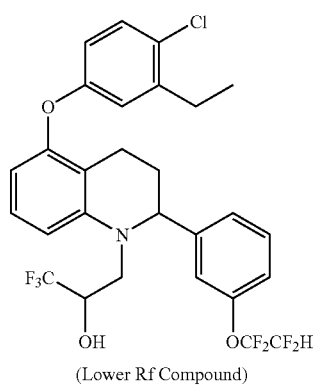

(Lower Rf Compound)

3-{5-(4-Chloro-3-ethyl-phenoxy)-2-[3-(1,1,2,2-tetrafluoro-ethoxy)-
phenyl]-3,4-dihydro-2H-quinolin-1-yl}-1,1,1-trifluoro-propan-2-ol $^1$H NMR (400 MHz, CDCl$_3$) δ 7.30 (t, J=8.0 Hz, 1H), 7.18 (d, J=8.7 Hz, 1H), 7.15-7.05 (m, 2H), 7.02 (d, J=7.7 Hz, 1H), 6.96 (s, 1H), 6.78 (d, J=2.9 Hz, 1H), 6.65 (d, J=8.3 Hz, 1H), 6.61 (dd, J=8.5, 2.9 Hz, 1H), 6.34 (d, J=8.0 Hz, 1H), 5.87 (tt, J=53.1, 2.8 Hz, 1H), 4.61 (bs, 1H), 4.35-4.25 (bs, 1H), 3.78 (dd, J=15.6, 6.4 Hz, 1H), 3.51 (dd, J=15.7, 5.5 Hz, 1H), 2.80-2.71 (m, 1H), 2.66 (q, J=7.5 Hz, 2H), 2.34 (d, J=3.4 Hz, 1H), 2.21-2.08 (m, 2H), 2.06-2.02 (m, 1H), 1.16 (t, J=7.5, 3H).

Example 86

Compound 86

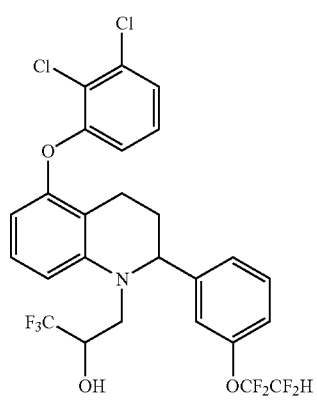

(Higher Rf Compound)

3-{5-(2,3-Dichloro-phenoxy)-2-[3-(1,1,2,2-tetrafluoro-ethoxy)-
phenyl]-3,4-dihydro-2H-quinolin-1-yl}-1,1,1-trifluoro-propan-2-ol Scheme V V

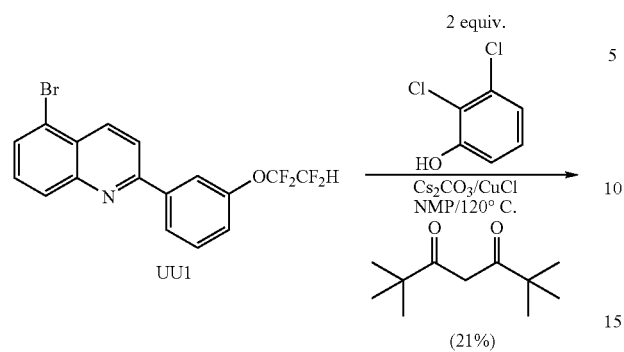

UU1

(21%)

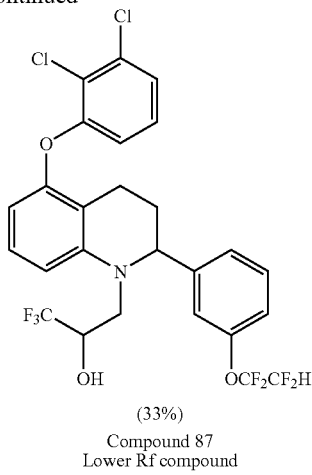

(33%)
Compound 87
Lower Rf compound

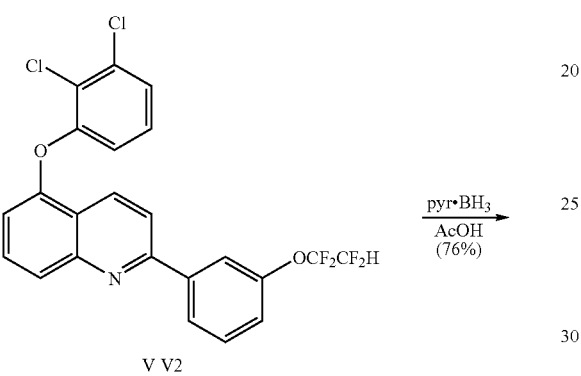

V V2

VV2

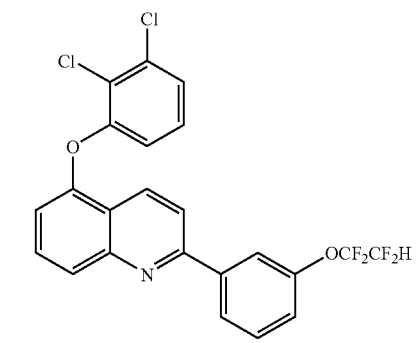

5-(2,3-Dichloro-phenoxy)-2-[3-(1,1,2,2-tetrafluoro-ethoxy)-phenyl]-quinoline

Replacing 3-ethyl-4-chloro-phenol with 2,3-dichloro-phenol and following the same procedure as for the preparation of UU2, VV2 was obtained: MS (ES) m/z: 482 (M+H⁺).

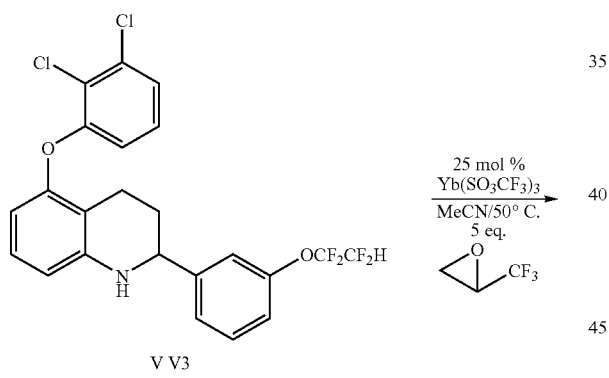

V V3

VV3

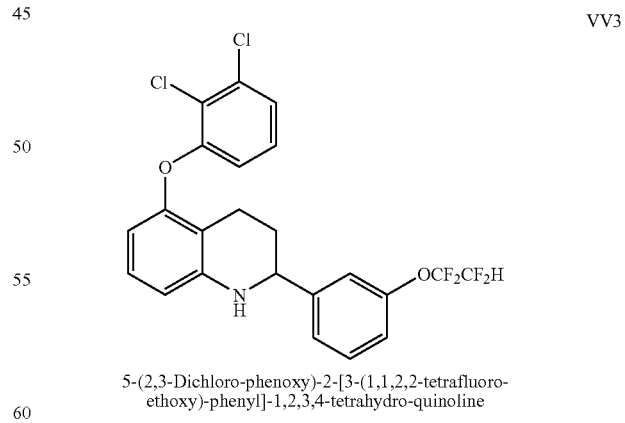

5-(2,3-Dichloro-phenoxy)-2-[3-(1,1,2,2-tetrafluoro-ethoxy)-phenyl]-1,2,3,4-tetrahydro-quinoline Replacing UU2 with VV2 and following the same procedure as for the preparation of UU3, VV3 was obtained (76%): $^1$H NMR (400 MHz, CDCl$_3$) δ 7.35-7.38 (m, 1H), 7.30-7.24 (m, 2H), 7.18-7.13 (m, 2H), 7.07 (t, J=8.2 Hz, 1H), 6.99 (t, J=8.0 Hz, 1H), 6.75 (dd, J=8.3, 2.4 Hz, 1H), 6.42 (d, J=7.9 Hz, 1H), 6.23 (d, J=8.0 Hz, 1H), 5.90 (tt, J=53.1, 2.8 Hz, 1H), 4.43

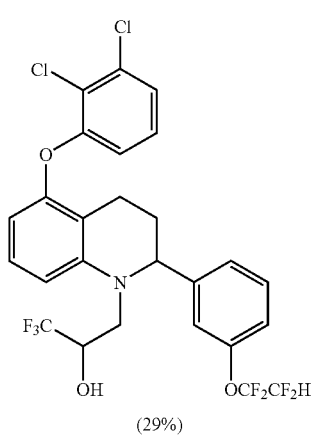

(29%)
Compound 86
Higher Rf compound (dd, J=9.2, 2.9 Hz, 1H), 4.20 (bs, 1H), 2.73-2.69 (m, 2H), 2.16-2.10 (m, 1H), 1.98-1.88 (m, 1H); MS (ES) m/z: 486 (M+H+).

Compound 86

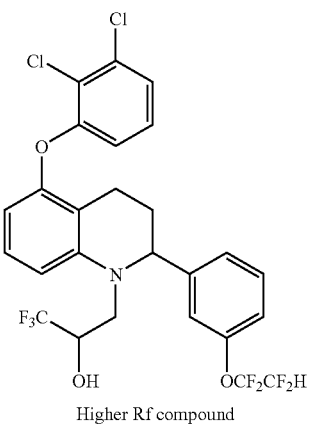

Higher Rf compound

3-{5-(2,3-Dichloro-phenoxy)-2-[3-(1,1,2,2-tetrafluoro-ethoxy)-phenyl]-3,4-dihydro-2H-quinolin-1-yl}-1,1,1-trifluoro-propan-2-ol Replacing A12 with VV3 and following the same procedure as in the preparation of compounds 1 and 2 gave compounds 86 and 87: $^1$H NMR (400 MHz, CDCl$_3$) δ 7.31 (t, J=7.9 Hz, 1H), 7.15-6.99 (m, 5H), 6.96 (s, 1H), 6.64 (dd, J=8.2, 1.4 Hz, 1H), 6.53 (d, J=8.3 Hz, 1H), 6.30 (dd, J=8.0, 0.6 Hz, 1H), 5.88 (tt, J=53.1, 2.8 Hz, 1H), 4.87 (t, J=3.3 Hz, 1H), 4.41-4.37 (m, 1H), 3.89 (dd, J=15.5, 1.7 Hz, 1H), 3.30 (dd, J=15.6, 9.6 Hz, 1H), 2.80-2.71 (m, 1H), 2.42 (bs, 1H), 2.23-2.13 (m, 2H), 2.09-2.02 (m, 1H); MS (ES) m/z: 598 (M+H+).

Example 87

Compound 87

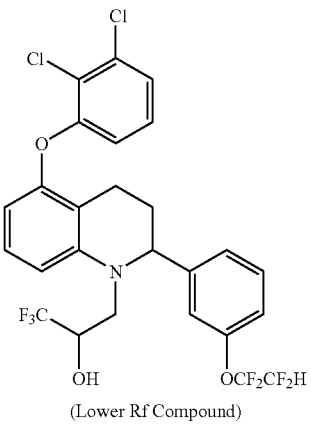

(Lower Rf Compound)

3-{5-(4-Chloro-3-ethyl-phenoxy)-2-[3-(1,1,2,2-tetrafluoro-ethoxy)-phenyl]-3,4-dihydro-2H-quinolin-1-yl}-1,1,1-trifluoro-propan-2-ol $^1$H NMR (400 MHz, CDCl$_3$) δ 7.31 (t, J=7.9 Hz, 1H), 7.15-7.00 (m, 5H), 6.94 (s, 1H), 6.68 (d, J=8.4 Hz, 1H), 6.63 (dd, J=8.0, 1.1 Hz, 1H), 6.32 (d, J=7.8 Hz, 1H), 5.88 (tt, J=53.1, 2.8 Hz, 1H), 4.62 (t, J=3.0 Hz, 1H), 4.35-4.25 (m, 1H), 3.77 (dd, J=15.7, 6.6 Hz, 1H), 3.52 (dd, J=15.9, 5.4 Hz, 1H), 2.80-2.71 (m, 1H), 2.22 (d, J=5.2 Hz, 1H), 2.18-2.01 (m, 2H); MS (ES) m/z: 598 (M+H+).

Example 88

Cmpd 88

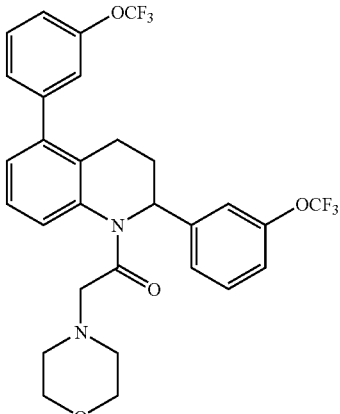

1-[2,5-Bis-(3-trifluoromethoxy-phenyl)-3,4-dihydro-2H-quinolin-1-yl]-2-morpholin-4-yl-ethanone Scheme WW

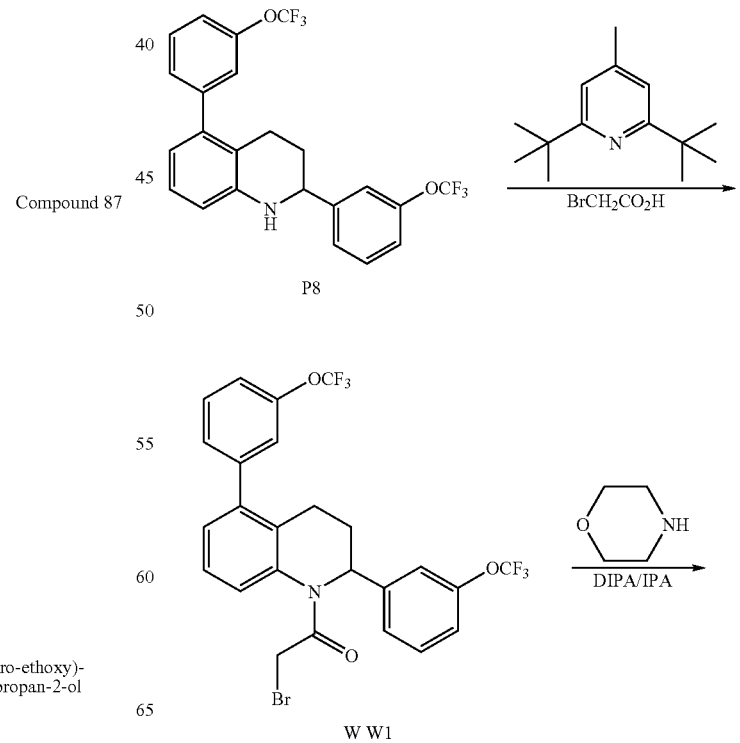

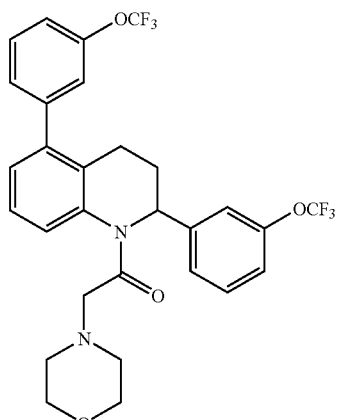
Cmpd 88

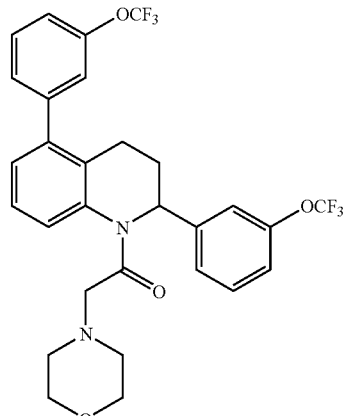
1-[2,5-Bis-(3-trifluoromethoxy-phenyl)-3,4-dihydro-2H-quinolin-1-yl]-2-morpholin-4-yl-ethanone A mixture of W W1 (68 mg; 0.119 mmol), morpholine (22 uL; 0.256 mmol) and DIPA (44 uL; 0.256 mmol) in IPA (1 mL) was heated to 35° C. Upon completion, the reaction was poured into EtOAc. The organic layer was then washed with saturated NaHCO$_3$ solution, water and brine. The organic layer was dried over MgSO$_4$, filtered and the solvent removed in vacuo. Purification by column chromatography (60% EtOAc/Hexanes) provided compound 88 (62 mg) in 90% yield. $^1$H NMR (300 MHz, CDCl$_3$) δ 7.48 (t, J=7.9 Hz, 2H), 7.39-7.24 (m, 7H), 7.09-7.01 (s, 2H), 5.71 (t, J=8.7 Hz, 1H), 3.69-3.61 (m, 4H), 3.37 (d, J=14.4 Hz, 1H), 3.19 (d, J=14.4 Hz, 1H), 2.77 (d, J=14.3 Hz, 1H), 2.66-2.39 (m, 6H), 1.62-1.50 (m, 1H); MS (ES) m/z: 581 (M+H$^+$).

Example 89

WW1

1-[2,5-Bis-(3-trifluoromethoxy-phenyl)-3,4,-dihydro-2H-quinolin-1-yl]-2-bromo-ethanone To P8 (82 mg; 0.18 mmol) in DCM (5mL) at 0° C. under an atmosphere of N$_2$ was added 2,6-di-tert-butyl-4-methylpyridine (60 mg; 0.29 mmol) followed by bromo acetylbromide (22 uL; 0.25 mmol). Upon completion, the reaction was poured into EtOAc. The organic layer was then washed with 1 N HCl (2×), water (2×), saturated NaHCO$_3$ solution and brine. The organic layer was dried over MgSO$_4$, filtered and the solvent removed in vacuo to provide 109 mg (97%) of W W1. $^1$H NMR (400 MHz, CDCl$_3$) δ 7.48 (bt, J=7.9 Hz, 1H), 7.42-7.38 (m, 2H), 7.33-7.24 (m, 4 H), 7.21 (s, 1H), 7.16 (d, J=7.6 Hz, 1H), 7.06 (d, J=8.2 Hz, 1H), 7.02 (s, 1H), 5.66 (t, J=9.0 Hz, 1H), 4.11 (t, J=10.9 Hz, 1H), 3.98 (d, J=11.3 Hz, 1H), 2.80 (dt, J=14.4, 3.3 Hz, 1H), 2.69-2.48 (m, 2H), 1.63-1.50 (m, 1H); MS (ES) m/z: 576 (M+2).

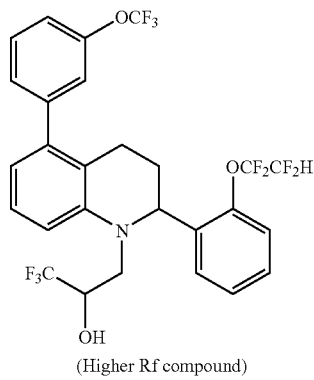
(Higher Rf compound)
1,1,1-Trifluoro-3-[2-[2-(1,1,2,2-tetrafluoro-ethoxy)-phenyl]-5-(3-trifluoromethoxy-phenyl)-3,4-dihydro-2H-quinolin-1-yl]-propan-2-ol Cmpd 89

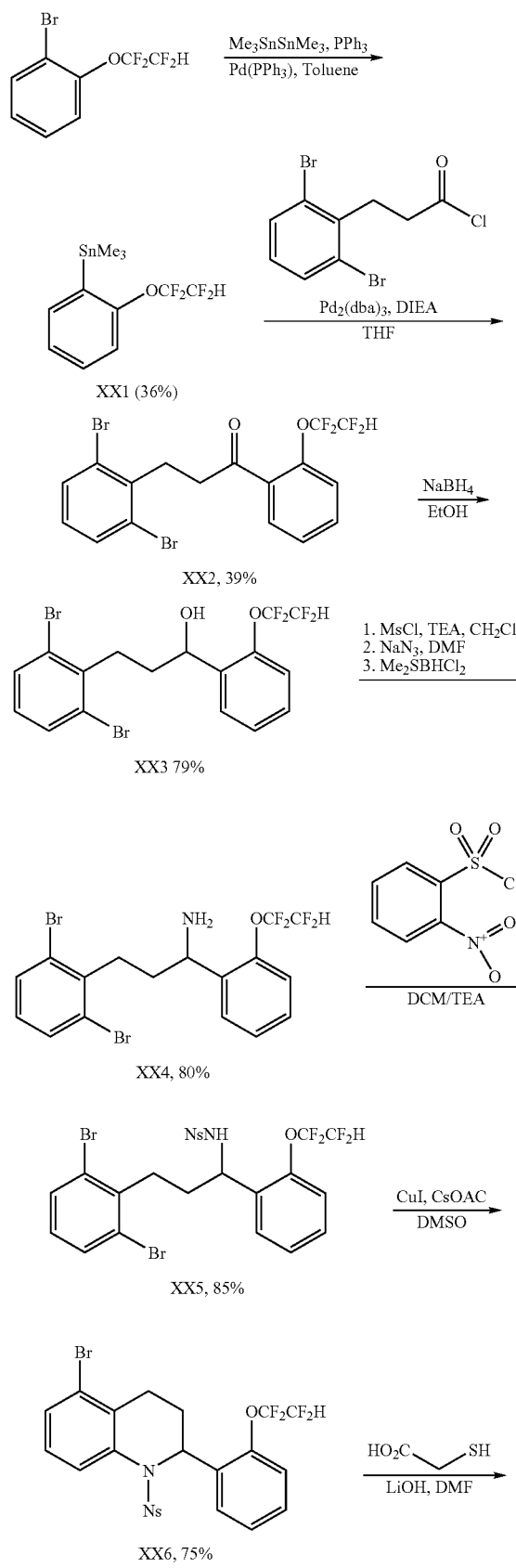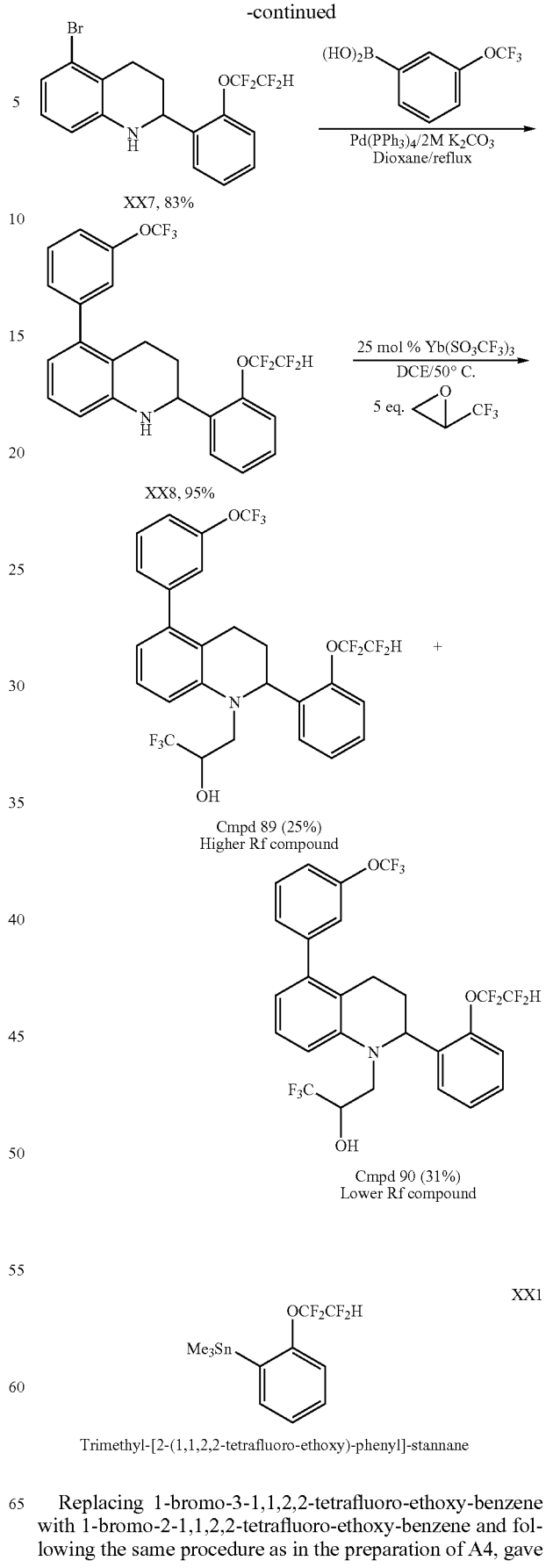
Replacing 1-bromo-3-1,1,2,2-tetrafluoro-ethoxy-benzene with 1-bromo-2-1,1,2,2-tetrafluoro-ethoxy-benzene and following the same procedure as in the preparation of A4, gave XX1 (36%) as an oil: $^1$H NMR (300 MHz, CDCl$_3$) δ 7.46 (dd, J=5.41, 1.60 Hz, 1H), 7.35-7.22 (m, 3H), 5.89 (tt, J=53.2, 2.9 Hz, 1H), 0.32 (s, 9H).

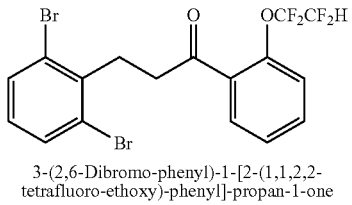

3-(2,6-Dibromo-phenyl)-1-[2-(1,1,2,2-tetrafluoro-ethoxy)-phenyl]-propan-1-one

Replacing A4 with XX1 and following the same procedure as in the preparation of A5 gave 206 mg (39%) of XX2 as a yellow solid: $^1$H NMR (300 MHz, CDCl$_3$) δ 7.74 (dd, J=6.10, 1.8 Hz, 1H), 7.53-7.49 (m, 3H), 7.45-7.32 (m, 2H), 6.94 (m, 1H), 5.97 (tt, J=53.0, 3.0 Hz, 1H), 3.42-3.36 (m, 2H), 3.22-3.15 (m, 2H); MS (ES) m/z: 485 (M+H$^+$).

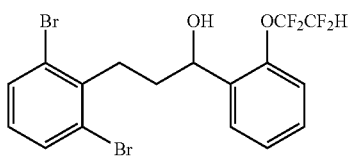

3-(2,6-Dibromo-phenyl)-1-[2-(1,1,2,2-tetrafluoro-ethoxy)-phenyl]-propan-1-ol

Replacing A5 with XX2 and following the same procedure as in the preparation of A6 gave 156 mg (79%) of XX3 as a clear oil. $^1$H NMR (300 MHz, CDCl$_3$) δ 7.67-7.64 (m, 1H), 7.48 (d, 8.0 Hz, 2H), 7.34-7.27 (m, 3H), 6.92-6.87 (m, 1H), 5.88 (tt, J=53.1, 2.19 Hz, 1H), 5.15 (t, J=6.27Hz, 1 H), 3.24-3.14 (m, 1H), 3.09-3.00 (m, 1H), 2.06-1.96 (m, 2H), 1.83-1.56 (brs, 1H); MS (ES) m/z: 509 (M+Na$^+$).

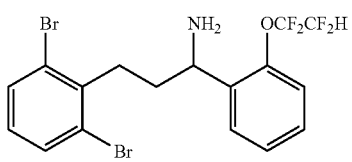

3-(2,6-Dibromo-phenyl)-1-[2-(1,1,2,2-tetrafluoro-ethoxy)-phenyl]-propylamine

Replacing A6 with XX3 and following the same procedure as in the preparation of A7 gave the crude azide intermediate.

Replacing A7 with the above azide intermediate and following the same procedure as in the preparation of A8 gave XX4 as an oil (80% for 3 steps): $^1$H NMR (400 MHz, CDCl$_3$) δ 7.59 (d, J=6.4 Hz, 1H), 7.46 (d, 7.99 Hz, 1H), 7.32-7.26 (m, 3H), 6.88 (t, J=8.0 Hz, 1H), 6.09-5.81 (tt, J=53.1, 2.4 Hz, 1H), 4.1 (t, J=6.75 Hz, 1H), 3.13-3.06 (m, 1H), 2.91-2.84 (m, 1H), 1.998-1.87 (m, 2H), 1.78-1.43 (brs, 1H); MS (ES) m/z: 486 (M+H$^+$).

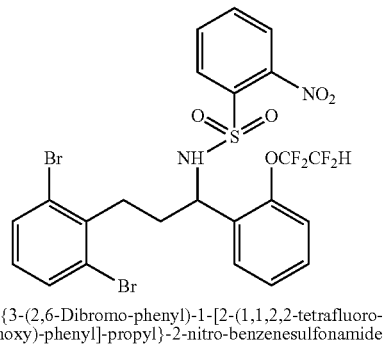

N-{3-(2,6-Dibromo-phenyl)-1-[2-(1,1,2,2-tetrafluoro-ethoxy)-phenyl]-propyl}-2-nitro-benzenesulfonamide Replacing A8 with XX4 and following the same procedure as in the preparation of A9 gave XX5 (85%): $^1$H NMR (400 MHz, CDCl$_3$) δ 7.80 (dd, J=6.5, 1.34 Hz, 1H), 7.73 (dd, J=6.8, 1.13 Hz, 1H), 7.58-7.54 (m, 1H), 7.48-7.44 (m, 3H), 7.32-7.30 (m, 1H), 7.14-7.01 (m, 1H), 6.89 (t. J=8.0 Hz, 1H), 6.02 (tt, J=53.1, 2.61 Hz, 1H), 5.00-4.94 (m, 1H), 3.22-3.15 (m, 1H), 2.91-2.84 (m, 1H), 2.05-1.97 (m, 2H); MS (ES) m/z: 693 (M+Na$^+$).

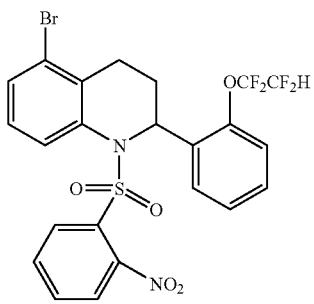

5-Bromo-1-(2-nitro-benzenesulfonyl)-2-[2-(1,1,2,2-tetrafluoro-ethoxy)-phenyl]-1,2,3,4-tetrahydro-quinoline Replacing A9 with XX6 and following the same preparation of A10 gave XX6 (75%) as an oil: $^1$H NMR (400 MHz, CDCl$_3$) δ 7.87 (d, J=8.1 Hz, 1H), 7.71-7.45 (m, 1H), 7.33-7.15 (m, 4H), 6.29-5.91 (tt, J=53.1, 3.1 Hz, 1H), 5.82 (t, J=7.71 Hz, 1H), 2.83-2.78 (m, 1H), 2.60-2.51 (m, 1 H), 2.13-2.03 (m, 1H), 1.75-1.62 (m, 1H); MS (ES) m/z: 590 (M+H$^+$).

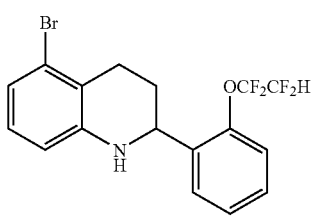

5-Bromo-2-[2-(1,1,2,2-tetrafluoro-ethoxy)-phenyl]-1,2,3,4-tetrahydro-quinoline

Replacing A10 with XX6 and following the same procedure as in the preparation of A11 gave XX7 (83%): $^1$H NMR (400 MHz, CDCl$_3$) δ 7.54-7.52 (m, 1H), 7.34-7.23 (m, 3H), 6.95-6.85 (m, 2H), 6.55-6.50 (m, 1H), 6.08-5.80 (tt, J=53.1, 2.38 Hz, 1H), 4.75-4.72 (dd, J=8.73, 3.2 Hz, 1H), 2.83-2.79 (m, 2H), 2.20-2.13 (m, 1H), 2.00-1.91 (m, 1H); MS (ES) m/z: 404 (M).

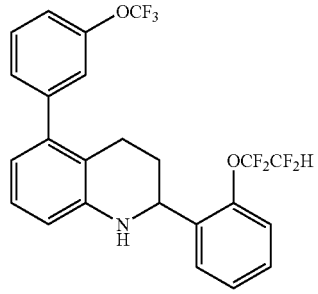

XX8

2-[3-(1,1,2,2-Tetrafluoro-ethoxy)-phenyl]-5-(3-trifluoromethoxy-phenyl)-1,2,3,4-tetrahydro-quinoline Replacing A11 with XX7 and following the same procedure as in the preparation of A12 gave 52 mg (95%) of XX8 as an oil: $^1$H NMR (300 MHz, CDCl$_3$) δ 7.63-7.60 (m, 1H), 7.40 (t, 7.8 Hz, 1H), 7.36-7.16 (m, 1H), 7.09 (t, 7.73, 1H), 6.50 (d, 7.6 Hz, 1H), 5.94 (tt, J=53.1, 2.45 Hz, 1H), 4.83 (dd, J=8.48, 3.49 Hz, 1H), 2.79-2.68 (m, 1H), 2.57-2.48 (tt, J=16.7, 5.1 Hz, H), 2.12-2.03 (m, 1H), 1.99-1.84 (m, 1H) 1.73-1.38 (brs, 1H); MS (ES) m/z: 486 (M+H$^+$).

Cmpd 89

1,1,1-Trifluoro-3-[2-[2-(1,1,2,2-tetrafluoro-ethoxy)-phenyl]-5-(3-trifluoromethoxy-phenyl)-3,4-dihydro-2H-quinolin-1-yl]-propan-2-ol Higher Rf compound Replacing A12 with XX8 and following the same procedure as in the preparation of compound 1 and 2 gave compounds 89 and 90. The spectra compound 89 are as follows: $^1$H NMR (300 MHz, CDCl$_3$) δ 7.37-7.14 (m, 9H), 6.73 (d, J=8.4 Hz, 1H), 6.67 (d, J=7.5 Hz, 1H), 5.92 (tt, J=53.0, 1.88 Hz, 1H), 5.16 (t, J=4.4 Hz, 1H), 4.38 (m, 1H), 3.84 (d, J=15.3 Hz, 1H), 3.25 (dd, J=15.6, 9.57 Hz, 1H), 2.50-2.31 (m, 3H), 2.14-1.93 (m, 2H); MS (ES) m/z: 598 (M+H$^+$).

Example 90

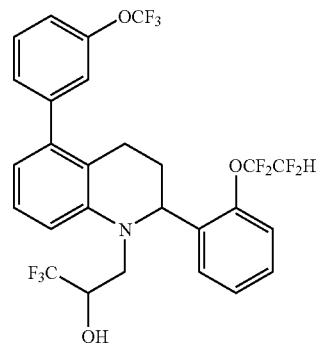

Cmpd 90

Lower Rf compound 1,1,1-Trifluoro-3-[2-[2-(1,1,2,2-tetrafluoro-ethoxy)-phenyl]-5-(3-trifluoromethoxy-phenyl)-3,4-dihydro-2H-quinolin-1-yl]-propan-2-ol Compound 90 was isolated as the other diasteriomer (31%) in the synthesis of compound 89. Spectra of compound 90 are as follows: $^1$H NMR (300 MHz, CDCl$_3$) δ 7.39-7.13 (m, 9H), 6.91 (d, J=8.36 Hz, 1H), 6.68 (d, J=7.52 Hz, 1H), 5.93 (tt, J=53.0, 2.8 Hz, 1H), 4.92 (m, 1H), 4.31 (m, 1H), 3.27 (dd, J=15.6, 6.69 Hz, 1H), 3.41 (dd, J=15.7, 5.30 Hz, 1H), 2.41-2.37 (m, 2H), 2.28 (d, J=4.58 Hz, 1H), 2.11-1.94 (m, 2H); MS (ES) m/z: 598 (M+H$^+$).

Compounds 1 through 90 of Formula (I), (Ia), (Ib), or (Ic) in Table 1 below were prepared according to the methods described by the Schemes and Examples described herein.

TABLE 1

Representative Compounds

| Cpd No. | Structure | Rf |
|---|---|---|
| 1 | 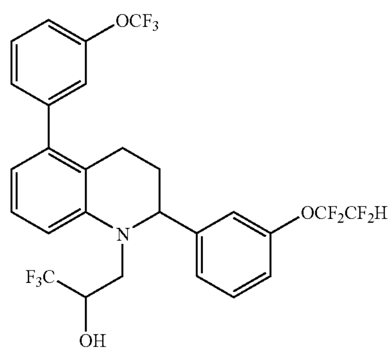 | Higher |

TABLE 1-continued

Representative Compounds

| Cpd No. | Structure | Rf |
|---|---|---|
| 2 | 3-OCF$_3$-phenyl at 5-position; 2-(3-OCF$_2$CF$_2$H-phenyl); N-CH$_2$CH(OH)CF$_3$ tetrahydroquinoline | Lower |
| 3 | 4-CF$_3$-phenyl at 5-position; 2-(3-OCF$_2$CF$_2$H-phenyl); N-CH$_2$CH(OH)CF$_3$ tetrahydroquinoline | Higher |
| 4 | 4-CF$_3$-phenyl at 5-position; 2-(3-OCF$_2$CF$_2$H-phenyl); N-CH$_2$CH(OH)CF$_3$ tetrahydroquinoline | Lower |
| 5 | 4-Cl-3-CH$_3$-phenyl at 5-position; 2-(3-OCF$_2$CF$_2$H-phenyl); N-CH$_2$CH(OH)CF$_3$ tetrahydroquinoline | Higher |
| 6 | 4-Cl-3-CH$_3$-phenyl at 5-position; 2-(3-OCF$_2$CF$_2$H-phenyl); N-CH$_2$CH(OH)CF$_3$ tetrahydroquinoline | Lower |
| 7 | 4-OCF$_3$-phenyl at 5-position; 2-(3-OCF$_2$CF$_2$H-phenyl); N-CH$_2$CH(OH)CF$_3$ tetrahydroquinoline | Higher |
| 8 | 4-OCF$_3$-phenyl at 5-position; 2-(3-OCF$_2$CF$_2$H-phenyl); N-CH$_2$CH(OH)CF$_3$ tetrahydroquinoline | Lower |
| 9 | 3-CN-phenyl at 5-position; 2-(3-OCF$_2$CF$_2$H-phenyl); N-CH$_2$CH(OH)CF$_3$ tetrahydroquinoline | Higher |

TABLE 1-continued

Representative Compounds

| Cpd No. | Structure | Rf |
|---|---|---|
| 10 | 3-CN-phenyl at C5; 2-(3-OCF₂CF₂H-phenyl); N-CH₂CH(OH)CF₃ tetrahydroquinoline | Lower |
| 11 | 3-F-phenyl at C5; 2-(3-OCF₂CF₂H-phenyl); N-CH₂CH(OH)CF₃ tetrahydroquinoline | Higher |
| 12 | 3-F-phenyl at C5; 2-(3-OCF₂CF₂H-phenyl); N-CH₂CH(OH)CF₃ tetrahydroquinoline | Lower |
| 13 | 3-CF₃-phenyl at C5; 2-(3-OCF₂CF₂H-phenyl); N-CH₂CH(OH)CF₃ tetrahydroquinoline | Higher |
| 14 | 3-CF₃-phenyl at C5; 2-(3-OCF₂CF₂H-phenyl); N-CH₂CH(OH)CF₃ tetrahydroquinoline | Lower |
| 15 | 3-Cl-phenyl at C5; 2-(3-OCF₂CF₂H-phenyl); N-CH₂CH(OH)CF₃ tetrahydroquinoline | Higher |
| 16 | 3-Cl-phenyl at C5; 2-(3-OCF₂CF₂H-phenyl); N-CH₂CH(OH)CF₃ tetrahydroquinoline | Lower |
| 17 | 3-OCF₃-phenyl at C5; 2-(3-CF₃-phenyl); N-CH₂CH(OH)CF₃ tetrahydroquinoline | Higher |

TABLE 1-continued

Representative Compounds

| Cpd No. | Structure | Rf |
|---|---|---|
| 18 | 5-(3-(trifluoromethoxy)phenyl)-2-(3-(trifluoromethyl)phenyl)-1-(3,3,3-trifluoro-2-hydroxypropyl)-1,2,3,4-tetrahydroquinoline | Lower |
| 19 | 5-(3-(trifluoromethoxy)phenyl)-2-phenyl-1-(3,3,3-trifluoro-2-hydroxypropyl)-1,2,3,4-tetrahydroquinoline | Higher |
| 20 | 5-(3-(trifluoromethoxy)phenyl)-2-phenyl-1-(3,3,3-trifluoro-2-hydroxypropyl)-1,2,3,4-tetrahydroquinoline | Lower |
| 21 | 5-(3-(trifluoromethoxy)phenyl)-2-(4-(OCF₂CF₂H)phenyl)-1-(3,3,3-trifluoro-2-hydroxypropyl)-1,2,3,4-tetrahydroquinoline | Higher |
| 22 | 5-(3-(trifluoromethoxy)phenyl)-2-(4-(OCF₂CF₂H)phenyl)-1-(3,3,3-trifluoro-2-hydroxypropyl)-1,2,3,4-tetrahydroquinoline | Lower |
| 23 | 5-(3-(trifluoromethoxy)phenyl)-2-(3-fluorophenyl)-1-(3,3,3-trifluoro-2-hydroxypropyl)-1,2,3,4-tetrahydroquinoline | Higher |
| 24 | 5-(3-(trifluoromethoxy)phenyl)-2-(3-fluorophenyl)-1-(3,3,3-trifluoro-2-hydroxypropyl)-1,2,3,4-tetrahydroquinoline | Lower |
| 25 | 5-(3-(trifluoromethoxy)phenyl)-2-(3-methoxyphenyl)-1-(3,3,3-trifluoro-2-hydroxypropyl)-1,2,3,4-tetrahydroquinoline | Higher |

TABLE 1-continued
Representative Compounds
| Cpd No. | Structure | Rf |
|---|---|---|
| 26 | 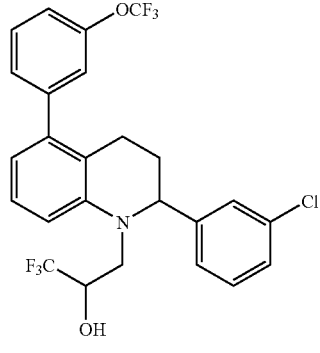 | Lower |
| 27 | 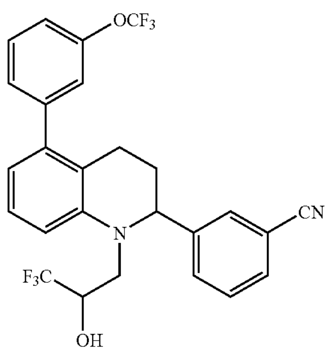 | Higher |
| 28 | 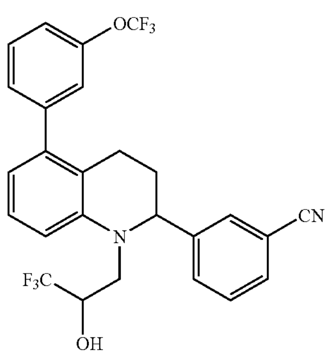 | Lower |
| 29 | 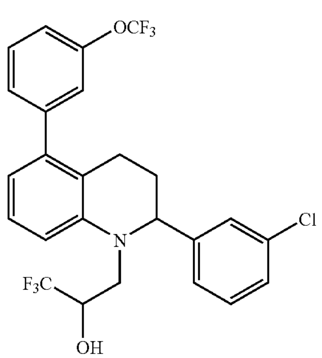 | Higher |
| 30 | 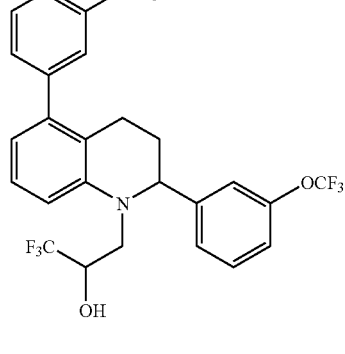 | Lower |
| 31 | 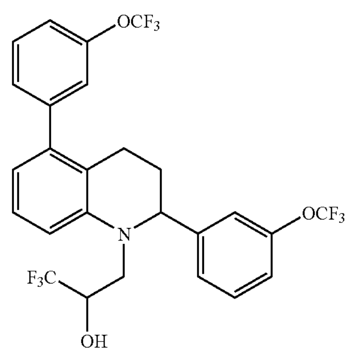 | Higher |
| 32 | 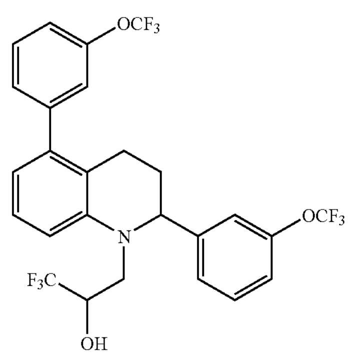 | Lower |
| 33 | 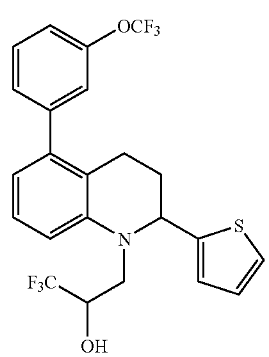 | Higher |

TABLE 1-continued

Representative Compounds

| Cpd No. | Structure | Rf |
|---|---|---|
| 34 | 5-(3-(trifluoromethoxy)phenyl)-2-(thiophen-2-yl)-1-(3,3,3-trifluoro-2-hydroxypropyl)-1,2,3,4-tetrahydroquinoline | Lower |
| 35 | 2-ethyl-5-(3-(trifluoromethoxy)phenyl)-1-(3,3,3-trifluoro-2-hydroxypropyl)-1,2,3,4-tetrahydroquinoline | Higher |
| 36 | 2-ethyl-5-(3-(trifluoromethoxy)phenyl)-1-(3,3,3-trifluoro-2-hydroxypropyl)-1,2,3,4-tetrahydroquinoline | Lower |
| 37 | 2-cyclohexyl-5-(3-(trifluoromethoxy)phenyl)-1-(3,3,3-trifluoro-2-hydroxypropyl)-1,2,3,4-tetrahydroquinoline | Higher |
| 38 | 2-cyclohexyl-5-(3-(trifluoromethoxy)phenyl)-1-(3,3,3-trifluoro-2-hydroxypropyl)-1,2,3,4-tetrahydroquinoline | Lower |
| 39 | 2-ethyl-1-(3-(trifluoromethoxy)benzyl)-5-(3-(trifluoromethoxy)phenyl)-1,2,3,4-tetrahydroquinoline | Not Applicable |
| 40 | 5-(3-chlorophenyl)-1-((S)-2-hydroxypropyl)-2-(3-(trifluoromethoxy)phenyl)-1,2,3,4-tetrahydroquinoline | Not Applicable |
| 41 | 5-(3-chlorophenyl)-1-((S)-2-hydroxypropyl)-2-(3-(trifluoromethoxy)phenyl)-1,2,3,4-tetrahydroquinoline | Not Applicable |

TABLE 1-continued

Representative Compounds

| Cpd No. | Structure | Rf |
|---|---|---|
| 42 | 5-(3-hydroxyphenyl)-2-(3-(OCF$_2$CF$_2$H)phenyl)-1-(3,3,3-trifluoro-2-hydroxypropyl)-1,2,3,4-tetrahydroquinoline | Higher |
| 43 | 5-(3-hydroxyphenyl)-2-(3-(OCF$_2$CF$_2$H)phenyl)-1-(3,3,3-trifluoro-2-hydroxypropyl)-1,2,3,4-tetrahydroquinoline | Lower |
| 45 | 5-(3-OCF$_3$-phenyl)-2-(3-OCF$_3$-phenyl)-1-(3-methyl-2-hydroxybutyl)-1,2,3,4-tetrahydroquinoline | Higher |
| 46 | 5-(3-OCF$_3$-phenyl)-2-(3-OCF$_3$-phenyl)-1-(3-methyl-2-hydroxybutyl)-1,2,3,4-tetrahydroquinoline | Lower |
| 47 | 5-(3-OCF$_3$-phenyl)-2-(3-OCF$_3$-phenyl)-1-(3-chloro-2-hydroxypropyl)-1,2,3,4-tetrahydroquinoline | Higher |
| 48 | 5-(3-OCF$_3$-phenyl)-2-(3-OCF$_3$-phenyl)-1-(3-chloro-2-hydroxypropyl)-1,2,3,4-tetrahydroquinoline | Lower |
| 49 | 5-(3-OCF$_3$-phenyl)-2-(3-OCF$_3$-phenyl)-1-(3-fluoro-2-hydroxypropyl)-1,2,3,4-tetrahydroquinoline | Higher |
| 50 | 5-(3-OCF$_3$-phenyl)-2-(3-OCF$_3$-phenyl)-1-(3-fluoro-2-hydroxypropyl)-1,2,3,4-tetrahydroquinoline | Lower |

TABLE 1-continued

Representative Compounds

| Cpd No. | Structure | Rf |
|---|---|---|
| 51 | [3-OCF3-phenyl at C5; 2-(3-OCF3-phenyl); N-CH2-CH(OH)-CH2-OCH3 tetrahydroquinoline] | Not Applicable |
| 52 | [3-OCF3-phenyl at C5; 2-(3-OCF3-phenyl); N-CH2-CH(OH)-CH2-OCH3 tetrahydroquinoline] | Not Applicable |
| 53 | [3-OCF3-phenyl at C5; 2-(3-OCF3-phenyl); N-CH2-CH(OH)-CH3 tetrahydroquinoline] | Not Applicable |
| 54 | [3-OCF3-phenyl at C5; 2-(3-OCF3-phenyl); N-CH2-CH(OH)-CH3 tetrahydroquinoline] | Not Applicable |
| 55 | [3-F-phenyl at C5; 2-(3-OCF3-phenyl); N-CH2-CH(OH)-CH3 tetrahydroquinoline] | Not Applicable |
| 56 | [3-F-phenyl at C5; 2-(3-OCF3-phenyl); N-CH2-CH(OH)-CH3 tetrahydroquinoline] | Not Applicable |
| 57 | [3-F-phenyl at C5; 2-(3-OCF3-phenyl); N-CH2-CH(OH)-CF3 tetrahydroquinoline] | Higher |
| 58 | [3-F-phenyl at C5; 2-(3-OCF3-phenyl); N-CH2-CH(OH)-CF3 tetrahydroquinoline] | Lower |

TABLE 1-continued

Representative Compounds

| Cpd No. | Structure | Rf |
|---|---|---|
| 59 | [structure] | Not Applicable |
| 60 | [structure] | Not Applicable |
| 61 | [structure] | Not Applicable |
| 62 | [structure] | Not Applicable |
| 63 | [structure] | Not Applicable |
| 64 | [structure] | Higher |
| 65 | [structure] | Lower |
| 66 | [structure] | Higher |

TABLE 1-continued

Representative Compounds

| Cpd No. | Structure | Rf |
|---|---|---|
| 67 | 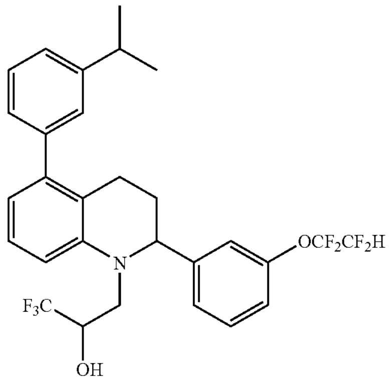 | Lower |
| 68 | 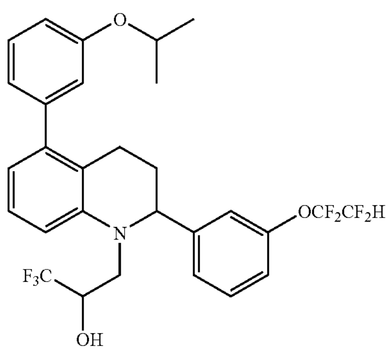 | Higher |
| 69 | 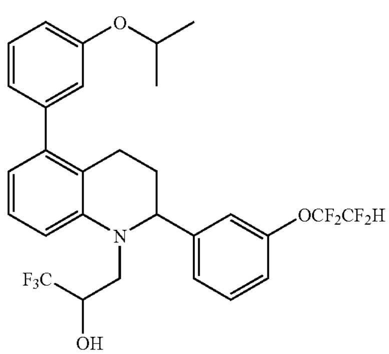 | Lower |
| 70 | 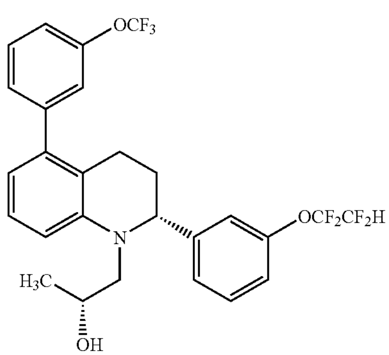 | Not Applicable |
| 72 | | Higher |
| 73 | | Lower |
| 74 | | Higher |
| 75 | | Lower |

TABLE 1-continued

Representative Compounds

| Cpd No. | Structure | Rf |
|---|---|---|
| 76 | 3-pyridyl at 5-position of 1,2,3,4-tetrahydroquinoline; N-substituted with (S)-CH₂CH(OH)CF₃; 2-(3-OCF₂CF₂H-phenyl) | Not Applicable |
| 77 | 3-F-phenyl at 5-position; N-substituted with (S)-CH₂CH(OH)CH₃; 2-(3-OCF₂CF₂H-phenyl) | Not Applicable |
| 78 | 3-OCF₃-phenyl at 5-position; N-substituted with (S)-CH₂CH(OH)CF₃; 2-(3-OCF₂CF₂H-phenyl) | Not Applicable |
| 79 | 3-OCF₃-phenyl at 5-position; N-substituted with (R)-CH₂CH(OH)CF₃; 2-(3-OCF₂CF₂H-phenyl) | Not Applicable |
| 80 | 3-OCF₃-phenyl at 5-position; N-substituted with CH₂CH(OH)CF₃; 2-(3-OCF₂CF₂H-phenyl) | Not Applicable |
| 81 | 3-OCF₃-phenyl at 5-position; N-substituted with (R)-CH₂CH(OH)CF₃; 2-(3-OCF₂CF₂H-phenyl) | Not Applicable |
| 82 | 3-F-phenyl at 5-position; N-substituted with (R)-CH₂CH(OH)CF₃; 2-(3-OCF₂CF₂H-phenyl) | Not Applicable |
| 83 | 3-OCH₃-phenyl at 5-position; N-substituted with (R)-CH₂CH(OH)CF₃; 2-(3-OCF₂CF₂H-phenyl) | Not Applicable |

TABLE 1-continued

Representative Compounds

| Cpd No. | Structure | Rf |
|---|---|---|
| 84 | [structure] | Higher |
| 85 | [structure] | Lower |
| 86 | [structure] | Higher |
| 87 | [structure] | Lower |
| 88 | [structure] | Not Applicable |
| 89 | [structure] | Higher |
| 90 | [structure] | Lower |

Biological Examples

CETP In Vitro Assay

The CETP inhibitory activity of the compounds was determined using a commercially available kit from Amersham Biosciences (Catalog #TRKQ7005).

For the measurement of inhibitory activity in human plasma, a modified protocol (Connolly, D. T. et al., Biochemistry, 39, 13870-13879, 2000) was used. Briefly, 80 µl of human plasma (obtained from normal volunteers), approximately 25 µg/ml (20 µl) of [$^3$H]CE-HDL (Amersham Biosciences from kit TRKQ7005) and 1 µl of compound dissolved in DMSO was incubated for at least 4 hrs at 37° C. and non-specific transfer was determined by incubating a corresponding plate at 4° C. (blank). After the incubation period, 10 μl of a solution of 1% Dextralip 50/0.5M MgCl$_2$, pH 7.4 was added, vortexed and incubated at room temperature for 10 min. The plate was then centrifuged for 30 min at 10° C. at 300 rpm in a Sorvall RT6000B centrifuge. Fifty microliters of the supernatant was transferred to a Picoplate (Packard) containing 100 μl of Microscint 40 (Perkin Elmer) and mixed for 30 min using a plate mixer. The radioactivity was counted using a TopCount (Perkin Elmer) and the % control was determined in the samples using the following formula: % transfer relative to vehicle controls (% control)=[cpm blank−cpm test]/cpm blank/cpm control]×100. IC$_{50}$s were calculated from plots of the % control versus compound concentration.

A variety of example compounds have been made and tested, with a range of in vitro results. Below, in Table 2, are representative compounds and the corresponding data; in some cases, where multiple IC$_{50}$'s are shown, multiple measurements were taken. Naturally, different compounds in Formula (I), (Ia), (Ib), and (Ic) may not have activities identical to any one compound below.

TABLE 2

In vitro data of representative compounds of the invention

| Cpd No. | % Inhibition @ 1 μM | IC$_{50}$ (nM) |
|---|---|---|
| 1 | 100 | 7, 25, 30 |
| 2 | 86 | 450, 150 |
| 3 | 85 | 500 |
| 4 | 1 | Not determined |
| 5 | 96 | 260, 381 |
| 6 | 42 | Not determined |
| 7 | 61, 61 | Not determined |
| 8 | 29, 36 | Not determined |
| 9 | 82, 85 | 177, 293 |
| 10 | 14, 29 | Not determined |
| 11 | 101, 99 79 | 70, 95, 187 |
| 12 | 41, 64 | Not determined |
| 13 | 98, 87 | 96 |
| 14 | 37 | Not determined |
| 15 | 68, 66 | 68, 59 |
| 16 | 55 | Not determined |
| 17 | 54, 43, 55 | 84, 202 |
| 18 | 40, 35 | 2900 |
| 19 | 21 | Not determined |
| 20 | 6 | Not determined |
| 21 | 5 | Not determined |
| 22 | 14 | Not determined |
| 23 | 33 | Not determined |
| 24 | 4 | Not determined |
| 25 | 59, 74 | 582 |
| 26 | 4 | Not determined |
| 27 | 48, 38 | 410 |
| 28 | 25 | Not determined |
| 29 | 39 | 290 |
| 30 | 13 | Not determined |
| 31 | 77, 72, 67, 66, 62 | 150, 100 |
| 32 | 34 | Not determined |
| 33 | 28 | Not determined |
| 34 | 12 | Not determined |
| 35 | 43, 45 | Not determined |
| 36 | 11, 13 | Not determined |
| 37 | 11 | Not determined |
| 38 | 2 | Not determined |
| 39 | 17 | Not determined |
| 40 | 37, 32 | 150 |
| 41 | 3 | Not determined |
| 42 | 97, 106 | 231 |
| 43 | 23 | Not determined |
| 45 | 74, 84 | 326 |
| 46 | 22 | Not determined |
| 47 | 68, 44 | 744 |
| 48 | 0 | Not determined |

TABLE 2-continued

In vitro data of representative compounds of the invention

| Cpd No. | % Inhibition @ 1 μM | IC$_{50}$ (nM) |
|---|---|---|
| 49 | 63, 77 | 331 |
| 50 | 13 | Not determined |
| 51 | 13 | Not determined |
| 52 | 0 | Not determined |
| 53 | 57, 57, 77, 84 | 90, 199, 85 |
| 54 | 13 | Not determined |
| 55 | 39, 34 | 110 |
| 56 | 0 | Not determined |
| 57 | 92, 97, 91 | 59, 253 |
| 58 | 40 | Not determined |
| 59 | 30 | Not determined |
| 60 | 5 | Not determined |
| 61 | 0 | Not determined |
| 62 | 30 | Not determined |
| 63 | 39 | Not determined |
| 64 | 61, 70, 78 | 300 |
| 65 | 16 | Not determined |
| 66 | 60, 65 | 181, 374 |
| 67 | 29 | Not determined |
| 68 | 49, 61 | 345 |
| 69 | 18 | Not determined |
| 70 | 61, 69, 59 | 63, 39 |
| 72 | 75, 62 | 160, 93 |
| 73 | 50, 26 | Not determined |
| 74 | 60, 66 | 380, 255 |
| 75 | 39 | Not determined |
| 76 | 57, 38 | >3000 |
| 77 | 38, 48 | Not determined |
| 78 | 85, 79 | 34, 44 |
| 79 | 62 | >3000 |
| 80 | 20 | Not determined |
| 81 | 46, 36 | 30 |
| 82 | 84, 76 | 122, 93 |
| 83 | 100, 98 | 140, 160 |
| 84 | 62 | 600 |
| 85 | 86 | 400 |
| 86 | 67 | Not determined |
| 87 | 86 | 400 |
| 88 | 0 | Not determined |
| 89 | 9 | Not determined |
| 90 | 0 | Not determined |

CETP In Vivo Assay

To determine the in vivo efficacy of a test compound, hamsters were first fed a moderately high cholesterol diet (Research Diets, D5012801) for two weeks before commencing treatment. The animals were orally gavaged with the vehicle (10% solutol, 5% ethanol, 85% D5W) and test compound for 5 days with the last dose being administered 2 hrs before sacrifice. Plasma was obtained and lipid parameters were measured.

The results for compound 78 is shown in Table 3.

TABLE 3

Effect of Compound 78 on lipid parameters in cholesterol-fed hamsters

| Dose (mg/kg) | HDL-C (mg/dL) | LDL-C (mg/dL) | Total Cholesterol (mg/dL) | HDL-C/ LDL-C | Triglycerides (mg/dL) |
|---|---|---|---|---|---|
| Vehicle | 87.0 ± 4.4 | 30.9 ± 1.6 | 149.6 ± 8.9 | 2.9 ± 0.1 | 315.7 ± 23.9 |
| 3 mg/kg | 96.2 ± 4.9 | 31.6 ± 1.9 | 149.3 ± 7.7 | 3.1 ± 0.2 | 217.7 ± 18.1 |
| 10 mg/kg | 117.9 ± 2.9 | 28.1 ± 1.8 | 178.5 ± 5.4 | 4.3 ± 0.3* | 325.6 ± 24.3 |
| 30 mg/kg | 121.4 ± 2.5** | 27.9 ± 2.5 | 188.4 ± 9.2** | 4.6 ± 0.4** | 350.8 ± 10.9 |

Data are expressed as the mean ± SEM
n = 8 per group
*p < 0.05,
**p < 0.001, compared to vehicle control While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I)

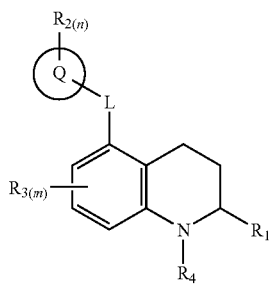

Formula (I)

wherein:
L is a covalent bond or O;
Q is $C_{6-10}$ aryl or 5- or 6-membered heteroaryl;
n is 0 to 3;
m is 0 to 3;
$R_1$ is $C_{1-10}$ alkyl, $C_{2-10}$ alkenyl, $C_{2-10}$ alkynyl, $C_{3-10}$ cycloalkyl, 5- or 6-membered heteroaryl, wherein each of $C_{1-10}$ alkyl, $C_{2-10}$ alkenyl, $C_{2-10}$ alkynyl, $C_{3-10}$ cycloalkyl, and 5- or 6-membered heteroaryl may be optionally substituted;
or $R_1$ is phenyl optionally substituted with 1 or 2 members selected from $R_a$ and $R_b$, wherein $R_a$ and $R_b$ are independently selected from the group consisting of optionally substituted $C_{1-4}$ alkyl, halogenated $C_{1-4}$alkyl, optionally substituted $C_{2-4}$ alkenyl, optionally substituted $C_{2-4}$ alkynyl, optionally substituted $C_{1-4}$ alkoxy, halogenated $C_{1-4}$alkoxy, optionally substituted $C_{1-4}$ alkylthio, halo, cyano, and hydroxy, or
$R_a$ and $R_b$ together with the carbon atoms of the phenyl ring to which they are attached form an optionally substituted 5- or 6-membered heterocyclyl fused to the phenyl ring;
each $R_2$ is independently selected from halo, hydroxy, cyano, $C_{1-4}$ alkoxy, halogenated $C_{1-4}$alkoxy, $C_{1-4}$ alkyl, halogenated $C_{1-4}$alkyl, $C_{2-4}$ alkenyl, $C_{2-4}$ alkynyl and —C(O)H;

each $R_3$ is independently selected from $C_{1-4}$ alkyl, halogenated $C_{1-4}$alkyl, $C_{2-4}$ alkenyl, $C_{2-4}$alkynyl, $C_{1-4}$ alkoxy, halo, cyano, and hydroxy;
$R_4$ is $C_{1-10}$ alkyl optionally substituted with 1-3 members independently selected from halo, oxo, hydroxy, halogenated $C_{1-4}$alkyl, $C_{1-4}$ alkoxy, $C_{3-8}$ cycloalkyl, CN, tert-butyldimethylsilyloxy, heterocyclyl and —$NR_cR_d$, wherein $R_c$ and $R_d$ are independently selected from H, optionally substituted $C_{1-3}$ alkyl, —$C(O)C_{1-3}$alkyl, —$C(O)O$—$C_{1-3}$ alkyl, and —$SO_2C_{1-3}$alkyl; or
$R_4$ is $C_{1-6}$alkyl substituted with heteroaryl or phenyl substituted with 1 to 3 members independently selected from halo, hydroxy, $C_{1-3}$alkyl, halogenated $C_{1-3}$alkyl, $C_{1-4}$alkoxy, and halogenated $C_{1-4}$alkoxy;
or enantiomers, diastereomers, tautomers, or pharmaceutically acceptable salts thereof.

2. A compound according to claim 1 wherein n is 1 or 2.

3. A compound according to claim 1 wherein L is a covalent bond.

4. A compound according to claim 1 wherein Q is phenyl.

5. A compound according to claim 1 wherein Q is thienyl or pyridinyl.

6. A compound according to claim 1 wherein $R_1$ is phenyl substituted with $C_{1-4}$ alkyl, halogenated $C_{1-4}$alkyl, $C_{1-4}$ alkoxy, halogenated $C_{1-4}$alkoxy, halo, cyano, or hydroxy.

7. A compound according to claim 1 wherein $R_1$ is phenyl substituted with halogenated $C_{1-4}$alkyl or halogenated $C_{1-4}$alkoxy.

8. A compound according to claim 7 wherein $R_1$ is phenyl substituted with —$OCF_2CF_2H$, —$CF_3$, or —$OCF_3$.

9. A compound according to claim 1 wherein n is 1 and $R_2$ is halo, halogenated $C_{1-4}$alkyl, or halogenated $C_{1-4}$alkoxy.

10. A compound according to claim 9 wherein $R_2$ is —$OCF_2CF_2H$ or —$OCF_3$.

11. A compound according to claim 1 wherein $R_4$ is $C_{1-5}$ alkyl optionally substituted with 1 or 2 members each independently selected from halo, oxo, hydroxy, halogenated $C_{1-4}$alkyl, and heterocyclyl.

12. A compound according to claim 11, wherein $R_4$ is $C_{1-3}$ alkyl substituted with 2 members each independently selected from halo, hydroxy, and halogenated $C_{1-3}$alkyl.

13. A compound according to claim 1 wherein
Q is phenyl;
m is 0;
n is 1 or 2;
L is a covalent bond;
$R_1$ is phenyl optionally substituted with $C_{1-4}$ alkyl, halogenated $C_{1-4}$alkyl, $C_{1-4}$alkoxy, halogenated $C_{1-4}$ alkoxy, halo, or cyano;

Each $R_2$ is independently selected from halo, hydroxy, cyano, $C_{1-4}$ alkoxy, halogenated $C_{1-4}$ alkoxy, $C_{1-4}$alkyl, halogenated $C_{1-4}$alkyl, and —C(O)H; and $R_4$ is $C_{1-6}$ alkyl substituted with 1-3 members independently selected from halo, hydroxy, halogenated $C_{1-4}$alkyl, $C_{1-4}$alkoxy, halogenated $C_{1-4}$alkoxy, and heterocyclyl.

14. A compound according to claim 1 wherein
Q is 5- or 6-membered heteroaryl selected from thienyl and pyridinyl;
n is 0;
m is 0; and
L is a covalent bond.

15. A compound according to claim 1 wherein (n) is 1; (m) is 0; and the Q-$R_2$ group is

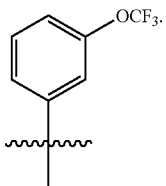

16. A compound according to claim 1 wherein (m) is 0; and $R_1$ is

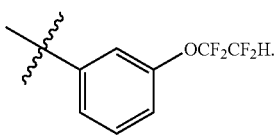

17. A compound according to claim 1 wherein (m) is 0, and $R_4$ is

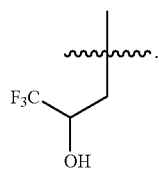

18. A compound of Formula (Ia)

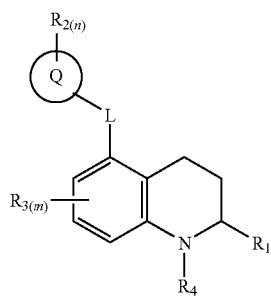

Formula (Ia)

wherein:
L is a covalent bond or O;
Q is phenyl, naphthalenyl, or a heteroaryl selected from the group consisting of thienyl, oxazolyl, thiazolyl, isoxazolyl, pyridinyl, and pyridazinyl;
n is 0 to 3;
m is 0 to 3;
$R_1$ is $C_{1-10}$ alkyl, $C_{2-10}$alkenyl, $C_{2-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with 1 to 3 substituents independently selected from halo, cyano, hydroxy, oxo, $C_{1-3}$alkyl, and $C_{1-3}$alkoxy;
or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated $C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated $C_{1-4}$alkylthio, halo, cyano, and hydroxy, or
$R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyan, and hydroxy;
each $R_2$ is independently selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;
each $R_3$ is independently selected from the group consisting of $C_{1-4}$ alkyl, $C_{1-4}$ alkoxy, halo, cyano, and hydroxy;
$R_4$ is $C_{1-10}$ alkyl, halogenated $C_{1-10}$alkyl, or phenyl $C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated $C_{1-4}$ alkoxy, $C_{3-8}$ cycloalkyl, cyano, heterocyclyl, and —$NR_cR_d$, wherein
$R_c$ and $R_d$ are independently selected from H, optionally substituted $C_{1-3}$ alkyl, —C(O)$C_{1-3}$alkyl, —C(O)O—$C_{1-3}$ alkyl, and $SO_2C_{1-3}$alkyl;
and enantiomers, diastereomers, tautomers, or pharmaceutically acceptable salts thereof.

19. A compound according to claim 18 wherein m is 0.
20. A compound according to claim 18 wherein n is 1 or 2.
21. A compound according to claim 18 wherein L is a covalent bond.
22. A compound according to claim 18 wherein Q is phenyl.
23. A compound according to claim 18 wherein Q is thienyl or pyridinyl.
24. A compound according to claim 18 wherein m is 0 and n is 1.
25. A compound according to claim 18 wherein L is a bond.
26. A compound according to claim 18, wherein $R_1$ is

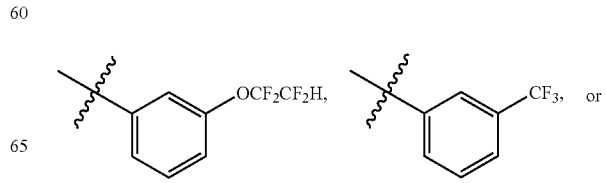

27. A compound according to claim 18, wherein $R_1$ is

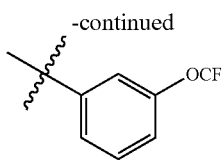

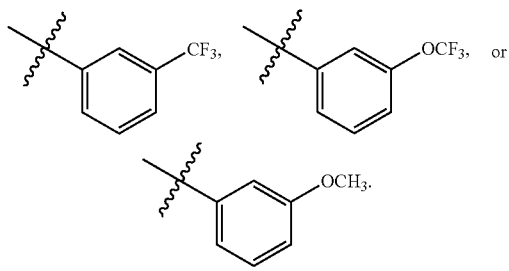

28. A compound according to claim 18 wherein $R_1$ is

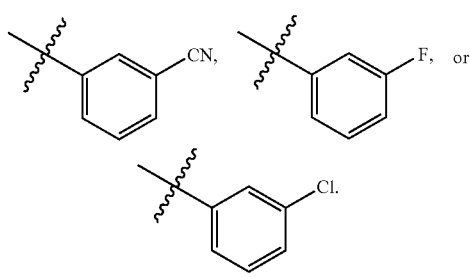

29. A compound according to claim 18 wherein n is 1 and Q is

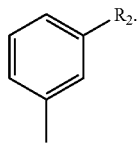

30. A compound according to claim 18 wherein $R_2$ is —O—$CF_3$.

31. A compound according to claim 18, wherein $R_2$ is F.

32. A compound according to claim 18, wherein $R_2$ is —$CH_3$, —$CH_2CH_3$, or —$CH(CH_3)_2$.

33. A compound according to claim 18, wherein $R_4$ is $C_{1-5}$alkyl substituted with 1 or 2 members independently selected from oxo, hydroxy, and —O—$CH_3$.

34. A compound according to claim 18, wherein $R_4$ is halogenated $C_{1-4}$ alkyl substituted with oxo, hydroxy, or —O—$CH_3$.

35. A compound according to claim 18, wherein $R_4$ is —$CH_2CH(OH)CF_3$.

36. A compound according to claim 18, wherein $R_4$ is —$CH_2CH(OH)CH(CH_3)_2$.

37. A compound according to claim 18, wherein m is 0, n is 1, L is a bond, and $R_1$ is

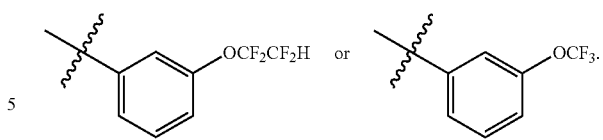

38. A compound according to claim 18, wherein m is 0, n is 1, L is a bond, $R_1$ is

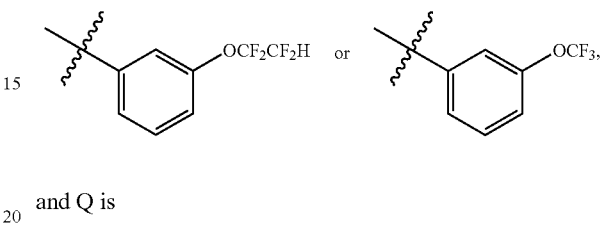

and Q is

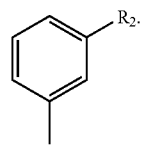

39. A compound of Formula (Ib)

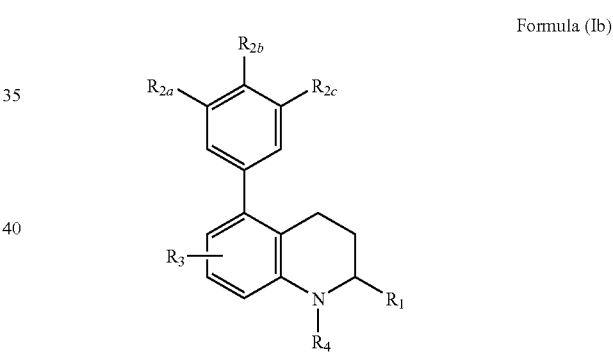

Formula (Ib)

wherein:

$R_1$ is $C_{1-10}$ alkyl, $C_{2-10}$alkenyl, $C_{2-10}$alkynyl, $C_{3-10}$cycloalkyl, or a 5- or 6-membered heteroaryl; wherein said $C_{1-10}$ alkyl, $C_{2-10}$alkenyl, $C_{2-10}$alkynyl, $C_{3-10}$cycloalkyl, or 5- or 6-membered heteroaryl is optionally substituted with halo, cyano, or hydroxy, oxo, $C_{1-3}$alkyl, or $C_{1-3}$alkoxy;

or $R_1$ is phenyl optionally substituted with 1 to 2 members selected from $R_a$ and $R_b$, wherein $R_a$ and $R_b$ are independently selected from the group consisting of $C_{1-4}$ alkyl, halogenated $C_{1-4}$alkyl, phenyl$C_{1-4}$alkyl, $C_{1-4}$ alkoxy, halogenated $C_{1-4}$ alkoxy, phenyl$C_{1-4}$ alkoxy, $C_{1-4}$ alkylthio, halogenated $C_{1-4}$alkylthio, halo, cyano, and hydroxy, or $R_a$ and $R_b$ together with the carbon atoms of the phenyl ring to which they are attached form a 5- or 6-membered heterocyclyl fused to the phenyl ring; said heterocyclyl optionally substituted with 1 or 2 members independently selected from halo, $C_{1-3}$alkyl, cyano, and hydroxy;

each of $R_{2a}$, $R_{2b}$, $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;

$R_3$ is absent or selected from the group consisting of $C_{1-4}$ alkyl, $C_{1-4}$ alkoxy, halo, cyano, and hydroxy;

$R_4$ is $C_{1-10}$ alkyl, halogenated $C_{1-10}$alkyl, or phenyl $C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of oxo, hydroxy, $C_{1-4}$ alkoxy, halogenated $C_{1-4}$ alkoxy, $C_{3-8}$ cycloalkyl, cyano, heterocyclyl, and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and $SO_2C_{1-3}$alkyl;

or enantiomers, diastereomers, tautomers, or pharmaceutically acceptable salts thereof.

40. A compound according to claim 39, wherein $R_4$ is $C_{1-5}$ alkyl substituted with 1 or 2 members each independently selected from oxo, hydroxy, $C_{1-4}$alkoxy, cyano, and heterocyclyl.

41. A compound according to claim 39, wherein $R_4$ is $C_{1-3}$ alkyl substituted with hydroxy, $C_{1-4}$alkoxy, or cyano.

42. A compound according to claim 39 wherein $R_4$ is halogenated $C_{1-4}$ alkyl substituted with oxo, hydroxy, $C_{1-4}$alkoxy, or cyano.

43. A compound according the claim 39, wherein $R_4$ is fluorinated $C_{1-3}$ alkyl substituted with hydroxy.

44. A compound according to claim 39, wherein $R_{2a}$ and $R_{2b}$ are both absent and $R_{2c}$ is selected from halo, halogenated $C_{1-4}$alkyl, and halogenated $C_{1-4}$alkoxy.

45. A compound according to claim 44, wherein $R_{2c}$ is —$OCF_2CF_2H$ or —$OCF_3$.

46. A compound of Formula (Ic)

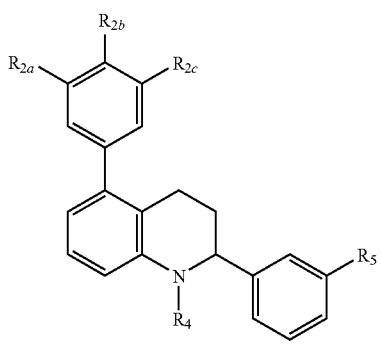

Formula (Ic)

wherein:
each $R_{2a}$, $R_{2b}$, $R_{2c}$ is independently absent or selected from the group consisting of halo, hydroxy, cyano, $C_{1-4}$ alkoxy, halogenated $C_{1-4}$alkoxy, $C_{1-4}$ alkyl, halogenated $C_{1-4}$ alkyl, and —C(O)H;

$R_4$ is $C_{1-10}$ alkyl, halogenated $C_{1-10}$alkyl, or phenyl $C_{1-3}$alkyl, wherein said $C_{1-10}$ alkyl, halogenated $C_{1-10}$alkyl, or phenyl$C_{1-3}$alkyl is optionally substituted with 1-3 members independently selected from the group consisting of halo, oxo, hydroxy, $C_{1-4}$ alkoxy, $C_{3-8}$ cycloalkyl, cyano, heterocyclyl, heteroaryl, tert-butyldimethylsilyloxy, and —$NR_cR_d$, wherein $R_c$ and $R_d$ are independently selected from H, optionally substituted $C_{1-3}$ alkyl, —C(O)$C_{1-3}$alkyl, —C(O)O—$C_{1-3}$ alkyl, and $SO_2C_{1-3}$alkyl;

$R_5$ is selected from the group consisting of $C_{1-4}$ alkyl, halogenated $C_{1-4}$alkyl, $C_{1-4}$ alkoxy, halogenated $C_{1-4}$ alkoxy, $C_{1-4}$ alkylthio, halo, cyano, and hydroxy;

or enantiomers, diastereomers, tautomers, or pharmaceutically acceptable salts thereof.

47. A compound according to claim 46 wherein $R_{2a}$ is absent or halo.

48. A compound according to claim 46 wherein $R_{2b}$ is absent, halo, $C_{1-4}$ alkoxy, halogenated $C_{1-4}$alkoxy, $C_{1-4}$ alkyl, or halogenated $C_{1-4}$ alkyl.

49. A compound according to claim 46 wherein $R_{2c}$ is halo, hydroxy, cyano, $C_{1-4}$ alkoxy, halogenated $C_{1-4}$alkoxy, $C_{1-4}$ alkyl, or halogenated $C_{1-4}$ alkyl.

50. A compound according to claim 46 wherein $R_4$ is $C_{1-5}$ alkyl substituted with 1 or 2 members each independently selected from oxo, hydroxy, $C_{1-4}$alkoxy, cyano, and heterocyclyl.

51. A compound according to claim 46, wherein $R_5$ is $C_{1-4}$ alkyl, halogenated $C_{1-4}$alkyl, $C_{1-4}$alkoxy, halogenated $C_{1-4}$alkoxy, $C_{1-4}$alkylthio, halo, cyano, or hydroxy.

52. A compound according to claim 46, wherein $R_5$ is halogenated $C_{1-4}$alkyl, halogenated $C_{1-4}$alkoxy, or halo.

53. A compound according to claim 46, wherein $R_5$ is —$OCF_3$ or —$OCF_2CF_2H$.

54. A compound selected from the group consisting of
1-[2,5-Bis-(3-trifluoromethoxy-phenyl)-3,4-dihydro-2H-quinolin-1-yl]-2-morpholin-4-yl-ethanone;
1,1,1-Trifluoro-3-[2-[3-(1,1,2,2-tetrafluoro-ethoxy)-phenyl]-5-(3-trifluoromethoxy-phenyl)-3,4-dihydro-2H-quinolin-1-yl]-propan-2-ol;
1,1,1-Trifluoro-3-[2-[3-(1,1,2,2-tetrafluoro-ethoxy)-phenyl]-5-(4-trifluoromethyl-phenyl)-3,4-dihydro-2H-quinolin-1-yl]-propan-2-ol;
3-{5-(4-Chloro-3-methyl-phenyl)-2-[3-(1,1,2,2-tetrafluoro-ethoxy)-phenyl]-3,4-dihydro-2H-quinolin-1-yl}-1,1,1-trifluoro-propan-2-ol;
1,1,1-Trifluoro-3-[2-[3-(1,1,2,2-tetrafluoro-ethoxy)-phenyl]-5-(4-trifluoromethoxy-phenyl)-3,4-dihydro-2H-quinolin-1-yl]-propan-2-ol;
3-[2-[3-(1,1,2,2-Tetrafluoro-ethoxy)-phenyl]-1-(3,3,3-trifluoro-2-hydroxy-propyl)-1,2,3,4-tetrahydro-quinolin-5-yl]-benzonitrile;
1,1,1-Trifluoro-3-{5-(3-fluoro-phenyl)-2-[3-(1,1,2,2-tetrafluoro-ethoxy)-phenyl]-3,4-dihydro-2H-quinolin-1-yl}-propan-2-ol;
1,1,1-Trifluoro-3-[2-[3-(1,1,2,2-tetrafluoro-ethoxy)-phenyl]-5-(3-trifluoromethyl-phenyl)-]3,4-dihydro-2H-quinolin-1-yl]-propan-2-ol;
3-{5-(3-Chloro-phenyl)-2-[3-(1,1,2,2-tetrafluoro-ethoxy)-phenyl]-3,4-dihydro-2H-quinolin-1-yl}-1,1,1-trifluoro-propan-2-ol;
1,1,1-Trifluoro-3-[5-(3-trifluoromethoxy-phenyl)-2-(3-trifluoromethyl-phenyl)-3,4-dihydro-2H-quinolin-1-yl]-propan-2-ol;
1,1,1-Trifluoro-3-[2-phenyl-5-(3-trifluoromethoxy-phenyl)-3,4-dihydro-2H-quinolin-1-yl]-propan-2-ol;
1,1,1-Trifluoro-3-[2-[4-(1,1,2,2-tetrafluoro-ethoxy)-phenyl]-5-(3-trifluoromethoxy-phenyl)-3,4-dihydro-2H-quinolin-1-yl]-propan-2-ol;
1,1,1-Trifluoro-3-[2-(3-fluoro-phenyl)-5-(3-trifluoromethoxy-phenyl)-3,4-dihydro-2H-quinolin-1-yl]-propan-2-ol;
1,1,1-Trifluoro-3-[2-(3-methoxy-phenyl)-5-(3-trifluoromethoxy-phenyl)-3,4-dihydro-2H-quinolin-1-yl]-propan-2-ol;

3-[1-(3,3,3-Trifluoro-2-hydroxy-propyl)-5-(3-trifluoromethoxy-phenyl)-1,2,3,4-tetrahydro-quinolin-2-yl]-benzonitrile;

3-[2-(3-Chloro-phenyl)-5-(3-trifluoromethoxy-phenyl)-3,4-dihydro-2H-quinolin-1-yl]-1,1,1-trifluoro-propan-2-ol;

3-[2,5-Bis-(3-trifluoromethoxy-phenyl)-3,4-dihydro-2H-quinolin-1-yl]-1,1,1-trifluoro-propan-2-ol;

1,1,1-Trifluoro-3-[2-thiophen-2-yl-5-(3-trifluoromethoxy-phenyl)-3,4-dihydro-2H-quinolin-1-yl]-propan-2-ol;

3-[2-Ethyl-5-(3-trifluoromethoxy-phenyl)-3,4-dihydro-2H-quinolin-1-yl]-1,1,1-trifluoro-propan-2-ol;

3-[2-Cyclohexyl-5-(3-trifluoromethoxy-phenyl)-3,4-dihydro-2H-quinolin-1-yl]-1,1,1-trifluoro-propan-2-ol;

2-Ethyl-1-(3-trifluoromethoxy-benzyl)-5-(3-trifluoromethoxy-phenyl)-1,2,3,4-tetrahydro-quinoline;

(αR,2R)-5-(3-Chlorophenyl)-3,4-dihydro-α-methyl-2-[3-(trifluoromethoxy)phenyl]-1(2H)-quinolineethanol;

(αR,2S)-5-(3-Chlorophenyl)-3,4-dihydro-α-methyl-2-[3-(trifluoromethoxy)phenyl]-1(2H)-quinolineethanol;

3-[2-[3(1,1,2,2-Tetrafluoro-ethoxy)-phenyl]-1-(3,3,3-trifluoro-2-hydroxypropyl)-1,2,3,4-tetrahydro-quinolin-5-yl]-phenol;

1-[3-(tert-Butyl-dimethyl-silanyloxy)-propyl]-2,5-bis-(3-trifluoromethoxy-phenyl)-1,2,3,4-tetrahydro-quinoline;

1-[2,5-Bis-(3-trifluoromethoxy-phenyl)-3,4-dihydro-2H-quinolin-1-yl]-3-methyl-butan-2-ol;

1-[2,5-Bis-(3-trifluoromethoxy-phenyl)-3,4-dihydro-2H-quinolin-1-yl]-3-chloro-propan-2-ol;

1-[2,5-Bis-(3-trifluoromethoxy-phenyl)-3,4-dihydro-2H-quinolin-1-yl]-3-fluoro-propan-2-ol;

(αS,2R)-3,4-Dihydro-α-(methoxymethyl)-2,5-bis-[3-(trifluoromethoxy)phenyl]-1(2H)-quinolineethanol;

(αS,2S)-3,4-Dihydro-α-(methoxymethyl)-2,5-bis-[3-(trifluoromethoxy)phenyl]-1(2H)-quinolineethanol;

(αR,2R)-3,4-Dihydro-α-methyl-2,5-bis-[3-(trifluoromethoxy)phenyl]-1(2H)-quinolineethanol;

(αR,2S)-3,4-Dihydro-α-methyl-2,5-bis-[3-(trifluoromethoxy)phenyl]-1(2H)-quinolineethanol;

(αR,2R)-5-(3-Fluorophenyl)-3,4-dihydro-α-methyl-2-[3-(trifluoromethoxy)phenyl]-1(2H)-quinolineethanol;

(αR,2S)-5-(3-Fluorophenyl)-3,4-dihydro-α-methyl-2-[3-(trifluoromethoxy)phenyl]-1(2H)-quinolineethanol;

1,1,1-Trifluoro-3-[5-(3-fluoro-phenyl)-2-(3-trifluoromethoxy-phenyl)-3,4-dihydro-2H-quinolin-1-yl]-propan-2-ol;

(αR,2R)-3,4-Dihydro-5-(3-methoxyphenyl)-α-methyl-2-[3-(trifluoromethoxy)phenyl]-1(2H)-quinolineethanol;

(αR,2S)-3,4-Dihydro-5-(3-methoxyphenyl)-α-methyl-2-[3-(trifluoromethoxy)phenyl]-1(2H)-quinolineethanol;

(αR,2S)-3,4-Dihydro-5-(3-methoxyphenyl)-α-methyl-2-[3-(trifluoromethoxy)phenyl]-1(2H)-quinolineethanol;

(αS,2R)-3,4-Dihydro-α-methyl-2-[3-(1,1,2,2-tetrafluoroethoxy)phenyl]-5-[3-(trifluoromethoxy)phenyl]-1(2H)-quinolineethanol;

(αS,2S)-3,4-Dihydro-α-methyl-2-[3-(1,1,2,2-tetrafluoroethoxy)phenyl]-5-[3-(trifluoromethoxy)phenyl]-1(2H)-quinolineethanol;

3-[2-[3-(1,1,2,2-Tetrafluoro-ethoxyyphenyl]-1-(3,3,3-trifluoro-2-hydroxy-propyl)-1,2,3,4-tetrahydro-quinolin-5-yl]-benzaldehyde;

1,1,1-Trifluoro-3-{2-[3-(1,1,2,2-tetrafluoro-ethoxy)-phenyl]-5-thiophen-3-yl-3,4-dihydro-2H-quinolin-1-yl}-propan-2-ol;

1,1,1-Trifluoro-3-{5-(3-isopropyl-phenyl)-2-[3-(1,1,2,2-tetrafluoro-ethoxy)-phenyl]-3,4-dihydro-2H-quinolin-1-yl}-propan-2-ol;

1,1,1-Trifluoro-3-{5-(3-isopropoxy-phenyl)-2-[3-(1,1,2,2-tetrafluoro-ethoxy)-phenyl]-3,4-dihydro-2H-quinolin-1-yl}-propan-2-ol;

(αR,2R)-3,4-Dihydro-α-methyl-2-[3-(1,1,2,2-tetrafluoroethoxy)phenyl]-5-[3-(trifluoromethoxy)phenyl]-1(2H)-quinolineethanol;

1,1,1-Trifluoro-3-{5-(3-methoxy-phenyl)-2-[3-(1,1,2,2-tetrafluoro-ethoxy)-phenyl]-3,4-dihydro-2H-quinolin-1-yl}-propan-2-ol;

1,1,1-Trifluoro-3-{2-[3-(1,1,2,2-tetrafluoro-ethoxy)-phenyl]-5-thiophen-2-yl-3,4-dihydro-2H-quinolin-1-yl}-propan-2-ol;

1,1,1-Trifluoro-3-{5-pyridin-3-yl-2-[3-(1,1,2,2-tetrafluoro-ethoxy)-phenyl]-3,4-dihydro-2H-quinolin-1-yl}-propan-2-ol;

(αR,2R)-5-(3-Fluorophenyl)-3,4-dihydro-α-methyl-2-[3-(1,1,2,2-tetrafluoroethoxy)phenyl]-1(2H)-quinolineethanol;

(2R,αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2R,αR)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2S,αS)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2S,αS)-3,4-Dihydro-2-[3-(1,1,2,2-tetrafluoroethoxy)phenyl]-5-[3-(trifluoromethoxy)phenyl]α-(trifluoromethyl)-1(2H)-quinolineethanol;

(2S,αR)-3,4-Dihydro-2-[3-(1,1,2,2-tetrafluoroethoxy)phenyl]-5-[3-(trifluoromethoxy)phenyl]-α-(trifluoromethyl)-1(2H)-quinolineethanol;

(2R,αS)-3,4-Dihydro-2-[3-(1,1,2,2-tetrafluoroethoxy)phenyl]-5-[3-(fluoro)phenyl]-α-(trifluoromethyl)-1(2H)-quinolineethanol;

(2R,αS)-3,4-Dihydro-2-[3-(1,1,2,2-tetrafluoroethoxy)phenyl]-5-[3-(fluoro)phenyl]-α-(trifluoromethyl)-1(2H)-quinolineethanol;

(2R,αS)-3,4-Dihydro-2-[3-(1,1,2,2-tetrafluoroethoxy)phenyl]-5-[3-(methoxy)phenyl]-α-(trifluoromethyl)-1(2H)-quinolineethanol;

3-{5-(4-Chloro-3-ethyl-phenoxy)-2-[3-(1,1,2,2-tetrafluoro-ethoxy)-phenyl]-3,4-dihydro-2H-quinolin-1-yl}-1,1,1-trifluoro-propan-2-ol;

3-{5-(2,3-Dichloro-phenoxy)-2-[3-(1,1,2,2-tetrafluoro-ethoxy)-phenyl]-3,4-dihydro-2H-quinolin-1-yl}-1,1,1-trifluoro-propan-2-ol;

1,1,1-Trifluoro-3-[2-[2-(1,1,2,2-tetrafluoro-ethoxy)-phenyl]-5-(3-trifluoromethoxy-phenyl)-3,4-dihydro-2H-quinolin-1-yl]-propan-2-ol; and enantiomers, diastereomers, tautomers, or pharmaceutically acceptable salts thereof.

55. A compound selected from the group consisting of
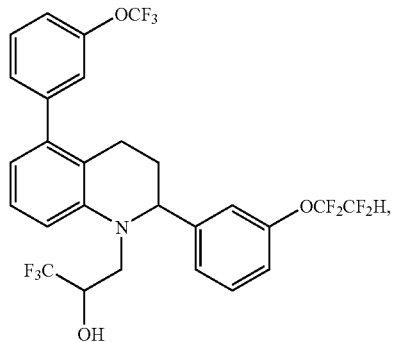
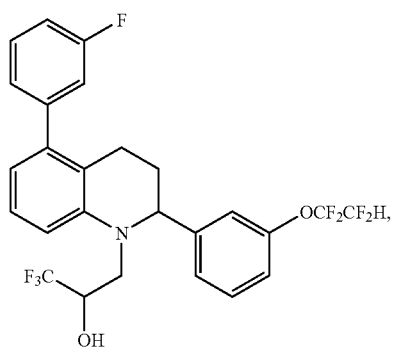
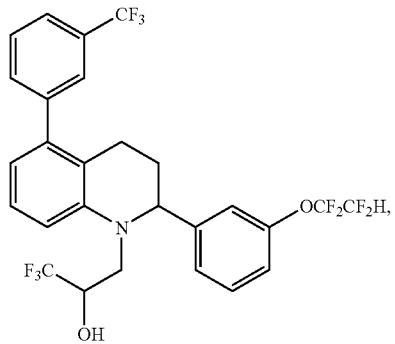
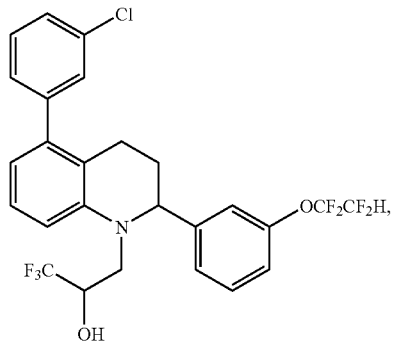
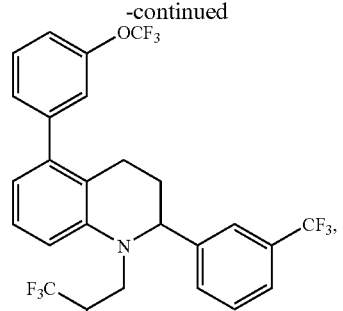
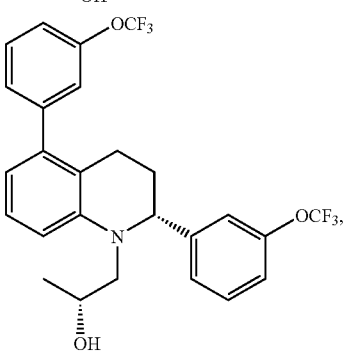
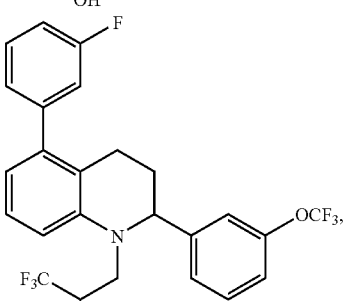
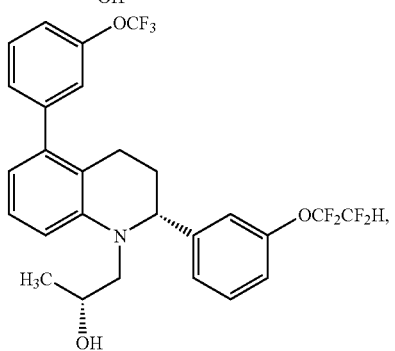
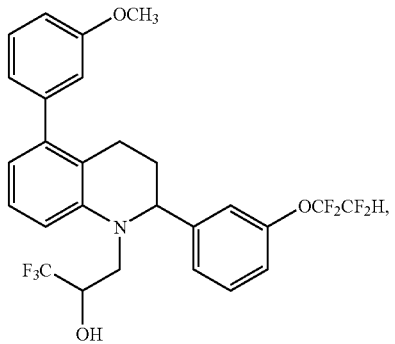

-continued
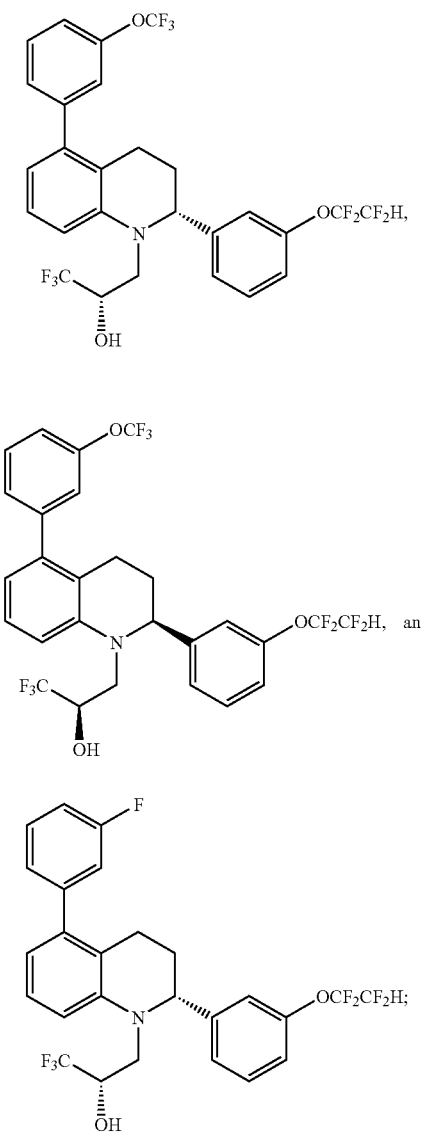
and enantiomers, diastereomers, tautomers, or pharmaceutically acceptable salts thereof.
56. A compound of the formula
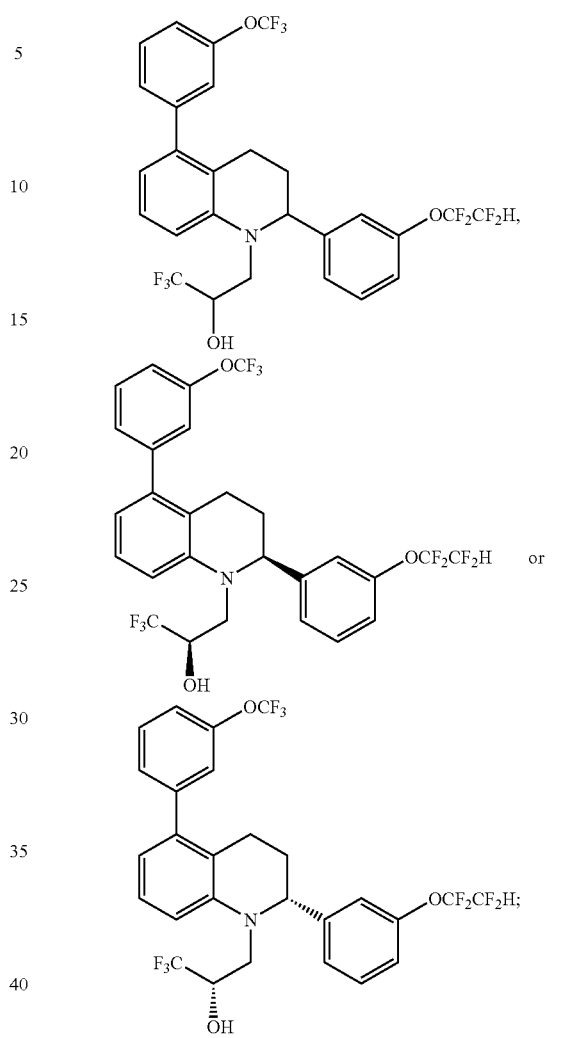
or pharmaceutically acceptable salts thereof.
57. A pharmaceutical composition comprising a compound or salt according to claim 1 admixed with a pharmaceutically acceptable carrier, excipient or diluent.
* * * * *